(12) United States Patent
Damokosh et al.

(10) Patent No.: US 7,470,509 B2
(45) Date of Patent: Dec. 30, 2008

(54) COMPOSITIONS AND METHODS FOR THE IDENTIFICATION, ASSESSMENT, PREVENTION AND THERAPY OF OVARIAN CANCER

(75) Inventors: Andrew I. Damokosh, West Hartford, CT (US); Natalia Iartchouk, Wayland, MA (US); James J. Stec, II, Plymouth, MA (US); Edwin A. Clark, Pennington, NJ (US); Karen Lu, Houston, TX (US); Lynn Hartmann, Rochester, MN (US); Robert C. Bast, Jr., Houston, TX (US); Gordon B. Mills, Houston, TX (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 338 days.

(21) Appl. No.: 10/361,112

(22) Filed: Feb. 7, 2003

(65) Prior Publication Data

US 2003/0180770 A1    Sep. 25, 2003

Related U.S. Application Data

(60) Provisional application No. 60/384,042, filed on May 29, 2002, provisional application No. 60/355,388, filed on Feb. 8, 2002.

(51) Int. Cl.
*C12Q 1/68* (2006.01)
(52) U.S. Cl. .................. 435/6; 536/23.1; 536/23.5; 435/4
(58) Field of Classification Search .............. 435/6, 435/4; 536/23.1, 23.5
See application file for complete search history.

(56) References Cited

U.S. PATENT DOCUMENTS 6,258,536 B1    7/2001    Oliner et al.

OTHER PUBLICATIONS

Engblom et al. (Anticancer Res. Jul.-Aug. 1997; 17 (4A): 2475-2479).*
Gyorffy et al. (Oncogene. 2005; 24: 7542-751).*
Duan et al. (Cancer Chemother. Pharmacol. Mar. 2005; 55 (3): 277-285).*
Kolfschoten et al. (Br. J. Cancer. 2000; 83 (7): 921-927).*
Hannermann et al. (J. Clin. Oncol. May 2005; 23 (15): 3331-3342).*
Hogberg et al. (Acta Oncologica. 2001; 40 (2/3): 340-360).*
Hough et al. (Cancer Res. Nov. 15, 2000; 60: 6281-6287).*
Tewari et al. (Cur. Oncol. Rep. 1999; 1: 77-84).*
Xiong et al. (Mol. Genetics Metab. 2001; 73: 239-247).*
Nguyen et al. (Bioinformatics. 2002; 18 (1): 39-50).*
Hagopian et al. (Clin. Cancer Res. Mar. 1999; 5: 655-63).*
Byvatov et al. (Appl. Bioinformatics. 203; 2 (2): 67-77).*
Somorjai et al. (Bioinformatics. 2003; 19 (12): 1484-1491).*
Hartmann et al. (Clin. Cancer Res. Mar. 15, 2005; 11: 2149-2155.*
Spentzos et al. (J. Clin. Oncol. Nov. 1, 2005; 23 (31): 7911-7918).*
Goto et al. (Oncol. Rep. 2006; 15: 1265-1271).*
Komatsu et al. (Mol. Cancer Ther. Mar. 2006; 5 (3): 767-775).*
Lavarino et al. (J. Clin. Oncol. 2000; 18 (23): 3936-3945).*
Ripley, B.D., "Pattern Recognition and Neural Networks," *Cambridge University Press*, (1996), pp. 91-93, 191, 365.

* cited by examiner

*Primary Examiner*—Stephen L Rawlings

(57) ABSTRACT

The present invention is directed to the identification of markers that can be used to determine whether ovarian cancer is sensitive or resistant to a therapeutic agent. In particular, the present invention is directed to the use of certain combinations of markers, wherein the expression of the markers correlates with sensitivity or resistance to a therapeutic agent. Thus, by examining the expression of the individual markers of a marker set, also referred to as the expression profile of the marker set, it is possible to determine whether a therapeutic agent, or combination of agents, will be most likely to reduce the growth rate of the ovarian cancer.

19 Claims, No Drawings

COMPOSITIONS AND METHODS FOR THE IDENTIFICATION, ASSESSMENT, PREVENTION AND THERAPY OF OVARIAN CANCER

RELATED APPLICATIONS

This Application claims the benefit of U.S. Provisional Application No. 60/384,042 filed May 29, 2002, and U.S. Provisional Application No. 60/355,388, filed Feb. 8, 2002. The teachings of each of these referenced applications are incorporated herein by reference in their entirety.

BACKGROUND OF THE INVENTION

The increased number of cancer cases reported in the United States, and, indeed, around the world, is a major concern. Currently there are only a handfull of detection and treatment methods available for specific types of cancer, and these provide no absolute guarantee of success. In order to be most effective, these treatments require not only an early detection of the malignancy, but also a reliable assessment of the severity of the malignancy.

Ovarian cancer is responsible for significant morbidity and mortality in populations around the world. Ovarian cancer is classified, on the basis of clinical and pathological features, in three groups, namely epithelial ovarian cancer (EOC; >90% of ovarian cancer in Western countries), germ cell tumors (circa 2-3% of ovarian cancer), and stromal ovarian cancer (circa 5% of ovarian cancer; Ozols et al., 1997, *Cancer Principles and Practice of Oncology*, 5th ed., DeVita et al. Eds. pp. 1502). Relative to EOC, germ cell tumors and stromal ovarian cancers are more easily detected and treated at an early stage, translating into higher/better survival rates for patients afflicted with these two types of ovarian cancer.

There are numerous types of ovarian tumors, some of which are benign, and others of which are malignant. Treatment (including non-treatment) options and predictions of patient outcome depend on accurate classification of the ovarian cancer. Ovarian cancers are named according to the type of cells from which the cancer is derived and whether the ovarian cancer is benign or malignant. Recognized histological tumor types include, for example, serous, mucinous, endometrioid, and clear cell tumors. In addition, ovarian cancers are classified according to recognized grade and stage scales.

In grade I, the tumor tissue is well differentiated from normal ovarian tissue. In grade II, tumor tissue is moderately well differentiated. In grade III, the tumor tissue is poorly differentiated from normal tissue, and this grade correlates with a less favorable prognosis than grades I and II. Stage I is generally confined within the capsule surrounding one (stage IA) or both (stage IB) ovaries, although in some stage I (i.e. stage IC) cancers, malignant cells may be detected in ascites, in peritoneal rinse fluid, or on the surface of the ovaries. Stage II involves extension or metastasis of the tumor from one or both ovaries to other pelvic structures. In stage IIA, the tumor extends or has metastasized to the uterus, the fallopian tubes, or both. Stage IIB involves extension of the tumor to the pelvis. Stage IIC is stage IIA or IIB in which malignant cells may be detected in ascites, in peritoneal rinse fluid, or on the surface of the ovaries. In stage III, the tumor comprises at least one malignant extension to the small bowel or the omentum, has formed extrapelvic peritoneal implants of microscopic (stage IIIA) or macroscopic (<2 centimeter diameter, stage IIIB; >2 centimeter diameter, stage IIIC) size, or has metastasized to a retroperitoneal or inguinal lymph node (an alternate indicator of stage IIIC). In stage IV, distant (i.e. non-peritoneal) metastases of the tumor can be detected.

The durations of the various stages of ovarian cancer are not presently known, but are believed to be at least about a year each (Richart et al., 1969, *Am. J. Obstet. Gynecol.* 105: 386). Prognosis declines with increasing stage designation. For example, 5-year survival rates for patients diagnosed with stage I, II, III, and IV ovarian cancer are 80%, 57%, 25%, and 8%, respectively.

Despite being the third most prevalent gynecological cancer, ovarian cancer is the leading cause of death among those afflicted with gynecological cancers. The disproportionate mortality of ovarian cancer is attributable to a substantial absence of symptoms among those afflicted with early-stage ovarian cancer and to difficulty diagnosing ovarian cancer at an early stage. Patients afflicted with ovarian cancer most often present with non-specific complaints, such as abnormal vaginal bleeding, gastrointestinal symptoms, urinary tract symptoms, lower abdominal pain, and generalized abdominal distension. These patients rarely present with paraneoplastic symptoms or with symptoms which clearly indicate their affliction. Presently, less than about 40% of patients afflicted with ovarian cancer present with stage I or stage II. Management of ovarian cancer would be significantly enhanced if the disease could be detected at an earlier stage, when treatments are much more generally efficacious.

Ovarian cancer may be diagnosed, in part, by collecting a routine medical history from a patient and by performing physical examination, x-ray examination, and chemical and hematological studies on the patient. Hematological tests which may be indicative of ovarian cancer in a patient include analyses of serum levels of proteins designated CA125 and DF3 and plasma levels of lysophosphatidic acid (LPA). Palpation of the ovaries and ultrasound techniques (particularly including endovaginal ultrasound and color Doppler flow ultrasound techniques) can aid detection of ovarian tumors and differentiation of ovarian cancer from benign ovarian cysts. However, a definitive diagnosis of ovarian cancer typically requires performing exploratory laparotomy of the patient.

Potential tests for the detection of ovarian cancer (e.g., screening, reflex or monitoring) may be characterized by a number of factors. The "sensitivity" of an assay refers to the probability that the test will yield a positive result in an individual afflicted with ovarian cancer. The "specificity" of an assay refers to the probability that the test will yield a negative result in an individual not afflicted with ovarian cancer. The "positive predictive value" (PPV) of an assay is the ratio of true positive results (i.e. positive assay results for patients afflicted with ovarian cancer) to all positive results (i.e. positive assay results for patients afflicted with ovarian cancer + positive assay results for patients not afflicted with ovarian cancer). It has been estimated that in order for an assay to be an appropriate population-wide screening tool for ovarian cancer the assay must have a PPV of at least about 10% (Rosenthal et al., 1998, *Sem. Oncol.* 25:315-325). It would thus be desirable for a screening assay for detecting ovarian cancer in patients to have a high sensitivity and a high PPV. Monitoring and reflex tests would also require appropriate specifications.

Owing to the cost, limited sensitivity, and limited specificity of known methods of detecting ovarian cancer, screening is not presently performed for the general population. In addition, the need to perform laparotomy in order to diagnose ovarian cancer in patients who screen positive for indications of ovarian cancer limits the desirability of population-wide screening, such that a PPV even greater than 10% would be desirable.

Prior use of serum CA125 level as a diagnostic marker for ovarian cancer indicated that this method exhibited insufficient specificity for use as a general screening method. Use of a refined algorithm for interpreting CA125 levels in serial retrospective samples obtained from patients improved the specificity of the method without shifting detection of ovarian cancer to an earlier stage (Skakes, 1995, *Cancer* 76:2004). Screening for LPA to detect gynecological cancers including ovarian cancer exhibited a sensitivity of about 96% and a specificity of about 89%. However, CA125-based screening methods and LPA-based screening methods are hampered by the presence of CA125 and LPA, respectively, in the serum of patients afflicted with conditions other than ovarian cancer. For example, serum CA125 levels are known to be associated with menstruation, pregnancy, gastrointestinal and hepatic conditions such as colitis and cirrhosis, pericarditis, renal disease, and various non-ovararian malignancies. Serum LPA is known, for example, to be affected by the presence of non-ovarian gynecological malignancies. A screening method having a greater specificity for ovarian cancer than the current screening methods for CA125 and LPA could provide a population-wide screening for early stage ovarian cancer.

Presently greater than about 60% of ovarian cancers diagnosed in patients are stage III or stage IV cancers. Treatment at these stages is largely limited to cytoreductive surgery (when feasible) and chemotherapy, both of which aim to slow the spread and development of metastasized tumor. Substantially all late stage ovarian cancer patients currently undergo combination chemotherapy as primary treatment, usually a combination of a platinum compound and a taxane. Median survival for responding patients is about one year. Combination chemotherapy involving agents such as doxorubicin, cyclophosphamide, cisplatin, hexamethylmelamine, paclitaxel, and methotrexate may improve survival rates in these groups, relative to single-agent therapies. Various recently-developed chemotherapeutic agents and treatment regimens have also demonstrated usefulness for treatment of advanced ovarian cancer. For example, use of the topoisomerase I inhibitor topectan, use of amifostine to minimize chemotherapeutic side effects, and use of intraperitoneal chemotherapy for patients having peritoneally implanted tumors have demonstrated at least limited utility. Presently, however, the 5-year survival rate for patients afflicted with stage III ovarian cancer is 25%, and the survival rate for patients afflicted with stage IV ovarian cancer is 8%.

It would therefore be beneficial to provide specific methods and reagents for the diagnosis, staging, prognosis, monitoring, and treatment of diseases associated with ovarian cancer, or to indicate a predisposition to such for preventative measures. The present invention is directed towards these needs.

SUMMARY OF THE INVENTION

The present invention is directed to the identification of markers that can be used to determine the sensitivity or resistance of ovarian cancer to a therapeutic agent. By examining the expression of one or more of the identified markers, whose expression correlates with sensitivity to a therapeutic agent or resistance to a therapeutic agent, in a sample of ovarian cancer cells, it is possible to determine whether a therapeutic agent or combination of agents will be most likely to reduce the growth rate of the ovarian cancer cells and can further be used in selecting appropriate treatment agents. In one embodiment, the invention is further directed to the identification of markers that can be used to determine the sensitivity or resistance of ovarian tumors to a therapeutic agent. By examining the expression of one or more of the identified markers, whose expression correlates with sensitivity to a therapeutic agent or resistance to a therapeutic agent, in a sample of ovarian tumor cells, it is possible to determine whether a therapeutic agent or combination of agents will be most likely to reduce the growth rate of the ovarian tumor cells and can further be used in selecting appropriate treatment agents. The markers of the present invention, whose expression correlates with sensitivity or with resistance to an agent, are identified in Table 1 as n1-n78 and further characterized in Table 16.

The invention further comprises the use of certain combinations of markers, wherein the expression of one or more markers, correlates with sensitivity or resistance to a therapeutic agent. Preferred combinations of markers referred to herein as "marker sets" are set forth in Tables 2-15. In addition, by examining the expression of the individual markers of the newly-identified marker sets (also referred to as the "expression profile" of the marker set), it is possible to determine whether a therapeutic agent or combination of agents will be most likely to reduce the growth rate of the ovarian cancer cells and can further be used in selecting appropriate treatment agents. Moreover, by examining the expression of individual markers and marker sets, it is also possible to determine whether a patient will most likely experience early or late recurrence of ovarian cancer growth. This information can be used in selecting an appropriate treatment.

Table 1 lists all of the markers of the invention (and comprises markers listed in Tables 2-16) which are designated with a marker identification number ("No."), the image Clone ID ("Image Clone ID"), the gene corresponding to the marker ("Gene Name"), the Accession Number ("Accession"), the GeneBank number ("GI number"), and the Reference Sequence Nucleic Accession Number ("RefSeq").

Tables 2-15 list marker sets, comprised of multiple individual markers, which are designated with a marker identification number within each marker set ("Number"), the marker identification numbers set forth in Table 1 ("Marker Number"), the Image clone identification number ("Image Clone Id"), the feature selection ("Feature Selection"), and the classification error rate of the model ("Classification Error Rate of the Model"). Table 2 is a preferred marker set.

Table 16 identifies the 78 individual markers of the present invention (n1-n78). The marker identification numbers are set forth in Table 16 ("No"), the Image clone identification number ("Image Clone Id"), and the Signal-to-noise ("SNR score"). Table 16 lists markers using SNR statistics applied to 18,539 genes of the 51 ovarian samples. In particular, the markers in Table 16 with negative SNR values are correlated with resistance to an agent (referred to herein as "resistance markers"), and the markers with positive SNR scores are correlated with sensitivity to an agent (referred to herein as "sensitivity markers").

By examining the expression of one or more of the identified markers or marker sets in ovarian cancer, it is possible to determine which therapeutic agent or combination of agents will be most likely to reduce the growth rate of the ovarian cancer. By examining the expression of one or more of the identified markers or marker sets in ovarian cancer, it is also possible to determine which therapeutic agent or combination of agents will be the least likely to reduce the growth rate of the ovarian cancer. By examining the expression of one or more of the identified markers or marker sets, it is therefore possible to eliminate ineffective or inappropriate therapeutic agents. Moreover, by examining the expression of one or more of the identified markers or marker sets in an ovarian cancer sample taken from a patient during the course of therapeutic treatment, it is possible to determine whether the therapeutic treatment is continuing to be effective or whether the ovarian cancer has become resistant (refractory) to the therapeutic treatment. It is also possible to identify new anti-cancer agents by examining the expression of one or more markers or marker sets when ovarian cancer cells are exposed to a potential anti-cancer agent. Thus, in one embodiment, the ovarian cancer cells used in the methods of the present invention are from an ovarian tumor sample. Importantly, these determinations can be made on a patient by patient basis or on an agent by agent (or combination of agents) basis. Thus, one can determine whether or not a particular therapeutic treatment is likely to benefit a particular patient or group/class of patients, or whether a particular treatment should be continued.

The invention also relates to various methods, reagents and kits for diagnosing, staging, prognosing, monitoring and treating cancers, particularly ovarian cancer. "Ovarian cancer" as used herein includes ovarian tumors, carcinomas, (e.g., carcinoma in situ, invasive carcinoma, metastatic carcinoma) and pre-malignant conditions. Thus, in one embodiment, the ovarian cancer cells used in the methods of the present invention are from an ovarian tumor sample.

In one embodiment, the invention provides a diagnostic method of assessing whether a patient has ovarian cancer or has higher than normal risk for developing ovarian cancer, comprising the steps of comparing the level of expression of a marker of the invention in a patient sample and the normal level of expression of the marker in a control, e.g., a sample from a patient without ovarian cancer. A significantly higher level of expression of the marker in the patient sample as compared to the normal level is an indication that the patient is afflicted with ovarian cancer or has higher than normal risk for developing ovarian cancer.

According to the invention, the markers are selected such that the positive predictive value of the methods of the invention is at least about 10%, preferably about 25%, more preferably about 50% and most preferably about 90%. Also preferred for use in the methods of the invention are markers that are differentially expressed, as compared to normal ovarian cells, by at least two-fold in at least about 20%, more preferably about 50%, and most preferably about 75% of any of the following conditions: stage I ovarian cancer patients, stage II ovarian cancer patients, stage III ovarian cancer patients, stage IV ovarian cancer patients, grade I ovarian cancer patients, grade II ovarian cancer patients, grade III ovarian cancer patients, epithelial ovarian cancer patients, stromal ovarian cancer patients, germ cell ovarian cancer patients, malignant ovarian cancer patients, benign ovarian cancer patients, serous neoplasm ovarian cancer patients, mucinous neoplasm ovarian cancer patients, endometrioid neoplasm ovarian cancer patients and/or clear cell neoplasm ovarian cancer patients.

The present invention further provides previously unknown or unrecognized targets for the development of anti-cancer agents, such as chemotherapeutic compounds. The markers and marker sets of the present invention can be used as targets in developing treatments (either single agent or multiple agent) for ovarian cancer, which displays resistance to agents and exhibits expression of one or more of the markers identified herein.

Other features and advantages of the invention will be apparent from the detailed description and from the claims. Although materials and methods similar or equivalent to those described herein can be used in the practice or testing of the invention, the preferred materials and methods are described below.

DETAILED DESCRIPTION OF THE INVENTION

The present invention is based, in part, on the identification of individual markers and marker sets that can be used to determine whether ovarian cancer is sensitive or resistant to a therapeutic agent. Based on these identifications, the present invention provides, without limitation: 1) methods for determining whether a therapeutic agent (or combination of agents) will or will not be effective in stopping or slowing ovarian cancer; 2) methods for determining the likelihood of recurrence and time of recurrence of ovarian cancer; 3) methods for monitoring the effectiveness of a therapeutic agent (or combination of agents) used for the treatment of ovarian cancer; 4) methods for identifying new therapeutic agents for the treatment of ovarian cancer; 5) methods for identifying combinations of therapeutic agents for use in treating ovarian cancer; 6) methods for identifying specific therapeutic agents and combinations of therapeutic agents that are effective for the treatment of ovarian cancer in specific patients; and 7) methods for identifying therapeutic agents and combinations of therapeutic agents that are effective for treating ovarian cancer that is likely to recur.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. The content of all GenBank and IMAGE Consortium database records cited throughout this application (including the Tables) are also hereby incorporated by reference. In the case of conflict, the present specification, including definitions, will control. In addition, the materials, methods, and examples are illustrative only and are not intended to be limiting.

The articles "a" and "an" are used herein to refer to one or to more than one (i.e. to at least one) of the grammatical object of the article. By way of example, "an element" means one element or more than one element.

A "marker" is a naturally-occurring polymer corresponding to at least one of the nucleic acids listed in Table 1. For example, markers include, without limitation, sense and anti-sense strands of genomic DNA (i.e. including any introns occurring therein), RNA generated by transcription of genomic DNA (i.e. prior to splicing), RNA generated by splicing of RNA transcribed from genomic DNA, and proteins generated by translation of spliced RNA (i.e. including proteins both before and after cleavage of normally cleaved regions such as transmembrane signal sequences). As used herein, "marker" may also include a cDNA made by reverse transcription of an RNA generated by transcription of genomic DNA (including spliced RNA).

A "marker set" is a group of markers. Preferred marker sets of the present invention are identified in Tables 2-15.

The term "probe" refers to any molecule which is capable of selectively binding to a specifically intended target molecule, for example a marker of the invention. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

The "normal" level of expression of a marker is the level of expression of the marker in cells of a patient not afflicted with cancer. A normal level of expression of a marker may also refer to the level of expression of a "control sample", (e.g., sample from a healthy subjects not having the marker associated disease). A control sample may be comprised of a control database.

"Over-expression" and "under-expression" of a marker refer to expression of the marker of a patient at a greater or lesser level, respectively, than normal level of expression of the marker (e.g. at least two-fold greater or lesser level).

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" is a polynucleotide (e.g. an RNA, a cDNA, or an analog of one of an RNA or cDNA) which is complementary to or homologous with all or a portion of a mature RNA made by transcription of a genomic DNA corresponding to a marker of the invention and normal post-transcriptional processing (e.g. splicing), if any, of the transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

A marker is "fixed" to a substrate if it is covalently or non-covalently associated with the substrate such the substrate can be rinsed with a fluid (e.g. standard saline citrate, pH 7.4) without a substantial fraction of the marker dissociating from the substrate.

As used herein, a "naturally-occurring" nucleic acid molecule refers to an RNA or DNA molecule having a nucleotide sequence that occurs in nature (e.g. encodes a natural protein).

Expression of a marker or marker set in a patient is "significantly" higher or lower than the normal level of expression of a marker or marker set if the level of expression of the marker or marker set is greater or less, respectively, than the normal level by an amount greater than the standard error of the assay employed to assess expression, and preferably at least twice, and more preferably three, four, five or ten times that amount. Alternately, expression of the marker or marker set in the patient can be considered "significantly" higher or lower than the normal level of expression if the level of expression is at least about two, and preferably at least about three, four, or five times, higher or lower, respectively, than the normal level of expression of the marker or marker set.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

"Ovarian cancer" as used herein includes ovarian tumors, carcinomas, (e.g., carcinoma in situ, invasive carcinoma, metastatic carcinoma) and pre-malignant conditions. By "ovarian tumor" is meant both benign and malignant tumors, such as ovarian germ cell tumors, e.g. teratomas, dysgerminoma, endodermal sinus tumor and embryonal carcinoma, and ovarian stromal tumors, e.g. granulosa, theca, Sertoli, Leydig, and collagen-producing stromal cells. Ovarian cancers as used herein also includes art recognized histological tumor types, which include, for example, serous, mucinous, endometrioid, and clear cell tumors. The term ovarian cancer as used herein further includes art recognized grade and stage scales: grade I, II and III and stage I (including stage 1A, 1B and 1C), II (including stage IIA, IIB and IIC), III (including stage IIIA, IIIB and IIIC), and IV.

"Early recurrence" refers to recurrence of ovarian cancer in less than 21 months from removal of an original ovarian tumor.

"Late recurrence" refers to recurrence of ovarian cancer in greater than 21 months from removal of an original ovarian tumor.

Ovarian cancer, including an ovarian tumor, is "sensitive" to a therapeutic agent if its rate of growth is inhibited as a result of contact with the therapeutic agent, compared to its growth in the absence of contact with the therapeutic agent. The quality of being sensitive to a therapeutic agent is a variable one, with different ovarian cancers exhibiting different levels of "sensitivity" to a given therapeutic agent, under different conditions. In one embodiment of the invention, ovarian cancers may be predisposed to sensitivity to an agent if one or more of the corresponding sensitivity markers are expressed. In another embodiment of the invention, the predisposition of ovarian cancer to be sensitive to an agent is determined by the methods of the present invention, wherein expression of the individual markers of the marker sets identified in Tables 2-15, is evaluated.

Ovarian cancer, including an ovarian tumor and ovarian tumor cells, is "resistant" to a therapeutic agent if its rate of growth is not inhibited, or inhibited to a very low degree, as a result of contact with the therapeutic agent when compared to its growth in the absence of contact with the therapeutic agent. The quality of being resistant to a therapeutic agent is a highly variable one, with different ovarian cancers exhibiting different levels of "resistance" to a given therapeutic agent, under different conditions. In another embodiment of the invention, ovarian cancers may be predisposed to resistance to an agent if one or more of the corresponding resistance markers are expressed. In another embodiment of the invention, the predisposition of ovarian cancer to be resistant to an agent is determined by the methods of the present invention, wherein expression of the individual markers of the marker sets identified in Tables 2-15, is evaluated.

A kit is any manufacture (e.g. a package or container) comprising at least one reagent, e.g. a probe, for specifically detecting a marker or marker set of the invention. The manufacture may be promoted, distributed, or sold as a unit for performing the methods of the present invention. The reagents included in such a kit comprise probes/primers and/or antibodies for use in detecting sensitivity and resistance marker expression. In addition, the kits of the present invention may preferably contain instructions which describe a suitable detection assay. Such kits can be conveniently used, e.g., in clinical settings, to diagnose patients exhibiting symptoms of ovarian cancer, in particular patients exhibiting the possible presence of an ovarian tumor.

SPECIFIC EMBODIMENTS

I. Identification of Sensitivity and Resistance Markers

The present invention provides markers that are expressed in ovarian cancer that are sensitive to a given therapeutic agent and whose expression correlates with sensitivity to that therapeutic agent. The present invention also provides markers that are expressed in ovarian cancer that are resistant to a given therapeutic agent and whose expression correlates with resistance to that therapeutic agent. Accordingly, one or more of the markers can be used to identify ovarian cancer that can be successfully treated by that agent. In one embodiment, one or more of the markers of the present invention can be used to identify ovarian tumor cells that can be successfully treated by that agent. In addition, the markers of the present invention can be used to identify ovarian cancer that has become or is at risk of becoming refractory to treatment with the agent. The invention also features combinations of marker sets, referred to herein as "marker sets," that can predict patients that are likely to respond or not to respond to an agent.

Table 1 identifies markers whose expression correlates with sensitivity or resistance to a taxane compound and/or a platinum compound. In particular, Table 1 sets forth 78 markers identified in ovarian tumor samples as sensitive or resistant to the combination therapy of TAXOL and cisplatin. It is preferable to determine the expression of two or more of the identified sensitivity or resistance markers, more preferably, three or more of the identified sensitivity or resistance markers, most preferably, a set of the identified sensitivity and/or resistance markers, such as the sets identified in Tables 2-15. Thus, it is preferable to assess the expression of a set or panel of sensitivity and resistance markers, i.e., the expression profile of a marker set.

Table 16 identifies the 78 individual markers of the present invention whose expression correlates with sensitivity or resistance to a taxane compound and/or a platinum compound. Table 16 lists markers using SNR statistics applied to 18,539 genes of the 51 ovarian tumor samples. In particular, the markers in Table 16 with negative SNR values are correlated with resistance to an agent (referred to herein as "resistance markers"), and the markers with positive SNR scores are correlated with sensitivity to an agent (referred to herein as "sensitivity markers").

II. Determining Sensitivity or Resistance to an Agent

The expression level (including protein level) of the identified sensitivity and resistance markers may be used to: 1) determine if ovarian cancer can be treated by an agent or combination of agents; 2) determine if ovarian cancer is responding to treatment with an agent or combination of agents; 3) select an appropriate agent or combination of agents for treating ovarian cancer; 4) monitor the effectiveness of an ongoing treatment; 5) identify new treatments (either single agent or combination of agents); 6) differentiate early versus late recurrence of the ovarian cancer; and 7) select an appropriate agent or combination of agents in treating early and late recurrence of the ovarian cancer In particular, the identified sensitivity and resistance markers may be utilized to determine appropriate therapy, to monitor clinical therapy and human trials of a drug being tested for efficacy, and to develop new agents and therapeutic combinations.

The present invention provides methods for determining whether an agent, e.g., a chemotherapeutic agent, can be used to reduce the growth rate of ovarian cancer comprising the steps of:
  a) obtaining a sample of ovarian cancer cells;
  b) evaluating the expression of the individual markers of a marker set; and
  c) identifying that an agent is or is not appropriate to reduce the growth rate of the ovarian cancer cells based on the evaluation.

In a preferred embodiment, the marker set is selected from those set forth in Tables 2-15.

In another embodiment, the invention provides a method for determining whether an agent, e.g., a chemotherapeutic agent, can be used to reduce the growth rate of ovarian cancer comprising the steps of:
  a) obtaining a sample of ovarian cancer cells;
  b) determining the expression profile of a marker set; and c) identifying that an agent is or is not appropriate to reduce the growth rate of the ovarian cancer cells based on the expression profile.

In a preferred embodiment, the marker set is selected from those set forth in Tables 2-15.

In another embodiment, the invention provides a method for determining whether an agent can be used to reduce the growth of ovarian cancer, comprising the steps of:
 a) obtaining a sample of ovarian cancer cells;
 b) exposing some of the ovarian cancer cells to one or more test agents;
 c) evaluating the expression of the individual markers of a marker set, both in ovarian cancer cells exposed to the agent and in ovarian cancer cells that have not been exposed to the agent; and
 d) identifying that an agent is or is not appropriate to treat the ovarian cancer based on the evaluation.

In a preferred embodiment, the marker set is selected from those set forth in Tables 2-15.

In another embodiment, the invention provides a method for determining whether an agent can be used to reduce the growth of ovarian cancer, comprising the steps of:
 a) obtaining a sample of ovarian cancer cells;
 b) exposing some of the ovarian cancer cells to one or more test agents;
 c) determining the expression profile of the marker set, both in ovarian cancer cells exposed to the agent and in ovarian cancer cells that have not been exposed to the agent; and
 d) identifying that an agent is appropriate to treat the ovarian cancer when the expression profile of the marker set demonstrates decreased resistance or increased sensitivity in the presence of the agent.

Alternatively, in step (d), an agent can be identified as not being appropriate to treat the ovarian cancer when the expression profile of the marker set demonstrates decreased sensitivity or increased resistance in the presence of the agent. In a preferred embodiment, the marker set is selected from those set forth in Tables 2-15.

In another embodiment, the invention provides a method for determining whether treatment with an anti-cancer agent should be continued in an ovarian cancer patient, comprising the steps of:
 a) obtaining two or more samples of ovarian cancer cells from a patient at different times during the course of anti-cancer agent treatment;
 b) evaluating the expression of the individual markers of a marker set, in the two or more samples; and
 c) continuing or discontinuing the treatment based on the evaluation.

In a preferred embodiment, the marker set is selected from those set forth in Tables 2-15.

In another embodiment, the invention provides a method for determining whether treatment with an anti-cancer agent should be continued in an ovarian cancer patient, comprising the steps of:
 a) obtaining two or more samples of ovarian cancer cells from a patient at different times during the course of anti-cancer agent treatment;
 b) determining the expression profile a marker set, in the two or more samples; and
 c) continuing the treatment when the expression profile of the marker set does not demonstrate decreased sensitivity and/or does not demonstrate increased resistance during the course of treatment.

Alternatively, in step (c), the treatment is discontinued when the expression profile of the marker set demonstrates decreased sensitivity and/or increased resistance during the course of treatment. In a preferred embodiment, the marker set is selected from those set forth in Tables 2-15.

In a further embodiment, the invention provides a method for determining whether treatment with an anti-cancer agent should be continued in an ovarian cancer patient, comprising the steps of:
 a) obtaining two or more samples of ovarian cancer cells from a patient at different times during the course of anti-cancer agent treatment;
 b) determining the expression profile of a marker set, in the two or more samples; and
 c) continuing the treatment when the expression profile of the marker set demonstrates increased sensitivity and/or decreased resistance during the course of treatment.

Alternatively, in step (c), the treatment is discontinued when the expression profile of the marker set demonstrates decreased sensitivity and/or increased resistance during the course of treatment. In a preferred embodiment, the marker set is selected from those set forth in Tables 2-15.

The present invention further provides methods for determining whether an agent, e.g., a chemotherapeutic agent, can be used to reduce the growth rate of ovarian cancer comprising the steps of:
 a) obtaining a sample of ovarian cancer cells;
 b) determining whether the ovarian cancer cells express one or more markers identified in Table 16; and
 c) identifying that an agent is or is not appropriate to treat the ovarian cancer based on the expression of one or more markers identified in Table 16.

In another embodiment, the invention provides a method for determining whether an agent can be used to reduce the growth of ovarian cancer, comprising the steps of:
 a) obtaining a sample of ovarian cancer cells;
 b) determining whether the ovarian cancer cells express one or more markers identified in Table 16; and
 c) identifying that an agent is appropriate to treat the ovarian cancer when the expression of the sensitivity markers identified in Table 16 is increased and/or the expression of the resistance markers identified in Table 16 is decreased in the presence of the agent.

Alternatively, in step (c), an agent can be identified as not being appropriate to treat the ovarian cancer when the expression of the sensitivity markers identified in Table 16 is decreased and/or the expression of the resistance markers identified in Table 16 is increased in the presence of the agent.

In another embodiment, the invention provides a method for determining whether an agent can be used to reduce the growth of ovarian cancer, comprising the steps of:
 a) obtaining a sample of ovarian cancer cells;
 b) exposing some of the ovarian cancer cells to one or more test agents;
 c) determining the level of expression of one or more markers identified in Table 16 both in ovarian cancer cells exposed to the agent and in ovarian cancer cells that have not been exposed to the agent; and
 d) identifying that an agent is appropriate to treat the ovarian cancer when the expression of the sensitivity markers identified in Table 16 is increased and/or the expression of the resistance markers identified in Table 16 is decreased in the presence of the agent.

Alternatively, in step (d), an agent can be identified as not being appropriate to treat the ovarian cancer when the expression of the sensitivity markers identified in Table 16 is decreased and/or the expression of the resistance markers identified in Table 16 is increased in the presence of the agent.

In another embodiment, the invention provides a method for determining whether treatment with an anti-cancer agent should be continued in an ovarian cancer patient, comprising the steps of:
- a) obtaining two or more samples of ovarian cancer cells from a patient at different times during the course of anti-cancer agent treatment;
- b) determining the level of expression in the ovarian cancer cells of one or more genes which correspond to markers identified in Table 16 in the two or more samples; and
- c) continuing the treatment when the expression level of the sensitivity markers identified in Table 16 does not decrease and/or the expression level of the resistance markers identified in Table 16 does not increase during the course of treatment.

Alternatively, in step (c), the treatment is discontinued when the expression level of the sensitivity markers identified in Table 16 is decreased and/or the expression level of the resistance markers identified in Table 16 is increased, during the course of treatment.

The markers and marker sets of the present invention are predictive of chemotherapeutic agents, generally. In one embodiment of the invention, the agent used in methods of the invention is a taxane compound. In another embodiment, the agent is a platinum compound. In yet another embodiment, the agent is a combination of a taxane compound and a platinum compound e.g., TAXOL and cisplatin, respectively.

In another embodiment of the invention, the expression of markers identified in Tables 1-16 is detected by measuring mRNA which corresponds to the marker. In yet another embodiment of the invention, the expression of markers which correspond to markers or marker sets identified in Tables 1-16 is detected by measuring protein which corresponds to the marker.

In another embodiment, the invention provides a method of treating a patient with ovarian cancer by administering to the patient a compound which has been identified as being effective against ovarian cancer by the methods of the invention described herein.

As used herein, the term "agent" is defined broadly as anything that cancer cells, including tumor cells, may be exposed to in a therapeutic protocol. In the context of the present invention, such agents include, but are not limited to, chemotherapeutic agents, such as anti-metabolic agents, e.g., Ara AC, 5-FU and methotrexate, antimitotic agents, e.g., TAXOL, inblastine and vincristine, alkylating agents, e.g., melphanlan, BCNU and nitrogen mustard, Topoisomerase II inhibitors, e.g., VW-26, topotecan and Bleomycin, strand-breaking agents, e.g., doxorubicin and DHAD, cross-linking agents, e.g., cisplatin and CBDCA, radiation and ultraviolet light. In a preferred embodiment, the agent is a taxane compound (e.g., TAXOL) and/or a platinum compound (e.g., cisplatin).

Further to the above, the language "chemotherapeutic agent" is intended to include chemical reagents which inhibit the growth of proliferating cells or tissues wherein the growth of such cells or tissues is undesirable. Chemotherapeutic agents are well known in the art (see e.g., Gilman A. G., et al., *The Pharmacological Basis of Therapeutics*, 8th Ed., Sec 12:1202-1263 (1990)), and are typically used to treat neoplastic diseases. The chemotherapeutic agents generally employed in chemotherapy treatments are listed below in Table A.

TABLE A

| CLASS | TYPE OF AGENT | NONPROPRIETARY NAMES (OTHER NAMES) |
|---|---|---|
| Alkylating | Nitrogen Mustards | Mechlorethamine (HN$_2$) |
| | | Cyclophosphamide |
| | | Ifosfamide |
| | | Melphalan (L-sarcolysin) |
| | | Chlorambucil |
| | Ethylenimines And Methylmelamines | Hexamethylmelamine Thiotepa |
| | Alkyl Sulfonates | Busulfan |
| Alkylating | Nitrosoureas | Carmustine (BCNU) |
| | | Lomustine (CCNU) |
| | | Semustine (methyl-CCNU) |
| | | Streptozocin (streptozotocin) |
| | Triazenes | Decarbazine (DTIC; dimethyltriazenoimi-dazolecarboxamide) |
| | Alkylator | cis-diamminedichloroplatinum II (CDDP) |
| Antimeta-bolites | Folic Acid Analogs | Methotrexate (amethopterin) |
| | Pyrimidine Analogs | Fluorouracil ('5-fluorouracil; 5-FU) |
| | | Floxuridine (fluorode-oxyuridine; FUdR) |
| | | Cytarabine (cytosine arabinoside) |
| | Purine Analogs and Related Inhibitors | Mercaptopuine (6-mercaptopurine; 6-MP) |
| | | Thioguanine (6-thioguanine; TG) |
| | | Pentostatin (2'-deoxycoformycin) |
| Natural Products | Vinca Alkaloids | Vinblastin (VLB) |
| | | Vincristine |
| | Topoisomerase Inhibitors | Etoposide |
| | | Teniposide |
| | | Camptothecin |
| | | Topotecan |
| | | 9-amino-campotothecin CPT-11 |
| | Antibiotics | Dactinomycin (actinomycin D) |
| | | Adriamycin |
| | | Daunorubicin (daunomycin; rubindomycin) |
| | | Doxorubicin |
| | | Bleomycin |
| | | Plicamycin (mithramycin) |
| | | Mitomycin (mitomycin C) |
| | | TAXOL |
| | | Taxotere |
| | Enzymes | L-Asparaginase |
| | Biological Response Modifiers | Interfon alfa interleukin 2 |
| Miscella-neous Agents | Platinum Coordination Complexes | cis-diamminedichloroplatinum II (CDDP) Carboplatin |
| | Anthracendione | Mitoxantrone |
| | Substituted Urea | Hydroxyurea |
| | Methyl Hydraxzine Derivative | Procarbazine (N-methylhydrazine, (MIH) |
| | Adrenocortical Suppressant | Mitotane (o,p'-DDD) Aminoglutethimide |
| Hormones and Antago-nists | Adrenocorticosteroids Progestins | Prednisone Hydroxyprogesterone caproate |
| | | Medroxyprogesterone acetate |
| | | Megestrol acetate |
| | Estrogens | Diethylstilbestrol |
| | | Ethinyl estradiol |
| | Antiestrogen | Tamoxifen |

TABLE A-continued

| CLASS | TYPE OF AGENT | NONPROPRIETARY NAMES (OTHER NAMES) |
|---|---|---|
| | Androgens | Testosterone propionate |
| | | Fluoxymesterone |
| | Antiandrogen | Flutamide |
| | Gonadotropin-releasing Hormone analog | Leuprolide |

The agents tested in the present methods can be a single agent or a combination of agents. For example, the present methods can be used to determine whether a single chemotherapeutic agent, such as methotrexate, can be used to treat a cancer or whether a combination of two or more agents can be used. Preferred combinations will include agents that have different mechanisms of action, e.g., the use of an anti-mitotic agent in combination with an alkylating agent.

As used herein, cancer cells, including tumor cells, refer to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarconia, angiosarcoma, endotheliosarcoma, lymphangiosarcoma, synoviosarcoma and mesotheliosarcoma; leukemias and lymphomas such as granulocytic leukemia, monocytic leukemia, lymphocytic leukemia, malignant lymphoma, plasmocytoma, reticulum cell sarcoma, or Hodgkins disease; and tumors of the nervous system including glioma, meningoma, medulloblastoma, schwannoma or epidymoma.

The source of the cancer cells used in the present method will be based on how the method of the present invention is being used. For example, if the method is being used to determine whether a patient's cancer can be treated with an agent, or a combination of agents, then the preferred source of cancer cells will be cancer cells obtained from a cancer biopsy from the patient, e.g., a tumor biopsy. Alternatively, a cancer cell line similar to the type of cancer being treated can be assayed. For example if ovarian cancer is being treated, then an ovarian cancer cell line can be used. If the method is being used to monitor the effectiveness of a therapeutic protocol, then a tissue sample from the patient being treated is the preferred source. If the method is being used to identify new therapeutic agents or combinations, any cancer cells, e.g., cells of a cancer cell line, can be used.

A skilled artisan can readily select and obtain the appropriate cancer cells that are used in the present method. For cancer cell lines, sources such as The National Cancer Institute, for the NCI-60 cells, are preferred. For cancer cells obtained from a patient, standard biopsy methods, such as a needle biopsy, can be employed.

Ovarian tumor samples were used to obtain the markers of the present invention. It will thus be appreciated that cells from ovarian tumors are particularly useful in the methods of the present invention.

In the methods of the present invention, the level or amount of expression of one or more markers selected from the group consisting of the markers identified in Table 1 is determined. As used herein, the level or amount of expression refers to the absolute level of expression of an mRNA encoded by the marker or the absolute level of expression of the protein encoded by the marker (i.e., whether or not expression is or is not occurring in the cancer cells).

Generally, it is preferable to determine the expression of two or more of the identified sensitivity or resistance markers, more preferably, three or more of the identified sensitivity or resistance markers, most preferably, a set of the identified sensitivity and/or resistance markers, such as the marker sets identified in Tables 2-15. Thus, it is preferable to assess the expression of a panel of sensitivity and resistance markers.

As an alternative to making determinations based on the absolute expression level of selected markers, determinations may be based on the normalized expression levels. Expression levels are normalized by correcting the absolute expression level of a sensitivity or resistance marker by comparing its expression to the expression of a marker that is not a sensitivity or resistance marker, e.g., a housekeeping gene that is constitutively expressed. Suitable markers for normalization include housekeeping genes, such as the actin gene. This normalization allows one to compare the expression level in one sample, e.g., a tumor sample, to another sample, e.g., a non-tumor sample, or between samples from different sources.

Alternatively, the expression level can be provided as a relative expression level. To determine a relative expression level of a marker or marker set, the level of expression of the marker or marker set is determined for 10 or more samples, preferably 50 or more samples, prior to the determination of the expression level for the sample in question. The mean expression level of each of the markers or marker sets assayed in the larger number of samples is determined and this is used as a baseline expression level for the markers or marker sets in question. The expression level of the marker or marker set determined for the test sample (absolute level of expression) is then divided by the mean expression value obtained for that marker or marker set. This provides a relative expression level and aids in identifying extreme cases of sensitivity or resistance.

Preferably, the samples used will be from similar tumors or from non-cancerous cells of the same tissue origin as the tumor in question. The choice of the cell source is dependent on the use of the relative expression level data. For example, using tumors of similar types for obtaining a mean expression score allows for the identification of extreme cases of sensitivity or resistance. Using expression found in normal tissues as a mean expression score aids in validating whether the sensitivity/resistance marker or marker set assayed is tumor specific (versus normal cells). Such a later use is particularly important in identifying whether a sensitivity or resistance marker or marker set can serve as a target marker or marker set. In addition, as more data is accumulated, the mean expression value can be revised, providing improved relative expression values based on accumulated data.

III. Isolated Nucleic Acid Molecules

One aspect of the invention pertains to isolated nucleic acid molecules that correspond to a marker of the invention, including nucleic acids which encode a polypeptide corresponding to a marker of the invention or a portion of such a polypeptide. Isolated nucleic acids of the invention also include nucleic acid molecules sufficient for use as hybridization probes to identify nucleic acid molecules that correspond to a marker of the invention, including nucleic acids which encode a polypeptide corresponding to a marker of the invention, and fragments of such nucleic acid molecules, e.g., those suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid encoding a protein corresponding to a marker listed in Tables 1-16, can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a nucleic acid corresponding to a marker of the invention or to the nucleotide sequence of a nucleic acid encoding a protein which corresponds to a marker of the invention. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker of the invention or which encodes a polypeptide corresponding to a marker of the invention. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ, due to degeneracy of the genetic code, from the nucleotide sequence of nucleic acids encoding a protein which corresponds to a marker of the invention, and thus encode the same protein.

In addition to the nucleotide sequences described in the database records described herein, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a nucleic acid corresponding to a marker of the invention or to a nucleic acid encoding a protein corresponding to a marker of the invention. As used herein, the term "hybridizes under stringent conditions" is intended to describe conditions for hybridization and washing under which nucleotide sequences at least 75% (80%, 85%, preferably 95%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions for annealing two single-stranded DNA each of which is at least about 100 bases in length and/or for annealing a single-stranded DNA and a single-stranded RNA each of which is at least about 100 bases in length, are hybridization in 6× sodium chloride/sodium citrate (SSC) at about 45° C., followed by one or more washes in 0.2×SSC, 0.1% SDS at 50-65° C. Further preferred hybridization conditions are taught in Lockhart, et al., Nature Biotechnology, Volume 14, 1996 August: 1675-1680; Breslauer, et al., Proc. Natl. Acad. Sci. USA, Volume 83, 1986 June: 3746-3750; Van Ness, et al., Nucleic Acids Research, Volume 19, No. 19, 1991 September: 5143-5151; McGraw, et al., BioTechniques, Volume 8, No. 6 1990: 674-678; and Milner, et al., Nature Biotechnology, Volume 15, 1997 June: 537-541, all expressly incorporated by reference.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, such a protein has an amino acid sequence that is at least about 40% identical, 50%, 60%, 70%, 80%, 90%, 95%, or 98% identical to the amino acid sequence of one of the proteins which correspond to the markers of the invention.

An isolated nucleic acid molecule encoding a variant protein can be created by introducing one or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid of the invention, e.g., complementary to the coding strand of a double-stranded cDNA molecule corresponding to a marker of the invention or complementary to an mRNA sequence corresponding to a marker of the invention. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a polypeptide corresponding to a selected marker of the invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into an ovary-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an a-anomeric nucleic acid molecule. An a-anomeric nucleic acid molecule forms specific double-standed hybrids with complementary RNA in which, contrary to the usual a-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the invention can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

IV. Isolated Proteins and Antibodies

One aspect of the invention pertains to isolated proteins which correspond to individual markers of the invention, and biologically active portions thereof, as well as polypeptide fragments suitable for use as immunogens to raise antibodies directed against a polypeptide corresponding to a marker of the invention. In one embodiment, the native polypeptide corresponding to a marker can be isolated from cells or tissue sources by an appropriate purification scheme using standard protein purification techniques. In another embodiment, polypeptides corresponding to a marker of the invention are produced by recombinant DNA techniques. Alternative to recombinant expression, a polypeptide corresponding to a marker of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide corresponding to a marker of the invention include polypeptides comprising amino acid sequences sufficiently identical to or derived from the amino acid sequence of the protein corresponding to the marker, which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence listed in the one of the GenBank and NUC database records described herein. Other useful proteins are substantially identical (e.g., at least about 40%, preferably 50%, 60%, 70%, 80%, 90%, 95%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et at. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et at. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See the website of the National Center for Biotechnology Information, Bethesda, Md. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALTGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a marker of the invention. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which a polypeptide corresponding to a marker of the invention is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a polypeptide corresponding to a marker of the invention can be removed and replaced with a signal sequence from another protein. For example, the gp67 secretory sequence of the baculovirus envelope protein can be used as a heterologous signal sequence (Ausubel et al., ed., *Current Protocols in Molecular Biology*, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide corresponding to a marker of the invention is fused to sequences derived from a member of the iumunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the polypeptides corresponding to individual markers of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983,

*Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

An isolated polypeptide corresponding to a marker of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the polypeptides of the invention, and encompasses an epitope of the protein such that an antibody raised against the peptide forms a specific immune complex with a marker of the invention to which the protein corresponds. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions.

An immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the invention pertains to antibodies directed against a polypeptide of the invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of the invention. Particularly preferred polyclonal antibody preparations are ones that contain only antibodies directed against a polypeptide or polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be harvested or isolated from the subject (e.g., from the blood or serum of the subject) and further purified by well-known techniques, such as protein A chromatography to obtain the IgG fraction. Alternatively, antibodies specific for a protein or polypeptide of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Antibodies of the invention may be used as therapeutic agents in treating cancers. In a preferred embodiment, completely human antibodies of the invention are used for therapeutic treatment of human cancer patients, particularly those having ovarian cancer. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

An antibody directed against a polypeptide corresponding to a marker of the invention (e.g., a monoclonal antibody) can be used to isolate the polypeptide by standard techniques, such as affinity chromatography or immunoprecipitation. Moreover, such an antibody can be used to detect the marker (e.g., in a cellular lysate or cell supernatant) in order to evaluate the level and pattern of expression of the marker. The antibodies can also be used diagnostically to monitor protein levels in tissues or body fluids (e.g. in an ovary-associated body fluid) as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Further, an antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include TAXOL, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

Accordingly, in one aspect, the invention provides substantially purified antibodies or fragments thereof, and non-human antibodies or fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 15 amino acid residues of an amino acid sequence of the present invention, an amino acid sequence which is at least 95% identical to the amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. In various embodiments, the substantially purified antibodies of the invention, or fragments thereof, can be human, non-human, chimeric and/or humanized antibodies.

In another aspect, the invention provides non-human antibodies or fragments thereof, which antibodies or fragments specifically bind to a polypeptide comprising an amino acid sequence selected from the group consisting of: the amino acid sequence of the present invention, an amino acid sequence encoded by the cDNA of the present invention, a fragment of at least 15 amino acid residues of the amino acid sequence of the present invention, an amino acid sequence which is at least 95% identical to the amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 15 amino acid residues of an amino acid sequence of the present invention, an amino acid sequence which is at least 95% identical to an amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. The monoclonal antibodies can be human, humanized, chimeric and/or non-human antibodies.

The substantially purified antibodies or fragments thereof may specifically bind to a signal peptide, a secreted sequence, an extracellular domain, a transmembrane or a cytoplasmic domain or cytoplasmic membrane of a polypeptide of the invention. In a particularly preferred embodiment, the substantially purified antibodies or fragments thereof, the non-human antibodies or fragments thereof, and/or the monoclonal antibodies or fragments thereof, of the invention specifically bind to a secreted sequence or an extracellular domain of the amino acid sequences of the present invention.

Any of the antibodies of the invention can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Still another aspect of the invention is a method of making an antibody that specifically recognizes a polypeptide of the present invention, the method comprising immunizing a mammal with a polypeptide. The polypeptide used as an immungen comprises an amino acid sequence selected from the group consisting of the amino acid sequence of the present invention, an amino acid sequence encoded by the cDNA of the nucleic acid molecules of the present invention, a fragment of at least 15 amino acid residues of the amino acid sequence of the present invention, an amino acid sequence which is at least 95% identical to the amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C.

After immunization, a sample is collected from the mammal that contains an antibody that specifically recognizes the polypeptide. Preferably, the polypeptide is recombinantly produced using a non-human host cell. Optionally, the antibodies can be further purified from the sample using techniques well known to those of skill in the art. The method can further comprise producing a monoclonal antibody-producing cell from the cells of the mammal. Optionally, antibodies are collected from the antibody-producing cell.

V. Recombinant Expression Vectors and Host Cells

Another aspect of the invention pertains to vectors, preferably expression vectors, containing a nucleic acid encoding a polypeptide corresponding to a marker of the invention (or a portion of such a polypeptide). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated-viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide corresponding to a marker of the invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant-protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, p. 119-128, *In Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant manunalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Baneiji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., 1986, *Trends in Genetics*, Vol. 1(1).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker will survive, while the other cells die).

A host cell of the invention, such as a prokaryotic or eukaryotic host cell in culture, can be used to produce a polypeptide corresponding to a marker of the invention. Accordingly, the invention further provides methods for producing a polypeptide corresponding to a marker of the invention using the host cells of the invention. In one embodiment, the method comprises culturing the host cell of invention (into which a recombinant expression vector encoding a polypeptide of the invention has been introduced) in a suitable medium such that the marker is produced. In another embodiment, the method further comprises isolating the marker polypeptide from the medium or the host cell.

The host cells of the invention can also be used to produce nonhuman transgenic animals. For example, in one embodiment, a host cell of the invention is a fertilized oocyte or an embryonic stem cell into which a sequences encoding a polypeptide corresponding to a marker of the invention have been introduced. Such host cells can then be used to create non-human transgenic animals in which exogenous sequences encoding a marker protein of the invention have been introduced into their genome or homologous recombinant animals in which endogenous gene(s) encoding a polypeptide corresponding to a marker of the invention sequences have been altered. Such animals are useful for studying the function and/or activity of the polypeptide corresponding to the marker and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid encoding a polypeptide corresponding to a marker of the invention into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide corresponding to a marker of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecch, 1987, *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, *Cell* 69:915). The selected cells are then injected into a blastocyst of an animal (e.g., a mouse) to form aggregation chimeras (see, e.g., Bradley, *Teratocarcinomas and Embryonic Stem Cells: A Practical Approach*, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

VI. Pharmaceutical Compositions

The nucleic acid molecules, polypeptides, and antibodies (also referred to herein as "active compounds") corresponding to a marker of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid corresponding to a marker of the invention. Such methods comprise formulating a pharmaceutically acceptable carrier with an agent which modulates expression or activity of a polypeptide or nucleic acid corresponding to a marker of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid corresponding to a marker of the invention and one or more additional active compounds.

The invention also provides methods (also referred to herein as "screening assays") for identifying modulators, i.e., candidate or test compounds or agents (e.g., peptides, peptidomimetics, peptoids, small molecules or other drugs) which (a) bind to the marker, or (b) have a modulatory (e.g., stimulatory or inhibitory) effect on the activity of the marker or, more specifically, (c) have a modulatory effect on the interactions of the marker with one or more of its natural substrates (e.g., peptide, protein, hormone, co-factor, or nucleic acid), or (d) have a modulatory effect on the expression of the marker. Such assays typically comprise a reaction between the marker and one or more assay components. The other components may be either the test compound itself, or a combination of test compound and a natural binding partner of the marker.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

In one embodiment, the invention provides assays for screening candidate or test compounds which are substrates of a marker or biologically active portion thereof. In another embodiment, the invention provides assays for screening candidate or test compounds which bind to a marker or biologically active portion thereof. Determining the ability of the test compound to directly bind to a marker can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{125}$I, $^{35}$S, $^{14}$C, or $^{3}$H, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

In another embodiment, the invention provides assays for screening candidate or test compounds which modulate the activity of a marker or a biologically active portion thereof In all likelihood, the marker can, in vivo, interact with one or more molecules, such as but not limited to, peptides, proteins, hormones, cofactors and nucleic acids. For the purposes of this discussion, such cellular and extracellular molecules are referred to herein as "binding partners" or marker "substrate".

One necessary embodiment of the invention in order to facilitate such screening is the use of the marker to identify its natural in vivo binding partners. There are many ways to accomplish this which are known to one skilled in the art. One example is the use of the marker protein as "bait protein" in a two-hybrid assay or three-hybrid assay (see, e.g., U.S. Pat. No. 5,283,317; Zervos et al, 1993, *Cell* 72:223-232; Madura et al, 1993, *J. Biol. Chem.* 268:12046-12054; Bartel et al , 1993, *BioTechniques* 14:920-924; Iwabuchi et al, 1993 *Oncogene* 8:1693-1696; Brent WO94/10300) in order to identify other proteins which bind to or interact with the marker (binding partners) and, therefore, are possibly involved in the natural function of the marker. Such marker binding partners are also likely to be involved in the propagation of signals by the marker or downstream elements of a marker-mediated signaling pathway. Alternatively, such marker binding partners may also be found to be inhibitors of the marker.

The two-hybrid system is based on the modular nature of most transcription factors, which consist of separable DNA-binding and activation domains. Briefly, the assay utilizes two different DNA constructs. In one construct, the gene that encodes a marker protein fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a marker-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be readily detected and cell colonies containing the functional transcription factor can be isolated and used to obtain the cloned gene which encodes the protein which interacts with the marker protein.

In a further embodiment, assays may be devised through the use of the invention for the purpose of identifying compounds which modulate (e.g., affect either positively or negatively) interactions between a marker and its substrates and/or binding partners. Such compounds can include, but are not limited to, molecules such as antibodies, peptides, hormones, oligonucleotides, nucleic acids, and analogs thereof. Such compounds may also be obtained from any available source, including systematic libraries of natural and/or synthetic compounds. The preferred assay components for use in this embodiment is an ovarian cancer marker identified herein, the known binding partner and/or substrate of same, and the test compound. Test compounds can be supplied from any source.

The basic principle of the assay systems used to identify compounds that interfere with the interaction between the marker and its binding partner involves preparing a reaction mixture containing the marker and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of the marker and its binding partner. Control reaction mixtures are incubated without the test compound or with a placebo. The formation of any complexes between the marker and its binding partner is then detected. The formation of a complex in the control reaction, but less or no such formation in the reaction mixture containing the test compound, indicates that the compound interferes with the interaction of the marker and its binding partner. Conversely, the formation of more complex in the presence of compound than in the control reaction indicates that the compound may enhance interaction of the marker and its binding partner.

The assay for compounds that interfere with the interaction of the marker with its binding partner may be conducted in a heterogeneous or homogeneous format. Heterogeneous assays involve anchoring either the marker or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the markers and the binding partners (e.g., by competition) can be identified by conducting the reaction in the presence of the test substance, i.e., by adding the test substance to the reaction mixture prior to or simultaneously with the marker and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the marker or its binding partner is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the marker or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione SEPHAROSE beads (Sigma Chemical, St. Louis, Mo.) or glutathione derivatized microtiter plates, which are then combined with the test compound or the test compound and either the non-adsorbed marker or its binding partner, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above. Alternatively, the complexes can be dissociated from the matrix, and the level of marker binding or activity determined using standard techniques.

Other techniques for immobilizing proteins on matrices can also be used in the screening assays of the invention. For example, either a marker or a marker binding partner can be immobilized utilizing conjugation of biotin and streptavidin. Biotinylated marker protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is pre-labeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibit or enhance) complex formation or which disrupt preformed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August;18(8): 284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J Mol. Recognit.* 11:141-148; Hage and Tweed, 1997, *J. Chromatogr. B. Biomed. Sci. Appl.*, 699:499-525). Gel electrophoresis may also be employed to separate complexed molecules from unbound species (see, e.g., Ausubel et al (eds.), In: Current Protocols in Molecular Biology, J. Wiley & Sons, New York, 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the marker and its binding partner.

Also within the scope of the present invention are methods for direct detection of interactions between the marker and its natural binding partner and/or a test compound in a homogeneous or heterogeneous assay system without further sample manipulation. For example, the technique of fluorescence energy transfer may be utilized (see, e.g.,. Lakowicz et al, U.S. Pat. No. 5,631,169; Stavrianopoulos et al, U.S. Pat. No. 4,868,103). Generally, this technique involves the addition of a fluorophore label on a first 'donor' molecule (e.g., marker or test compound) such that its emitted fluorescent energy will be absorbed by a fluorescent label on a second, 'acceptor' molecule (e.g., marker or test compound), which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between a marker and its binding partner can be identified in controlled assays.

In another embodiment, modulators of marker expression are identified in a method wherein a cell is contacted with a candidate compound and the expression of mRNA or protein, corresponding to a marker in the cell, is determined. The level of expression of mRNA or protein in the presence of the candidate compound is compared to the level of expression of mRNA or protein in the absence of the candidate compound. The candidate compound can then be identified as a modulator of marker expression based on this comparison. For example, when expression of marker mRNA or protein is greater (statistically significantly greater) in the presence of the candidate compound than in its absence, the candidate compound is identified as a stimulator of marker mRNA or protein expression. Conversely, when expression of marker mRNA or protein is less (statistically significantly less) in the presence of the candidate compound than in its absence, the candidate compound is identified as an inhibitor of marker mRNA or protein expression. The level of marker mRNA or protein expression in the cells can be determined by methods described herein for detecting marker mRNA or protein.

In another aspect, the invention pertains to a combination of two or more of the assays described herein. For example, a modulating agent can be identified using a cell-based or a cell free assay, and the ability of the agent to modulate the activity of a marker protein can be further confirmed in vivo, e.g., in a whole animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an marker modulating agent, an antisense marker nucleic acid molecule, an marker-specific antibody, or an marker-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

It is understood that appropriate doses of small molecule agents and protein or polypeptide agents depends upon a number of factors within the knowledge of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g. about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g. about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g. a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, CREMOPHOR EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the ovarian epithelium). A method for lipidation of antibodies is described by Cruikshank et al. (1997) *J. Acquired Immune Deficiency Syndromes and Human Retrovirology* 14:193.

The nucleic acid molecules corresponding to a marker of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., 1994, *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

VII. Monitoring the Effectiveness of an Anti-Cancer Agent

As discussed above, the identified sensitivity and resistance markers can also be used as markers to assess whether the ovarian cancer has become refractory to an ongoing treatment (e.g., a chemotherapeutic treatment). When the ovarian cancer is no longer responding to a treatment the expression profile of the ovarian cancer cells will change: the level of expression of one or more of the sensitivity markers will be reduced and/or the level of expression of one or more of the resistance markers will increase.

In such a use, the invention provides methods for determining whether an anti-cancer treatment should be continued in a cancer patient, comprising the steps of:

a) obtaining two or more samples of ovarian cancer cells from a patient undergoing anti-cancer therapy;

b) determining the expression of the individual markers of a marker set, wherein the marker set is selected from those set forth in Tables 2-15 in the sample exposed to the agent and in a sample of ovarian cancer cells that is not exposed to the agent; and c) discontinuing or altering treatment when the expression profile of the marker sets identified in Tables 2-15 demonstrates increased resistance or decreased sensitivity to the agent being used.

As used herein, a patient refers to any subject undergoing treatment for ovarian cancer. In one embodiment, the subject will be a human patient undergoing chemotherapy treatment. This embodiment of the present invention relies on comparing two or more samples obtained from a patient undergoing anti-cancer treatment. In general, it is preferable to obtain a first sample from the patient prior to beginning therapy and one or more samples during treatment. In such a use, a baseline of expression prior to therapy is determined and then changes in the baseline state of expression is monitored during the course of therapy. Alternatively, two or more successive samples obtained during treatment can be used without the need of a pre-treatment baseline sample. In such a use, the first sample obtained from the subject is used as a baseline for determining whether the expression of a particular marker or marker set is increasing or decreasing.

In general, when monitoring the effectiveness of a therapeutic treatment, two or more samples from the patient are examined. Preferably, three or more successively obtained samples are used, including at least one pretreatment sample.

VIII. Detection Assays

An exemplary method for detecting the presence or absence of a polypeptide or nucleic acid corresponding to a marker of the invention in a biological sample involves obtaining a biological sample (e.g. an ovarian tumor sample) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a polypeptide corresponding to a marker of the invention include enzyme linked immunosorbent assays (ELISAs), Western blots, irmnunoprecipitations and immunofluorescence. In vitro techniques for detection of genomic DNA include Southern hybridizations. Furthermore, in vivo techniques for detection of a polypeptide corresponding to a marker of the invention include introducing into a subject a labeled antibody directed against the polypeptide. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). AS used herein, "BIA" or "surface plasmon resonance" is a technology for studying biospecific interactions in real time, without labeling any of the interactants (e.g., BIACORE). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit.* Winter 11(1-6):141-8; Hage, D. S., and Tweed, S. A. *J Chromatogr B Biomed Sci Appl* 1997 October 10;699(1-2):499-525). Gel electrophoresis may also be employed to separate complexed assay components from unbound components (see, e.g., Ausubel et al, ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of mRNA corresponding to the marker can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from ovarian cells (see, e.g., Ausubel et al., ed., *Current Protocols in Molecular Biology*, John Wiley & Sons, New York, 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the ovarian cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-ovarian cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the markers and marker sets assayed in the larger number of samples is determined and this is used as a baseline expression level for the marker. The expression level of the marker determined for the test sample (absolute level of expression) is then divided by the mean expression value obtained for that marker. This provides a relative expression level.

In another embodiment of the present invention, a polypeptide corresponding to a marker is detected. A preferred agent for detecting a polypeptide of the invention is an antibody capable of binding to a polypeptide corresponding to a marker of the invention, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

A variety of formats can be employed to determine whether a sample contains a protein that binds to a given antibody. Examples of such fonnats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether ovarian cells express a marker of the present invention.

In one format, antibodies, or antibody fragments, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from ovarian cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a polypeptide or nucleic acid corresponding to a marker of the invention in a biological sample (e.g. an ovary-associated body fluid such as a urine sample). Such kits can be used to determine if a subject is suffering from or is at increased risk of developing ovarian cancer. For example, the kit can comprise a labeled compound or agent capable of detecting a polypeptide or an mRNA encoding a polypeptide corresponding to a marker of the invention in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for interpreting the results obtained using the kit.

For antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

IX. Electronic Apparatus Readable Media and Arrays

Electronic apparatus readable media comprising a marker of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the markers of the present invention.

A variety of software programs and formats can be used to store the marker information of the present invention on the electronic apparatus readable medium. For example, the nucleic acid sequence corresponding to the markers or marker sets can be represented in a word processing text file, formatted in commercially-available software such as WORDPERFECT and MICROSOFT WORD, or represented in the form of an ASCII file, stored in a database application, such as DB2, SYBASE, ORACLE, or the like, as well as in other forms. Any number of dataprocessor structuring formats (e.g., text file or database) may be employed in order to obtain or create a medium having recorded thereon the markers and marker sets of the present invention.

By providing the markers and marker sets of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The invention also includes an array comprising a marker or marker set of the present invention. The array can be used to assay expression of one or more markers or marker sets in the array. In one embodiment, the array can be used to assay marker or marker set expression in a tissue to ascertain tissue specificity of markers in the array. In this manner, up to about 36,000 markers can be simultaneously assayed for expression. This allows a profile to be developed showing a battery of markers specifically expressed in one or more tissues.

In addition to such qualitative determination, the invention allows the quantitation of marker expression. Thus, not only tissue specificity, but also the level of expression of a battery of markers in the tissue is ascertainable. Thus, markers can be grouped on the basis of their tissue expression per se and level of expression in that tissue. This is useful, for example, in ascertaining the relationship of marker expression between or among tissues. Thus, one tissue can be perturbed and the effect on marker expression in a second tissue can be determined. In this context, the effect of one cell type on another cell type in response to a biological stimulus can be determined. Such a determination is useful, for example, to know the effect of cell-cell interaction at the level of marker expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target marker can be ascertained and counteracted.

In another embodiment, the array can be used to monitor the time course of expression of one or more markers in the array.

The array is also useful for ascertaining the effect of the expression of a marker on the expression of other markers in the same cell or in different cells. This provides, for example, for a selection of alternate molecular targets for therapeutic intervention if the ultimate or downstream target cannot be regulated.

The array is also useful for ascertaining differential expression patterns of one or more markers in normal and abnormal cells. This provides a battery of markers that could serve as a molecular target for diagnosis or therapeutic intervention.

SPECIFIC EXAMPLES

A. Therapeutic Agents

The markers of the present invention are shown to be sensitive or resistant to TAXOL. TAXOL is a chemical compound within a family of taxane compounds which are art-recognized as being a family of related compounds. The language "taxane compound" is intended to include TAXOL, compounds which are structurally similar to TAXOL and/or analogs of TAXOL. The language "taxane compound" can also include "mimics". "Mimics" is intended to include compounds which may not be structurally similar to TAXOL but mimic the therapeutic activity of TAXOL or structurally similar taxane compounds in vivo. The taxane compounds of this invention are those compounds which are useful for inhibiting ovarian cancer growth, including ovarian tumor growth in subjects (patients). The term taxane compound also is intended to include pharmaceutically acceptable salts of the compounds. Taxane compounds have previously been described in U.S. Pat. Nos. 5,641,803, 5,665,671, 5,380,751, 5,728,687, 5,415,869, 5,407,683, 5,399,363, 5 5,424,073, 5,157,049, 5,773,464, 5,821,263, 5,840,929, 4,814,470, 5,438,072, 5,403,858, 4,960,790, 5,433,364, 4,942,184, 5,362,831, 5,705,503, and 5,278,324, all of which are expressly incorporated by reference.

The structure of TAXOL, shown below, offers many groups capable of being synthetically functionalized to alter the physical or pharmaceutical properties of TAXOL.

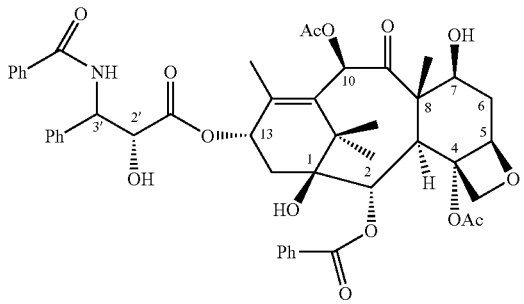

For example, a well known semi-synthetic analog of TAXOL, named Taxotere (docetaxel), has also been found to have good anti-tumor activity in animal models. Taxotere has t-butoxy amide at the 3' position and a hydroxyl group at the C10 position (U.S. Pat. No. 5,840,929).

Other examples of TAXOL derivatives include those mentioned in U.S. Pat. No. 5,840,929 which are directed to derivatives of TAXOL having the formula:

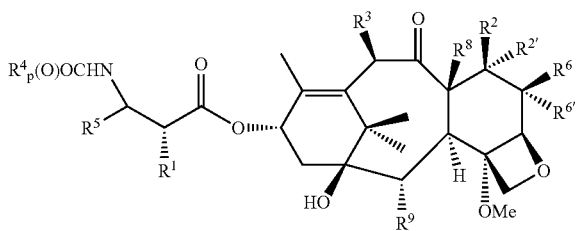

wherein $R^1$ is hydroxy, —OC(O)$R^x$, or —OC(O)O$R^x$; $R^2$ is hydrogen, hydroxy, —OC(O)$R^x$, or —OC(O)O$R^x$; $R^{2'}$ is hydrogen, hydroxy, or fluoro; $R^{6'}$ is hydrogen or hydroxy or $R^{2'}$ and $R^{6'}$ can together form an oxirane ring; $R^3$ is hydrogen, $C_{1-6}$ alkyloxy, hydroxy, —OC(O)$R^x$, —OC(O)O$R^x$, —OCON$R^7R^{11}$; $R^8$ is methyl or $R^8$ and $R^2$ together can form a cyclopropane ring; $R^6$ is hydrogen or $R^6$ and $R^2$ can together form a bond; $R^9$ is hydroxy or —OC(O)$R^x$; $R^7$ and $R^{11}$ are independently $C_{1-6}$ alkyl, hydrogen, aryl, or substituted aryl; $R^4$ and $R^5$ are independently $C_{1-6}$ alkyl, $C_{2-6}$ alkenyl, $C_{2-6}$ alkynyl, or -Z-$R^{10}$; Z is a direct bond, $C_{1-6}$ alkyl, or $C_{2-6}$ alkenyl; $R^{10}$ is aryl, substituted aryl, $C_{3-6}$ cycloalkyl, $C_{2-6}$ alkenyl, $C_{1-6}$ alkyl, all can be optionally substituted with one to six same or different halogen atoms or hydroxy; $R^x$ is a radical of the formula:

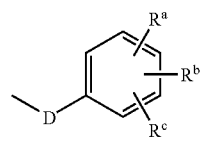

wherein D is a bond or $C_{1-6}$ alkyl; and $R^a$, $R^b$ and $R^c$ are independently hydrogen, amino, $C_{1-6}$ alkyl or $C_{1-6}$ alkoxy.

Further examples of $R^x$ include methyl, hydroxymethyl, ethyl, n-propyl, isopropyl, n-butyl, isobutyl, chloromethyl, 2,2,2-trichloroethyl, cyclopropyl, cyclobutyl, cyclopentyl, cyclohexyl, ethenyl, 2-propenyl, phenyl, benzyl, bromophenyl, 4-aminophenyl, 4-methylaminophenyl, 4-methylphenyl, 4-methoxyphenyl and the like. Examples of $R^4$ and $R^5$ include 2-propenyl, isobutenyl, 3-furanyl (3-furyl), 3-thienyl, phenyl, naphthyl, 4-hydroxyphenyl, 4-methoxyphenyl, 4-fluorophenyl, 4-trifluoromethylphenyl, methyl, ethyl, n-propyl, isopropyl, n-butyl, isobutyl, t-butyl, ethenyl, 2-propenyl, 2-propynyl, benzyl, phenethyl, phenylethenyl, 3,4-dimethoxyphenyl, 2-furanyl (2-furyl), 2-thienyl, 2-(2-furanyl)ethenyl, 2-methylpropyl, cyclopropyl, cyclobutyl, cyclopentyl, cyclohexyl, cyclohexylmethyl, cyclohexylethyl and the like.

TAXOL derivatives can be readily made by following the well established paclitaxel chemistry. For example, C2, C6, C7, C10, and/or C8 position can be derivatized by essentially following the published procedure, into a compound in which $R^3$, $R^8$, $R^2$, $R^{2'}$, $R^9$, $R^{6'}$ and $R^6$ have the meanings defined earlier. Subsequently, C4-acetyloxy group can be converted to the methoxy group by a sequence of steps. For example, for converting C2-benzoyloxy to other groups see, S. H. Chen et al, *Bioorganic and Medicinal Chemistry Letters*, Vol. 4, No. 3, pp 479-482 (1994); for modifying C10-acetyloxy see, J. Kant et al, *Tetrahedron Letters*, Vol. 35, No. 31, pp 5543-5546 (1994) and U.S. Pat. No. 5,294,637 issued Mar. 15, 1994; for making C10 and/or C7 unsubstituted (deoxy) derivatives see, European Patent Application 590 267A2 published Apr. 6, 1994 and PCT application WO 93/06093 published Apr. 1, 1993; for making 7β,8β-methano, 6,7-α,α-dihydroxy and 6,7-olefinic groups see, R. A. Johnson, *Tetrahedron Letters*, Vol. 35, No 43, pp 7893-7896 (1994), U.S. Pat. No. 5,254, 580, issued Oct. 19, 1993, and European Patent Application 600 517A1 published Jun. 8, 1994; for making C7/C6 oxirane see, U.S. Pat. No. 5,395,850 issued Mar. 7, 1995; for making C7-epi-fluoro see, G. Roth et al, *Tetrahedron Letters*, Vol 36, pp 1609-1612 (1993); for forming C7 esters and carbonates see, U.S. Pat. No. 5,272,171 issued Dec. 21, 1993 and S. H. Chen et al., *Tetrahedron*, 49, No. 14, pp 2805-2828 (1993).

In U.S. Pat. No. 5,773,464, TAXOL derivatives containing epoxides at the $C_{10}$ position are disclosed as antitumor agents. Other C-10 taxane analogs have also appeared in the literature. Taxanes with alkyl substituents at C-10 have been reported in a published PCT patent application WO 9533740. The synthesis of C-10 epi hydroxy or acyloxy compounds is disclosed in PCT application WO 96/03394. Additional C-10 analogs have been reported in *Tetrahedron Letters* 1995, 36(12), 1985-1988; *J. Org. Chem.* 1994, 59, 4015-4018 and references therein; K. V. Rao et. al. *Journal of Medicinal Chemistry* 1995, 38 (17), 3411-3414; J. Kant et. al. *Tetrahe-* dron Lett. 1994, 35(31), 5543-5 546; WO 9533736; WO 93/02067; U.S. Pat. No. 5,248,796; WO 9415929; and WO 94/15599.

Other relevant TAXOL derivatives include the sulfenamide taxane derivatives described in U.S. Pat. No. 5,821,263. These compounds are characterized by the C3' nitrogen bearing one or two sulfur substituents. These compounds have been useful in the treatment of cancers such as ovarian, breast, lung, gastic, colon, head, neck, melanoma, and leukemia.

U.S. Pat. No. 4,814,470 discusses TAXOL derivatives with hydroxyl or acetyl group at the C10 position and hydroxy or t-butylcarbonyl at C2' and C3' positions.

U.S. Pat. No. 5,438,072 discusses TAXOL derivatives with hydroxyl or acetate groups at the C10 position and a C2' substitutuent of either t-butylcarbonyl or berizoylamino.

U.S. Pat. No. 4,960,790 discusses derivatives of TAXOL which have, at the C2' and/or C7 position a hydrogen, or the residue of an amino acid selected from the group consisting of alanine, leucine, isoleucine, saline, phenylalanine, proline, lysine, and arginine, or a group of the formula:

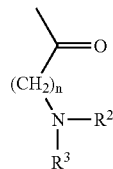

wherein n is an integer of 1 to 3 and $R^2$ and $R^3$ are each hydrogen on an alkyl radical having one to three carbon atoms or wherein $R^2$ and $R^3$ together with the nitrogen atom to which they are attached form a saturated heterocyclic ring having four to five carbon atoms, with the proviso that at least one of the substituents are not hydrogen.

Other similar water soluble TAXOL derivatives are discussed in U.S. Pat. No. 4,942,184, U.S. Pat. No. 5,433,364, and in U.S. Pat. No. 5,278,324.

Many TAXOL derivatives may also include protecting groups such as, for example, hydroxy protecting groups. "Hydroxy protecting groups" include, but are not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, fornyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, *Protective Groups in Organic Synthesis,* 2d Ed., 1991, John Wiley & Sons, and McOmie; and *Protective Groups in Organic Chemistry,* 1975, Plenum Press. Methods for introducing and removing protecting groups are also found in such textbooks.

The markers and marker sets of the present invention are also shown to be sensitive to cis-Diamminedichloroplatinum (II), otherwise known as cisplatin. Cisplatin is a chemical compound within a family of platinum coordination complexes which are art-recognized as being a family of related compounds. Cisplatin was the first platinum compound shown to have anti-malignant properties. The language "platinum compounds" is intended to include cisplatin, compounds which are structurally similar to cisplatin, as well as analogs and derivatives of cisplatin. The language "platinum compounds" can also include "mimics." "Mimics" is intended to include compounds which may not be structurally similar to cisplatin but mimic the therapeutic activity of cisplatin or structurally related compounds in vivo.

The platinum compounds of this invention are those compounds which are useful for inhibiting ovarian cancer growth in subjects (patients). More than 1000 platinum-containing compounds have been synthesized and tested for therapeutic properties. One of these, carboplatin, has been approved for treatment of ovarian cancer. Both cisplatin and carboplatin are amenable to intravenous delivery. However, compounds of the invention can be formulated for therapeutic delivery by any number of strategies. The term platinum compounds also is intended to include pharmaceutically acceptable salts and related compounds. Platinum compounds have previously been described in U.S. Pat. Nos. 6,001,817, 5,945,122, 5,942, 389, 5,922,689, 5,902,610, 5,866,617, 5,849,790, 5,824,346, 5,616,613, and 5,578,571, all of which are expressly incorporated by reference.

Cisplatin and related compounds are thought to enter cells through diffusion, whereupon the molecule likely undergoes metabolic processing to yield the active metabolite of the drug, which then reacts with nucleic acids and proteins. Cisplatin has biochemical properties similar to that of bifunctional alkylating agents, producing interstrand, intrastrand, and monofunctional adduct cross-linking with DNA.

B. Sensitivity Assays and Identification of Therapeutic and Drug Screening Targets A sample of cancerous cells with unknown sensitivity to a given therapeutic agent is obtained from a patient. An expression level is measured in the sample for a marker corresponding to one of the markers identified in Table 1. In a preferred embodiment, the expression level for a set of markers (e.g., the marker sets of Tables 2-15) is determined (also referred to herein as the "expression profile"). An evaluation of the expression level is then made employing the methods described herein. Based on the outcome of this evaluation, it is possible to determine which therapeutic agent, or combination of agents, to use as the appropriate treatment.

A therapeutic agent may be identified as appropriate to treat the ovarian cancer when the outcome of the evaluation demonstrates decreased resistance or increased sensitivity in the presence of the agent. The invention further comprises identifying that a therapeutic agent may be identified as not being appropriate to treat the ovarian cancer when the outcome of the evaluation demonstrates increased resistance or decreased sensitivity in the presence of the agent.

By examining the expression of one or more of the identified markers or marker sets in a sample of ovarian cancer cells taken from a patient during the course of therapeutic treatment, it is also possible to determine whether the therapeutic agent is continuing to work or whether the ovarian cancer has become resistant (refractory) to the treatment protocol. For example, an ovarian cancer patient receiving a treatment of TAXOL would have ovarian cancer cells removed and monitored for the expression of a marker or marker set. If the expression profile of one or more marker sets identified in Tables 2-15 demonstrates decreased resistance or increased sensitivity in the presence of the agent, the treatment with TAXOL would continue. However, if the expression profile of one or more marker sets identified in Tables 2-15 demonstrates increased resistance or decreased sensitivity in the presence of the agent, then the ovarian cancer may have become resistant to TAXOL and another chemotherapy protocol should be initiated to treat the patient.

Importantly, these determinations can be made on a patient by patient basis or on an agent by agent (or combinations of agents). Thus, one can determine whether or not a particular therapeutic treatment is likely to benefit a particular patient or group/class of patients, or whether a particular treatment should be continued.

The identified markers and marker sets further provide previously unknown or unrecognized targets for the development of anti-cancer agents, such as chemotherapeutic compounds, and can be used as targets in developing single agent treatment as well as combinations of agents for the treatment of ovarian cancer.

C. Identification of Sensitivity and Resistant Markers

Tumors from 79 ovarian cancer patients were used in this study. In particular, RNA was isolated from ovarian tumors using a Qiagen RNEASY kit according to the manufacturers directions. Probes for transcriptional profiling were generated by reverse transcribing the RNA into cDNA with SUPERSCRIPT II Reverse transcriptase, done in the presence of 33P-dCTP. Transcriptional profiling was then performed using the radio labeled cDNA probe by hybridizing the probe to nylon filter arrays on which were spotted >36,000 target cDNAs. Hybridization of the specific cDNA probes to the target cDNAs was done for 18 hours at 65° C. in the presence of Cot1 and Salmon sperm DNA to block non-specific binding. The filters were then washed once with 4% SDS-low stringency wash buffer and twice with 1% SDS-high stringency wash buffer. After drying the filters they were placed on a Fuji phosphoimager screen for 48 hours. The image was then read on a Fuji phosphoimager, the intensity of the cDNA probe bound to target cDNA digitized using GRID GURU and AIMZOO software packages.

The response of the 79 ovarian cancer patients was determined by analyzing clinical oncologist reports. 21 month outcome was used to define those patients that had no evidence of disease (NED) for the 21 months following disease identification. NED was determined by either a second-look surgery or by increasing levels of the serum marker, CA125 (see, supra).

Candidate markers that are likely to predict the outcome of ovarian cancer patients to a combined TAXOL/cisplatin therapy were selected by using a combination of predictive algorithms. Statistical algorithms were then used to identify the markers of the present invention.

D. Data Analysis

A data set was comprised of 51 discovery samples, classified as sensitive ($N_S$=25) or resistant ($NR_2$=26), based on the time to recurrence of cancer or a tumor growth off of 21 months, and 28 validation samples ($N_S$=7, $N_R$=21). For each sample, 30,512 transcripts (image clones) were profiled on 5 nylon arrays.

Initial Clone Filtering. For duplicate hybridizations, expression values for all markers on an array were normalized to a median value of 1 and then averaged. Three filtering steps were applied to the initial 30,512 clones. First, the frequency filter was applied to the clones, wherein none of the 51 samples had an intensity value of greater than one. Second, the clones with annotation suggested the presence of Alu repeats. Third, clones that were not printed on the array were removed from analysis. This process resulted in an analytic set of 18,539 clones.

Model Selection. Determining which combination of clone(s) and clinical phenotypes best classify samples into sensitive and resistant groups are referred to as a "model." This section describes the process of how the models of the present invention were identified.

1. Multiple Random Sampling Method

A 70% training fraction was obtained from the 51 discovery samples using block randomized sampling with blocking on outcome and several covariates of interest including debulking status, histology, and stage of tumor for the 18,539 clones.

Using this training fraction, signal-to-noise ratio ("SNR") values [absolute$(\mu_S - \mu_R)/(\sigma_S + \sigma_R)$, where $\mu$ and $\sigma$ represent the mean and standard deviation of expression for each class S (sensitive) and R (resistant)] were calculated for each clone. Feature selection and classification were carried out using the top 500 SNR clones which resulted in a best model for this training fraction. The random sampling method was repeated 100 times resulting in, possibly, 100 different best models.

2. Feature Selection

Feature selection is the process of grouping a combination of individual markers into a marker set. The feature selection process involves determining the best combination of individual markers, that form a marker set, in order to classify patients into sensitive and resistant groups. Four different feature selection methods were considered for determining the best classifier for each of the 100 patient fractions: 1) Stepwise linear discriminant analysis; 2) Signal-to-noise; 3) Fisher score; and 4) Support Vector Feature selection. In preferred embodiments, Support Vector Feature selection was used as the feature selection method.

3. Classifiers

Various algorithms are currently available that can be used to classify patient samples into prior defined groups using the models discovered through the feature selection process described above. Therefore, the combination of markers selected through the feature selection process may be used in one of the following classifying algorithms in order to derive a prediction equation as to whether the patient sample is sensitive or resistant. The classifiers used in the present invention were: 1) K-nearest neighbors ("KNN"); 2) Linear Discriminant Analysis ("LDA"); 3) Weighted Voting Scheme ("WTV"); and 4) Support Vector Machines ("SVM"). In preferred embodiments, Support Vector Feature selection was used as the classifier.

Each classifier can have several user selected parameters. The classifier KNN was performed by averaging the 5 closest gene neighbors using Euclidean distance to define closeness. A Standard linear discriminant analysis was performed using proportional priors and estimating a quadratic discriminant function. A weighted voting scheme was implemented as described by Golub et al., "Molecular Classification of Cancer: Class discovery and class prediction by marker expression monitoring." *Science,* 286:531-537 (1999), the contents of which are incorporated herein by reference. A support vector machine was also used for classification using a $2^{nd}$ order polynomial kernal function. A detailed description of the support vector machine classifier may be found in the following references, Hastie et al., "The Elements of Statistical Learning: Data Mining, Inference and Prediction." Springer-Verlag, New York, (2001) and Ramaswamy et al., "Multiclass cancer diagnosis using tumor marker expression signatures." *PNAS (USA)* 98(26):15149-15154 (2001), the contents of which are incorporated herein by reference.

4. Classification Error

To determine the ability of a model to predict sensitivity or resistance in an independent group of tumors, all of the models were refit using 51 discovery samples. Classification error rates and the proportion of incorrect predictions were estimated for each model using the 28 validation samples. The best models were defined as those with the fewest classification errors.

Model Performance. To determine if the most highly predictive models could be obtained by chance alone, a permutation test was performed. The labels were permuted on the 51 discovery samples 10 times and performed the entire marker selection procedure resulting in 1,000 random models. The overall error rate for the 1,000 permuted models was 50%, compared to 44% for the observed labels using the SVM models. The best two models generated from the training data lay outside the 99% confidence interval for the best model from the permuted data, suggesting that it is unlikely that those models could be identified by chance alone.

It will be appreciated that additional marker sets may thus be obtained by employing the methods described herein for identifying models.

E. Specific Application of Class Prediction

1. Linear Discriminant Analysis

The Support Vector Machines feature selection and classification were used to select the individual markers of Table 2. The following algorithms were then used to determine the classification error rate and class prediction, i.e., to determine the group, either sensitive or resistant, to which a sample may be classified. Classification error rates and the proportion of incorrect predictions were estimated for each marker set using 28 validation samples. The following example details the process that was used on each of the 28 validation samples.

The criterion used for predicting the specific group to which a patient is classified, is given by the following formula:

$$c = \frac{1}{2}(\overline{x}_R - \overline{x}_S)'S^{-1}(\overline{x}_R + \overline{x}_S)$$

where $\overline{X}_R$, $X_s$ are the vector of means for the markers in the marker set for each group (resistant and sensitive, respectively) and S is the pooled covariance matrix of predictors.

Using the 51 discovery samples, the following coefficients were obtained from estimating the linear discriminant analysis model for each of the 14 markers of Table 2:

$\beta = [\beta_1 = -3.70, \beta_2 = 0.90, \beta_3 = -0.71, \beta_4 = -0.25, \beta_5 = 0.49,$
$\beta_6 = -0.84, \beta_7 = 0.31, \beta_8 = 0.76, \beta_9 = -0.52,$
$\beta_{10} = 0.40, \beta_{11} = 4.04, \beta_{12} = 0.43, \beta_{13} = -0.25, \beta_{14} = -0.14],$ wherein $\beta_1$-$\beta_{14}$ represents parameter estimates for markers 1-14 of Table 2, respectively.

By assessing the following patient validation sample, the following expression values were attained:

$Z = [z_1 = 1.57, z_2 = 1.93, z_3 = 0.96, z_4 = 3.32, z_5 = 0.70,$
$z_6 = 3.68, z_7 = 5.10, z_8 = 5.48, z_9 = 1.34, z_{10} = 2.33,$
$z_{11} = 1.91, z_{12} = 4.29, z_{13} = 5.33, z_{14} = 2.97],$ wherein $z_1$-$z_{14}$ represent the expression of the markers 1-14 of Table 2 in the patient validation sample.

By using the equation, $\beta z' \geq c$, it is possible to predict whether a patient is resistant or sensitive. The value for c from the model using the patient samples is −4.33. Therefore, $$\sum_{i=1}^{14} \beta_i z_i = -3.21$$

The resulting expression profile of the patient validation sample shown above is −3.21, which is greater than c=−4.33. Therefore, the patient sample at issue is predicted to be resistant based on the expression profile.

It will be appreciated that similar methods may be employed utilizing the marker sets of the present invention.

2. Weighted Voting

For weighted voting, the criterion was developed from a weighted voting scheme using the following:

$$V_j = \frac{(\overline{x}_R - \overline{x}_S)}{S_S + S_R}\left[z_j - \left(\frac{\overline{x}_R + \overline{x}_S}{2}\right)\right]_j$$

where $z_j$ represents the expression value for the $j^{th}$ marker for in the LDA example above and S represents the standard deviation for the class indicated by the subscript. The first term in the equation is signal-to-noise ratio while the second term is called the decision boundary. A positive value of $V_j$ is a vote for being a resistant sample, while a negative value is a vote for being sensitive value. The majority vote provides the class prediction.

For the above patient, 9/14 votes were for resistant therefore by WTV, this patient would be predicted to be resistant. A summary of the calculations are provided in the following table.

| SNR | Decision Boundry | $V_j$ | Vote |
|---|---|---|---|
| −0.67 | 0.86 | −0.32 | S |
| 0.53 | 1.03 | 0.48 | R |
| −0.41 | 1.17 | −0.48 | S |
| −0.52 | 1.71 | −0.10 | S |
| 0.45 | 1.22 | 1.39 | R |
| 0.28 | 1.33 | 1.14 | R |
| 0.37 | 1.35 | 0.60 | R |
| 0.49 | 0.63 | 0.16 | R |
| −0.47 | 1.79 | 0.10 | R |
| 0.34 | 1.40 | 0.66 | R |
| 0.24 | 0.76 | −0.01 | S |
| 0.37 | 1.18 | 0.92 | R |
| 0.30 | 1.47 | 1.10 | R |
| −0.36 | 2.23 | −1.17 | S |

It will be appreciated that similar methods may be employed utilizing the marker sets of the present invention.

3. K-nearest neighbors

For the K nearest neighbors, prediction of how "close" the sample to be predicted is to its K nearest neighbors. K=5 was selected for the analyses and Euclidean distance as the measure of "distance" given by $$d_i = \sqrt{\sum_{j=1}^{14}(x_{ij} - z_j)^2}$$

and i is the $i^{th}$ sample in the training set. Thus for prediction, one needs the expression values for all training samples for the 14 markers. These are provided below after log transformation along with identifiers for the samples contained in the training set, class designation, and $d_i$ for each training sample using log transformed values of Z from above.

| Sample ID | $x_{i1}$ | $x_{i2}$ | $x_{i3}$ | $x_{i4}$ | $x_{i5}$ | $x_{i6}$ | $x_{i7}$ | $x_{i8}$ | $x_{i9}$ | $x_{i10}$ | $x_{i11}$ | $x_{i12}$ | $x_{i13}$ | $x_{i14}$ | $d_i$ | Class |
|---|---|---|---|---|---|---|---|---|---|---|---|---|---|---|---|---|
| 1 | 1.89 | 0.93 | 0.41 | 0.88 | 0.70 | 1.15 | 1.57 | 2.31 | 1.29 | 0.86 | 2.36 | 1.10 | 1.88 | 1.67 | 2.03 | S |
| 2 | 1.61 | 1.24 | 0.81 | 1.80 | 0.83 | 1.10 | 1.94 | 2.80 | 1.07 | 0.75 | 1.72 | 1.64 | 2.02 | 1.11 | 1.60 | S |
| 3 | 1.68 | 1.36 | 0.54 | 1.28 | 0.99 | 1.29 | 1.66 | 2.17 | 0.58 | 0.96 | 1.72 | 1.34 | 1.09 | 1.76 | 1.56 | R |
| 4 | 1.80 | 0.88 | 0.69 | 1.95 | 0.94 | 1.34 | 1.50 | 1.90 | 0.89 | 1.38 | 1.34 | 1.26 | 1.60 | 1.66 | 1.31 | R |
| 5 | 1.65 | 0.96 | 0.67 | 1.25 | 0.93 | 1.35 | 1.25 | 2.30 | 0.83 | 1.02 | 1.70 | 1.35 | 1.50 | 2.48 | 1.76 | R |
| 6 | 2.06 | 1.03 | 0.72 | 1.39 | 0.73 | 1.00 | 1.36 | 1.88 | 0.88 | 1.40 | 1.84 | 1.20 | 1.51 | 1.13 | 1.67 | S |
| 7 | 1.90 | 0.42 | 0.60 | 1.26 | 0.75 | 1.26 | 1.30 | 2.54 | 0.76 | 1.39 | 3.09 | 1.02 | 0.96 | 1.38 | 2.75 | S |
| 8 | 1.55 | 1.17 | 0.70 | 2.08 | 0.70 | 1.35 | 1.99 | 2.24 | 0.80 | 0.71 | 0.91 | 1.27 | 1.48 | 1.46 | 1.25 | R |
| 9 | 1.96 | 0.64 | 0.54 | 1.09 | 0.82 | 0.84 | 1.21 | 3.02 | 1.01 | 1.45 | 2.37 | 0.96 | 0.67 | 0.98 | 2.73 | S |
| 10 | 1.80 | 1.08 | 0.51 | 1.70 | 0.76 | 1.20 | 1.73 | 1.86 | 0.75 | 1.17 | 1.37 | 1.03 | 1.27 | 1.30 | 1.35 | R |
| 11 | 1.69 | 0.86 | 0.73 | 1.79 | 0.78 | 0.95 | 1.51 | 1.95 | 0.96 | 0.92 | 0.83 | 0.89 | 2.19 | 1.67 | 1.48 | S |
| 12 | 1.72 | 1.43 | 0.54 | 1.61 | 0.72 | 1.41 | 1.20 | 2.29 | 0.65 | 0.92 | 0.60 | 1.28 | 1.99 | 1.66 | 1.40 | R |
| 13 | 1.53 | 0.64 | 0.67 | 1.44 | 1.12 | 1.28 | 1.54 | 2.13 | 1.09 | 0.82 | 1.52 | 1.19 | 1.31 | 1.77 | 1.47 | S |
| 14 | 1.98 | 0.59 | 0.53 | 1.46 | 0.77 | 0.91 | 1.42 | 2.54 | 1.01 | 1.04 | 2.44 | 1.24 | 0.76 | 1.24 | 2.39 | S |
| 15 | 1.63 | 2.18 | 0.89 | 1.40 | 0.37 | 1.04 | 1.85 | 2.21 | 0.63 | 0.90 | 1.59 | 1.11 | 1.52 | 1.33 | 1.72 | R |
| 16 | 1.64 | 1.45 | 0.40 | 0.97 | 0.70 | 1.19 | 1.90 | 1.92 | 0.66 | 1.45 | 1.10 | 1.18 | 1.25 | 1.66 | 1.37 | R |
| 17 | 2.38 | 0.99 | 0.73 | 1.30 | 0.51 | 1.16 | 1.41 | 2.67 | 1.01 | 1.27 | 0.67 | 1.01 | 1.18 | 0.70 | 2.14 | S |
| 18 | 1.86 | 0.66 | 0.57 | 0.91 | 0.77 | 0.91 | 1.50 | 2.50 | 1.08 | 1.22 | 1.67 | 1.42 | 1.23 | 0.69 | 1.90 | S |
| 19 | 2.09 | 0.82 | 0.56 | 1.31 | 0.50 | 1.19 | 1.32 | 2.11 | 0.94 | 0.68 | 0.85 | 1.42 | 0.81 | 1.36 | 1.81 | S |
| 20 | 1.96 | 0.92 | 0.24 | 1.26 | 0.77 | 0.96 | 1.39 | 1.96 | 0.97 | 1.13 | 2.96 | 0.73 | 1.02 | 1.12 | 2.67 | S |
| 21 | 1.28 | 1.33 | 1.22 | 2.04 | 0.72 | 1.58 | 2.22 | 2.10 | 0.77 | 0.81 | 1.40 | 1.81 | 1.61 | 2.17 | 1.43 | R |
| 22 | 1.64 | 0.94 | 0.47 | 1.27 | 0.79 | 0.78 | 1.24 | 2.48 | 0.81 | 1.31 | 1.51 | 1.73 | 0.79 | 0.92 | 1.87 | R |
| 23 | 2.26 | 0.68 | 0.65 | 1.95 | 0.89 | 1.18 | 1.38 | 1.81 | 0.94 | 2.15 | 3.29 | 1.17 | 1.11 | 1.68 | 3.05 | S |
| 24 | 1.93 | 0.67 | 0.50 | 0.71 | 0.67 | 0.67 | 1.21 | 2.51 | 0.92 | 1.86 | 1.90 | 0.77 | 1.09 | 1.03 | 2.43 | S |
| 25 | 1.69 | 1.07 | 0.54 | 1.33 | 0.68 | 1.09 | 1.44 | 2.35 | 0.66 | 1.21 | 1.93 | 1.07 | 1.27 | 1.09 | 1.65 | S |
| 26 | 1.38 | 0.72 | 0.38 | 1.24 | 0.66 | 1.03 | 1.19 | 2.55 | 0.95 | 1.35 | 2.91 | 1.18 | 1.27 | 1.28 | 2.37 | S |
| 27 | 2.37 | 0.96 | 0.56 | 1.53 | 0.75 | 0.90 | 1.52 | 2.28 | 0.98 | 0.75 | 2.37 | 0.80 | 0.66 | 1.16 | 2.63 | S |
| 28 | 1.67 | 0.99 | 0.47 | 1.44 | 0.67 | 1.15 | 1.51 | 2.21 | 0.93 | 0.84 | 1.61 | 1.61 | 1.58 | 1.28 | 1.21 | R |
| 29 | 2.14 | 0.73 | 0.44 | 1.26 | 0.73 | 1.11 | 1.11 | 2.93 | 1.00 | 1.72 | 2.82 | 0.91 | 1.20 | 0.85 | 2.85 | S |
| 30 | 1.58 | 0.58 | 0.60 | 1.68 | 0.90 | 1.39 | 1.63 | 2.18 | 0.72 | 1.00 | 1.93 | 1.22 | 1.68 | 1.03 | 1.46 | R |
| 31 | 1.81 | 1.17 | 0.48 | 1.35 | 0.74 | 1.11 | 0.96 | 2.60 | 1.13 | 1.90 | 2.28 | 1.13 | 0.69 | 0.99 | 2.47 | S |
| 32 | 1.57 | 0.92 | 1.15 | 1.21 | 0.95 | 0.98 | 1.07 | 2.19 | 0.84 | 1.13 | 1.74 | 1.11 | 1.54 | 1.58 | 1.65 | R |
| 33 | 1.98 | 1.16 | 0.93 | 1.94 | 1.00 | 2.12 | 1.11 | 2.21 | 0.82 | 0.92 | 0.54 | 0.98 | 1.54 | 1.33 | 1.86 | R |
| 34 | 1.73 | 1.31 | 0.56 | 1.19 | 0.72 | 1.21 | 1.28 | 2.10 | 0.72 | 1.83 | 1.32 | 1.28 | 1.08 | 1.27 | 1.57 | R |
| 35 | 1.81 | 1.07 | 0.48 | 0.77 | 0.62 | 1.36 | 1.25 | 1.71 | 0.87 | 1.60 | 1.05 | 1.71 | 1.23 | 1.01 | 1.52 | S |
| 36 | 1.63 | 0.65 | 0.73 | 1.69 | 0.82 | 1.20 | 1.19 | 1.72 | 0.86 | 1.02 | 1.72 | 1.16 | 1.16 | 1.51 | 1.59 | R |
| 37 | 1.53 | 1.18 | 0.57 | 1.53 | 0.94 | 1.39 | 1.35 | 1.73 | 0.88 | 1.02 | 1.28 | 0.93 | 1.60 | 1.13 | 1.24 | R |
| 38 | 2.23 | 1.36 | 0.93 | 0.97 | 0.83 | 1.25 | 1.55 | 1.88 | 1.02 | 0.73 | 0.99 | 1.64 | 1.48 | 1.17 | 1.65 | R |
| 39 | 1.73 | 1.62 | 0.84 | 1.88 | 0.69 | 1.39 | 2.02 | 2.41 | 0.83 | 1.03 | 0.76 | 1.70 | 1.73 | 1.01 | 1.33 | R |
| 40 | 1.99 | 1.15 | 0.51 | 1.22 | 0.71 | 0.87 | 1.41 | 2.15 | 1.14 | 1.33 | 1.88 | 0.83 | 1.28 | 1.60 | 1.93 | S |
| 41 | 1.42 | 1.43 | 0.58 | 1.16 | 0.78 | 1.38 | 1.76 | 2.27 | 0.80 | 1.28 | 1.27 | 1.24 | 2.18 | 1.13 | 1.05 | S |
| 42 | 1.95 | 0.97 | 0.50 | 0.70 | 0.49 | 1.03 | 1.25 | 1.99 | 0.87 | 1.71 | 1.34 | 1.08 | 1.19 | 1.04 | 1.86 | S |
| 43 | 1.82 | 1.05 | 0.42 | 1.51 | 0.55 | 1.37 | 1.17 | 2.18 | 1.03 | 1.59 | 1.68 | 1.08 | 1.26 | 1.42 | 1.62 | S |
| 44 | 1.69 | 1.12 | 0.59 | 1.12 | 1.00 | 1.05 | 1.08 | 1.84 | 0.75 | 1.13 | 1.36 | 1.46 | 0.95 | 1.76 | 1.66 | R |
| 45 | 1.51 | 1.53 | 0.77 | 1.42 | 1.03 | 0.83 | 2.10 | 1.85 | 0.68 | 1.08 | 1.77 | 1.67 | 1.25 | 1.57 | 1.52 | R |
| 46 | 1.54 | 1.42 | 1.09 | 1.87 | 0.87 | 1.59 | 1.24 | 2.01 | 0.86 | 0.54 | 1.02 | 1.34 | 2.11 | 1.87 | 1.47 | R |
| 47 | 1.61 | 1.45 | 0.72 | 1.68 | 0.94 | 1.10 | 2.00 | 2.23 | 0.50 | 1.19 | 2.02 | 1.47 | 1.81 | 1.09 | 1.52 | R |
| 48 | 1.99 | 0.67 | 0.40 | 0.99 | 0.21 | 1.02 | 1.34 | 2.48 | 0.90 | 1.03 | 1.70 | 1.21 | 0.70 | 1.06 | 2.14 | R |
| 49 | 1.71 | 0.90 | 0.84 | 1.54 | 0.85 | 1.34 | 2.00 | 2.53 | 0.72 | 0.87 | 1.82 | 1.19 | 1.67 | 1.89 | 1.58 | R |
| 50 | 1.76 | 0.76 | 0.48 | 1.08 | 0.86 | 1.52 | 1.46 | 2.27 | 0.68 | 1.30 | 3.67 | 0.94 | 0.81 | 1.24 | 3.13 | S |
| 51 | 1.82 | 0.46 | 0.36 | 1.63 | 0.63 | 1.01 | 1.51 | 2.56 | 0.72 | 1.25 | 1.73 | 1.17 | 0.84 | 1.52 | 1.97 | S |

Since K=5, the 5 nearest neighbors are considered, that is the 5 smallest values of $d_i$ with class prediction based on a majority vote. For this example, 4/5 of the closest neighbors were resistant, therefore this sample is predicted to be resistant.

It will be appreciated that similar methods may be employed utilizing the marker sets of the present invention.

4. Support Vector Machine

A support vector machine using a second order polynomial kernel has the form $$d(Z) = \sum_{i=1}^{S} \alpha_i \frac{\left(1 + \sum_{j=1}^{14} z_j x_{ij}\right)^2}{c} + b$$

where $z_j$ (log transformed) and $x_{ij}$ are the same as in above examples, C is a scaling constant set to 200, b is a penalty term (=−4.4675), and $\alpha_i$ is the $i^{th}$ support vector estimated from the training data. They are listed below.

| Sample ID | $\alpha_i$ |
|---|---|
| 1 | 0 |
| 2 | 70.0164 |
| 3 | 0 |
| 4 | −0.282 |
| 5 | 0 |
| 6 | 32.281 |
| 7 | 0 |
| 8 | 0 |
| 9 | 0 |
| 10 | −23.3735 |
| 11 | 3.3081 |

-continued

| Sample ID | $\alpha_i$ |
|---|---|
| 12 | −12.8285 |
| 13 | 0 |
| 14 | 0 |
| 15 | 0 |
| 16 | 0 |
| 17 | 0 |
| 18 | 0 |
| 19 | 100 |
| 20 | 0 |
| 21 | 0 |
| 22 | −42.1717 |
| 23 | 0 |
| 24 | 0 |
| 25 | 100 |
| 26 | 0 |
| 27 | 0 |
| 28 | −90.7953 |
| 29 | 0 |
| 30 | −83.4233 |
| 31 | 0 |
| 32 | −0.7843 |
| 33 | 0 |
| 34 | −100 |
| 35 | 100 |
| 36 | 0 |
| 37 | 0 |
| 38 | −42.3951 |
| 39 | −11.9709 |
| 40 | 0 |
| 41 | 37.9963 |
| 42 | 0 |
| 43 | 0 |
| 44 | 0 |
| 45 | 0 |
| 46 | 0 |
| 47 | 0 |
| 48 | −100 |
| 49 | −33.8659 |
| 50 | 15.3422 |
| 51 | 82.9463 |

Values of d(Z) represent the distance the sample Z is from the decision boundary (often referred to as the margin). Values less than the margin (0.04 for these data) are predicted to be resistant while larger values are sensitive. For this example, d(z) is equal to −3.19 and is therefore predicted to be resistant.

It will be appreciated that similar methods may be employed utilizing the marker sets of the present invention.

F. Summary of the Data Provided in the Tables

The following terms are used throughout the Tables:

"No." or "Number" corresponds to an identification number for the markers.

"Image Clone Id" corresponds to the cDNA clone number from the IMAGE Consortium. All referenced IMAGE clone sequences are expressly incorporated herin by reference.

"Accession" the GenBank accession number assigned to the particular sequence. All referenced GenBank sequences are expressly incorporated herein by reference.

"Gene name" corresponds to the name the gene is commonly known by.

"GI number" to the GenBank number.

"RefSeq" corresponds to the Reference Sequence Nucleic Accession Number.

"Market Number" corresponds the marker identification numbers set forth in Table 1.

"Feature Selection" corresponds to the process of determining which individual markers may be used in combination to group or classify a sample, for example, as sensitive or resistant. Four different feature selection methods were utilized for determining the best classifier: 1) Stepwise linear discriminant analysis ("LDA"); 2) Signal-to-noise ("SNR"); 3) Fisher score ("FISHER"); and 4) Support Vector Feature Selection ("SVM").

"Classification Error Rate of the Model" corresponds to the classification algorithm which uses the model established in the feature selection process to make predictions as to the group, for example, either sensitive or resistant, to which each validation sample may be classified. The error rate is simply the proportion of occurrences in which the algorithm predicted a sample incorrectly, e.g., 1 error in 10 predictions would be a Classification Error Rate of 10% for the model.

Table 1 lists all of the markers of the invention (and comprises the markers listed in Tables 2-16), which are designated with a marker identification number ("No."), the Image Clone ID ("Image Clone ID"), the gene corresponding to the marker ("Gene Name"), the Accession Number ("Accession"), the GeneBank number ("GI number"), and the Reference Sequence Nucleic Accession Number ("RefSeq").

TABLE 1

| No | Image Clone Id | Gene name | Accession | GI number | RefSeq |
|---|---|---|---|---|---|
| n1 | 31866 | splicing factor 3a, subunit 3 | R43015 (SEQ ID NO:1) | 820077 | NM_006802 (SEQ ID NO:3) |
|  |  |  | R17811 (SEQ ID NO:2) | 771421 |  |
| n2 | 43936 | unnamed | H05777 (SEQ ID NO:4) | 869329 |  |
| n3 | 51970 | NAG14 protein | H23117 (SEQ ID NO:5) | 891812 | NM_022143 (SEQ ID NO:6) |
| n4 | 52724 | hypothetical protein FLJ20241 | H29399 (SEQ ID NO:7) | 900309 | NM_017721 (SEQ ID NO:9) |
|  |  |  | H29307 | 900217 |  |

TABLE 1-continued

| No | Image Clone Id | Gene name | Accession | GI number | RefSeq |
|---|---|---|---|---|---|
| n5 | 77577 | FOS-like antigen 2 | (SEQ ID NO:8) T58873 T58932 (SEQ ID NO:11) | 660710 660769 | NM_005253 |
| n6 | 110812 | unnamed | T83174 (SEQ ID NO:13) T90647 (SEQ ID NO:14) | 711462 719160 | |
| n7 | 124575 | zinc finger protein 200 | R01941 (SEQ ID NO:15) R01991 (SEQ ID NO:16) | 751677 751727 | NM_003454 (SEQ ID NO:17) |
| n8 | 133872 | hypothetical protein FLJ12716 | R28239 (SEQ ID NO:18) R27982 (SEQ ID NO:19) | 784374 784117 | NM_021942 (SEQ ID NO:20) |
| n9 | 149895 | unnamed | H00660 (SEQ ID NO:21) H00752 (SEQ ID NO:22) | 863593 863685 | |
| n10 | 182818 | pre-mRNA processing factor 31 homolog | H45335 (SEQ ID NO:23) H45266 (SEQ ID NO:24) | 921387 921318 | NM_015629 (SEQ ID NO:25) |
| n11 | 187147 | ras association (RalGDS/AF-6) domain | R83224 (SEQ ID NO:26) R83223 (SEQ ID NO:27) | 928101 928100 | |
| n12 | 244055 | CCR4-NOT transcription complex | N34048 (SEQ ID NO:28) | 1154448 | NM_014516 (SEQ ID NO:29) |
| n13 | 277403 | Homo sapiens mRNA cDNA DKFZp586D0918 | N47672 (SEQ ID NO:30) N57522 (SEQ ID NO:31) | 1188838 1201412 | |
| n14 | 283301 | KIAA0914 gene product | N51424 (SEQ ID NO:32) | 1192590 | NM_014883 (SEQ ID NO:33) |
| n15 | 284497 | Homo sapiens mRNA cDNA DKFZp586E1624 | N52362 (SEQ ID NO:34) N75133 (SEQ ID NO:35) | 1193528 1237711 | |
| n16 | 289652 | none | N59881 (SEQ ID NO:36) N77022 (SEQ ID NO:37) | 1203771 1239600 | |
| n17 | 306921 | eukaryotic translation elongation factor 1 | W24209 (SEQ ID NO:38) N91962 (SEQ ID NO:39) | 1301121 1264271 | NM_004280 (SEQ ID NO:40) |
| n18 | 308412 | unnamed | N93790 (SEQ ID NO:41) W31338 | 1266099 1312329 | |

TABLE 1-continued

| No | Image Clone Id | Gene name | Accession | GI number | RefSeq |
|---|---|---|---|---|---|
| | | | (SEQ ID NO:42) | | |
| n19 | 342082 | *Homo sapiens* cDNA FLJ30816 | W60310 (SEQ ID NO:43) | 1367069 | |
| | | | W60401 (SEQ ID NO:44) | 1367160 | |
| n20 | 342181 | B-cell CLL/lymphoma 2 | W61100 (SEQ ID NO:45) | 1367877 (SEQ ID NO:47); (SEQ ID NO:48) | NM_000633NM_000657 |
| | | | W63749 (SEQ ID NO:46) | 1371329 | |
| n21 | 343174 | *Homo sapiens* cDNA FLJ31204 | W67536 (SEQ ID NO:49) | 1376407 | |
| n22 | 380245 | protein kinase C | AA047803 (SEQ ID NO:50) | 1527482 | NM_006255 (SEQ ID NO:51) |
| n23 | 416049 | unnamed | W85947 (SEQ ID NO:52) | 1398375 | |
| | | | W85843 (SEQ ID NO:53) | 1398292 | |
| n24 | 428296 | unnamed | AA004944 (SEQ ID NO:54) | 1447731 | |
| n25 | 449126 | unnamed | AA777493 (SEQ ID NO:55) | 2836972 | |
| n26 | 451706 | polymerase (DNA directed), alpha | AA707650 (SEQ ID NO:56) | 2717568 | NM_016937 (SEQ ID NO:57) |
| n27 | 454798 | unnamed | AA677295 (SEQ ID NO:58) | 2657817 | |
| n28 | 491184 | unnamed | AA137072 (SEQ ID NO:59) | 1698289 | |
| | | | AA137144 (SEQ ID NO:60) | 1698379 | |
| n29 | 509887 | non-POU-domain-containing, octamer-binding | AA056465 (SEQ ID NO:61) | 1548805 | NM_007363 (SEQ ID NO:63) |
| | | | AA054701 (SEQ ID NO:62) | 1545625 | |
| n30 | 513200 | 60S ribosomal protein L30 isolog | AA063398 (SEQ ID NO:64) | 1557267 | NM_016304 (SEQ ID NO:65) |
| n31 | 565235 | spermine synthase | AA136125 (SEQ ID NO:66) | 1697335 | NM_00459 (SEQ ID NO:68) |
| | | | AA136221 (SEQ ID NO:67) | 1697431 | |
| n32 | 611532 | troponin I | AA181334 (SEQ ID NO:69) | 1764986 | NM_003282 (SEQ ID NO:71) |
| | | | AA182927 (SEQ ID NO:70) | 1766096 | |
| n33 | 681910 | unnamed | AA256174 (SEQ ID NO:72) | 1891713 | |
| | | | AA256233 (SEQ ID NO:73) | 1891772 | |
| n34 | 682088 | unnamed | AA256824 (SEQ ID NO:74) | 1890970 | |

TABLE 1-continued

| No | Image Clone Id | Gene name | Accession | GI number | RefSeq |
|---|---|---|---|---|---|
| | | | AA256482 (SEQ ID NO:75) | 1892020 | |
| n35 | 703838 | chromosome 8 open reading frame 1 | AA279100 (SEQ ID NO:76) | 1920583 | NM_004337 (SEQ ID NO:78) |
| | | | AA278836 (SEQ ID NO:77) | 1920357 | |
| n36 | 740620 | tropomyosin 2 | AA479560 (SEQ ID NO:79) | 2205446 | NM_003289 (SEQ ID NO:81) |
| | | | AA477400 (SEQ ID NO:80) | 2206034 | |
| n37 | 740672 | polymerase (RNA) II (DNA directed) polypeptide G | AA479589 (SEQ ID NO:82) | 2205475 | NM_002696 (SEQ ID NO:84) |
| | | | AA477428 (SEQ ID NO:83) | 2206062 | |
| n38 | 745158 | *Homo sapiens* mRNA; cDNA DKFZp434A1635 | AA626716 (SEQ ID NO:85) | 2539103 | |
| n39 | 753587 | butyrophilin, subfamily 3 | AA478585 (SEQ ID NO:86) | 2207219 | NM_006994 (SEQ ID NO:88) |
| | | | AA479322 (SEQ ID NO:87) | 2207878 | |
| n40 | 767388 | unnamed | AA418593 (SEQ ID NO:89) | 2080394 | |
| | | | AA418655 (SEQ ID NO:90) | 2080474 | |
| n41 | 781109 | KIAA1488 protein | AA430052 (SEQ ID NO:91) | 2113226 | |
| n42 | 789369 | inhibitor of DNA binding 4 | AA464856 (SEQ ID NO:92) | 2189740 | NM_001546 (SEQ ID NO:94) |
| | | | AA453341 (SEQ ID NO:93) | 2167010 | |
| n43 | 795847 | COP9 subunit 5 | AA461527 (SEQ ID NO:95) | 2185391 | NM_006837 (SEQ ID NO:97) |
| | | | AA460599 (SEQ ID NO:96) | 2185719 | |
| n44 | 809828 | E2F transcription factor 5 | AA464403 (SEQ ID NO:98) | 2189287 | NM_001951 (SEQ ID NO:100) |
| | | | AA455521 (SEQ ID NO:99) | 2178297 | |
| n45 | 810027 | mitochondrial ribosomal protein S26 | AA464995 (SEQ ID NO:101) | 2189879 | NM_030811 (SEQ ID NO:103) |
| | | | AA455275 (SEQ ID NO:102) | 2178051 | |
| n46 | 810237 | hypothetical protein MGC4248 | AA464708 (SEQ ID NO:104) | 2189592 | NM_032333 (SEQ ID NO:105) |
| n47 | 810305 | *Homo sapiens* cDNA FLJ30463 | AA463961 (SEQ ID NO:106) | 2188845 | |
| | | | AA464098 (SEQ ID NO:107) | 2188982 | |
| n48 | 810671 | hypothetical protein FLJ22269 | AA464121 (SEQ ID NO:108) | 2189005 | NM_032219 (SEQ ID NO:110) |
| | | | AA463986 | 2188870 | |

TABLE 1-continued

| No | Image Clone Id | Gene name | Accession | GI number | RefSeq |
|---|---|---|---|---|---|
| | | | (SEQ ID NO:109) | | |
| n49 | 814595 | protein kinase C binding protein 1 | AA480969 (SEQ ID NO:111) | 2210521 | NM_012408 (SEQ ID NO:113) |
| | | | AA480906 (SEQ ID NO:112) | 2210458 | |
| n50 | 815563 | DKFZp434J1813 protein | AA456833 (SEQ ID NO:114) | 2179553 | |
| n51 | 825083 | mitogen-activated protein kinase 8 | AA489245 (SEQ ID NO:115) | 2218847 | NM_015133 (SEQ ID NO:117) |
| | | | AA504316 (SEQ ID NO:116) | 2240476 | |
| n52 | 837904 | ribosomal protein L15 | AA434360 (SEQ ID NO:118) | 2139274 | NM_002948 (SEQ ID NO:120) |
| | | | AA434088 (SEQ ID NO:119) | 2139002 | |
| n53 | 884867 | eukaryotic translation initiation factor 5 | AA669443 (SEQ ID NO:121) | 2630942 | NM_001969 (SEQ ID NO:122) |
| n54 | 897656 | FERM, RhoGEF (ARHGEF) and pleckstrin domain protein 1 | AA496796 (SEQ ID NO:123) | 2230117 | NM_005766 (SEQ ID NO:124) |
| n55 | 897722 | HMBA-inducible | AA598983 (SEQ ID NO:125) | 2432023 | NM_006460 (SEQ ID NO:126) |
| n56 | 1031717 | unnamed | AA609584 (SEQ ID NO:127) | 2458012 | |
| n57 | 1240298 | low density lipoprotein receptor-related protein 5 | AA788645 (SEQ ID NO:128) | 2848765 | NM_002335 (SEQ ID NO:129) |
| n58 | 1536925 | 3-phosphoinositide dependent protein kinase-1 | AA973277 (SEQ ID NO:130) | 3148457 | NM_002613 (SEQ ID NO:131) |
| n59 | 1558940 | *Homo sapiens* cDNA FLJ20046 fis | AA917744 (SEQ ID NO:132) | 3057634 | |
| n60 | 1650934 | *Homo sapiens* cDNA FLJ11472 fis | AI022993 (SEQ ID NO:133) | 3238234 | |
| n61 | 1901754 | *Homo sapiens* cDNA FLJ10500 fis | AI302412 (SEQ ID NO:134) | 3961758 | |
| n62 | 1908973 | cocaine-and amphetamine-regulated transcript | AI300511 (SEQ ID NO:135) | 3959857 | NM_004291 (SEQ ID NO:136) |
| n63 | 1916700 | kallikrein 1, renal/pancreas/salivary | AI347629 (SEQ ID NO:137) | 4084835 | NM_002257 (SEQ ID NO:138) |
| n64 | 269663 | unnamed | N24785 (SEQ ID NO:139) | 1138935 | |
| n65 | 278137 | none | N63520 (SEQ ID NO:140) | 1211349 | |
| n66 | 289499 | unnamed | N63996 (SEQ ID NO:141) | 1211825 | |
| n67 | 384634 | none | AA708997 (SEQ ID NO:142) | 2718915 | |
| n68 | 399440 | semaphorin sem2 | AA732915 (SEQ ID NO:143) | 2754274 | NM_020163 (SEQ ID NO:144) |
| n69 | 743211 | | AA400125 (SEQ ID NO:145) | 2053927 | |

TABLE 1-continued

| No | Image Clone Id | Gene name | Accession | GI number | RefSeq |
|---|---|---|---|---|---|
| n70 | 745190 | unnamed | AA626846 (SEQ ID NO:146) | 2539233 | |
| n71 | 753794 | small inducible cytokine B subfamily | AA406115 (SEQ ID NO:147) | 2064231 | NM_006419 |
| | | | AA410383 (SEQ ID NO:148) | 2069486 | |
| n72 | 1293184 | Homo sapiens unknown mRNA | AA682767 (SEQ ID NO:150) | 2669450 | |
| n73 | 1534173 | frequenin | AA918755 (SEQ ID NO:151) | 3058645 (SEQ ID NO:152) | NM_014286 |
| n74 | 1583344 | *Homo sapiens* mRNA; cDNA DKFZp434D115 | AA983933 (SEQ ID NO:153) | 3162458 | |
| n75 | 275060 | none | R85700 (SEQ ID NO:154) | 944106 | |
| n76 | 381036 | unnamed | AA054643 (SEQ ID NO:155) | 1545567 | |
| n77 | 504630 | S164 protein | AA150143 (SEQ ID NO:156) | 1721364 | |
| | | | AA152212 (SEQ ID NO:157) | 1721413 | |
| n78 | 897950 | ATPase | AA598814 (SEQ ID NO:158) | 2432486 | NM_001677 (SEQ ID NO:159) |

Tables 2-15 list marker sets, comprised of multiple individual markers, which are designated with a marker identification number within each marker set ("Number"), the marker identification numbers set forth in Table 1 ("Marker Number"), the Image clone identification number ("Image Clone Id"), the feature selection ("Feature Selection"), and the classification error rate of the model ("Classification Error Rate of the Model").

TABLE 2

| Number | Marker number | Image clone Id | Feature selection | Classification error rate of the model |
|---|---|---|---|---|
| 1 | n35 | 703838 | SVM | SVM - 0.14286 |
| 2 | n4 | 52724 | SVM | |
| 3 | n39 | 753587 | SVM | |
| 4 | n42 | 789369 | SVM | |
| 5 | n48 | 810671 | SVM | |
| 6 | n54 | 897656 | SVM | |
| 7 | n55 | 897722 | SVM | |
| 8 | n7 | 124575 | SVM | |
| 9 | n1 | 31866 | SVM | |
| 10 | n10 | 182818 | SVM | |
| 11 | n19 | 342082 | SVM | |
| 12 | n22 | 380245 | SVM | |
| 13 | n28 | 491184 | SVM | |
| 14 | n30 | 513200 | SVM | |

TABLE 3

| Number | Marker number | Image clone Id | Feature selection | Classification error rate of the model |
|---|---|---|---|---|
| 1 | n33 | 681910 | SVM | KNN = 0.21429 |
| 2 | n3 | 51970 | SVM | |
| 3 | n40 | 767388 | SVM | |
| 4 | n43 | 795847 | SVM | |
| 5 | n46 | 810237 | SVM | |
| 6 | n49 | 814595 | SVM | |
| 7 | n1 | 31866 | SVM | |
| 8 | n13 | 277403 | SVM | |
| 9 | n65 | 278137 | SVM | |
| 10 | n18 | 308412 | SVM | |
| 11 | n20 | 342181 | SVM | |
| 12 | n25 | 449126 | SVM | |

TABLE 4

| Number | Marker number | Image clone Id | Feature selection | Classification error rate of the model |
|---|---|---|---|---|
| 1 | n34 | 682088 | SNR | SVM = 0.21429 |
| 2 | n44 | 809828 | SNR | |
| 3 | n49 | 814595 | SNR | |
| 4 | n56 | 1031717 | SNR | |
| 5 | n59 | 1558940 | SNR | |
| 6 | n62 | 1908973 | SNR | |
| 7 | n63 | 1916700 | SNR | |
| 8 | n12 | 244055 | SNR | |
| 9 | n21 | 343174 | SNR | |
| 10 | n2 | 43936 | SNR | |
| 11 | n27 | 454798 | SNR | |
| 12 | n32 | 611532 | SNR | |

TABLE 5

| Number | Marker number | Image clone Id | Feature selection | Classification error rate of the model |
|---|---|---|---|---|
| 1 | n36 | 740620 | FISHER | WTV = SVM = 0.21429 |
| 2 | n37 | 740672 | FISHER | |
| 3 | n38 | 745158 | FISHER | |
| 4 | n39 | 753587 | FISHER | |
| 5 | n45 | 810027 | FISHER | |
| 6 | n58 | 1536925 | FISHER | |
| 7 | n61 | 1901754 | FISHER | |
| 8 | n17 | 306921 | FISHER | |
| 9 | n26 | 451706 | FISHER | |
| 10 | n27 | 454798 | FISHER | |
| 11 | n32 | 611532 | FISHER | |

TABLE 6

| Number | Marker number | Image clone Id | Feature selection | Classification error rate of the model |
|---|---|---|---|---|
| 1 | n3 | 51970 | SNR | SVM = 0.21429 |
| 2 | n4 | 52724 | SNR | |
| 3 | n42 | 789369 | SNR | |
| 4 | n47 | 810305 | SNR | |
| 5 | n48 | 810671 | SNR | |
| 6 | n54 | 897656 | SNR | |
| 7 | n10 | 182818 | SNR | |
| 8 | n11 | 187147 | SNR | |
| 9 | n64 | 269663 | SNR | |
| 10 | n18 | 308412 | SNR | |
| 11 | n24 | 428296 | SNR | |
| 12 | n28 | 491184 | SNR | |
| 13 | n29 | 509887 | SNR | |

TABLE 7

| Number | Marker number | Image clone Id | Feature selection | Classification error rate of the model |
|---|---|---|---|---|
| 1 | n35 | 703838 | SVM | SVM = 0.21429 |
| 2 | n4 | 52724 | SVM | |
| 3 | n39 | 753587 | SVM | |
| 4 | n42 | 789369 | SVM | |
| 5 | n48 | 810671 | SVM | |
| 6 | n54 | 897656 | SVM | |
| 7 | n55 | 897722 | SVM | |
| 8 | n7 | 124575 | SVM | |
| 9 | n1 | 31866 | SVM | |
| 10 | n10 | 182818 | SVM | |
| 11 | n19 | 342082 | SVM | |
| 12 | n28 | 491184 | SVM | |
| 13 | n30 | 513200 | SVM | |

TABLE 8

| Number | Marker number | Image clone Id | Feature selection | Classification error rate of the model |
|---|---|---|---|---|
| 1 | n37 | 740620 | SVM | WTV = 0.21429 |
| 2 | n39 | 753587 | SVM | |
| 3 | n42 | 789369 | SVM | |
| 4 | n52 | 837904 | SVM | |
| 5 | n53 | 884867 | SVM | |
| 6 | n60 | 1650934 | SVM | |
| 7 | n8 | 133872 | SVM | |
| 8 | n1 | 31866 | SVM | |
| 9 | n14 | 283301 | SVM | |
| 10 | n15 | 284497 | SVM | |
| 11 | n67 | 384634 | SVM | |
| 12 | n29 | 509887 | SVM | |

TABLE 9

| Number | Marker number | Image clone Id | Feature selection | Classification error rate of the model |
|---|---|---|---|---|
| 1 | n34 | 682088 | SNR | WTV = 0.21429 |
| 2 | n38 | 745158 | SNR | |
| 3 | n41 | 781109 | SNR | |
| 4 | n49 | 814595 | SNR | |
| 5 | n5 | 77577 | SNR | |
| 6 | n56 | 1031717 | SNR | |
| 7 | n57 | 1240298 | SNR | |
| 8 | n9 | 149895 | SNR | |
| 9 | n16 | 289652 | SNR | |
| 10 | n2 | 43936 | SNR | |
| 11 | n27 | 454798 | SNR | |
| 12 | n32 | 611532 | SNR | |

TABLE 10

| Number | Marker number | Image clone Id | Feature selection | Classification error rate of the model |
|---|---|---|---|---|
| 1 | n33 | 681910 | SVM | KNN = 0.21429 |
| 2 | n38 | 745158 | SVM | |
| 3 | n4 | 52724 | SVM | |
| 4 | n39 | 753587 | SVM | |
| 5 | n50 | 815563 | SVM | |
| 6 | n51 | 825083 | SVM | |
| 7 | n54 | 897656 | SVM | |
| 8 | n6 | 110812 | SVM | |
| 9 | n8 | 133872 | SVM | |
| 10 | n15 | 284497 | SVM | |
| 11 | n23 | 416049 | SVM | |
| 12 | n26 | 451706 | SVM | |
| 13 | n31 | 565235 | SVM | |
| 14 | n32 | 611532 | SVM | |

TABLE 11

| Number | Marker number | Image clone Id | Feature selection | Classification error rate of the model |
|---|---|---|---|---|
| 1 | n3 | 51970 | SNR | SVM = 0.21429 |
| 2 | n4 | 52724 | SNR | |
| 3 | n42 | 789369 | SNR | |
| 4 | n47 | 810305 | SNR | |
| 5 | n48 | 810671 | SNR | |
| 6 | n54 | 897656 | SNR | |
| 7 | n10 | 182818 | SNR | |
| 8 | n11 | 187147 | SNR | |
| 9 | n64 | 269663 | SNR | |
| 10 | n66 | 289499 | SNR | |
| 11 | n18 | 308412 | SNR | |
| 12 | n24 | 428296 | SNR | |
| 13 | n28 | 491184 | SNR | |
| 14 | n29 | 509887 | SNR | |

TABLE 12

| Number | Marker number | Image clone Id | Feature selection | Classification error rate of the model |
|---|---|---|---|---|
| 1 | n33 | 681910 | SVM | KNN = 0.21429 |
| 2 | n38 | 745158 | SVM | |
| 3 | n4 | 52724 | SVM | |
| 4 | n39 | 753587 | SVM | |
| 5 | n50 | 815563 | SVM | |
| 6 | n51 | 825083 | SVM | |
| 7 | n54 | 897656 | SVM | |
| 8 | n6 | 110812 | SVM | |
| 9 | n8 | 133872 | SVM | |
| 10 | n15 | 284497 | SVM | |
| 11 | n23 | 416049 | SVM | |

TABLE 12-continued

| Number | Marker number | Image clone Id | Feature selection | Classification error rate of the model |
|---|---|---|---|---|
| 12 | n26 | 451706 | SVM | |
| 13 | n31 | 565235 | SVM | |
| 14 | n32 | 611532 | SVM | |

TABLE 13

| Number | Marker number | Image clone Id | Feature selection | Classification error rate of the model |
|---|---|---|---|---|
| 1 | n38 | 745158 | FISHER | KNN = 0.14286 |
| 2 | n4 | 52724 | FISHER | |
| 3 | n71 | 753794 | FISHER | |
| 4 | n49 | 814595 | FISHER | |
| 5 | n58 | 1536925 | FISHER | |
| 6 | n74 | 1583344 | FISHER | |
| 7 | n62 | 1908973 | FISHER | |
| 8 | n12 | 244055 | FISHER | |
| 9 | n75 | 275060 | FISHER | |
| 10 | n65 | 278137 | FISHER | |
| 11 | n68 | 399440 | FISHER | |
| 12 | n32 | 611532 | FISHER | |

TABLE 14

| Number | Marker number | Image clone Id | Feature selection | Classification error rate of the model |
|---|---|---|---|---|
| 1 | n35 | 703838 | SNR | KNN = 0.14286 |
| 2 | n69 | 743211 | SNR | |
| 3 | n38 | 745158 | SNR | |
| 4 | n70 | 745190 | SNR | |
| 5 | n78 | 897950 | SNR | |
| 6 | n72 | 1293184 | SNR | |
| 7 | n73 | 1534173 | SNR | |
| 8 | n9 | 149895 | SNR | |
| 9 | n65 | 278137 | SNR | |
| 10 | n76 | 381036 | SNR | |
| 11 | n27 | 454798 | SNR | |
| 12 | n77 | 504630 | SNR | |

TABLE 15

| Number | Marker number | Image clone Id | Feature selection | Classification error rate of the model |
|---|---|---|---|---|
| 1 | n35 | 703838 | FISHER | WTV = 0.14286 |
| 2 | n69 | 743211 | FISHER | |
| 3 | n70 | 745190 | FISHER | |
| 4 | n71 | 753794 | FISHER | |
| 5 | n72 | 1293184 | FISHER | |
| 6 | n73 | 1534173 | FISHER | |
| 7 | n62 | 1908973 | FISHER | |
| 8 | n9 | 149895 | FISHER | |
| 9 | n13 | 277403 | FISHER | |
| 10 | n65 | 278137 | FISHER | |
| 11 | n76 | 381036 | FISHER | |
| 12 | n27 | 454789 | FISHER | |

Table 16 identifies the 78 individual markers of the present invention (n1-n78). The marker identification numbers are set forth in Table 16 ("No"), the Image clone identification number ("Image Clone Id"), and the Signal-to-noise ("SNR score"). Table 16 lists markers using SNR statistics applied to 18,539 genes of the 51 ovarian tumor samples. In particular, the markers in Table 16 with negative SNR values are correlated with resistance to an agent (referred to herein as "resistance markers"), and the markers with positive SNR scores are correlated with sensitivity to an agent (referred to herein as "sensitivity markers").

TABLE 16

| No | Image Clone Id | SNR score |
|---|---|---|
| n1 | 31866 | 0.520 |
| n2 | 43936 | −0.331 |
| n3 | 51970 | −0.495 |
| n4 | 52724 | −0.454 |
| n5 | 77577 | −0.463 |
| n6 | 110812 | −0.411 |
| n7 | 124575 | −0.486 |
| n8 | 133872 | −0.371 |
| n9 | 149895 | −0.414 |
| n10 | 182818 | −0.349 |
| n11 | 187147 | 0.443 |
| n12 | 244055 | −0.453 |
| n13 | 277403 | −0.537 |
| n14 | 283301 | 0.364 |
| n15 | 284497 | −0.474 |
| n16 | 289652 | 0.329 |
| n17 | 306921 | 0.300 |
| n18 | 308412 | −0.347 |
| n19 | 342082 | −0.253 |
| n20 | 342181 | 0.345 |
| n21 | 343174 | 0.323 |
| n22 | 380245 | −0.387 |
| n23 | 416049 | 0.404 |
| n24 | 428296 | −0.365 |
| n25 | 449126 | −0.376 |
| n26 | 451706 | 0.581 |
| n27 | 454798 | −0.604 |
| n28 | 491184 | −0.302 |
| n29 | 509887 | 0.456 |
| n30 | 513200 | 0.370 |
| n31 | 565235 | 0.382 |
| n32 | 611532 | 0.572 |
| n33 | 681910 | −0.489 |
| n34 | 682088 | 0.453 |
| n35 | 703838 | 0.565 |
| n36 | 740620 | 0.367 |
| n37 | 740672 | 0.374 |
| n38 | 745158 | 0.573 |
| n39 | 753587 | 0.396 |
| n40 | 767388 | −0.473 |
| n41 | 781109 | −0.366 |
| n42 | 789369 | 0.489 |
| n43 | 795847 | 0.355 |
| n44 | 809828 | 0.414 |
| n45 | 810027 | 0.474 |
| n46 | 810237 | 0.426 |
| n47 | 810305 | −0.432 |
| n48 | 810671 | −0.464 |
| n49 | 814595 | −0.386 |
| n50 | 815563 | 0.341 |
| n51 | 825083 | −0.402 |
| n52 | 837904 | 0.169 |
| n53 | 884867 | 0.301 |
| n54 | 897656 | −0.301 |
| n55 | 897722 | −0.430 |
| n56 | 1031717 | 0.506 |
| n57 | 1240298 | 0.432 |
| n58 | 1536925 | −0.575 |
| n59 | 1558940 | 0.365 |
| n60 | 1650934 | −0.379 |
| n61 | 1901754 | −0.390 |
| n62 | 1908973 | 0.149 |
| n63 | 1916700 | −0.482 |
| n64 | 269663 | 0.385 |
| n65 | 278137 | 0.520 |
| n66 | 289499 | 0.348 |
| n67 | 384634 | −0.521 |
| n68 | 399440 | −0.457 |
| n69 | 743211 | −0.398 |
| n70 | 745190 | 0.470 |
| n71 | 753794 | 0.475 |
| n72 | 1293184 | 0.447 |
| n73 | 1534173 | −0.394 |

TABLE 16-continued

| No | Image Clone Id | SNR score |
|---|---|---|
| n74 | 1583344 | 0.475 |
| n75 | 275060 | −0.290 |
| n76 | 381036 | −0.317 |
| n77 | 504630 | −0.286 |
| n78 | 897950 | 0.306 |

OTHER EMBODIMENTS

The present invention is not to be limited in scope by the specific embodiments described that are intended as single illustrations of individual aspects of the invention and functionally equivalent methods and components are within the scope of the invention, in addition to those shown and described herein will become apparent to those skilled in the art from the foregoing description and accompanying drawings. Such modifications are intended to fall within the scope of the appended claims.

All references cited herein, including journal articles, patents, and databases are expressly incorporated by reference.

The invention claimed is:

1. A method for determining whether a combination of paclitaxel and cisplatin can be used to reduce the growth of ovarian cancer, comprising the steps of:
   a. Obtaining a sample of ovarian cancer cells;
   b. Determining the level of expression in the ovarian cancer cells of each of the markers in the marker set identified in a table selected from the group consisting of: Table 2, Table 3, Table 4, Table 5, Table 6, Table 7, Table 8, Table 9, Table 10, Table 11, Table 12, Table 13, Table 14, and Table 15; and
   c. Evaluating the expression profile of the marker set, wherein over-expression as compared to expression in normal ovarian cells of the sensitivity markers identified in the table and under-expression as compared to expression in normal ovarian cells of the resistance markers identified in the table indicates that a combination of paclitaxel and cisplatin can be used.

2. The method of claim 1, wherein the ovarian cancer cells are selected from the group consisting of ovarian cancer cell lines and ovarian cancer cells obtained from a patient.

3. The method of claim 1, wherein the table is Table 2.

4. The method of claim 1, wherein the table is Table 3.

5. The method of claim 1, wherein the table is Table 4.

6. The method of claim 1, wherein the table is Table 5.

7. The method of claim 1, wherein the table is Table 6.

8. The method of claim 1, wherein the table is Table 7.

9. The method of claim 1, wherein the table is Table 8.

10. The method of claim 1, wherein the table is Table 9.

11. The method of claim 1, wherein the table is Table 10.

12. The method of claim 1, wherein the table is Table 11.

13. The method of claim 1, wherein the table is Table 12.

14. The method of claim 1, wherein the table is Table 13.

15. The method of claim 1, wherein the table is Table 14.

16. The method of claim 1, wherein the table is Table 15.

17. A method for determining whether a combination of paclitaxel and cisplatin can be used to reduce the growth of ovarian cancer, comprising the steps of:
   a. Obtaining a sample of ovarian cancer cells;
   b. Determining the level of expression in the ovarian cancer cells of each of the markers in the marker set identified in Table 2; and
   c. Evaluating the expression profile of the marker set, wherein over-expression as compared to expression in normal ovarian cells of the sensitivity markers identified in the table and under-expression as compared to expression in normal ovarian cells of the resistance markers identified in the table indicates that a combination of paclitaxel and cisplatin can be used.

18. The method of claim 1, wherein the over-expression is at least two-fold greater than expression in normal ovarian cells, and the under-expression is at least two-fold less than expression in normal ovarian cells.

19. The method of claim 17, wherein the over-expression is at least two-fold greater than expression in normal ovarian cells, and the under-expression is at least two-fold less than expression in normal ovarian cells.

* * * * *

SEQUENCE LISTING

```
<160> NUMBER OF SEQ ID NOS: 159

<210> SEQ ID NO 1
<211> LENGTH: 459
<212> TYPE: DNA
<213> ORGANISM: Homo sapiens

<400> SEQUENCE: 1
tttttttttt taatgagaca gggtctcact atgttaccta ggctagtctc aagcaaccct      60
cctgcctcag cctcccaagt agctgggact acaggcacaa gccactgcac ccagctccaa     120
ctcctttctt tatgcaaata caaaaggcaa accttggtgc gacacttagt ccttagtagc     180
aaccctgggc tcatcctcct agtctttccc tagtatttgc atcaatggct aactaagctg     240
atggcagacc tcatcctggg gtaatactca ttcagggaag cagcaacaaa ggagggtggg     300
gaaagaggtc aggtcagatt tacctaacat gatatgtagg cataataggt gcccattaaa     360
tctcagctac tagtaaagtt ggtgaggaag aggtatggag gcattaagac ctgaagcatt     420
gagttggtcc ttaacctggg ttttagaaca aggtttggt                           459

<210> SEQ ID NO 2
<211> LENGTH: 487
<212> TYPE: DNA
<213> ORGANISM: Homo sapiens
<220> FEATURE:
<221> NAME/KEY: misc_feature
<222> LOCATION: 383, 397, 408, 459, 467, 476
<223> OTHER INFORMATION: n = A,T,C or G

<400> SEQUENCE: 2
agaaatggga gaatgggacc tttcctggat ggccgaaaga gacaagcagt gccctgaccc      60
atgctggagc ccatcttgac ctctctgcat tctcctcctg ggaggagttg gcttctctgg     120
gtttggacag attgaaatct gctctcttag ctttaggctt gaaatgtggc gggaccctag     180
aagagcgagc ccagagacta ttcagtacca aaggaaagtc cctggagtca cttgatacct     240
ctttgtttgc caaaaatccc aagtcaaagg gcaccaagcg agacactgaa aggaacaaag     300
acattgcttt tctagaagcc cagatctatg gaatatgtag gagattcttc gggggaacag     360
cgacattctt cactcatgga aantgttaca gcgcaanaag gccagggnca gggagaagga     420
gcgaggaagg aaggagggag gaaggggcag ttccagttna ggagttnagg atttanggtt     480
gaaggag                                                              487

<210> SEQ ID NO 3
<211> LENGTH: 2733
<212> TYPE: DNA
```

<213> ORGANISM: Homo sapiens

<400> SEQUENCE: 3

| | | | | | |
|---|---|---|---|---|---|
| aagggaagat | ggagacaata | ctggagcagc | agcggcgcta | tcatgaggag | aaggaacggc | 60 |
| tcatggacgt | catggctaaa | gagatgctca | ccaagaagtc | cacgctccgg | gaccagatca | 120 |
| attctgatca | ccgcactcgg | gccatgcaag | ataggtatat | ggaggtcagt | gggaacctga | 180 |
| gggatttgta | tgatgataag | gatggattac | gaaaggagga | gctcaatgcc | atttcaggac | 240 |
| ccaatgagtt | tgctgaattc | tataatagac | tcaagcaaat | aaaggaattc | caccggaagc | 300 |
| acccaaatga | gatctgtgtg | ccaatgtcag | tggaatttga | ggaactcctg | aaggctcgag | 360 |
| agaatccaag | tgaagaggca | caaaacttgg | tggagttcac | agatgaggag | ggatatggtc | 420 |
| gttatctcga | tctccatgac | tgttacctca | agtacattaa | cctgaaggca | tctgagaagc | 480 |
| tggattatat | cacatacctg | tccatctttg | accaattatt | tgacattcct | aaagaaagga | 540 |
| agaatgcaga | gtataagaga | tacctagaga | tgctgcttga | gtaccttcag | gattacacag | 600 |
| atagagtgaa | gcctctccaa | gatcagaatg | aacttttggg | aagattcag | gctgagtttg | 660 |
| agaagaaatg | ggagaatggg | acctttcctg | gatggccgaa | agagacaagc | agtgccctga | 720 |
| cccatgctgg | agcccatctt | gacctctctg | cattctcctc | ctgggaggag | ttggcttctc | 780 |
| tgggtttgga | cagattgaaa | tctgctctct | tagcttagg | cttgaaatgt | ggcgggaccc | 840 |
| tagaagagcg | agcccagaga | ctattcagta | ccaaaggaaa | gtccctggag | tcacttgata | 900 |
| cctctttgtt | tgccaaaaat | cccaagtcaa | agggcaccaa | gcgagacact | gaaaggaaca | 960 |
| aagacattgc | ttttctagaa | gcccagatct | atgaatatgt | agagattctc | ggggaacagc | 1020 |
| gacatctcac | tcatgaaaat | gtacagcgca | agcaagccag | gacaggagaa | gagcgagaag | 1080 |
| aagaggaaga | agagcagatc | agtgagagtg | agagtgaaga | tgaagagaac | gagatcattt | 1140 |
| acaaccccaa | aaacctgcca | cttggctggg | atggcaaacc | tattccctac | tggctgtata | 1200 |
| agcttcatgg | cctaaatatc | aactacaact | gtgagatttg | tggaaactac | acctaccgag | 1260 |
| ggcccaaagc | cttccagcga | cactttgctg | aatggcgtca | tgctcatggc | atgaggtgtt | 1320 |
| tgggcatccc | aaatactgct | cactttgcta | atgtgacaca | gattgaagat | gctgtctcct | 1380 |
| tgtgggccaa | actgaaattg | cagaaggctt | cagaacgatg | gcagcctgac | actgaggaag | 1440 |
| aatatgaaga | ctcaagtggg | aatgttgtga | ataagaagac | atacgaggat | ctgaaaagac | 1500 |
| aaggactgct | ctagtgttga | gggatgtagc | tcagcttttg | ggctagccca | ggcttcccta | 1560 |
| agatctgctt | tttctatttc | tcccaaccaa | atcctcttaa | agacccttg | ctatgtagtc | 1620 |
| tcatggtcta | gcatgcatct | tgtagaaaca | aggcatgctg | gcagattgca | gggttgagat | 1680 |
| gtgttttatc | tgttttatat | tttaaaagat | tctgccagaa | aataaaacca | gaccttgttc | 1740 |
| taaagcccag | ggttatggac | caactcagtg | cttcaggtct | taatgcctcc | atacctcttc | 1800 |
| ctcaccaact | ttactagtag | ctgagattta | atgggcacct | attatgctac | atatcatgtt | 1860 |
| aggtaaatct | gacctgacct | ctttccccac | cctcctttgt | tgctgcttcc | ctgaatgagt | 1920 |
| attaccccag | gatgaggtct | gccatcagct | tagttagcca | ttgatgcaaa | tactagggaa | 1980 |
| agactaggag | gatgagccag | ggttgctact | aaggactaag | tgtcgcacca | aggtttgcct | 2040 |
| tttgtatttg | cataaagaaa | ggagttggag | ctgggtgcag | tggcttgtgc | ctgtagtccc | 2100 |
| agctacttgg | gaggctgagg | caggagggtt | gcttgagact | agcctaggta | acatagtgag | 2160 |
| accctgtctc | attaaaaaaa | aaaaaaaaag | gcatggtggc | acgcactgta | gtcccagcta | 2220 |
| ctcaggagac | tgaggctaga | agatcctttg | aacctaggag | tttgagacca | gcctgggcga | 2280 |

```
tatagtgagg cccatctca aaaaaaaaaa aaagcggggg gggggagttg ggctgtgttg    2340
gaatgggcct gcagcccaac aaacaaggga actaggaccg acagtgactt caccagcttg    2400
ctaggtcaga atgagagact ggtgggtctg tctacctgtt tcttctacaa gatccctatt    2460
tgactgtaaa agtagctaat actcacatgt tctccaatcc caggtagcca tggtagagtt    2520
gggtagagtt gagcagccgc cccaggatcc aaatgtggtg tctgaaatgg aaagaactaa    2580
ggcaaccagg aaggcactga tctgccttat aagcacagtc atctgaaagt caggcctgct    2640
gcaggacagg atcccccaga gaccccattt gcctctcaac actcagacct tcaactgttt    2700
tttaataaat ctactttta aaaaaaaaaa ata                                 2733

<210> SEQ ID NO 4
<211> LENGTH: 441
<212> TYPE: DNA
<213> ORGANISM: Homo sapiens
<220> FEATURE:
<221> NAME/KEY: misc_feature
<222> LOCATION: 200, 248, 362, 393, 429
<223> OTHER INFORMATION: n = A,T,C or G

<400> SEQUENCE: 4
tttttttttt tttttttatt tatttaaagt tttatttgct agctaataaa taccactgaa     60
actatgcact tttaaacaaa gtataattgt acatgagtgg gggcagagtg gaatgcaaca    120
tagtaattca tttcacatct tgcataccat taaggtgcct tccagtttgc ctgtaattgc    180
atgaaatgag tatctgagcn taacttcttt taccacaaag gccactaaca ctgtagaggg    240
tgccaggnaa aggtccctga ttcccggggc ttaattaacg aaactggaaa ggcaaaatca    300
aacttcaata caaatggaat gtacagatcc atcacttttct tacttcattc taggattcta    360
angtcagggc tctcaaaccc ttgggtttat ggncttacct atgtgctgag gacatctttt    420
tttcatacna gtccttttgg a                                              441

<210> SEQ ID NO 5
<211> LENGTH: 483
<212> TYPE: DNA
<213> ORGANISM: Homo sapiens
<220> FEATURE:
<221> NAME/KEY: misc_feature
<222> LOCATION: 424, 442, 458, 481
<223> OTHER INFORMATION: n = A,T,C or G

<400> SEQUENCE: 5
tttttttttt tgttttgact ttttgtcttt aaattttaat ataatctgtt tttttttaacc    60 agcccataga cttaatatat aagcatatac aagaaaaagt ctctccccac tctgtacaaa   120
agttgctgtc tttgtgtgca ttctattgca ttttataagt ttttgggggg aggggagtca   180
tatttgagtt tcctgtacct tgtccttggt atgggtctga attatataag gttcagagat   240
agtggtgact gtggggtgca gagagttccc cagggctgtt ttctgtccag tgggcccat    300 gtgctggttt gtaggtgttg tagttaatat gggtcatgaa ttgtggggca gcactactgc   360 cccttcacc tgatacaccg gacgggagct gctgttgctg ctgcggatgt tggctgctgg    420
ggangtcttc gtccacccgg gnttatctca acagtccngg cggctgtgac tgtaactccg   480 ngc                                                                  483

<210> SEQ ID NO 6
<211> LENGTH: 2306
<212> TYPE: DNA
```

<213> ORGANISM: Homo sapiens

<400> SEQUENCE: 6

```
cggggacacc acgccagtgc tttcctgcct tccttccgag atggaaagag gagctcctag      60
ctcacttaag ccggggtagg gctggttctc ctttccgagc caaaatccca ggcgatggtg     120
aattatgaac gtgccacacc atgaagctct tgtggcaggt aactgtgcac caccacacct     180
ggaatgccat cctgctcccg ttcgtctacc tcacggcgca agtgtggatt ctgtgtgcag     240
ccatcgctgc tgccgcctca gccgggcccc agaactgccc ctccgtctgc tcgtgcagta     300
accagttcag caaggtggtg tgcacgcgcc ggggcctctc cgaggtcccg cagggtattc     360
cctcgaacac ccggtacctc aacctcatgg agaacaacat ccagatgatc caggccgaca     420
ccttccgcca cctccaccac ctggaggtcc tgcagttggg caggaactcc atccggcaga     480
ttgaggtggg ggccttcaac ggcctggcca gcctcaacac cctggagctg ttcgacaact     540
ggctgacagt catccctagc ggggcctttg aatacctgtc caagctgcgg agctctggc     600
ttcgcaacaa ccccatcgaa agcatcccct cttacgcctt caaccgggtg ccctccctca     660
tgcgcctgga cttgggggag ctcaagaagc tggagtatat ctctgaggga gcttttgagg     720
ggctgttcaa cctcaagtat ctgaacttgg gcatgtgcaa cattaaagac atgcccaatc     780
tcaccccct ggtggggctg gaggagctgg agatgtcagg gaaccacttc ctgagatca     840
ggcctggctc cttccatggc ctgagctccc tcaagaagct ctgggtcatg aactcacagg     900
tcagcctgat tgagcggaat gcttttgacg ggctggcttc acttgtgaa ctcaacttgg     960
cccacaataa cctctcttct ttgccccatg acctctttac cccgctgagg tacctggtgg    1020
agttgcatct acaccacaac ccttggaact gtgattgtga cattctgtgg ctagcctggt    1080
ggcttcgaga gtatataccc accaattcca cctgctgtgg ccgctgtcat gctcccatgc    1140
acatgcgagg ccgctacctc gtggaggtgg accaggcctc cttccagtgc tctgcccct    1200
tcatcatgga cgcacctcga gacctcaaca tttctgaggg tcggatggca gaacttaagt    1260
gtcggactcc ccctatgtcc tccgtgaagt ggttgctgcc caatgggaca gtgctcagcc    1320
acgcctcccg ccacccaagg atctctgtcc tcaacgacgg caccttgaac ttttcccacg    1380
tgctgctttc agacactggg gtgtacacat gcatggtgac caatgttgca ggcaactcca    1440
acgcctcggc ctacctcaat gtgagcacgg ctgagcttaa cacctccaac tacagcttct    1500
tcaccacagt aacagtggag accacggaga tctcgcctga ggacacaacg cgaaagtaca    1560
agcctgttcc taccacgtcc actggttacc agccggcata taccacctct accacggtgc    1620
tcattcagac taccgtgtg cccaagcagg tggcagtacc cgcgacagac accactgaca    1680
agatgcagac cagcctggat gaagtcatga agaccaccaa gatcatcatt ggctgctttg    1740
tggcagtgac tctgctagct gccgccatgt tgattgtctt ctataaactt cgtaagcggc    1800
accagcagcg gagtacagtc acagccgccc ggactgttga taatccag gtggacgaag    1860
acatcccagc agcaacatcc gcagcagcaa cagcagctcc gtccggtgta tcaggtgagg    1920
gggcagtagt gctgcccaca attcatgacc atattaacta caacacctac aaaccagcac    1980
atgggggcca ctggacagaa aacagcctgg ggaactctct gcaccccaca gtcaccacta    2040
tctctgaacc ttatataatt cagacccata ccaaggacaa ggtacaggaa actcaaatat    2100
gactcccctc ccccaaaaaa cttataaaat gcaatagaat gcacacaaag acagcaactt    2160
ttgtacagag tggggagaga cttttcttg tatatgctta tatattaagt ctatgggctg    2220
gttaaaaaaa acagattata ttaaaattta aagacaaaaa gtcaaaacaa aaaaaaaaaa    2280
```

```
aaaaaaaaat tccgagatgt caggga                                        2306
```

<210> SEQ ID NO 7
<211> LENGTH: 438
<212> TYPE: DNA
<213> ORGANISM: Homo sapiens
<220> FEATURE:
<221> NAME/KEY: misc_feature
<222> LOCATION: 206, 334, 366, 408, 425, 431
<223> OTHER INFORMATION: n = A,T,C or G

<400> SEQUENCE: 7

```
tctccccacg cccaccgccc gctttgagca aaggaccttc agcgtcatca agatcttccc    60
tgacctcagc agcaacgaca tgctcctctt catcgtgaag ggcatcaact tgcccacacc   120
cccaggactg tcccctggcg atctggatgt ctttgttcgg tttgacttcc cctatcccaa   180
cgtggaagaa gctcagaaag acaagnccag tgtgatcaag aacacagact cccctgagtt   240
caaggagcag ttcaaactct gcatcaaccg cagccaccgt ggcttccgaa gggccatcca   300
gaccaagggc atcaagttcg aagtggtttc acanggggg gctgttcaa gatttaccgg    360
gtgttngggg acagcccagt tgaagttggg ttgcattggg agatagcntt tgaagttccg   420
ggagntcttt naggttct                                                 438
```

<210> SEQ ID NO 8
<211> LENGTH: 108
<212> TYPE: DNA
<213> ORGANISM: Homo sapiens
<220> FEATURE:
<221> NAME/KEY: misc_feature
<222> LOCATION: 15, 17, 42, 93
<223> OTHER INFORMATION: n = A,T,C or G

<400> SEQUENCE: 8

```
tttttttttt gagtntngcc ctggctattt tattccatgt gnctggccct ggggacccag    60
ctgggccagg tcgacgcccc tggggagaca gtntggctcg gccagcct                108
```

<210> SEQ ID NO 9
<211> LENGTH: 2126
<212> TYPE: DNA
<213> ORGANISM: Homo sapiens

<400> SEQUENCE: 9

```
agctcaaagg caaaggtccc ttgccgatgg aggccattga gaagatggcc agcctgtgca    60
tgagagaccc ggatgaggat gaggaggagg ggacggatga ggacgacttg gaggctgatg   120
atgacctgct ggcggagcta aatgaggtcc ttggagagga gcagaaggct tcagagaccc   180
cacctcctgt ggcccagccg aagcctgagg cccctcatcc ggggctggag accaccttgc   240
aggagaggct ggcgctctat cagacagcaa ttgaaagcgc cagacaagct ggagacagcg   300
ccaagatgcg gcgctacgat cggggggctta aaacactgga aaacctgctc gcctccatcc   360
gtaagggcaa tgccattgac gaagcggaca tcccgccgcc agtggccata ggaaaaggcc   420
cggcgtccac tcaaaccaat tcacccagct gggcaacatc actgaaacca ccaagtttga   480
aaagttggcg gaggactgta agcggagcat ggacattctg aagcaagcct tcgtccgggg   540
tctccccacg cccaccgccc gctttgagca aaggaccttc agcgtcatca agatcttccc   600
tgacctcagc agcaacgaca tgctcctctt catcgtgaag ggcatcaact tgcccacacc   660
cccaggactg tcccctggcg atctggatgt ctttgttcgg tttgacttcc cctatcccaa   720
```

```
cgtggaagaa gctcagaaag acaagaccag tgtgatcaag aacgcagact cccctgagtt      780
caaggagcag ttcaaactct gcatcaaccg cagccaccct ggccctctgg cccagttgca      840
gagccgccag cgcgactaca agctggctgc cctccacgcc aagcagcagg agataccac      900 tgctgccgct agacacttcc gcgtggctaa gagctttgat gctgtcttgg aggccctgag      960
ccggggtgag cccgtggacc tctcctgcct gccccctcca cccgaccagc tgccccccaga    1020 cccaccgtca ccaccgtcgc agcctccgac ccccgctacg gcgccctcca aacagaggt    1080 gcccccaccc ccgaggaccc tgctggaggc gctggagcag cggatggagc ggtaccaggt   1140
ggccgcagcc caggccaaga gcaagggggga ccagcggaaa gctcgaatgc acgagcgcat   1200
cgtcaagcaa taccaagatg ccatccgagc cacaaggct ggccgagccg tggatgtcgc     1260
tgaattgccc gtgcccccag gcttcccccc aatccagggc ctggaggcca caagcccac    1320 ccagcagagt ctggtgggtg tcctggagac tgccatgaag ctggccaacc aggatgaagg   1380
cccagaggat gaagaggatg aggtgcctaa gaagcagaac agccctgtgg cccccacagc   1440
ccagcccaaa gccccaccct caagaactcc ccagtcggga tcagccccaa cagccaaagc   1500
gccccccaaa gccacatcca ccagagccca gcagcagctg gccttcctag agggccgcaa   1560
gaagcagctc ctgcaggccg cactgcgagc caagcagaaa aacgacgtgg agggtgccaa   1620
gatgcacctg cgccaagcca agggactgga gcctatgctg gaggcctcgc gcaatgggct   1680
gcctgtggac atcaccaagg tgccgcctgc ccctgtcaac aaggacgact ttgccctggt   1740
ccagcggcct ggcccgggtc tgtctcagga ggccgcccgg cgctatggtg aactcaccaa   1800
gctcatacgg cagcagcacg agatgtgcct gaaccactca aaccaattca cccagctggg   1860
caacatcact gaaaccatcc tggctaacat ggtgaaaccc tgtttctact aaaatacaaa   1920
aaaattagcc aggcatggtg gcgggcgcct gtagtcccag ctactcggga ggctgaggca   1980
ggagaatggc gtaagtaaac ccaggaggcg gagcttgcag tgagcccaga ttgcaccact   2040
gcactccagc ctggacaaca gagcgagact ctatctcaaa aaaaaaaaa aaaaaaaaa    2100 aaaaaaaaa aaaaaaaaa aaaaaa                                         2126
```

<210> SEQ ID NO 10
<211> LENGTH: 326
<212> TYPE: DNA
<213> ORGANISM: Homo sapiens
<220> FEATURE:
<221> NAME/KEY: misc_feature
<222> LOCATION: 170, 268, 279, 284, 303, 308, 320
<223> OTHER INFORMATION: n = A,T,C or G

<400> SEQUENCE: 10

```
gatgaaatgt catggcaaat ttgataaaaa ccaagaggga gtgaaactga cgctggggga     60
gggaagggtc aagtcgaggg aaggtgaaac caaaaggcac tgagcatgcg tggtggggca   120
gggaaggaca ccatcactcc agagacagta tggtaacaaa gggacaggan tggtccaggc   180
cagcttcagg ctcttcagaa gccagagaga tgtccaagtc taccaaaccc gagttctcca   240
aggcttttca agaaatgggg tttgcttnca agatgaatna gggnggaggt cccatggctt   300
ctnagggntc caccccagtn ttccca                                        326
```

<210> SEQ ID NO 11
<211> LENGTH: 360
<212> TYPE: DNA
<213> ORGANISM: Homo sapiens
<220> FEATURE:
<221> NAME/KEY: misc_feature
<222> LOCATION: 257, 274, 312, 340
<223> OTHER INFORMATION: n = A,T,C or G

<400> SEQUENCE: 11

| | | | | | |
|---|---|---|---|---|---|
| ctcggtgggc | gctgtagtgg | tgaaacagga | gccoctggaa | gaggacagcc | cctcgtcctc | 60 |
| gtcggcgggg | ctggacaagg | cccagcgctc | tgtcatcaag | cccatcagca | ttgctggggg | 120 |
| cttctacggt | gaggagcccc | tgcacacccc | catcgtggtg | acctccacac | ctgctgtcac | 180 |
| tccgggcacc | tcgaacctcg | tcttcaccta | tcctagcgtc | ctgggagcag | gagtcacccg | 240 |
| catcttccct | ccgaatnctt | gcttccaagg | gttnaccgca | gaagcagtta | gcagcggggg | 300 |
| accaattcat | tnagattcct | ttgaaattcc | cccatttttn | ttgggttttt | taaacccagt | 360 |

<210> SEQ ID NO 12
<211> LENGTH: 1007
<212> TYPE: DNA
<213> ORGANISM: Homo sapiens

<400> SEQUENCE: 12

| | | | | | |
|---|---|---|---|---|---|
| atcatgtacc | aggattatcc | cgggaacttt | gacacctcgt | cccggggcag | cagcggctct | 60 |
| cctgcgcacg | ccgagtccta | ctccagcggc | ggcggcggcc | agcagaaatt | ccgggtagat | 120 |
| atgcctggct | caggcagtgc | attcatcccc | accatcaacg | ccatcacgac | cagccaggac | 180 |
| ctgcagtgga | tggtgcagcc | cacagtgatc | acctccatgt | ccaacccata | ccctcgctcg | 240 |
| caccoctaca | gccccctgcc | gggcctggcc | tctgtccctg | acacatggc | cctcccaaga | 300 |
| cctggcgtga | tcaagaccat | tggcaccacc | gtgggccgca | ggaggagaga | tgagcagctg | 360 |
| tctcctgaag | aggaggagaa | gcgtcgcatc | cggcgggaga | ggaacaagct | ggctgcagcc | 420 |
| aagtgccgga | accgacgccg | ggagctgaca | gagaagctgc | aggcggagac | agaggagctg | 480 |
| gaggaggaga | agtcaggcct | gcagaaggag | attgctgagc | tgcagaagga | gaaggagaag | 540 |
| ctggagttca | tgttggtggc | tcacggccca | gtgtgcaaga | ttagccccga | ggagcgccga | 600 |
| tcgcccccag | cccctgggct | gcagcccatg | cgcagtgggg | gtggctcggt | gggcgctgta | 660 |
| gtggtgaaac | aggagcccct | ggaagaggac | agccoctcgt | cctcgtcggc | ggggctggac | 720 |
| aaggcccagc | gctctgtcat | caagcccatc | agcattgctg | ggggcttcta | cggtgaggag | 780 |
| cccctgcaca | ccccatcgt | ggtgacctcc | acacctgctg | tcactccggg | cacctcgaac | 840 |
| ctcgtcttca | cctatcctag | cgtcctggag | caggagtcac | ccgcatctcc | ctccgaatcc | 900 |
| tgctccaagg | gtcaccgcag | aagcagtagc | agcgggacc | aatcatcaga | ctccttgaac | 960 |
| tcccccactc | tgctggctct | gtaacccagt | gcacctccct | ccggagc | | 1007 |

<210> SEQ ID NO 13
<211> LENGTH: 373
<212> TYPE: DNA
<213> ORGANISM: Homo sapiens
<220> FEATURE:
<221> NAME/KEY: misc_feature
<222> LOCATION: 140, 367
<223> OTHER INFORMATION: n = A,T,C or G

<400> SEQUENCE: 13

| | | | | | |
|---|---|---|---|---|---|
| tgatcatagc | tcactgcagc | ctcagcctcc | tgagctcaag | taatcctacc | acttcagcct | 60 |
| cctgagtagc | tcggactacg | tctggacctc | atttatttat | ttattttgta | gagatagggt | 120 |
| cttgtcacgt | tgtccagggn | tggtcttgaa | ctcctgggcc | tcaagcaatc | ttcccacctc | 180 |
| agcctcccaa | agtgctgaga | ctacaggtgt | gagccatgat | tgccagtcca | cgtcttagtt | 240 |

```
tttaatctcc cctgcatggc tgaggggcag aggccagcca gggagcatct gaggagaccc      300
aaattttgca tcccaccatg ggccagttag tagttgtgtg acctttggtg atgggcatca      360
cttttgntga ggc                                                         373

<210> SEQ ID NO 14
<211> LENGTH: 457
<212> TYPE: DNA
<213> ORGANISM: Homo sapiens
<220> FEATURE:
<221> NAME/KEY: misc_feature
<222> LOCATION: 372, 437
<223> OTHER INFORMATION: n = A,T,C or G

<400> SEQUENCE: 14
gtcgccgagg ctgaagtgca gaggtacgac catagctcag ttcagaagcc tcgacctccc       60
atgcttaagt tatcctcctg cctcagcctc ccaagtaact gggattatga gattacaggt      120
gcaccaccac acccagctaa tttcttaact ttttgtagag acaagggtct cacactgtgt      180
tgcccgggct ggtctcaaac tcgtggcctc cagtgatact tccacctcaa cctcgcaaag      240
tgctgggatt ttaagtgtga gccaccgcac ctgggccaaa tctttactct gttaagcaac      300
tgcagccagg ggacttttgg ttactgcagc ataacccaac ctgttctgcc caattctggg      360
tacatgagag antgcaagga agaaaaaaag gaggaggca ggagaaagga gggaggagat       420
gagagttgct gggtctntcg gaggcctgct gtgacca                               457

<210> SEQ ID NO 15
<211> LENGTH: 222
<212> TYPE: DNA
<213> ORGANISM: Homo sapiens
<220> FEATURE:
<221> NAME/KEY: misc_feature
<222> LOCATION: 21, 157, 168, 176, 199, 205, 215
<223> OTHER INFORMATION: n = A,T,C or G

<400> SEQUENCE: 15 tttttttct tgtagatgg ngtcatttta ccaaaagtta acagaactaa accaagaaac         60
tattgaaaat taacaacagt gagatgacta tacaaatata taattaaaaa taactttccc      120
atgtaaaagc aataatcaac tataaaaata taatggnaaa aactacanta acaaanttgt      180
gtaaaacaag tgaagaaant taggnaaatt tttcncaggg gt                         222

<210> SEQ ID NO 16
<211> LENGTH: 402
<212> TYPE: DNA
<213> ORGANISM: Homo sapiens
<220> FEATURE:
<221> NAME/KEY: misc_feature
<222> LOCATION: 273, 290
<223> OTHER INFORMATION: n = A,T,C or G

<400> SEQUENCE: 16
ttgaaaggaa ttgtttactt tggaatatag gaaacagtt gaatgtcaga ctctcatttg        60
tatgtgatct aaatttgcaa tcaatttcaa taatatttac aatttgtgat aaaactgact      120
tttacagatt ccttttcaca acataattta ggtgtctact gttcttattg tattttgttc      180
tgctgttgat ctctccagca gccgtctcat gcttctccct tgctaaaaga agtttggatt      240
actcaggcag ggccatccca gccccaccca ctnagaaaag ctcttcagan tcttgtcccc      300
tctgttgagc cccagatctc catgtgctac ggagggaaac ccccaagacc ccagagaggg      360
aaggggtcaa ccctggggag ggccagggga aaaagtttgg ct                         402
```

<210> SEQ ID NO 17
<211> LENGTH: 2098
<212> TYPE: DNA
<213> ORGANISM: Homo sapiens

<400> SEQUENCE: 17

```
gcggcgcgaa cgaatagtcg ccggcgacct gtgagggcac tcggaagggc gaggggaggg      60
ctcgaccgct cgcgcctagt ttttctatct ctcccggagc ctgagtctct gagccgtccc     120
cagcaaacgc tcaggggctg cagaggcccc gagagcttgg ctctctggca gatttcctct     180
agtaagaggt ggctctggag gccccgcgaa acgagtgtgg tgtgtggttg caaggcatga     240
tggctgcaaa agtggttcct atgccccaa agccaaagca gtcctttata ctgagagttc      300
cgccagactc caagctgggc caagacctac ttcgagatgc cactaacggg cccaagacca     360
tccaccagct agtgctggag cacttcctca ccttcttgcc caagccaagc ctggtccagc     420
ccagtcagaa agtcaaggag accttggtta ttatgaaaga tgtgagctca agccttcaga     480
acagagtgca tcctcgtccc ttggtgaagc ttctgcccaa aggagtccaa aaggaacaag     540
agacagtgtc tctgtatttg aaagctaacc ctgaggagct ggtggtcttt gaggatttga     600
atgtatttca ctgccaggaa gaatgtgtga gcttggatcc tactcaacaa ctcacgtcag     660
agaaggaaga tgacagcagt gtcggggaaa tgatgttact ggcagtcaat ggcagtaatc     720
ctgaaggtga agatcctgag agggaacctg tagaaaatga agattataga gaaaagtctt     780
cagatgatga tgaaatggat tcttccttgg tctctcagca gcctcccgat aaccaggaaa     840
aggaacgact aaatacatcc attccacaaa aaggaaaat gagaaatctg ttagttacca      900
ttgagaatga tactcctcta gaggaactct caaaatatgt agacatcagt attattgccc     960
ttactcgaaa tcggaggaca aggagatggt acacttgtcc actgtgtggg aaacagttta    1020
atgaaagttc ttacctcatt tcccaccaga ggacccacac tggagaaaaa ccctatgact    1080
gtaatcactg tgggaaaagc ttcaatcata aacaaaccct caataaacat gagcgaattc    1140
atacaggaga gaaaccttat tcctgttctc agtgtggaaa aaacttccgt cagaattctc    1200
atcggagtcg tcatgaagga atccatataa gggagaagat atttaagtgt ccagaatgtg    1260
ggaaaacctt cccaaagaat gaggagtttg tgcttcatct gcagagtcat gaggctgaga    1320
gaccatatgg ttgcaaaaaa tgtgggagaa gatttggtcg gctgtcaaac tgtacccggc    1380
atgagaaaac ccactcagcc tgtaagaccc gaaagcagaa gtaatactgg gaacccttc     1440
tgggtctgat ggtgctgcct caacctgaga gctttcataa gtagttctga attcccaagc    1500
tgcctaaaaa ggtataaatg tgtaaaaatc tcattattgc caaaattgga taatgccca     1560
tcttagctaa aaccctcaaat tgctagaaaa ttcacaggga agaaaacatt tcaagggcta    1620
tacctcagca tctaggcttt ttggactaag gagctttcct tttgaagtt atatgataat      1680
gtacaggtca cagatcccct ttcccaacac tttgaagatg aatctggagt ctgcttactt    1740
ggaaggcaaa gagtgacttg tgtctattga aagtatatcc gttttccccc cacatgggga    1800
ttcatacttg agaaatagtg caaagatgct tatctggaac tgtgttctgg tgaaagaacc    1860
aaattactgg cttgttagcc aacagcttct gatagcaatt catataaccc tctaagaata    1920
cctgtttaag tcttgagtgt tgaaaggaat tgtttacttt ggaatatagg aaaacagttg    1980
aatgtcagac tctcatttgt atgtgatcta aatttgcaat caatttcaat aatatttaca    2040
atttgtgata aaaaaaaaa aaaaaaaaa aaaaaaaaa aaaaaaaaa aaaaaaa          2098
```

<210> SEQ ID NO 18
<211> LENGTH: 383
<212> TYPE: DNA
<213> ORGANISM: Homo sapiens
<220> FEATURE:
<221> NAME/KEY: misc_feature
<222> LOCATION: 282, 328, 341, 371
<223> OTHER INFORMATION: n = A,T,C or G

<400> SEQUENCE: 18

| | | | | | |
|---|---|---|---|---|---|
| gttacagaga | tgttgggcag | agtatgcagg | tgtttcattg | tgaactctag | ctttgatcat | 60 |
| ggtaaaaagt | taaccttttc | tattttttaa | tggatgttat | accaactatt | cagaggaact | 120 |
| catacttcaa | aaatattagg | aaaatctgtc | ttatagtttc | tctaataaat | atctgaaatc | 180 |
| tcagtacgac | atgaaagaat | gtcagaccat | tgttattgtt | gaaagtcatt | tgatgatggg | 240 |
| taaattctat | ggaaaagtaa | gtgatttgca | tgtataatat | cngggaaaat | ttaggcatcc | 300 |
| ccagtgtgac | tggggccaag | gaggagcngg | tgcacccgtg | ncccgtggcc | ctaaggtccc | 360 |
| gattcccccc | ngtgtcccct | ttt | | | | 383 |

<210> SEQ ID NO 19
<211> LENGTH: 311
<212> TYPE: DNA
<213> ORGANISM: Homo sapiens
<220> FEATURE:
<221> NAME/KEY: misc_feature
<222> LOCATION: 8, 39, 101, 120, 175, 231, 289, 295, 306
<223> OTHER INFORMATION: n = A,T,C or G

<400> SEQUENCE: 19

| | | | | | |
|---|---|---|---|---|---|
| ttttttntt | tacttgaaag | agaacatgtt | tatttacanc | actatttcct | ttttacaatg | 60 |
| cctccacctt | tgaataata | aaattttcca | gggaatcagg | ncattttaaa | ttattaaggn | 120 |
| attttaacaa | atacaatttt | caccctatga | ttttttattta | catgagtttt | caagngtttt | 180 |
| aaataggttc | ttttggaaac | tgcacaatat | aaccaggagg | gcctgactcg | naccctggca | 240 |
| tcttttccaa | aaactttcag | tctgggggaa | ttatggttta | taatcaaanc | cttgncactt | 300 |
| gggggncttt | t | | | | | 311 |

<210> SEQ ID NO 20
<211> LENGTH: 1951
<212> TYPE: DNA
<213> ORGANISM: Homo sapiens

<400> SEQUENCE: 20

| | | | | | |
|---|---|---|---|---|---|
| aaaaatttaa | ctcagaagac | tcacgtgact | cttcatggaa | cagaactgtg | tgatgaatcc | 60 |
| tacccggctt | tactcactga | cattcctgtt | ggagacttac | atccagggga | acagctggaa | 120 |
| aaatgttgt | atgttcgctg | tggaacagtg | ggttccagaa | tgtttcttgt | atatgtttct | 180 |
| tacctgataa | atacaaccat | tgaagaaaaa | gaaattgttt | gcaagtgtca | caaggatgaa | 240 |
| actgtaacaa | ttgaaacagt | ctttccattt | gatgttgcgg | ttaaatttgt | ttctaccaag | 300 |
| tttgagcacc | tggaaagggt | ttatgctgac | atcccctttc | tgttgatgac | ggacctctta | 360 |
| agtgcctcac | cctgggccct | cactattgtt | tccagtgagc | tccagcttgc | tccatccatg | 420 |
| accacagtgg | accagctcga | gtctcaagtg | gacaatgtta | tcttacagac | tggagagagt | 480 |
| gctagtgaat | gcttttgtct | tcaatgccca | tctcttggaa | atattgaagg | tggagtagca | 540 |
| accgggcatt | atattatctc | ttggaaaagg | acctcagcaa | tggagaatat | ccccatcatc | 600 |
| acaactgtca | tcactctgcc | gcacgtgatt | gtggagagta | tccctctcca | tgtgaatgca | 660 |

-continued

```
gatctgccgt catttgggcg tgtcagagag tcgttacctg tcaagtatca cctacagaat    720
aagaccgact tagttcaaga tgtagaaatt tctgtggagc ccagtgatgc cttcatgttc    780
tcaggtctca aacagattcg attacgtatc ctccctggca cggagcagga aatgctatat    840
aatttctatc ctctgatggc tggataccag cagctgccat ctctcaacat caacttgctt    900
agatttccta acttcacaaa tcagctgctc aggcgtttta tacctaccag tattttgtc     960 aagccacagg gtcgactcat ggatgatacc tctattgctg ctgcatgatg ttcaagaccg    1020
gcccttggct gttgttacag agatgttggg cagagctatg caggtgtttc attgtgaact    1080
ctagctttga tcatggtaaa aagctaacct tttctatttt ttaatggatg ttataccaac    1140
tattcagagg aactcatact tcaaaaatat taggaaaatc tgtcttatag tttctctaat    1200
aaatatctga atctcagta cgacatgaaa gaatgtcaga ccattgttat tgttgaaagt     1260
catttgatga atggtaaatt ctatgaaaag taagtgattt gcatgtataa tatcaggaaa    1320
attaagcatc ccaagtgtga ctggacaaag agagcagatg caccagtgcc tgtgccataa    1380
agttccgaat cccccatgtg tctctttcag agctggccag accggaaata aatcattctc    1440
ataaattcag tgtgtactca gaacacatac acaacaacat agtgagttgt atgactgata    1500
cggaaaactt ccagaaagtt ttaatcaaag cagtttaatt aaggtatcaa aaatatcttt    1560
gcttactatc aagaagtgtc aaataggttc agcttgctgc caaatatgg atcatttatg     1620 aagcaggttc atattttaga ggtgttaata aaatcctcat cggaaaagat ccaaagtgca    1680
aggatttgat tataaacata atttcctaga ctgaaagttt ttggaaaaga tgcagggtct    1740
gagtcaggcc ttctggttat attgtgcagt ttcaaaagaa ctatttaaaa ctcttgaaaa    1800
ctcatgtaaa taaaaatcat agggtgaaaa ttgtatttgt taaaataccct taataattta    1860 aaatgacctg atttcctgga aaattttatt attcaaaagg tggaggcatt gtaaaaagga    1920
aatagtgatg taaataaaca tgttctcttt c                                    1951
```

<210> SEQ ID NO 21
<211> LENGTH: 245
<212> TYPE: DNA
<213> ORGANISM: Homo sapiens
<220> FEATURE:
<221> NAME/KEY: misc_feature
<222> LOCATION: 132, 149, 174, 241
<223> OTHER INFORMATION: n = A,T,C or G

<400> SEQUENCE: 21

```
attaagtata tataatatta cagggtaata tttacaaagt tatgtttttt tttaaataaa     60
aaagtacctt ggcaaagatt gcagatattc aaagctttaa acagtgataa attgatttaa    120
tacatataaa anaaaaaacc tttaacggna acacagctgt aaaacaactt tggncttcaa    180
atcactggca aaaaatggg ctactgacaa atgggcacac ctttaattgc tatgcaaaaa     240 ngctc                                                                245
```

<210> SEQ ID NO 22
<211> LENGTH: 424
<212> TYPE: DNA
<213> ORGANISM: Homo sapiens
<220> FEATURE:
<221> NAME/KEY: misc_feature
<222> LOCATION: 345, 395
<223> OTHER INFORMATION: n = A,T,C or G

<400> SEQUENCE: 22

```
tttactcctc catctcagta ataaaaatta agctgtaatc aaccttctag gtttctcttg    60
tcttaaaatg ggtattcaaa aatggggatc tgtggtgtat gtatggaaac acatactcct   120
taatttacct gttgttggaa actggagaaa tgattgtcgg gcaaccgttt attttttatt   180
gtattttatt tggttgaggg attttttttat aaacagtttt acttgtgtca tattttaaaa   240
ttactaactg ccatcacctg ctggggtcct ttgttaggtc attttcagtg actaataggg   300
gataatccag ggtaactttg gaagaggatg agcagtgagt gaccngggca gttttctgg    360 cctttaggct tttggacagt tcttaatttt aaggntccat tgaaggaccc agcttttctc   420
atta                                                                424
```

```
<210> SEQ ID NO 23
<211> LENGTH: 311
<212> TYPE: DNA
<213> ORGANISM: Homo sapiens
<220> FEATURE:
<221> NAME/KEY: misc_feature
<222> LOCATION: 105, 303
<223> OTHER INFORMATION: n = A,T,C or G

<400> SEQUENCE: 23 tttttcttgac aatgtccttt taattgtact cttttcaaaa aatctccttt ctcagttaaa   60
aaagacaagg catgatgaag acctgctcta gcccatactg ggggntgatc tcggtcctgg   120
gggaggccag gccggactct tccaaggcct cctccctggg cagtcccagc aatggggcca   180
gtggcagggc aggttctccc tgccagaacc cgatcctagc ccttcagaag gactggacct   240
ctgtgtccct tcagtgggaa gccaccttgg gacacacgca gtcattcagg tgggacataa   300
ggncactttt t                                                        311
```

```
<210> SEQ ID NO 24
<211> LENGTH: 450
<212> TYPE: DNA
<213> ORGANISM: Homo sapiens
<220> FEATURE:
<221> NAME/KEY: misc_feature
<222> LOCATION: 196, 338, 355, 363, 406, 415, 434, 439
<223> OTHER INFORMATION: n = A,T,C or G

<400> SEQUENCE: 24
tgatccggaa gcaggccaac cgtatgagct tcggagagat cgaggaggac gcctaccagg    60
aggacctggg attcagcctg ggccacctgg gcaagtcggg cagtgggcgt gtgcggcaga   120
cacaggtaaa cgaggccacc aaggccagga tctccaagac gctgcaggta tgggccagac   180
ccaggtgggg ctgggngacc gagggacaca aggtgggggg agcccagatc gcagcctccc   240
tgtcctcccc acagcggacc ctgcagaagc agagcttcgt atatgcgggg aagtccacca   300
tccgcgaccg ctccttcggg gcacggcctt ccagcgtngg cctttcaccc cattncaggg   360
gcntgggaga tttttgaaac ccacagggcg gcagagaaga aggttnggtt taggncaacc   420 agaattttttt tttncagant ggtttaattt                                    450
```

```
<210> SEQ ID NO 25
<211> LENGTH: 1834
<212> TYPE: DNA
<213> ORGANISM: Homo sapiens

<400> SEQUENCE: 25
agaaacagtg gtgcgcggag aggagaggcc tcgggatgtc tctggcagat gagctcttag    60
ctgatctcga agaggcagca gaagaggagg aaggaggaag ctatggggag gaagaagagg   120
```

| | |
|---|---|
| agccagcgat cgaggatgtg caggaggaga cacagctgga tctttccggg gattcagtca | 180 |
| agaccatcgc caagctatgg gatagtaaga tgtttgctga gattatgatg aagattgagg | 240 |
| agtatatcag caagcaagcc aaagcttcag aagtgatggg accagtggag gccgcgcctg | 300 |
| aataccgcgt catcgtggat gccaacaacc tgaccgtgga gatcgaaaac gagctgaaca | 360 |
| tcatccataa gttcatccgg gataagtact caaagagatt ccctgaactg gagtccttgg | 420 |
| tccccaatgc actggattac atccgcacgg tcaaggagct gggcaacagc ctggacaagt | 480 |
| gcaagaacaa tgagaacctg cagcagatcc tcaccaatgc caccatcatg gtcgtcagcg | 540 |
| tcaccgcctc caccacccag gggcagcagc tgtcggagga ggagctggag cggctggagg | 600 |
| aggcctgcga catggcgctg agctgaacg cctccaagca ccgcatctac gagtatgtgg | 660 |
| agtcccggat gtccttcatc gcacccaacc tgtccatcat tatcggggca tccacggccg | 720 |
| ccaagatcat gggtgtggcc ggcggcctga ccaacctctc caaggtgccc gcctgcaaca | 780 |
| tcatgctgct cggggcccag cgcaagacgc tgtcgggctt ctcgtctacc tcagtgctgc | 840 |
| cccacaccgg ctacatctac cacagtgaca tcgtgcagtc cctgccaccg gatctgcggc | 900 |
| ggaaagcggc ccggctggtg gccgccaagt gcacactggc agcccgtgtg gacagtttcc | 960 |
| acgagagcac agaagggaag gtgggctacg aactgaagga tgagatcgag cgcaaattcg | 1020 |
| acaagtggca ggagccgccg cctgtgaagc aggtgaagcc gctgcctgcg cccctggatg | 1080 |
| gacagcggaa gaagcgaggc ggccgcaggt accgcaagat gaaggagcgg ctggggctga | 1140 |
| cggagatccg gaagcaggcc aaccgtatga gcttcggaga gatcgaggag gacgcctacc | 1200 |
| aggaggacct gggattcagc ctgggccacc tgggcaagtc gggcagtggg cgtgtgcggc | 1260 |
| agacacaggt aaacgaggcc accaaggcca ggatctccaa gacgctgcag cggaccctgc | 1320 |
| agaagcagag cgtcgtatat ggcgggaagt ccaccatccg cgaccgctcc tcgggcacgg | 1380 |
| cctccagcgt ggccttcacc ccactccagg gcctggagat tgtgaaccca caggcggcag | 1440 |
| agaagaaggt ggctgaggcc aaccagaagt atttctccag catggctgag ttcctcaagg | 1500 |
| tcaagggcga gaagagtggc cttatgtcca cctgaatgac tgcgtgtgtc caaggtggct | 1560 |
| tcccactgaa gggacacaga ggtccagtcc ttctgaaggg ctaggatcgg ttctggcag | 1620 |
| ggagaacctg ccctgccact ggccccattg ctgggactgc ccaggaggga ggccttggaa | 1680 |
| gagtccggcc tggcttcccc caggaccgag atcaccgccc agtatgggct agagcaggtc | 1740 |
| ttcatcatgc cttgtctttt ttaactgaga aaggagattt tttgaaaaga gtacaattaa | 1800 |
| aaggacattg tcaagaaaaa aaaaaaaaaa aaaa | 1834 |

<210> SEQ ID NO 26
<211> LENGTH: 251
<212> TYPE: DNA
<213> ORGANISM: Homo sapiens
<220> FEATURE:
<221> NAME/KEY: misc_feature
<222> LOCATION: 3, 30, 36, 116, 122, 143, 239
<223> OTHER INFORMATION: n = A,T,C or G

<400> SEQUENCE: 26

| | |
|---|---|
| aangttaaaa tcacatgcat aattatagan tatttnaaag ttacaaaaat attttaaaac | 60 |
| caatcctgac agtttacctg caactgctat aaaaatttct atgaaatata taaaancatg | 120 |
| anggctcttt gtaaaaaaaa aanggaaaaa gaaaggaagg aaggcaggga tgaagccatc | 180 |
| cacaggagtg agaatcacct gacgcactgc atcgcaagca tctgctgttg aattcaaang | 240 |

```
aacttgtatc t                                                            251
```

<210> SEQ ID NO 27
<211> LENGTH: 472
<212> TYPE: DNA
<213> ORGANISM: Homo sapiens
<220> FEATURE:
<221> NAME/KEY: misc_feature
<222> LOCATION: 24, 25, 365, 392, 405, 420, 426, 433, 445, 458, 467
<223> OTHER INFORMATION: n = A,T,C or G

<400> SEQUENCE: 27

```
ggagaaccac caaccggacc atcnnctctg tggacgactt ccagaattac ctccgagttg        60
catttcagga ggtcaacagt ggttgcacag gaaagaccct ccttgtgaga ccttacatca       120
ccactgagga tgtgtgtcag atctgcgctg agaagttcaa ggtggggac cctgaggagt        180
acagcctctt tctcttcgtt gacgagacat ggcagcagct ggcagaggac acttaccctc       240
aaaaaatcaa ggcggactgc cacagccgac cacagcccca catcttccac tttgtctaca       300
aacgcatcaa ggaacgatcc ttatgggcat cattttccag gaacggggaa ggaggacctc       360
accanctcct aggaaggaca gggcgggatt tnccagttgg ttgcntccaa aggggagtn        420
gggagnctttg gcntttcccg ttttnaacat gtttgagntt gaaaagnagt tc              472
```

<210> SEQ ID NO 28
<211> LENGTH: 416
<212> TYPE: DNA
<213> ORGANISM: Homo sapiens
<220> FEATURE:
<221> NAME/KEY: misc_feature
<222> LOCATION: 105, 119, 123, 188, 215, 216, 217, 223, 224, 416
<223> OTHER INFORMATION: n = A,T,C or G

<400> SEQUENCE: 28

```
ttcatataaa actatttatt cataaatatt ttccaaaatg aaaataggtt taccaaaaaa        60
tgtccctcac tgggagggg aggagggggc agccctcgcc cccgngcccc cagggtggna       120
tcnagaggaa aacctcccgg cccctccct gcttcctggg agaggggat gcccgtcgg        180
cttgggnct ccctccagtc ttccagggca gggcnnnacc tgnncagggg gatcagcatg       240
agggggaagg gggtgggtag agggaggggc cggtgtcact ggaggtcccg gtcctccagg      300
tagcggtact caaaggtgaa gccttccttc ttccgctggc cccacttctc gtagtcaaag      360
tagatgtagg tgccctggcc gggggagaag gcggtcagtg agtggacgag gaggtn         416
```

<210> SEQ ID NO 29
<211> LENGTH: 4133
<212> TYPE: DNA
<213> ORGANISM: Homo sapiens

<400> SEQUENCE: 29

```
aaattctccc tggggtaag gtaccagccc tgtcctttat gggcttcttg ttctaaagca        60
tatccgtccc atatggttgc tgctagtcac atgtggtgat tagtaactag ttaaaaatga      120
aaaattcagt tcctccatta cacttgccac atttcagatg ttcagtggcc aacagatatg      180
cgcaaataga gtgtttccag cattgcaaag ttctgttgga tagcactgtt tgccagatgt      240
tcccttcttt gtgggtgagg actcttttgg tgtgacttcc ctctgtattg aggctcttgt      300
tcctcagtat ggggctgttt ctgtctttac agtaagtgac tactccaggg ttccctgccc      360
tgcacacgta gagtgggagc ggcccgtgga tcccaggaa ctgtgctttt cattgtaggc       420
cccctccctg gaggggaaga gggcaatctc cgctggtatc tcagaagtct tcttctgagg      480
```

```
cataagcctc tcttcccagg gctcccctgg tctcgctgtc aggccctaag gtatgtcttc      540
ccttggacta aagctccttg gaactccctt ttgacctcag tcttctctgg gttccaggta      600
acttccttta aaataaagac gctcctctct tgaagttttg ggttcctgcc ctgatggtct      660
atgtctccct gactctaaat taccaatcca cttgctatgg gattcctcca tgagtgcaga      720
ttggctccct cacagctgcg gtacctttgc accctcttat cttagtaaga tttctgtctt      780
ctcccaggtc tctcttgggt actgccttct gcccccaaat ctctaagcct tcttggtatt      840
agcttctttg ggttaggagt gttatttcct tttggtttaa ggatcctgct ctggaataaa      900
tgtcttggtg gtttgagtcc cttctacttg gcattcagcc ctgtctgcat gagcgggttc      960
agctcttcac agctttcggc atctctgctc gccgtcgttt tcccccaccc ccaatctttc     1020
ttctcctacc tacagcttac acacacacac acacacacac acacacacac acgcccttct     1080
ctgtgagctg ccagtttcat ttgtctcctg acttgtctga gggatgacct ctcctagcca     1140
cctctgccca gcccctctga gtaggaagtg tgatttccag ggctaatgcc tccatcccag     1200
tcatcgactg tgtgcagcat gactgtcctg ctctgaaaaa ccttttttgag tgtattctgg     1260 gggaaggtac tccatgctct aggaattttc cacttcctga gtcagaggca cacaaaaaag     1320
tatgtaactt ttcttgtttc aacaaactta tggggtcccc tgttggccag acactatgct     1380
gggcagtcaa gcgagcatca ggagaactgg ggctggtctc ttgtcagata gcaaatgctt     1440
cttctcttta ccagtcccac ctacctcact atgctgacta ggtccatgtc tctgggtttt     1500
taccagccag ggaatacgtg ttaattcctc tccaatctct cctagcagcg tccgtctcca     1560
agagagtatg aagagagtgc gtctgtaggg cagggaagat ggcggacaag cgcaaactcc     1620
aaggtgagat tgatcgctgc ctcaagaagg tgtccgaggg cgtggagcag tttgaagata     1680
tttggcagaa gctccacaat gcagccaacg cgaaccagaa agaaaagtat gaggctgacc     1740
taaagaagga gattaagaag ctacaacggc tgagggacca aatcaagaca tgggtagcgt     1800
ccaacgagat caaggacaag aggcagctta tagacaaccg caagctcatt gagacgcaaa     1860
tggaacggtt caaagttgtg gaacgagaga ccaaaaccaa agcttacagc aaagagggcc     1920
tgggcctggc ccagaaggta gatcctgccc agaaggagaa ggaagaggtt ggccagtggc     1980
tcacgaatac catcgacacg ctcaacatgc aggtggacca gtttgagagt gaagtggagt     2040
cactgtcagt gcagacacgc aagaagaagg gcgacaagga taagcaggac cggattgagg     2100
gcttgaagcg gcacatcgag aagcaccgct accacgtgcg catgctagag accatcctgc     2160
gcatgctgga caatgactcc atcctcgttg acgccatccg caagatcaag gacgacgttg     2220
agtactatgt tgactcatcc caggaccccg acttcgagga gaacgagttt ctctacgatg     2280
acctggacct cgaggacatt ccacaggcgc tggtcgccac ctcccccccc agccacagcc     2340
acatggagga tgagatcttc aaccagtcca gcagcacgcc cacctcaacc acctccagct     2400
ctcccatccc gcccagccca gccaactgta ccacggaaaa ctctgaagat gataagaaga     2460
ggggacgttc cacagacagt gaagtcagcc agtctccagc caaaaacggc tccaagcctg     2520
tccacagcaa ccagcaccct cagtccccag ctgtgccgcc cacctacccc tccggccccc     2580
cgcctgctgc ctctgccttg agcaccactc ctggcaacaa tggggtcccc gccccgcag     2640 cacccccaag tgccctgggc cccaaggcca gtccagctcc cagccacaac tcgggcaccc     2700
ctgctcccta tgcccaggct gtggcccac cagctcccag tgggcccagc acgacccagc     2760
cccggccccc cagcgtccag cctagcggag gcggaggcgg cggcagcgga ggcggaggga     2820
```

```
gcagcagcag tagtaacagc agtgccggtg gaggggctgg caagcagaat ggcgccacca    2880
gttacagctc agttgtggca gacagcccgg cagaggtggc tttgagcagc agtgggggca    2940
acaatgccag cagccaggcc ttgggccccc cttccggccc ccacaaccca cctcccagca    3000
cctcgaagga acccagtgcg gcagcccaaa cgggggctgg gggcgtggcc ccaggctcag    3060
ggaacaactc aggggjaccc agcctcctgg tgccactgcc tgtgaatcct cccagctccc    3120
caacgcccag cttcagtgat gccaaggcag ccggtgccct gctcaatggg cctccacagt    3180
tcagcaccgc cccagaaatc aaggcccctg agcctctgag ctccttgaag tccatggcgg    3240
aacgggcagc catcagctct ggcattgagg accctgtgcc aacgctgcac ctgaccgagc    3300
gagacatcat cctgagcagt acatcagcac ctccggcctc agcccagccg ccctgcagc    3360 tgtcagaggt gaacataccg ctgtcgctgg tgtctgtcc actgggccct gtgcccctca    3420
ccaaggagca gctctatcag caggccatgg aagaggccgc ctggcaccac atgcctcacc    3480
cctctgactc tgagcgtatt cggcagtacc tcccccggaa ccctgtccg acgccccct     3540 accaccacca gatgccaccc ccacactcgg acactgtgga attctaccag cgcctgtcga    3600
ccgagacact cttcttcatc ttctactatc tggagggcac taaggcacag tatctggcag    3660
ccaaggccct aaagaagcag tcatggcgat ccacaccaa gtacatgatg tggttccaga    3720
ggcacgagga gccaagacc atcactgacg agtttgagca gggcacctac atctactttg    3780
actacgagaa gtgggggccag cggaagaagg aaggcttcac ctttgagtac cgctacctgg    3840
aggaccggga cctccagtga caccggcccc tccctctacc cacccccttc ccccgcatgc    3900
tgatccccct gcccaggtga gggccctgcc ctggaagact ggagggaggc cccaagccac    3960
ggggcatccc cctctcccag gaagcaggga ggggccgggg aggttttcct ctcagcccca    4020
ccctgggggc ccggggggcga gggctgcccc ctcctcccct cccagtgag ggacatttt     4080 tggtaaacct attttcattt tggaaaatat ttatgaataa atagttttat atg            4133

<210> SEQ ID NO 30
<211> LENGTH: 145
<212> TYPE: DNA
<213> ORGANISM: Homo sapiens
<220> FEATURE:
<221> NAME/KEY: misc_feature
<222> LOCATION: 28, 29, 31, 117, 130
<223> OTHER INFORMATION: n = A,T,C or G

<400> SEQUENCE: 30
tatgagaaat gcccagaaag gctttgcnnc ntccatccgt ctgtggaggc tgcctgcctc      60
cggggtggga tgggtggttt ctcctccaat tcagacccaa gaggtagccc ccgaggnaat    120
gtacctggtn ggaagcagct caagt                                          145

<210> SEQ ID NO 31
<211> LENGTH: 444
<212> TYPE: DNA
<213> ORGANISM: Homo sapiens
<220> FEATURE:
<221> NAME/KEY: misc_feature
<222> LOCATION: 13, 98, 359, 379, 431
<223> OTHER INFORMATION: n = A,T,C or G

<400> SEQUENCE: 31
attagactag ganatatat ttatttcata aaaattaatt ttgttacaat aggaatgcta      60
aaggttattt ataggttgca gtttacagaa taaacagngg tgggattggg ggccatccct    120
ggggccctgc accccctct cccgggcata taaccatgtc cacagacctg gcaggggtcc    180
```

```
agcccttttgc cccaccaaga gctccctgca ccaaagctcc tggtcacctc ccctaaggga      240
cccggctcag ctgcctagga gctggggaat agggaccaga gtgccctgga agggtccagg      300
aaattgagaa ggatcccctg caccctcaag gagaacccct accccttgag ctcttgganc      360
cgggggcact tgttgagang aaggccagaa gggagaggca ccttagaaag atacatttga      420 cttgaacccct ntgggcttca ggga                                            444
```

```
<210> SEQ ID NO 32
<211> LENGTH: 513
<212> TYPE: DNA
<213> ORGANISM: Homo sapiens
<220> FEATURE:
<221> NAME/KEY: misc_feature
<222> LOCATION: 41
<223> OTHER INFORMATION: n = A,T,C or G

<400> SEQUENCE: 32
```

```
acatgatctc gaaaatagtg tgatttagat tctgccttgg ntgagctctg agggctacat       60
ttacctgtca gtttggggat tttagtgcag attttttttta aaaaaattaa actctggtaa     120
gtactcagga ggctgagaac acaggcccct tctctccccg atcctctgta tgcaggctga     180
cttaagcccc tttatgtttg gctagtgcca caacaaaaca gccccaaaca gattgccata     240
agcatgctag cctggcttgg tgtttgacga taaaatcaga ctggtaagtg cagtcagtgt     300
tcaggaaaga atctccaggc tcttctccca tgacctggtt ttaaaatcag cattcataca     360
gctgctttac catctctctg tcctctgcag atgacccggt cctaggcagg ggaccaaaat     420
tccttggtca gctgaggaag tcctgaagaa acatcctgaa gatgatgact gcactggcca     480
tcgtggggca gatgcagctt ccatctacct gat                                   513
```

```
<210> SEQ ID NO 33
<211> LENGTH: 4491
<212> TYPE: DNA
<213> ORGANISM: Homo sapiens

<400> SEQUENCE: 33
```

```
aaatgtagag aagcagccga taaaatagca ttgcctgaag aagtttggag gctgagagca       60
gcagtagact ggccaactgc agagcaagtt gtttctccag ccgtgcggtg cagcctcatg     120
cccccaaccc agcttagcca ctgtaagaag acgttcactg tacagacgac caaacttgcc     180
gtggaagaga cagttgtgag attcccttgc aaatttacat acgagaatgg cttgtgaaat     240
catgcctctg caaagttcac aggaagatga aagacctctg tcacctttct atttgagtgc     300
tcatgtaccc caagtcagca atgtgtctgc aaccggagaa ctcttagaaa gaaccatccg     360
atcagctgta gaacaacatc ttttttgatgt taataactct ggaggtcaaa gttcagagga     420
ctcagaatct ggaacactat cagcatcttc tgccacatct gccagacagc gccgccgcca     480
gtccaaggag caggatgaag ttcgacatgg gagagacaag ggacttatca acaaagaaaa     540
tactccttct gggttcaacc accttgatga ttgtatttttg aatactcagg aagtcgaaaa     600
ggtacacaaa aatactttttg ttgtgctgg agaaaggagc aagcctaaac gtcagaaatc     660
cagtactaaa ctttctgagc ttcatgacaa tcaggacggt cttgtgaata tggaaagtct     720
caattccaca cgatctcatg agagaactgg acctgatgat tttgaatgga tgtctgatga     780
aaggaaagga aatgaaaaag atggtggaca cactcagcat tttgagagcc ccacaatgaa     840
gatccaggag catcccagcc tatctgacac caaacagcag agaaatcaag atgccggtga     900
```

```
ccaggaggag agctttgtct ccgaagtgcc ccagtcggac ctgactgcat tgtgtgatga      960
aaagaactgg gaagagccta tccctgcttt ctcctcctgg cagcgggaga acagtgactc     1020
tgatgaagcc cacctctcgc cgcaggctgg gcgcctgatc cgtcagctgc tggacgaaga     1080
cagcgacccc atgctctctc ctcggttcta cgcttatggg cagagcaggc aatacctgga     1140
tgacacagaa gtgcctcctt ccccaccaaa ctcccattct ttcatgaggc ggcgaagctc     1200
ctctctgggg tcctatgatg atgagcaaga ggacctgaca cctgcccagc tcacacgaag     1260
gattcagagc cttaaaaaga gatccggaa gtttgaagat agattcgaag aagagaagaa      1320
gtacagacct cccacagtg acaaagcagc caatccggag gttctgaaat ggacaaatga      1380
ccttgccaaa ttccggagac aacttaaaga atcaaaacta agatatctg aagaggacct      1440
aactcccagg atgcggcagc gaagcaacac actccccaag agttttggtt cccaacttga     1500
gaaagaagat gagaagaagc aagagctggt ggataaagca ataaagccca gtgttgaagc     1560
cacattggaa tctattcaga ggaagctcca ggagaagcga gcggaaagca gccgccctga    1620
ggacattaag gatatgacca agaccagat tgctaatgag aaagtggctc tgcagaaagc      1680
tctgttatat tatgaaagca ttcatggacg gccggtaaca aagaacgaac ggcaggtgat     1740
gaagccacta tacgacaggt accggctggt caaacagatc ctctcccgag ctaacaccat     1800
acccatcatt ggttccccct ccagcaagcg gagaagccct ttgctgcagc caattatcga     1860
gggcgaaact gcttccttct tcaaggagat aaaggaagaa gaggaggggt cagaagacga     1920
tagcaatgtg aagccagact tcatggtcac tctgaaaacc gatttcagtg cacgatgctt     1980
tctggaccaa ttcgaagatg acgctgatgg atttatttcc ccaatggatg ataaaaatacc    2040
atcaaaatgc agccaggaca cagggctttc aaatctccat gctgcctcaa tacctgaact    2100
cctggaacac ctccaggaaa tgagagaaga aaagaaaagg attcgaaaga aacttcggga    2160
ttttgaagac aacttttca gacagaatgg aagaaatgtc cagaaggaag accgcactcc     2220
tatggctgaa gaatacagtg aatataagca cataaaggcg aaactgaggc tcctggaggt    2280
gctcatcagc aagagagaca ctgattccaa gtccatgtga ggggcatggc caagcacagg    2340
gggctggcag ctgcggtgag agtttactgt ccccagagaa agtgcagctc tggaaggcag    2400
ccttgggggct ggccctgcaa agcatgcagc ccttctgcct ctagaccatt tggcatcggc    2460
tcctgttttcc attgcctgcc ttagaaactg gctggaagaa gacaatgtga cctgacttag    2520
gcatttgtga attggaaagt caagactgca gtatgtgcac atgcgcacgc gcatgcacgc    2580
acacacacac acagtagtgg agctttccta acactagcag agattaatca ctacattaga    2640
caacactcat ctacagagaa tatacactgt tcttccctgg ataactgaga aacaagagac    2700
cattctctgt ctaactgtga taaaaacaag ctcaggactt tattctatag agcaaacttg     2760
ctgtggaggg ccatgctctc cttggaccca gttaactgca aacgtgcatt ggagccctat    2820
ttgctgccgc tgccattcta gtgacctttc cacagagctg cgccttcctc acgtgtgtga    2880
aaggttttcc ccttcagccc tcaggtagat ggaagctgca tctgcccacg atggcagtgc    2940
agtcatcatc ttcaggatgt tcttcagga cttcctcagc tgacaaggaa ttttggtccc     3000
tgcctaggac cgggtcatct gcagaggaca gagagatggt aagcagctgt atgaatgctg    3060
attttaaaac caggtcatgg gagaagagcc tggagattct ttcctgaaca ctgactgcac    3120
ttaccagtct gattttatcg tcaaacacca agccaggcta gcatgctcat ggcaatctgt    3180
ttggggctgt tttgttgtgg cactagccaa acataaaggg gcttaagtca gcctgcatac    3240
agaggatcgg ggagagaagg ggcctgtgtt ctcagcctcc tgagtactta ccagagttta    3300
```

```
atttttttaa aaaaaatctg cactaaaatc cccaaactga caggtaaatg tagccctcag    3360
agctcagccc aaggcagaat ctaaatcaca ctattttcga gatcatgtat aaaaagaaaa    3420
aaaagaagtc atgctgtgtg gccaattata attttttca aagactttgt cacaaaactg     3480
tctatattag acattttgga gggaccagga aatgtaagac accaaatcct ccatctcttc    3540
agtgtgcctg atgtcacctc atgatttgct gttacttttt taactcctgc gccaaggaca    3600
gtgggttctg tgtccacctt tgtgctttgc gaggccgagc ccaggcatct gctcgcctgc    3660
cacggctgac cagagaaggt gcttcaggag ctctgcctta gacgacgtgt tacagtatga    3720
acacacagca gaggcaccct cgtatgtttt gaaagttgcc ttctgaaagg gcacagtttt    3780
aaggaaaaga aaaagaatgt aaaactatac tgacccgttt tcagttttaa agggtcgtga    3840
gaaactggct ggtccaatgg gatttacagc aacattttcc attgctgaag tgaggtagca    3900
gctctcttct gtcagctgaa tgttaaggat ggggaaaaag aatgcccttta agtttgctct    3960 taatcgtatg gaagcttgag ctatgtgttg gaagtgccct ggttaatcca tacacaaaga    4020
cggtacataa tcctacaggt ttaaatgtac ataaaaatat agtttggaat tctttgctct    4080
actgtttaca ttgcagattg ctataatttc aaggagtgag attataaata aaatgatgca    4140
ctttaggatg tttcctattt ttgaaatctg aacatgaatc attcacatga ccaaaaattg    4200
tgttttttta aaaatacatg tctagtctgt cctttaatag ctctcttaaa taagctatga    4260
tattaatcag atcattacca gttagctttt aaagcacatt tgtttaagac tatgtttttg    4320
gaaaaatacg ctacagaatt ttttttaag ctacaaataa atgagatgct actaattgtt     4380
ttggaatctg ttgtttctgc caaaggtaaa ttaactaaag atttattcag gaatccccat    4440
ttgaatttgt atgattcaat aaaagaaaac accaagtaag ttatataaaa t             4491
```

```
<210> SEQ ID NO 34
<211> LENGTH: 335
<212> TYPE: DNA
<213> ORGANISM: Homo sapiens
<220> FEATURE:
<221> NAME/KEY: misc_feature
<222> LOCATION: 42, 43, 53, 89, 90, 91, 97, 128, 182, 324
<223> OTHER INFORMATION: n = A,T,C or G

<400> SEQUENCE: 34
gagaatttaa gctttattta ataaatcatg attttctatt gnntacataa tanagtacaa     60
ttaacaataa cataacatta caacattann nattaaaact ttcagaatca ccttgatcaa    120
tatataangc tttagttcct tatttcaaca gtgttcttct catatgcaaa acagcttccc    180
anaataagag attcgtgaat gaaatttat aaagcttcct gtgtaccaaa gagattgact     240
ccacatcaac tgtccccctac tgaaaatcca aaccatacag gcttgaagga ccagaactga    300
gccacattct attaaagtta tcanagataa aatct                               335
```

```
<210> SEQ ID NO 35
<211> LENGTH: 410
<212> TYPE: DNA
<213> ORGANISM: Homo sapiens

<400> SEQUENCE: 35
ttcagaaaac taagaagtaa gtgtaacttt taaagtaagt atatatcagt gagagtaggc     60
ttgttttaca actatttcta gccagtgagt tgtgttttca tgtctcatca aaagacaata    120
ccacattgca tcattttaca aaatatgttg tcattttcat ttcagttgta acataggaaa    180
```

```
atagatattt cctagatgat ttctgagttt cttactgcaa agaacagtta taaattggta      240
tacatgtgtc tctgtaatag ggataatatt gatatatctg ttgctacata tttaagaatc      300
attctatctt atggttgtct tgaggccaag atttaccacc gtttgcccag tgtattgaat      360
tggtggtaga aggtagttcc atgttccatt ggtagatcct taagatttta                 410
```

<210> SEQ ID NO 36
<211> LENGTH: 455
<212> TYPE: DNA
<213> ORGANISM: Homo sapiens
<220> FEATURE:
<221> NAME/KEY: misc_feature
<222> LOCATION: 423, 429, 453
<223> OTHER INFORMATION: n = A,T,C or G

<400> SEQUENCE: 36

```
ccaactctgc gtatgtattt gaactttcta caaccattaa taacagaaat aattgaatgc      60
tagactaata ctgtgtaaag gagcaatggt caatcttaat ctgattacaa agtttgaaa       120 aaagaagcct cactcttctg attgccatta taataagtga tggctatact attgaatttg     180
taaagttatc ctaatcaaat actacttttc taatttatat atattttttat atacatgact    240 ccaaataaga ctgtttataa aatgggttcc atccagtaca agtttttaaa ctattgttgt     300
aacacataaa tttgtgctgc ctccaacagc aatgattcaa ctgttagtct ggattacatc     360
attcacatta tcaccaagta tatccccta aaagtggtcc aattatcccc tttaataaag      420
gcncattcnc aaaggttttg gcattcatca ccnct                                455
```

<210> SEQ ID NO 37
<211> LENGTH: 279
<212> TYPE: DNA
<213> ORGANISM: Homo sapiens
<220> FEATURE:
<221> NAME/KEY: misc_feature
<222> LOCATION: 276
<223> OTHER INFORMATION: n = A,T,C or G

<400> SEQUENCE: 37

```
ctaaataagg atggaacatt tattgaatga aaaatgcact tttgttttc cattttttta       60 aataataaaa atcagacaaa caggaactgg gtagtggtga tgaatgcaaa acttgtgaa      120 tgtgctttat aaaagtgata attagacact ttagaggata tacttggtga taatgtgaat    180
gatgtaatca gactaacagt tgaatcattg ctgttggagg cagcacaaat ttatgtgtta    240
caacaatagt ttaaaaactt gtactggatg ggcccnccc                            279
```

<210> SEQ ID NO 38
<211> LENGTH: 247
<212> TYPE: DNA
<213> ORGANISM: Homo sapiens
<220> FEATURE:
<221> NAME/KEY: misc_feature
<222> LOCATION: 3, 5, 239
<223> OTHER INFORMATION: n = A,T,C or G

<400> SEQUENCE: 38

```
tananagatt aagcccgatt tgcaacattt attgaaataa atgtcatcta ctaaaaacaa     60
ggttaattta taactggatc tcaacttgtt taatagcaat tgaattttga cataaaaatt    120
gcaaaacttc agctaaagaa caaataaaac attcagacac aagtttacac ttcaaaaatt    180
ctatcaactt caacaaataa tgaatgactg tatattaatt tacattagtc ctgtggtcna    240
gaggtca                                                              247
```

<210> SEQ ID NO 39
<211> LENGTH: 164
<212> TYPE: DNA
<213> ORGANISM: Homo sapiens
<220> FEATURE:
<221> NAME/KEY: misc_feature
<222> LOCATION: 95
<223> OTHER INFORMATION: n = A,T,C or G

<400> SEQUENCE: 39

| | | | | | |
|---|---|---|---|---|---|
| tcagacaaac | aatggtccaa | gtctaacagg | attgactact | atagcagctc | atctagtcaa | 60 |
| gcaagccaac | aaagaatatt | tgctggggag | tactncaga | agaaaaagca | atcgttcagc | 120 |
| agtggttaga | atacagggtc | actcaagtag | atgggcactc | cagt | | 164 |

<210> SEQ ID NO 40
<211> LENGTH: 840
<212> TYPE: DNA
<213> ORGANISM: Homo sapiens

<400> SEQUENCE: 40

| | | | | | |
|---|---|---|---|---|---|
| ggcgtctgcc | aggagctacg | gccggaagat | ggcggcggcc | gcagagttgt | cgctactgga | 60 |
| gaagtccctg | ggactgagta | agggaataa | atacagtgct | cagggcgagc | gacagattcc | 120 |
| agttcttcag | acaaacaatg | gtccaagtct | aacaggattg | actactatag | cagctcatct | 180 |
| agtcaagcaa | gccaacaaag | aatatttgct | ggggagtact | gcagaagaaa | aagcaatcgt | 240 |
| tcagcagtgg | ttagaataca | gggtcactca | agtagatggg | cactccagta | aaaatgacat | 300 |
| ccacacactg | ttgaaggatc | ttaattcata | tcttgaagat | aaagtctacc | ttacagggta | 360 |
| taactttaca | ttagcagata | tactattgta | ctatggactt | catcgcttta | tagttgacct | 420 |
| gacagttcaa | gaaaaggaga | aatatcttaa | tgtgtctcgc | tggttttgtc | acattcagca | 480 |
| ttatccaggc | atcaggcaac | atctgtctag | tgttgtcttc | atcaagaaca | gactatatac | 540 |
| taattcccac | tagaagctgt | ccatgccata | cagaagatct | attaaaaatg | ttttaaatgg | 600 |
| aaaatgtact | ctagaccaca | ggactaatgt | aaattaatat | acagtcattc | attatttgtt | 660 |
| gaagttgata | gaattttga | agtgtaaact | tgtgtctgaa | tgttttatt | gttctttagc | 720 |
| tgaagttttg | caattttat | gtcaaaattc | aattgctatt | aaacaagttg | agatccagtt | 780 |
| ataaattaac | cttgttttta | gtagatgaca | tttatttcaa | taaaagttgc | aaatcgggaa | 840 |

<210> SEQ ID NO 41
<211> LENGTH: 375
<212> TYPE: DNA
<213> ORGANISM: Homo sapiens
<220> FEATURE:
<221> NAME/KEY: misc_feature
<222> LOCATION: 299, 329, 351, 367
<223> OTHER INFORMATION: n = A,T,C or G

<400> SEQUENCE: 41

| | | | | | |
|---|---|---|---|---|---|
| ctcttcataa | aaaatattt | attagtttga | acatcgattt | aaaaaaaaat | cagtcacata | 60 |
| aaaaaaaccc | ttcatgacat | gtcttttccc | tccacgcctc | ctgagatgga | cgtgctcacc | 120 |
| tgggcctcgg | aaatcccaca | ctcttcagtc | ggcaaactcg | cgaacaagaa | caggaaatct | 180 |
| gccacgcagc | aaacacttgg | ggaggtcagt | gggacactgt | tggttttagg | gaagaaaatg | 240 |
| cccctgtagc | tccggcgggg | aaccccaaaa | cggtcagcaa | aggcaggcca | cacggagtng | 300 |
| ccgggcaaaa | ttgagcagga | catccttant | tttgaagggg | aagcggggcc | nggtccttgg | 360 |

```
caaggtngcc tctag                                                    375
```

<210> SEQ ID NO 42
<211> LENGTH: 481
<212> TYPE: DNA
<213> ORGANISM: Homo sapiens
<220> FEATURE:
<221> NAME/KEY: misc_feature
<222> LOCATION: 424, 443, 478
<223> OTHER INFORMATION: n = A,T,C or G

<400> SEQUENCE: 42

```
ggcaagccca tgtgtgttga gagcttctca gactatccac ctttgggtcg ctttgctgtt    60
cgtgatatga gacagacagt tgcggtgggt gtcatcaaag cagtggacaa aaggctgct    120
ggagctggca aggtcaccaa gtctgcccag aaagctcaga aggctaaatg aatattatcc   180
ctaatacctg ccaccccact cttaatcagt ggtggaagaa cggtctcaga actgtttgtt   240
tcaattggcc atttaagttt agtagtaaaa gactggttaa tgataacaat gcatcgtaaa   300
accttcagaa ggaaaggaga atgttttgtg gaccactttg gttttccttt ttttgccgtg   360
tggcagtttt aaagttaatt aagtttttaa aaatcagtac cttttttatt ggaacaactt   420
tggnccaaaa atttgtcccc agnatttttg agacccctttt aaaaagttta aatgggnaa    480
a                                                                   481
```

<210> SEQ ID NO 43
<211> LENGTH: 409
<212> TYPE: DNA
<213> ORGANISM: Homo sapiens
<220> FEATURE:
<221> NAME/KEY: misc_feature
<222> LOCATION: 409
<223> OTHER INFORMATION: n = A,T,C or G

<400> SEQUENCE: 43

```
tggacacgtt acgaagaaat atcacatagg taagagtaag aaaactgaac agcctgccac    60
attaaaatga tggagaacaa agaaaatctg gcccagtttt tctagaaatc tcctccttaa   120
ggtgtgagat gagagcccct agtggaatta agtcctattt ctctctacat ccttgctgca   180
atgaagttta cagcaggttc ccttatagag agcccactct cctaagcaga tggagttaca   240
aatgaaaacc catagccaca cacacacaca cacacacaca aaaggagaaa taagagcagc   300
aagatcatcc aagaatacta catgtgctgc cagaataatt cctttaaaag tcaaatccag   360
gaagcacaga tcaacatctc acaaaaaact ttagcagtgg gaggccccn               409
```

<210> SEQ ID NO 44
<211> LENGTH: 474
<212> TYPE: DNA
<213> ORGANISM: Homo sapiens

<400> SEQUENCE: 44

```
gagccaaggt atgtagggtg tgtggctggc catcagtgga gcacgaagag agaatgggat    60
accattgtgg gaagagaaga aaagttcctc aggggcctcc cactgctaaa gttttttgtg   120
agatgttgat ctgtgcttcc tggatttgac ttttaaagga attattctgg cagcacatgt   180
agtattcttg gatgatcttg ctgctcttat ttctcctttt gtgtgtgtgt gtgtgtgtgt   240
gtggctatgg gttttcattt gtaactccat ctgcttagga gagtgggctc tctataaggg   300
aacctgctgt aaacttcatt gcagcaagga tgtagagaga aataggactt aattccacta   360
ggggctctca tctcacacct taaggaggag atttctagaa aaactgggcc agattttctt   420
```

```
tgttctccat cattttaatg tggcaggctg ttcagttttc ttactcttac ctat        474

<210> SEQ ID NO 45
<211> LENGTH: 465
<212> TYPE: DNA
<213> ORGANISM: Homo sapiens

<400> SEQUENCE: 45
ggtatttaaa caataaatgt gcagttttaa ctaacaggat atttaatgac aaccttctgg   60
ttggtaggga catctgtttc taaatgttta ttatgtacaa tacagaaaaa aattttataa  120
aattaagcaa tgtgaaactg aattggagag tgataataca agtcctttag tcttacccag  180
tgaatcattc tgttccatgt ctttggacaa ccatgacctt ggacaatcat gaaatatgca  240
tctcactgga tgcaaagaaa atcagatgga gcatgaatgg tactgtaccg gttcatctgg  300
actgccccag aaaaataact tcaagcaaac atcctatcaa caacaaggtt gttctgcata  360
ccaagctgag cacagaagat gggaacactg gtggaggatg gaaaggctcg ctcaatcaag  420
aaaattctga gactattaat aaataagact gtagtgtaga tactg                 465

<210> SEQ ID NO 46
<211> LENGTH: 646
<212> TYPE: DNA
<213> ORGANISM: Homo sapiens
<220> FEATURE:
<221> NAME/KEY: misc_feature
<222> LOCATION: 539, 567, 619, 628
<223> OTHER INFORMATION: n = A,T,C or G

<400> SEQUENCE: 46
tatctcacac tgtactttat ttttcttcac aatattaact agacagacaa ggaaagttta   60
atggcaatgt gactttttcc aacaacacaa acaaagtgcc attatagcta atggtggcca  120
actggagact tactttacct taaccatgta aagtatcctt accgtatttt ttatgtgtac  180
agtgttgcag aatatcagcc acctcttaaa agtatcaatc ttaaaaagag ccatggaagg  240
taaaagtatg aaaatcttga taacaaaagc tttcaataca aaaacactta ttgtacactt  300
atttttattt aaaacaaaaa taacccccagt aactcaaaac aaaagcaaac cttggttgaa  360
aacttaagaa ggtataataa acaaaaccac caaaagaaag cttccccaaa agaaatgcaa  420
tccactgtca ctcttgcaaa ttctaccttg gagggaaaaa cttaatgaaa tgagctatct  480
ggagggccca cggagatttt ccaaaaggtt taggtgcatg gatttactca gtatctacnt  540
acagtcttat ttattaatag ctcagantto ctgattgagc gagcctttcc atctccacca  600
gtgtccccac ttctgtgcnc acttgggntg cagacaccct gtgttg                646

<210> SEQ ID NO 47
<211> LENGTH: 6030
<212> TYPE: DNA
<213> ORGANISM: Homo sapiens

<400> SEQUENCE: 47 gttggcccccc gttactttc ctctgggaaa tatggcgcac gctgggagaa cagggtacga   60
taaccgggag atagtgatga agtacatcca ttataagctg tcgcagaggg gctacgagtg  120
ggatgcggga gatgtgggcg ccgcgccccc ggggggccgcc ccgcgccgg gcatcttctc  180 ctcgcagccc gggcacacgc cccatacagc cgcatcccgg gacccggtcg ccaggacctc  240
gccgctgcag acccccggctg ccccccggcgc cgccgcgggg cctgcgctca gcccggtgcc  300
```

```
acctgtggtc cacctgaccc tccgccaggc cggcgacgac ttctcccgcc gctaccgccg    360
cgacttcgcc gagatgtcca ggcagctgca cctgacgccc ttcaccgcgc ggggacgctt    420
tgccacggtg gtggaggagc tcttcaggga cggggtgaac tggggagga ttgtggcctt     480
ctttgagttc ggtggggtca tgtgtgtgga gagcgtcaac cgggagatgt cgcccctggt    540
ggacaacatc gccctgtgga tgactgagta cctgaaccgg cacctgcaca cctggatcca    600
ggataacgga ggctgggatg cctttgtgga actgtacggc cccagcatgc ggcctctgtt    660
tgatttctcc tggctgtctc tgaagactct gctcagtttg gccctggtgg agcttgcat    720
caccctgggt gcctatctgg gccacaagtg aagtcaacat gcctgcccca acaaatatg    780
caaaaggttc actaaagcag tagaaataat atgcattgtc agtgatgttc catgaaacaa    840
agctgcaggc tgtttaagaa aaataacac acatataaac atcacacaca cagacagaca    900
cacacacaca caacaattaa cagtcttcag gcaaaacgtc gaatcagcta tttactgcca    960
aagggaaata tcatttattt tttacattat taagaaaaaa agatttattt atttaagaca   1020
gtcccatcaa aactcctgtc tttggaaatc cgaccactaa ttgccaagca ccgcttcgtg   1080
tggctccacc tggatgttct gtgcctgtaa acatagattc gctttccatg ttgttggccg   1140
gatcaccatc tgaagagcag acggatggaa aaaggacctg atcattgggg aagctggctt   1200
tctggctgct ggaggctggg gagaaggtgt tcattcactt gcatttcttt gccctggggg   1260
ctgtgatatt aacagaggga gggttcctgt gggggaagt ccatgcctcc ctggcctgaa    1320
gaagagactc tttgcatatg actcacatga tgcatacctg gtgggaggaa aagagttggg   1380
aacttcagat ggacctagta cccactgaga tttccacgcc gaaggacagc gatgggaaaa   1440
atgcccttaa atcataggaa agtatttttt taagctacca attgtgccga gaaaagcatt   1500
ttagcaattt atacaatatc atccagtacc ttaagccctg attgtgtata ttcatatatt   1560
ttggatacgc acccccccaac tcccaatact ggctctgtct gagtaagaaa cagaatcctc   1620
tggaacttga ggaagtgaac atttcggtga cttccgcatc aggaaggcta gagttaccca   1680
gagcatcagg ccgccacaag tgcctgcttt taggagaccg aagtccgcag aacctgcctg   1740
tgtcccagct tggaggcctg gtcctggaac tgagccgggg ccctcactgg cctcctccag   1800
ggatgatcaa cagggcagtg tggtctccga atgtctggaa gctgatggag ctcagaattc   1860
cactgtcaag aaagagcagt agaggggtgt ggctgggcct gtcaccctgg ggccctccag   1920
gtaggcccgt tttcacgtgg agcatgggag ccacgaccct tcttaagaca tgtatcactg   1980
tagagggaag gaacagaggc cctggggccct tcctatcaga aggacatggt gaaggctggg   2040
aacgtgagga gaggcaatgg ccacggccca ttttggctgt agcacatggc acgttggctg   2100
tgtggccttg gcccacctgt gagtttaaag caaggcttta aatgactttg gagagggtca   2160
caaatcctaa aagaagcatt gaagtgaggt gtcatggatt aattgacccc tgtctatgga   2220
attacatgta aaacattatc ttgtcactgt agtttggttt tatttgaaaa cctgacaaaa   2280
aaaaagttcc aggtgtggaa tatgggggtt atctgtacat cctggggcat taaaaaaaaa   2340
atcaatggtg gggaactata aagaagtaac aaaagaagtg acatcttcag caaataaact   2400
aggaaatttt tttttcttcc agtttagaat cagccttgaa acattgatgg aataactctg   2460
tggcattatt gcattatata ccatttatct gtattaactt tggaatgtac tctgttcaat   2520
gtttaatgct gtggttgata tttcgaaagc tgctttaaaa aaatacatgc atctcagcgt   2580
tttttgtt taattgtat ttagttatgg cctatacact atttgtgagc aaaggtgatc      2640
gttttctgtt tgagattttt atctcttgat tcttcaaaag cattctgaga aggtgagata   2700
```

```
agccctgagt ctcagctacc taagaaaaac ctggatgtca ctggccactg aggagctttg   2760
tttcaaccaa gtcatgtgca tttccacgtc aacagaattg tttattgtga cagttatatc   2820
tgttgtccct tgaccttgt tcttgaagg tttcctcgtc cctgggcaat tccgcattta     2880
attcatggta ttcaggatta catgcatgtt tggttaaacc catgagattc attcagttaa   2940
aaatccagat ggcaaatgac cagcagattc aaatctatgg tggtttgacc tttagagagt   3000
tgctttacgt ggcctgtttc aacacagacc cacccagagc cctcctgccc tccttccgcg   3060
ggggctttct catggctgtc cttcaggtc ttcctgaaat gcagtggtgc ttacgctcca     3120
ccaagaaagc aggaaacctg tggtatgaag ccagacctcc ccggcgggcc tcagggaaca   3180
gaatgatcag accttgaat gattctaatt tttaagcaaa atattatttt atgaaaggtt     3240
tacattgtca aagtgatgaa tatggaatat ccaatcctgt gctgctatcc tgccaaaatc   3300
attttaatgg agtcagtttg cagtatgctc acgtggtaa gatcctccaa gctgctttag    3360
aagtaacaat gaagaacgtg gacgctttta atataaagcc tgttttgtct tctgttgttg   3420
ttcaaacggg attcacagag tatttgaaaa atgtatatat attaagaggt cacgggggct   3480
aattgctggc tggctgcctt tgctgtgggg gttttgttac ctggttttaa taacagtaaa   3540
tgtgcccagc ctcttggccc cagaactgta cagtattgtg gctgcacttg ctctaagagt   3600
agttgatgtt gcatttttcct tattgttaaa aacatgttag aagcaatgaa tgtatataaa   3660
agcctcaact agtcattttt ttctcctctt cttttttttc attatatcta attattttgc   3720 agtgggcaa cagagaacca tccctatttt gtattgaaga gggattcaca tctgcatctt   3780
aactgctctt tatgaatgaa aaaacagtcc tctgtatgta ctcctcttta cactggccag   3840
ggtcagagtt aaatagagta tatgcacttt ccaaattggg gacaagggct ctaaaaaaag   3900
ccccaaaagg agaagaacat ctgagaacct cctcggccct cccagtccct cgctgcacaa   3960
atactccgca agagaggcca gaatgacagc tgacagggtc tatggccatc gggtcgtctc   4020
cgaagatttg gcaggggcag aaaaactctgg caggcttaag atttggaata aagtcacaga   4080
atcaaggaag cacctcaatt tagttcaaac aagacgccaa cattctctcc acagctcact   4140
tacctctctg tgttcagatg tggccttcca tttatatgtg atctttgttt tattagtaaa   4200
tgcttatcat ctaaagatgt agctctggcc cagtgggaaa aattaggaag tgattataaa   4260
tcgagaggag ttataataat caagattaaa tgtaaataat cagggcaatc ccaacacatg   4320
tctagctttc acctccagga tctattgagt gaacagaatt gcaaatagtc tctatttgta   4380
attgaactta tcctaaaaca aatagtttat aaatgtgaac ttaaactcta attaattcca   4440
actgtacttt taaggcagtg gctgttttta gactttctta tcacttatag ttagtaatgt   4500
acacctactc tatcagagaa aaacaggaaa ggctcgaaat acaagccatt ctaaggaaat   4560
tagggagtca gttgaaattc tattctgatc ttattctgtg gtgtcttttg cagcccagac   4620
aaatgtggtt acacactttt taagaaatac aattctacat tgtcaagctt atgaaggttc   4680
caatcagatc tttattgtta ttcaatttgg atctttcagg gatttttttt ttaaattatt   4740
atgggacaaa ggacatttgt tggagggggtg ggagggagga acaattttta aatataaaac   4800
attcccaagt ttggatcagg gagttggaag ttttcagaat aaccagaact aagggtatga   4860
aggacctgta ttgggtcga tgtgatgcct ctgcgaagaa ccttgtgtga caaatgagaa   4920
acattttgaa gtttgtggta cgaccttag attccagaga catcagcatg gctcaaagtg   4980
cagctccgtt tggcagtgca atggtataaa tttcaagctg gatatgtcta atgggtattt   5040
```

| | |
|---|---|
| aaacaataaa tgtgcagttt taactaacag gatatttaat gacaaccttc tggttggtag | 5100 |
| ggacatctgt ttctaaatgt ttattatgta caatacagaa aaaaatttta taaaattaag | 5160 |
| caatgtgaaa ctgaattgga gagtgataat acaagtcctt tagtcttacc cagtgaatca | 5220 |
| ttctgttcca tgtctttgga caaccatgac cttggacaat catgaaatat gcatctcact | 5280 |
| ggatgcaaag aaaatcagat ggagcatgaa tggtactgta ccggttcatc tggactgccc | 5340 |
| cagaaaaata acttcaagca aacatcctat caacaacaag gttgttctgc ataccaagct | 5400 |
| gagcacagaa gatgggaaca ctggtggagg atggaaaggc tcgctcaatc aagaaaattc | 5460 |
| tgagactatt aataaataag actgtagtgt agatactgag taaatccatg cacctaaacc | 5520 |
| ttttggaaaa tctgccgtgg gccctccaga tagctcattt cattaagttt ttccctccaa | 5580 |
| ggtagaattt gcaagagtga cagtggattg catttctttt ggggaagctt tcttttggtg | 5640 |
| gttttgttta ttataccttc ttaagttttc aaccaaggtt tgcttttgtt ttgagttact | 5700 |
| ggggttattt ttgttttaaa taaaaataag tgtacaataa gtgttttttgt attgaaagct | 5760 |
| tttgttatca agattttcat acttttacct tccatggctc tttttaagat tgatactttt | 5820 |
| aagaggtggc tgatattctg caacactgta cacataaaaa atacggtaag gatactttac | 5880 |
| atggttaagg taaagtaagt ctccagttgg ccaccattag ctataatggc actttgtttg | 5940 |
| tgttgttgga aaagtcaca ttgccattaa acttccttg tctgtctagt taatattgtg | 6000 |
| aagaaaaata aagtacagtg tgagatactg | 6030 |

<210> SEQ ID NO 48
<211> LENGTH: 911
<212> TYPE: DNA
<213> ORGANISM: Homo sapiens

<400> SEQUENCE: 48

| | |
|---|---|
| tgattgaaga cacccccctcg tccaagaatg caaagcacat ccaataaaat agctggatta | 60 |
| taactcctct tctttctctg ggggccgtgg ggtgggagct ggggcgagag gtgccgttgg | 120 |
| cccccgttgc ttttcctctg ggaaggatgg cgcacgctgg gagaacgggg tacgacaacc | 180 |
| gggagatagt gatgaagtac atccattata agctgtcgca gaggggctac gagtgggatg | 240 |
| cgggagatgt gggcgccgcg ccccggggg ccgccccgc accgggcatc ttctcctccc | 300 |
| agcccgggca cacgccccat ccagccgcat cccgcgaccc ggtcgccagg acctcgccgc | 360 |
| tgcagacccc ggctgccccc ggcgccgccg cggggcctgc gctcagcccg gtgccacctg | 420 |
| tggtccacct ggccctccgc caagccggcg acgacttctc ccgccgctac cgcggcgact | 480 |
| tcgccgagat gtccagccag ctgcacctga cgcccttcac cgcgcgggga cgcttttgcca | 540 |
| cggtggtgga ggagctcttc agggacgggg tgaactgggg gaggattgtg gccttctttg | 600 |
| agttcggtgg ggtcatgtgt gtggagagcg tcaaccggga gatgtcgccc ctggtggaca | 660 |
| acatcgccct gtggatgact gagtacctga accggcacct gcacacctgg atccaggata | 720 |
| acggaggctg ggtaggtgca tctggtgatg tgagtctggg ctgaggccac aggtccgaga | 780 |
| tcgggggttg gagtgcgggt gggctcctgg gcaatgggag gctgtggagc cggcgaaata | 840 |
| aaatcagagt tgttgcttcc cggcgtgtcc ctacctcctc ctctggacaa agcgttcact | 900 |
| cccaacctga c | 911 |

<210> SEQ ID NO 49
<211> LENGTH: 402
<212> TYPE: DNA
<213> ORGANISM: Homo sapiens

<400> SEQUENCE: 49

```
cagcatttag gaaactttat tgcacttatc catttacatg tcctaattt ccagtaacat    60
aaaagcaaga agcaaatatt accatttag taagaccaac agttagagaa ggaaataaaa   120
gtagaaagaa taactaaatg agtcaataaa ttccccagtt cgtttctctg cttgtctgct   180
ggtgcttggt ttcacccaat taatagaaac accaccacac gaacacaaac acacacacac   240
attaaccttg cagaaggtcc tcctaaaact ttcctggaca gacccagccc ccaaaagttt   300
tctccaagta ctgggccaca gccagggtca gatgatcatt aaagggtcca gccacaacct   360
gggatgccta aagggagtcc tttggcattc agtcccagtg gg                     402
```

<210> SEQ ID NO 50
<211> LENGTH: 463
<212> TYPE: DNA
<213> ORGANISM: Homo sapiens
<220> FEATURE:
<221> NAME/KEY: misc_feature
<222> LOCATION: 14, 30, 32, 55, 60, 79, 91
<223> OTHER INFORMATION: n = A,T,C or G

<400> SEQUENCE: 50

```
gcgaccgcgc ggtngaccga cgccggcatn gnaccgagtg ggggccccgc gcggngcctn    60
ccctctccgc gccgccaanc cggggactgc ncgcgggtcg ggtttcccgc cagctcaggt   120
ggatctcgag ccagagggga aagtatttgt ggtaataacc cttaccggga gtttcactga   180
agctactctc cagagagacc ggatcttcaa acatttacc aggaagcgcc aaagggctat   240
gcgaaggcga gtccaccaga tcaatggaca caagttcatg ccacgtatc tgaggcagcc   300
cacctactgc tctcactgca gggaagttta tctggggagt gtttgggaaa cagggttatc   360
agtgccaagt tgtgcacctg tgtccgtcca taaacgctgc catcatctaa tttgttacag   420
cctgtacttg ccaaaacaat attaacaaag tggattcaaa gat                    463
```

<210> SEQ ID NO 51
<211> LENGTH: 2389
<212> TYPE: DNA
<213> ORGANISM: Homo sapiens

<400> SEQUENCE: 51

```
gaattcggac ggaggaggca gaatggccag tcgaggggcg cttaggcgtg gccttccc     60
agggctgcct cgactcctgc acctgtcccg agggctggcc tgagacggga ctcccggttc   120
tcccgctgcg aagcaggccc cccggggccg gggcagcggc gccggcatgt cgtctggcac   180
catgaagttc aatggctatt tgaggtccg catcggtgag gcagtgggc tgcagcccac   240
ccgctggtcc ctgcgccact cgctcttcaa gaagggccac cagctgctgg accctatct   300
gacggtgagc gtggaccagg tgcgcgtggg ccagaccagc accaagcaga agaccaacaa   360
acccacgtac aacgaggagt tttgcgctaa cgtcaccgac ggcggccacc tcgagttggc   420
cgtcttccac gagacccccc tgggctacga cttcgtggcc aactgcaccc tgcagttcca   480
ggagctcgtc ggcacgaccg cgcctcgga caccttcgag ggttgggtgg atctcgagcc   540
agaggggaaa gtatttgtgg taataaccct taccgggagt ttcactgaag ctactctcca   600
gagagaccgg atcttcaaac attttaccag gaagcgccaa agggctatgc gaaggcgagt   660
ccaccagatc aatggacaca gttcatggc acgtatctg aggcagccca cctactgctc   720
tcactgcagg gagtttatct ggggagtgtt tgggaaacag ggttatcagt gccaagtgtg   780
```

-continued

```
cacctgtgtc gtccataaac gctgccatca tctaattgtt acagcctgta cttgccaaaa    840
caatattaac aaagtggatt caaagattgc agaacagagg ttcgggatca acatcccaca    900
caagttcagc atccacaact acaaagtgcc aacattctgc gatcactgtg gctcactgct    960
ctggggaata atgcgacaag acttcagtg taaaatatgt aaaatgaatg tgcatattcg   1020
atgtcaagcg aacgtggccc ctaactgtgg ggtaaatgcg gtggaacttg ccaagaccct   1080
ggcagggatg ggtctccaac ccggaaatat ttctccaacc tcgaaactcg tttccagatc   1140
gaccctaaga cgacagggaa aggagagcag caagaaggaa atgggattg gggttaattc   1200
ttccaaccga cttggtatcg acaactttga gttcatccga gtgttgggga aggggagttt   1260
tgggaaggtg atgcttgcaa gagtaaaaga acaggagac ctctatgctg tgaaggtgct   1320
gaagaaggac gtgattctgc tggatgatga tgtggaatgc accatgaccg agaaaaggat   1380
cctgtctctg gcccgcaatc accccttcct cactcagttg ttctgctgct ttcagacccc   1440
cgatcgtctg tttttgtga tggagtttgt gaatgggggt gacttgatgt tccacattca   1500
gaagtctcgt cgttttgatg aagcacgagc tcgcttctat gctgcagaaa tcatttcggc   1560
tctcatgttc ctccatgata aaggaatcat ctatagagat ctgaaactgg acaatgtcct   1620
gttggaccac gagggtcact gtaaactggc agacttcgga atgtgcaagg aggggatttg   1680
caatggtgtc accacggcca cattctgtgg cacgccagac tatatcgctc cagagatcct   1740
ccaggaaatg ctgtacgggc ctgcagtaga ctggtgggca atgggcgtgt tgctctatga   1800
gatgctctgt ggtcacgcgc cttttgaggc agagaatgaa gatgacctct ttgaggccat   1860
actgaatgat gaggtggtct accctacctg gctccatgaa gatgccacag ggatcctaaa   1920
atctttcatg accaagaacc ccaccatgcg cttgggcagc ctgactcagg aggcgagca   1980
cgccatcttg agacatcctt ttttaagga aatcgactgg gcccagctga accatcgcca   2040
aatagaaccg cctttcagac ccagaatcaa atcccgagaa gatgtcagta attttgaccc   2100
tgacttcata aaggaagagc cagttttaac tccaattgat gagggacatc ttccaatgat   2160
taaccaggat gagtttagaa acttttccta tgtgtctcca gaattgcaac catagcctta   2220
tggggagtga gagagagggc acgagaaccc aaaggaatag agattctcca ggaatttcct   2280
ctatcggacc ttcccagcat cagccttaga acaagaacct taccttcaag gagcaagtga   2340
agaactctgt cgaaggatgg aactttcaga tatcaactat ttagagtcc               2389
```

<210> SEQ ID NO 52
<211> LENGTH: 412
<212> TYPE: DNA
<213> ORGANISM: Homo sapiens

<400> SEQUENCE: 52

```
aggtgtccaa ggatgatcga agtgatattg agtctagctc agatgaggag gactcagaac    60
ctccgggaaa gaatccccac actgcgacaa ccaccaatgg gaccagtggt accaacgggt   120
atctcctgac tggctcctgc tccatggatg attaattact caaaactaca gtcccaagc   180
aaagtgaact atttgttcct ggaagtattt aataagttgc aaatgcagtt cctttcataa   240
tatctcagca ccagaaacaa aaattaagat tatcaaacgc attttgaata cgtgcactgc   300
catgtgtcct gtctgtgaat gaagaagaat taccattctc tctttgtagg catgctgtat   360
gtaatttgac acaagggaac agtatttgca tttgtactgt cttagaatat ta          412
```

<210> SEQ ID NO 53
<211> LENGTH: 449

```
<212> TYPE: DNA
<213> ORGANISM: Homo sapiens
<220> FEATURE:
<221> NAME/KEY: misc_feature
<222> LOCATION: 42, 355, 449
<223> OTHER INFORMATION: n = A,T,C or G

<400> SEQUENCE: 53
tttaatttga actgctaatt gaacatgaag agtgaaaatt anacacctag ttcgtccggt      60
ttaaatggtc actaagactg tataggcaat ttcaaaatgg gcactgtaac taaaagaaag    120
caaacctatt tagagctgaa cgagactctt gcactgggtt ttgcttgctc taagtgacaa    180
agtaagctga tgctcatagc acattggact acagcaagag aaaggggggag aagcagatgg   240 agcatctcct tcactgtcat gagcccagtg agtaaaagga gtgaggaaac cctcttttgt    300
ccacagattt acaaatacaa aaaaataaat aatattctaa gacagtacaa atgcnaatac    360
tgttcccttg tgtcaattac atacagcatg cctacaaaga gagaatggta attcttcttc    420
attcacagac aggacacatg gcagtgcan                                     449

<210> SEQ ID NO 54
<211> LENGTH: 449
<212> TYPE: DNA
<213> ORGANISM: Homo sapiens
<220> FEATURE:
<221> NAME/KEY: misc_feature
<222> LOCATION: 299, 423, 431, 442
<223> OTHER INFORMATION: n = A,T,C or G

<400> SEQUENCE: 54
aaaattggtc tgcaattaga acatgtaaga ggagattagg aattaaaatg gattctgaga     60
ggcaatttct aactactgaa cttttataac aggagtatct ttgattaaat aaggagctag   120
tctaaactaa aagcaaaact gtaccataat aacccaactt aattatcttt gcagaataca   180
tttataaatg attggctcat ttctaccttt acttgactaa gtaaatatgc ctcttaaatt   240
ctcaaacatt gaaaattctg attctcacag ttgcacagac ttatctaaat caaaacttnc   300
aaaaagttac aatataatta ctgactccca ttggctaaga tgccagtaca agttccaagt   360
aaggaagttt aagctctggt aacttccact cctcaaccta gaacctccaa ggtcacttgt   420
tcnggttaaa ngggtggggc gnttttatt                                    449

<210> SEQ ID NO 55
<211> LENGTH: 521
<212> TYPE: DNA
<213> ORGANISM: Homo sapiens

<400> SEQUENCE: 55
caaatcataa ggaagttttt attgggtcct gtacagaaga gaaatgctcc gttgtcaaaa     60
aactacaaag ggatccctgg ctctgggtgt gctatgaaga caactccctc cccagtgagc   120
ccagggaaca ggctggatgc tggacaaagt tagggaggga gctccaggcc cagggtcctc   180
cacttggggt ctcccctta tgtttgtaaa aaccgcagac ttggagtatt tagaggactc   240 tgtcccctg caagtattgc cgttggatat gaaacacaca gagcaaaacc ccaaggtgac    300
aaatgagtga aaacctaagg tgacaagtgg acagacgccc cccagatgga ggagacactg   360
gctagctggc gacctctgcc cctacgtaac ttgtcagtcc ttgaaggcac agcagcattg   420
gccagagatg gcccctcccg cggccagggc tggattgcag ttccctgcct tgctcacctg   480
tggccacagc tcataccccc agttacccca cagccaggga c                       521
```

<210> SEQ ID NO 56
<211> LENGTH: 639
<212> TYPE: DNA
<213> ORGANISM: Homo sapiens

<400> SEQUENCE: 56

| | | | | | |
|---|---|---|---|---|---|
| acatactttt | tcttttataa | aaacacacag | gtcaatgttt | tttaaaaaca | cagcataatt | 60 |
| gtacaagggg | aaacattttg | ttagtataat | cttaccaata | atgtaagaga | ggaaagactg | 120 |
| ccatactgaa | atacattttg | ctgctgccaa | agacggtcct | attgtgaaga | aatgagaaag | 180 |
| aaatagcaag | cgccagggcc | aattaagcat | ccctctcccc | gttttctga | atacaacaca | 240 |
| gtgatcctca | ccgtaacccc | tacacatgtt | aatggattgt | tagagtatca | aattattttc | 300 |
| aatgtgcttt | cttgttgtat | aaaccttaac | ctgcactttc | tatttagggg | gcaaaaggg | 360 |
| aatgtgagtg | taaaaaccct | gctcagtgtg | tgtgtgttgg | actttggagc | aattcaacaa | 420 |
| acaagcctgc | tctctttaaa | ctaattatgg | agtggaaggc | ttacaaaatt | ctcccctcag | 480 |
| ctcctatata | aaagaccatg | actggaagga | cagccacctc | tgggtgtgct | ggagaaactt | 540 |
| tgagatttaa | acgggttttg | attgcatgag | agaaagcaaa | cggttagtct | ctcgtcagtc | 600 |
| ctcaagaact | tacttaattg | tggtggtgac | taagcataa | | | 639 |

<210> SEQ ID NO 57
<211> LENGTH: 5433
<212> TYPE: DNA
<213> ORGANISM: Homo sapiens

<400> SEQUENCE: 57

| | | | | | |
|---|---|---|---|---|---|
| ggggagattc | gggaccatgg | cacctgtgca | cggcgacgac | tctctgtcag | attcagggag | 60 |
| ttttgtatct | tctcgagccc | ggcgagaaaa | aaatcaaag | aaggggcgcc | aagaagccct | 120 |
| agaaagactg | aaaaaggcta | aagctggtga | aagtataaa | tatgaagtcg | aggacttcac | 180 |
| aggtgtttat | gaagaagttg | atgaagaaca | gtattcgaag | ctggttcagg | cacgccagga | 240 |
| tgatgactgg | attgtggatg | atgatggtat | tggctatgtg | gaagatggcc | gagagatttt | 300 |
| tgatgatgac | cttgaagatg | atgcccttga | tgctgatgag | aaaggaaaag | atggtaaagc | 360 |
| acgcaataaa | gacaagagga | atgtaaagaa | gctcgcagtg | acaaaaccga | acaacattaa | 420 |
| gtcaatgttc | attgcttgtg | ctggaaagaa | aactgcagat | aaagctgtag | acttgtccaa | 480 |
| ggatggtctg | ctaggtgaca | ttctacagga | tcttaacact | gagacacctc | aaataactcc | 540 |
| accacctgta | atgatactga | agaagaaag | atccattgga | gcttcaccga | atccctctctc | 600 |
| tgtgcacacc | gccacggcag | ttccttcagg | aaaaattgct | tcccctgtct | ccagaaagga | 660 |
| gcctccatta | actcctgttc | ctcttaaacg | tgctgaattt | gctggcgatg | atgtacaggt | 720 |
| cgagagtaca | gaagaagagc | aggagtcagg | ggcaatggag | tttgaagatg | gtgactttga | 780 |
| tgagcccatg | gaagttgaag | aggtggaacct | ggagcctatg | gctgccaagg | cttgggacaa | 840 |
| agagagtgag | ccagcagagg | aagtgaaaca | agaggcggat | tctgggaaag | gaccgtgtc | 900 |
| ctacttagga | agttttctcc | cggatgtctc | ttgttgggac | attgatcaag | aaggtgatag | 960 |
| cagtttctca | gtgcaagaag | ttcaagtgga | ttccagtcac | ctcccattgg | taaaagggc | 1020 |
| agatgaggaa | caagtattcc | acttttattg | gttggatgct | tatgaggatc | agtacaacca | 1080 |
| accaggtgtg | gtatttctgt | ttgggaaagt | ttggattgaa | tcagccgaga | cccatgtgag | 1140 |
| ctgttgtgtc | atggtgaaaa | atatcgagcg | aacgctttac | ttccttcccc | gtgaaatgaa | 1200 |
| aattgatcta | aatacgggga | aagaaacagg | aactccaatt | tcaatgaagg | atgttttatga | 1260 |

-continued

```
ggaatttgat gagaaaatag caacaaaata taaaattatg aagttcaagt ctaagccagt    1320
ggaaaagaac tatgcttttg agatacctga tgttccagaa aaatctgagt acttggaagt    1380
taaatactcg gctgaaatgc cacagcttcc tcaagatttg aaaggagaaa cttttttctca   1440
tgtatttggg accaacacat ctagcctgga actgttcttg atgaacagaa agatcaaagg    1500
accttgttgg cttgaagtaa aaaagtccac agctcttaat cagccagtca gttggtgtaa    1560
agttgaggca atggctttga aaccagacct ggtgaatgta attaaggatg tcagtccacc    1620
accgcttgtc gtgatggctt tcagcatgaa gacaatgcag aatgcaaaga accatcaaaa    1680
tgagattatt gctatggcag ctttggtcca tcacagtttt gcattggata aagcagcccc    1740
aaagcctccc tttcagtcac acttctgtgt tgtgtctaaa ccaaaggact gtattttcc     1800
atatgctttc aaagaagtca ttgagaaaaa gaatgtgaag gttgaggttg ctgcaacaga    1860
aagaacactg ctaggttttt tccttgcaaa agttcacaaa attgatcctg atatcattgt    1920
gggtcataat atttatgggt ttgaactgga agtactactg cagagaatta atgtgtgcaa    1980
agctcctcac tggtccaaga taggtcgact gaagcgatcc aacatgccaa agcttggggg    2040
ccggagtgga tttggtgaaa gaaatgctac ctgtggtcga atgatctgtg atgtggaaat    2100
ttcagcaaag gaattgattc gttgtaaaag ctaccatctg tctgaacttg ttcagcagat    2160
tctaaaaact gaaagggttg taatcccaat ggaaaatata caaaatatgt acagtgaatc    2220
ttctcaactg ttatacctgt tggaacacac ctggaaagat gccaagttca ttttgcagat    2280
catgtgtgag ctaaatgttc ttccattagc attgcagatc actaacatcg ctgggaacat    2340
tatgtccagg acgctgatgg gtggacgatc cgagcgtaac gagttcttgt tgcttcatgc    2400
attttacgaa aacaactata ttgtgcctga caagcagatt ttcagaaagc ctcagcaaaa    2460
actgggagat gaagatgaag aaattgatgg agataccaat aaatacaaga aaggacgtaa    2520
gaaaggagct tatgctggag gcttggtttt ggaccccaaa gttggttttt atgataagtt    2580
cattttgctt ctggacttca acagtctata tccttccatc attcaggaat ttaacatttg    2640
ttttacaaca gtacaaagag ttgcttcaga ggcacagaaa gttacagagg atggagaaca    2700
agaacagatc cctgagttgc cagatccaag cttagaaatg ggcattttgc ccagagagat    2760
ccggaaactg gtagaacgga gaaaacaagt caaacagcta atgaaacagc aagacttaaa    2820
tccagacctt attcttcagt atgacattcg acagaaggct ttgaagctca cagcgaacag    2880
tatgtatggt tgcctgggat tttcctatag cagatttac gccaaaccac tggctgcctt     2940
ggtgacatac aaaggaaggg agattttgat gcatacgaaa gagatggtac aaaagatgaa    3000
tcttgaagtt atttatggag atacagattc aattatgata acaccaata gcaccaatct     3060
ggaagaagta tttaagttgg gaaacaaggt aaaaagtgaa gtgaataagt tgtacaaact    3120
gcttgaaata gacattgatg ggttttcaa gtctctgcta ctgctgaaaa aaagaagta     3180
cgctgctctg gttgttgagc aacgtcgga tgggaattat gtcaccaaac aggagctcaa    3240
aggattagat atagttagaa gagattggtg tgatcttgct aaagacactg gaaactttgt    3300
gattggccag attctttctg atcaaagccg ggacactata gtggaaaaca ttcagaagag    3360
gctgatagaa attggagaaa atgtgctaaa tggcagtgtc ccagtgagcc agtttgaaat    3420
taacaaggca ttgacaaagg atccccagga ttaccctgat aaaaaaagcc tacctcatgt    3480
acatgttgcc ctctggataa attctcaagg aggcagaaag gtgaaagctg agatactgt     3540
gtcatatgtc atctgtcagg atggatcaaa cctcactgca agtcagaggg cctatgcgcc    3600
```

```
tgagcagctg cagaaacagg ataatctaac cattgacacc cagtactacc tggcccagca     3660
gatccaccca gtcgtggctc ggatctgtga accaatagac ggaattgatg ctgtcctcat     3720
tgcaacgtgg ttgggacttg accccaccca atttagagtt catcattatc ataaagatga     3780
agagaatgat gctctacttg gtggcccagc acagctcact gatgaagaga aatacaggga     3840
ctgtgaaaga ttcaaatgtc catgccctac atgtggaact gagaatattt atgataatgt     3900 cttttgatggt tcgggaacag atatggagcc cagcttgtat cgttgcagta acatcgattg     3960
taaggcttca cctctgacct ttacagtaca actgagcaac aaattgatca tggacattag     4020
acgtttcatt aaaaagtact atgatggctg gttgatatgt gaagagccaa cctgtcgcaa     4080
tcgaactcgt caccttcccc ttcaattctc ccgaactggg cctctttgcc cagcctgcat     4140
gaaagctaca cttcaaccag agtattctga caagtccctg tacacccagc tgtgctttta     4200
ccggtacatt tttgatgcgg agtgtgcact ggagaaactt actaccgatc atgagaaaga     4260
taaattgaag aagcaatttt ttaccccccaa agttctgcag gactacagaa aactcaagaa     4320
cacagcagag caattcttgt cccgaagtgg ctactccgaa gtgaatctga gcaaactctt     4380
cgctggttgt gccgtgaaat cctaagggaa tcccaggagt aaccaaggag ggggtagttg     4440
aaaaatccca gcttcctctg tgcctccact ctggccctaa atgctcctcc agcatctgtt     4500
tctcccttgg gactgtgtct catgtttgtg tgaatgtaga ccaggaaagg gggctgcaaa     4560
aatgttgagt ctaatgttcg taagcatcat agaaattcct gtcttcatat aagatgtac      4620 tgctttaaaa cacaactcca gagccccctcc ccaagctccc ctcccccaagc tcctgaagac     4680 ccggtttctg agggagggaa attgctactt ggattgagag tagctggaat gtaagtgacc     4740
ccaggctttg ctcagggcct ttagcctatg tccccccac ataaagagag cttctcagag       4800
cctgactgaa gagctgacgt tttgcttttt catatgccaa ttaaacccgg tctaaatcca     4860
aatgcttctc cagccatcca ggagtggctg tccttttcag tcttgtcttt tatataggta     4920 gctgagggggg aagatttaga agccttgcac tcactaaata gattaaacag agcaggcttg    4980
tttgttgaat tgctccaaag tccaacagac acacactgag caggtgtttt acactcacat     5040
tccctttttg ccccttaaat agaaagtgca ggtaaaggtt tatacaacaa gaaagcacat     5100
tgaaaataat ttgatactct aacaatccat taacatgtgt aggggttacg gtgaggatca     5160
tgtgttgtat tcgaaaaacg gggagaggga tgcttaattg gccctcgctt gctatttttt     5220
tctcatttct tcacaatagg accgtctttg gcagcagcaa aatgtatttc agtatggcag     5280 tcttttcctct cttacattat tggtaagatt atactaacaa aatgtttccc cttgtacaat     5340
tatgctgtgt ttttaaaaaa cattgacctg tgtgttttta taaaagaaaa agtatgttgt     5400
gccttcttct taagaataaa gttttctaaa ggg                                   5433
```

<210> SEQ ID NO 58
<211> LENGTH: 126
<212> TYPE: DNA
<213> ORGANISM: Homo sapiens

<400> SEQUENCE: 58

```
gaaaactgca aaaggtggca aaaggtgaga atgggaggag actcatctgt gactaactcc        60
cccatcagcc tcacgggtgg gtgacttgga gctccccaac ccaatgggac ttccttcttt       120
cgccta                                                                  126
```

<210> SEQ ID NO 59
<211> LENGTH: 294

```
<212> TYPE: DNA
<213> ORGANISM: Homo sapiens

<400> SEQUENCE: 59
tcagacgatc ttcctttaat acaaagtcga tatatctaca tacacggggg tgggaaaacc    60
accggctgct tccgctggaa taaacagtgt tgaaagtaac cgcagatctg cccttgtaca   120
aagaggaaca actcgcttgc tcagggtagg cgggtagagg ggggcctgtc cttctggttt   180
tgctcccaaa ctgccccata gtcccagggg gaaagggtcc ctgatgtggg gcagaacagc   240
catacagcca ctggtccccg aagaagtagg atcctctctg tctccttggg ggcg         294

<210> SEQ ID NO 60
<211> LENGTH: 397
<212> TYPE: DNA
<213> ORGANISM: Homo sapiens
<220> FEATURE:
<221> NAME/KEY: misc_feature
<222> LOCATION: 1, 2, 202, 206, 305, 375, 387
<223> OTHER INFORMATION: n = A,T,C or G

<400> SEQUENCE: 60
nntgacattt catttttttt aaatagtgta ttttttttcc attttttttt ttaagagaaa    60
caaaagactc gccagtcaat gactttcaaa gagaactaac tttggcttat tcatattctg   120
ttcaaagaca gtctatttt tcactgtaga aagcgtcctt gtgtgatagt tacgttcgca    180
aacgcgcacg ccaggcccat gnctgntacc ttggcttttt tttttttttt tttttttttt   240 aattttcct accatcagaa agtgtgcttt gctcacagaa gaatgggatg tcctttttc     300 tttcntggct ttttttttcc cccttttttgt ttcattttta taaattaaat tttcagacat   360
atcaaataag gttcngaggg gtaaggncat gggggaa                             397

<210> SEQ ID NO 61
<211> LENGTH: 326
<212> TYPE: DNA
<213> ORGANISM: Homo sapiens
<220> FEATURE:
<221> NAME/KEY: misc_feature
<222> LOCATION: 275, 301, 313, 318
<223> OTHER INFORMATION: n = A,T,C or G

<400> SEQUENCE: 61
tttttttttt ttttaccac acagaattga cttgtttaat accaccctc ccttgccctc      60 tgcctccagc atactcccta gagtagtaca ggcagggtag atctaactat tggaaggaat   120
ccctaacact tttccagggt agaattctgg ctagtccaaa aagggtcctt cttttaaggg   180
ttttgagaaa ctagacactg caacttatta gtatcggcga cgtttgtttg gggcaaattc   240
agctccagga gctgcacggg ttgaatgcag gaggnagttc caccaattgc cccaattccc   300
ntccatttgg tangcaancc ttgacc                                         326

<210> SEQ ID NO 62
<211> LENGTH: 156
<212> TYPE: DNA
<213> ORGANISM: Homo sapiens

<400> SEQUENCE: 62
ggccgtcgta gcgtcgccgt tactccgagg agataccagt cggtagaggg gtgcaaaaat    60
gcagagtaat aaaactttta acttggagaa gcaaaaccat actccaagaa agcatcatca   120
acatcaccac cagcagcagc accaccagca gcaaca                              156
```

<210> SEQ ID NO 63
<211> LENGTH: 2690
<212> TYPE: DNA
<213> ORGANISM: Homo sapiens

<400> SEQUENCE: 63

| | | | | | |
|---|---|---|---|---|---|
| gctcttttct | cgggacggga | gaggccgtgt | agcgtcgccg | ttactccgag | gagataccag | 60 |
| tcggtagagg | agaagtcgag | gttagaggga | actgggaggc | actttgctgt | ctgcaatcga | 120 |
| agttgagggt | gcaaaaatgc | agagtaataa | aacttttaac | ttggagaagc | aaaaccatac | 180 |
| tccaagaaag | catcatcaac | atcaccacca | gcagcagcac | caccagcagc | aacagcagca | 240 |
| gccgccacca | ccgccaatac | ctgcaaatgg | gcaacaggcc | agcagccaaa | atgaaggctt | 300 |
| gactattgac | ctgaagaatt | ttagaaaacc | aggagagaag | accttcaccc | aacgaagccg | 360 |
| tcttttgtg | ggaaatcttc | ctcccgacat | cactgaggaa | gaaatgagga | aactatttga | 420 |
| gaaatatgga | aaggcaggcg | aagtcttcat | tcataaggat | aaaggatttg | gctttatccg | 480 |
| cttggaaacc | cgaaccctag | cggagattgc | caaagtggag | ctggacaata | tgccactccg | 540 |
| tggaaagcag | ctgcgtgtgc | gctttgcctg | ccatagtgca | tcccttacag | ttcgaaacct | 600 |
| tcctcagtat | gtgtccaacg | aactgctgga | agaagccttt | tctgtgtttg | ccaggtaga | 660 |
| gagggctgta | gtcattgtgg | atgatcgagg | aaggcccttca | ggaaaaggca | ttgttgagtt | 720 |
| ctcagggaag | ccagctgctc | ggaaagctct | ggacagatgc | agtgaaggct | ccttcctgct | 780 |
| aaccacattt | cctcgtcctg | tgactgtgga | gcccatggac | cagttagatg | atgaagaggg | 840 |
| acttccagag | aagctggtta | taaaaaacca | gcaatttcac | aaggaacgag | agcagccacc | 900 |
| cagatttgca | cagcctggct | cctttgagta | tgaatatgcc | atgcgctgga | aggcactcat | 960 |
| tgagatggag | aagcagcagc | aggaccaagt | ggaccgcaac | atcaaggagg | ctcgtgagaa | 1020 |
| gctggagatg | gagatggaag | ctgcacgcca | tgagcaccag | gtcatgctaa | tgagacagga | 1080 |
| tttgatgagg | cgccaagaag | aacttcggag | gatggaagag | ctgcacaacc | aagaggtgca | 1140 |
| aaaacgaaag | caactggagc | tcaggcagga | ggaagagcgc | aggcgccgtg | aagaagagat | 1200 |
| gcggcggcac | gaagaagaaa | tgatgcggcg | acacgaggaa | ggattcaagg | gaaccttccc | 1260 |
| tgatgcgaga | gagcaggaga | ttcggatggg | tcagatggct | atgggaggtg | ctatgggcat | 1320 |
| aaacaacaga | ggtgccatgc | ccctgctcc | tgtgccagct | ggtaccccag | ctcctccagg | 1380 |
| acctgccact | atgatgccgg | atggaacttt | gggattgacc | ccaccaacaa | ctgaacgctt | 1440 |
| tggtcaggct | gctacaatgg | aaggaattgg | ggcaattggt | ggaactcctc | ctgcattcaa | 1500 |
| ccgtgcagct | cctggagctg | aatttgcccc | aaacaaacgt | cgccgatact | aataagttgc | 1560 |
| agtgtctagt | ttctcaaaac | ccttaaaaga | aggaccctt | ttggactagc | cagaattcta | 1620 |
| ccctggaaaa | gtgttaggga | ttccttccaa | tagttagatc | taccctgcct | gtactactct | 1680 |
| aagggattcc | ttccaatagt | tagatctacc | ctgcctgtac | tactctaggg | agtatgctgg | 1740 |
| aggcagaggg | caagggaggg | gtggtattaa | acaatgcaat | tctgtgtggt | atattgttta | 1800 |
| atcagttctg | tgtggtgcat | tcctgaagtc | tctaatgtga | ctgttgaggg | cctggggaaa | 1860 |
| ccatggcaaa | gtggatccag | ttagagccca | ttaatcttga | tcattccggt | ttttttttt | 1920 |
| tttgtccatc | ttgttctcatt | tgcttgcccc | gccccgaga | cggagtctta | ctctgtcgcc | 1980 |
| caggctggag | tgtagtggca | tgatctcggc | tcactgcaat | ctctgcctcc | cgggttcaag | 2040 |
| cttgtccagg | ttgatcttga | actcctgacc | tcgtgatcta | cccacctcgg | tctcccaaaa | 2100 |
| tgctgggatt | acaggggtga | gccaccgtgc | ccaacctcac | ttgcttctta | tccttacact | 2160 |

```
cccccagccc cagagaaact gccacataca ccacaaaaac caaacatgcc ccaatgacct    2220 tagcccatt gctccattca ctcccaggtg agaattcagg caaacgtcca caaaggtcac    2280
aggcagcgta catacggttc tgttataccc catatattac cccttcatgt cctaaagaag    2340 acatttctc ttagagattt tcattttagt gtatctttaa aaaaaaaatc ttgtgttaac    2400
ttgcctccat ctttttcttg gggtgaggga caccagggaa tgacccttt gtgtctatga    2460 tgttgctgtt cacagctttt cttgataggc ctagtacaat cttgggaaca gggttactgt    2520
atactgaagg tctgacagta gctcttagac tcgcctatct taggtagtca tgctgtgcat    2580 ttttttttc attggtgtac tgtgtttgat ttgtctcata tatttggagt ttttctgaaa    2640
aatggagcag taatgcagca tcaacctatt aaaatacttt taagcctttt                2690

<210> SEQ ID NO 64
<211> LENGTH: 367
<212> TYPE: DNA
<213> ORGANISM: Homo sapiens
<220> FEATURE:
<221> NAME/KEY: misc_feature
<222> LOCATION: 41, 71, 341, 367
<223> OTHER INFORMATION: n = A,T,C or G

<400> SEQUENCE: 64
attttagtat ttcctgtttt ggtttatttg catcttagaa nagcataatg acattgtttg     60
atgaagccta nttatgctgg actgttttga cctggtttaa cccttctgat aggtagttgt    120
ggatgctggg gatgagaact gaataatctt tgcctggagt gacactacac tctagaattt    180
ccactttgga gaatactcag ttccaacttg tgattcctga tagaacagac tttacttttc    240
tagcccagca ttgatctaga agcagaggaa tcccagcgcc ttttaaaagt tgttatgtgg    300
gttttctttt aaaaagctcc tgttttggaa agtagaatt natgggtaca acgtatgttc    360 attattn                                                              367

<210> SEQ ID NO 65
<211> LENGTH: 1487
<212> TYPE: DNA
<213> ORGANISM: Homo sapiens

<400> SEQUENCE: 65
ctggtctaac agacccgcga gaacgaagga cgcttgcctt tttccggtcg gggaaggggg     60
aagaaggtaa cttccggtga cggggttgca tcacttcctc tcaagcttgg cgtttgtttg    120
gtggggttac acgcgggttc aacatgcgta tcgaaaagtg ttatttctgt tcggggccca    180
tctatcctgg cacggcatg atgttcgtcc gcaacgattg caaggtgttc agattttgca    240
aatctaaatg tcataaaaac tttaaaaaga agcgcaatcc tcgcaaagtt aggtggacca    300
aagcattccg gaaagcagct ggtaaagagc ttacagtgga taattcattt gaatttgaaa    360
aacgtagaaa tgaacctatc aaataccagc gagagctatg gaataaaact attgatgcga    420
tgaagagagt tgaagaaatc aaacagaagc gccaagctaa atttataatg aacagattga    480
agaaaaataa agagctacag aaagttcagg atatcaaaga agtcaagcaa acatccatc    540 ttatccgagc ccctcttgca ggcaaaggga acagttggga agagaaatg gtacagcagt    600 tacaagagga tgtggacatg aagatgctc cttaaaaatc tctgtaacca tttcttttat    660
gtacatttga aaatgccctt tggatacttg gaactgctaa attatttat tttttacata    720 aggtcactta aatgaaaagc gattaaaaga catctttcct gcattgccat ctacataata    780
```

-continued

| | |
|---|---|
| tcagatatta cggatgttag attgcatctc agtgttaaat ctttactgat agatgtactt | 840 |
| aagtaaatca tgaaaattct acttgtaact atagaagtga attgtggacg taaaatggtt | 900 |
| gtgctatttg gataatggca ctaggcagca tttgtatagt aactaatggc aaaaattcat | 960 |
| ggctagtgat gtataaaata aaatattctt tgcagtaaaa tattcccttt gttaatgtta | 1020 |
| tagaagggg gatacaaaaa ggaactaaca atttgtatgg cagtgtcaga tattttatt | 1080 |
| ttagtatttc ctgttttggt ttatttgcat cttagaagag cataatgaca ttgtttgatg | 1140 |
| aagcctaatt atgctggact gttttgacct ggtttaaccc ttctgatagg tagttgtgga | 1200 |
| tgctggggat gagaactgaa taatcttgc ctggagtgac actacactct agaatttcca | 1260 |
| ctttggagaa tactcagttc caacttgtga ttcctgatag aacagacttt acttttctag | 1320 |
| cccagcattg atctagaagc agaggaatcc cagcgccttt taaagttgt tatgtggttt | 1380 |
| tcttttaaaa agctcctgtt tttggaaagt agaatttatg ggtacaacgt atgttcatta | 1440 |
| tttgtacata aaataaaacc atttaaaaag taaaaaaaaa aaaaaa | 1487 |

<210> SEQ ID NO 66
<211> LENGTH: 366
<212> TYPE: DNA
<213> ORGANISM: Homo sapiens

<400> SEQUENCE: 66

| | |
|---|---|
| ccgcctccag caaaacaacg atgttcactc ctccaaatat ccaaattgaa gatctaccaa | 60 |
| aacaaaaaca aaaacaaaag cccacagaga aataaaaagg aacaaaaatc acattctaat | 120 |
| gggggggtc agtgcattta gcagtcttcg ctgtgctgtc taaccatcct tcagctgact | 180 |
| ttcaaaaaaa aaaacaccct aagctcatca aaatatacat tttccatttg cttttttaaa | 240 |
| ttaaaaataa ttattaaaaa aaggaaaact ttaaggaatt cacaatcaat tgcctgactc | 300 |
| attttgatgt catgtacagc atatggaggt caggaaggct atttgcagca catgtgatta | 360 |
| ggggct | 366 |

<210> SEQ ID NO 67
<211> LENGTH: 410
<212> TYPE: DNA
<213> ORGANISM: Homo sapiens
<220> FEATURE:
<221> NAME/KEY: misc_feature
<222> LOCATION: 389
<223> OTHER INFORMATION: n = A,T,C or G

<400> SEQUENCE: 67

| | |
|---|---|
| aaagatgtac tcattctggg aggtggagac ggaggcatat tgtgtgaaat agtcaaacta | 60 |
| aaaccaaaga tggtcactat ggtagagatt gaccaaatgg tgattgatgg gtgtaagaaa | 120 |
| tacatgcgaa aaacgtgtgg cgatgtctta gacaatctta aggagactg ctatcaggtt | 180 |
| ctaatagaag actgtatccc ggtacctgaa gaggtacgcc aaagaaggga gagaatttga | 240 |
| ttatgtgatt aatgatttga cagctgttcc aatctccacc gtctccagaa gaagattcca | 300 |
| catgggagtt tctcagactg attcttgacc tctcaatgaa agtgttgaaa caggatgggg | 360 |
| aaatatttta cacaggggga actgtgtcna tctgacagaa gcactgtcgc | 410 |

<210> SEQ ID NO 68
<211> LENGTH: 1612
<212> TYPE: DNA
<213> ORGANISM: Homo sapiens

<400> SEQUENCE: 68

```
tagtgaggcg aggccctgtg ccatgcctgg ggcagcagca cggcacagca cgctcgactt    60
catgctcggc gccaaagctg atggtgagac cattctaaaa ggcctccagt ccattttcca   120
ggagcagggg atggcggagt cggtgcacac ctggcaggac catggctatt tagcaaccta   180
cacaaacaag aacggcagct ttgccaattt gagaatttac ccacatggat tggtgttgct   240
ggaccttcag agttatgatg gtgatgcgca aggcaaagaa gagatcgaca gtattttgaa   300
caaagtagag gaaagaatga agaattgag tcaggacagt actgggcggg tgaaacgatt   360
accacccata gtgcgaggag gagccatcga cagatactgg cccaccgccg acgggcgcct   420
ggttgaatat gacatagatg aagtggtata tgacgaagat tcaccttatc aaaatataaa   480
aattctacac tcgaagcagt ttggaaatat tctcatcctt agtggggatg ttaatttggc   540
agagagtgat ttggcatata cccgggccat catgggcagt ggcaaagaag attacactgg   600
caaagatgta ctcattctgg gaggtggaga cggaggcata ttgtgtgaaa tagtcaaact   660
aaaaccaaag atggtcacta tggtagagat tgaccaaatg gtgattgatg ggtgtaagaa   720
atacatgcga aaaacgtgtg gcgatgtctt agacaatctt aaaggagact gctatcaggt   780
tctaatagaa gactgtatcc cggtactgaa gaggtacgcc aaagaaggga gagaatttga   840
ttatgtgatt aatgatttga cagctgttcc aatctccacg tctccagaag aagattccac   900
atgggagttt ctcagactga ttcttgacct ctcaatgaaa gtgttgaaac aggatgggaa   960
atattttaca caggggaact gtgtcaatct gacagaagca ctgtcgctct atgaagaaca  1020
gctgggcgc ctgtattgtc ctgtggaatt ttcaaaggag atcgtctgtg tcccttcata  1080
cttggaattg tgggtatttt acactgtttg gaagaaagct aaaccctgaa gatcagtagc  1140
ccctaatcac atgtgctgca aatagccttc ctgacctcca tatgctgtac atgacatcaa  1200
aatgagtcag gcaattgatt gtgaattcct taaagttttc ctttttttaa taattatttt  1260
taatttaaaa aagcaaatgg aaaatgtata ttttgatgag cttagggtgt ttttttttg  1320
aaagtcagct gaaggatggt tagacagcac agcgaagact gctaaatgca ctgacccccc  1380
ccattagaat gtgattttg ttccttttta tttctctgtg ggcttttgtt tttgtttttg  1440
ttttggtaga tcttcaattt ggatatttgg aggagtgaac atcgttgttt tgctggaggg  1500
aagatcttga tggtgtttct ttccccaaaa attgacttag atattaaaat ttggtgctta  1560
taagagagag ttaaaaaaaa ataggattgc ttcaattaaa attacaaaag ag          1612
```

<210> SEQ ID NO 69
<211> LENGTH: 267
<212> TYPE: DNA
<213> ORGANISM: Homo sapiens
<220> FEATURE:
<221> NAME/KEY: misc_feature
<222> LOCATION: 239, 243, 244
<223> OTHER INFORMATION: n = A,T,C or G

<400> SEQUENCE: 69

```
tttttttttt tttttttttt tttggggatt caaatccttt attgacggtg gtggtgaggc    60
cagccctccc tggcaggctc tgggtgcatc tccctagtat gttctgctgg gagccgggca   120
ccggggcagg cgtaggggca gcgagtggcc taggactcgg actcaaacat cttcttccgg   180
ccctccatgc cagacttctc ctcgatgttc ttcctccagt cacccacgtc tcgcaggtnc   240
cgnnccttct ctgtggtcct ccttctt                                      267
```

<210> SEQ ID NO 70

```
<211> LENGTH: 596
<212> TYPE: DNA
<213> ORGANISM: Homo sapiens
<220> FEATURE:
<221> NAME/KEY: misc_feature
<222> LOCATION: 54, 56, 127, 130, 151, 154, 164, 421, 449, 474, 487,
      516, 530, 540, 546, 562, 573
<223> OTHER INFORMATION: n = A,T,C or G

<400> SEQUENCE: 70
tcaggacctc aggatgggag atgaggagaa gcggaacagg gccatcacgg cgcnanggca     60
gcacctgaag agtgtgatgc tgcagatagc ggccacggag ctggagaagg aggagagccg    120
ccgtgangan gaagcagaac tacctggcgg nacntgcccg cgcntgcata tcccgggctc    180
catgtctgaa gtgcaggagc tctcaaacag ctgcacgcca agatcgatgc ggctgaagag    240
gagaagtacg acatggaggt gagggtgcag aagaccagca aggagctgga ggacatgaac    300
cagaagctat ttgatctgcg gggcaagttc aagcggcccc cactgcggag ggtgcgcatg    360
tcgaccgatg ccatgctcaa ggccctgctg cttcgaagca caaggtgttc atggacctga    420
nggcaacctg aagcaggttc aagaaggang acacagagaa ggagccggga cctncgagac    480
gttggtnact tgaagaagaa catcgaggga gaagtntggc atgaaggccn gaagaagatn    540
ttttanttcg agtctagcca tngctgccct aanctgcccg ttccggttcc agcaga        596

<210> SEQ ID NO 71
<211> LENGTH: 701
<212> TYPE: DNA
<213> ORGANISM: Homo sapiens

<400> SEQUENCE: 71
ctaggctcca agctcaggac ctcaggatgg gagatgagga gaagcggaac agggccatca     60
cggcccgcag gcagcacctg aagagcgtga tgctgcagat agcggccacg gagctggaga    120
aggaggagag ccgccgtgag gcagagaagc agaactacct ggcggagcac tgcccgccgc    180
tgcatatccc gggctccatg tctgaagtgc aggagctctg caaacagctg cacgccaaga    240
tcgatgcggc tgaagaggag aagtacgaca tggaggtgag ggtgcagaag accagcaagg    300
agctggagga catgaaccag aagctatttg atctgcgggg caagttcaag cggcccccac    360
tgcggagggt gcgcatgtcg ccgatgcca tgctcaaggc cctgctgggc tcgaagcaca    420
aggtgtgcat ggacctgagg gccaacctga agcaggtcaa gaaggaggac acagagaagg    480
agcgggacct gcgagacgtg ggtgactgga ggaagaacat cgaggagaag tctggcatgg    540
agggccggaa gaagatgttt gagtccgagt cctaggccac tcgctgcccc tacgcctgcc    600
ccggtgcccg gctcccagca gaacatacta gggagatgca cccagagcct gccagggagg    660
gctggcctca ccaccaccgt caataaagga tttgaatccc c                       701

<210> SEQ ID NO 72
<211> LENGTH: 282
<212> TYPE: DNA
<213> ORGANISM: Homo sapiens

<400> SEQUENCE: 72
tttttttttt tttggatttc acgaactcac atttattcac agacagacaa agggacaagg     60
acagaccttt gctcactggg gaccccagg gtctggcagt tccaaagagg tgatggtgtc     120
cagtgtgtga acggggggac agggaggcgg ggcgtccca ccagtctcca tccctctggc    180
caactgtccg ccgccttttt ttccaagtcg tcctgcctta agacacatgt tggggtgagc    240
```
ggttcctaac cagcatcagg ggttctgggg gcgggcgatg gg                         282

<210> SEQ ID NO 73
<211> LENGTH: 443
<212> TYPE: DNA
<213> ORGANISM: Homo sapiens
<220> FEATURE:
<221> NAME/KEY: misc_feature
<222> LOCATION: 419
<223> OTHER INFORMATION: n = A,T,C or G

<400> SEQUENCE: 73
agacagcaaa ctcacctgcg cgggctgggg ggcctggctc ctgaccttcg ccgccctgcc     60
ctccgccgct ccgcctgagc tccccggttt gcagaatgga ggagggaagt tgaaggagcc    120
acctcctctg tctacccacc cgtcccccttc acgcccttga cactaaggag tgggggggccc   180 tggactgccc cttcctcccc catcgcccgc cccagaaacc cctgatgctg gttaggaacc    240 gctcaccccca acatgtgtct taaggcagga cgacttggaa aaaaaggcgg cggacagttg    300
gccagaggga tggagactgg tggggacgcc ccgcctccct gtccccgtt tcacacactg     360 gacaccatca cctcttttgga actgccagac cctgggggtc ccagtgagca aggtctgnt    420 ccttgtcctt tgtctgtctg tga                                             443

<210> SEQ ID NO 74
<211> LENGTH: 310
<212> TYPE: DNA
<213> ORGANISM: Homo sapiens

<400> SEQUENCE: 74
ctaacgtgga ctagagaaac ttggcctgct gtgagtgggc cttctgttca acttaccctc     60
caccgctgac cctgtgtgaa gagagatggt gcgttactgc catctaatgg gaaaagagaa    120
aactgcagtt gggaaaagca gctgtcattt aagggtaggg cttttctgaag gatttctgat    180 acagtccaga aagggaaaa tgatgacaca gcagttgcca tcttgaaaaa tgcccttttcc    240 tgcggaaagg gtgttttgaa gtctaataca actatcatca caaggtccct ggactaaggc     300
tggatcgtgt                                                            310

<210> SEQ ID NO 75
<211> LENGTH: 408
<212> TYPE: DNA
<213> ORGANISM: Homo sapiens

<400> SEQUENCE: 75
ggaataatgt ttatttaaag ttacatttca gaggaaacta tcttcaggag ggcatgaagc     60
ctatattggc tactgcaaaa caaccagaag ttttataaaa tatttctgat ttaaattact    120
aaggcactat agataggcac ctatattaca tacaatcttc aaacattttt aaaagttgaa    180
actatgtatt agttgatatc taaaatatta agcccctga caaactgaac ggctaagaac    240
ttgacaaaat gagatgcctg tttcaatgat tcttgttgcc atgcatatta atttaaaatt    300 acaatttttgg aggatttcta aattacacga tcccagcctt taagttccag ggggacccctt   360 gtgattggat aggtttggaa ttaggacttt tcaaaaacac ccccctttt                408

<210> SEQ ID NO 76
<211> LENGTH: 439
<212> TYPE: DNA
<213> ORGANISM: Homo sapiens

<400> SEQUENCE: 76

```
aaagacgtac atttatattc ttcagccatg acaaaatcac aaatattttg aaattttcc    60 acattctctt tttcaacgta caccaaagaa ttttaataca gttcaatctt taccttcgtt   120
tacttgatac ccagtcctta aatttaagtc caggtagttc catccaactt ccaaagctga   180
ttgtcaacat ggagccttcc atattatgcc aagccccacc aggtggacct ttaccaagaa   240
ctacgtgagg gatataatga tgttgctcta atttccaatg caaaacggat ggataatcat   300
acccaaagtc agcatctgga tgaagaagtg tatcgaaaag tactgcaact ggattggatg   360
atcggccctc aaggcgctca gacaagtatt ctaagtcctg atcaacaatg aaagatgtc    420 ttgcttcttc taatttact                                                439

<210> SEQ ID NO 77
<211> LENGTH: 427
<212> TYPE: DNA
<213> ORGANISM: Homo sapiens

<400> SEQUENCE: 77
agaaactata gtgacactga aactgaagga gagattttta attccttagt gcaatacttt    60
ggtgacaact tggggcgaaa agttaaagcg atgccattag ttgaagaaac ttctttactg   120
gaagattcgt cagtgacttt tcctgtggta ataataggaa atggaccctc aggaatatgc   180
ctttcttata tgttatcagg ctacagaccg tatttatcat cagaagcaat acacccaaat   240
acaatcttaa atagtaaatt agaagaagca agacatcttt ccattgttga tcaggactta   300
gaatacttgt ctgagggcct tgagggccga tcatccaatc cagttgcagt acttttcgat   360
acacttcttc atccagatgc tgactttggg tatgattatc catccgtttt gcattggaaa   420
ttagagc                                                             427

<210> SEQ ID NO 78
<211> LENGTH: 4199
<212> TYPE: DNA
<213> ORGANISM: Homo sapiens

<400> SEQUENCE: 78
tggggcgggc tgatgagcac ctggattttc acccggcgtg ctggtaattc ctacacttgt    60
gggtgtttga gagacatgaa gaggggagga tgacctcttc ccggaagcgg gacttccata   120
aaagaagcgt ggtgggcggg tcccgggcac ctgtggtttg gtgagtcctc caggtaactg   180
tgatgcgggg gtcagcggga gaggcacccg gaagctcccg cgtctgcac cccggcagcg    240 cgaggaaatg cccaaagaaa ctatagtgac actgaaactg aaggagagat ttttaattcc   300
ttagtgcaat actttggtga caacttgggg cgaaaagtta aagcgatgcc attagttgaa   360
gaaacttctt tattggaaga ttcgtcagtg acttttcctg tggtaataat aggaaatgga   420
ccctcaggaa tatgccttt ctatatgtta tcaggctaca gaccgtattt atcatcagaa   480
gcaatacacc caaatacaat cttaaatagt aaattagaag aagcaagaca tctttccatt   540
gttgatcagg acttagaata cttgtctgag ggccttgagg ccgatcatc caatccagtt   600 gcagtacttt tcgatacact tcttcatcca gatgctgact ttgggtatga ttatccatcc   660
gttttgcatt ggaaattaga gcaacatcat tatatccctc acgtagttct ggtaaaggt    720 ccacctggtg gggcttggca taatatggaa ggctccatgt tgacaatcag ctttggaagt   780
tggatggaac tacctggact taaatttaag gactgggtat caagtaaacg aaggagccta   840 aaagggggatc gagttatgcc agaggaaata gctcgctact ataaacatta tgtaaaagtc   900
```

-continued

```
atgggtcttc agaagaattt cagagagaat acttacataa cttccgtatc aagactctac     960
agagatcaag atgatgatga tattcaagac agagatattt caacaaagca tttacagata    1020
gagaagtcaa actttatcaa gagaaactgg gaaattaggg gttatcagcg aatagctgat    1080
ggttctcatg ttcccttctg cctctttgct gagaatgtag cgctggcaac tggaacgctg    1140
gattctcctg cccatctgga aattgaaggg gaagattttc cttttgtgtt tcattcaatg    1200
cctgaatttg gagctgctat aaacaaagga agttgcgtg gcaaagtgga tccagtgtta     1260
attgtaggtt ctgggcttac tgccgctgac gcagtactgt gtgcttacaa cagtaatatc    1320
cctgtgattc atgtgtttcg cagacgagta actgatccaa gcttaatttt caaacagctt    1380
cccaaaaagc tgtatcctga atatcataaa gtctatcata tgatgtgtac tcagtcatat    1440
tctgtagact caaatctttt atctgattat accagctttc ccgagcaccg tgtgctttcc    1500
tttaagtcgg acatgaaatg tgttctccaa agcgtttctg gattgaagaa aatatttaag    1560
ctgtctgcag cagtagtatt gataggttct catcctaatc tgtctttttct gaaggatcaa   1620
gggtgttacc taggccataa gtcaagccag ccaatcacat gtaagggtaa tcctgtggaa    1680
atagatacat atacctatga gtgtattaaa gaagccaacc tttttgcatt gggtcctttg    1740
gttggagaca attttgttcg atttttaaag ggaggggcgc tgggtgttac acgctgttta    1800
gctacaagac agaagaaaaa gcatttgttt gttgaaagag gaggaggaga tgggatagct    1860
taaagcaagt ttacaagtaa ttaaaatgga cagtttgcca ttaaagatt ttaatagtgg     1920
ttttgcagtg tactggcttg aattttctgg acttgagtta actgaaggag agcctcaaac    1980
tatagtaact tcattttaa aagttactag aatttggtat cctgatttat attgcagtgt     2040
ttcaaaggtg tcactgtcag acaaatagaa acactgccaa cttggtgtaa cttaagcttt    2100
catttaacta aaacattctt ttcttgcaaa acttattttt catgatcatt tttggttatt    2160
tattatactt gattccaaaa tagtacagcc ttgaatctat aaaactgtgc agtcattatg    2220
ccagaaatta tcttaaatat ataatgggtc accttgctgt tcaagggtg gtgcaaggtc     2280
ctgcagcatc ttcatctgt agcttgttag aaatgtaaac tctcaggccc acaacttac     2340
ttcctgcatt ttaacaagat ccccaaggga tatgtatgct cataaaaatt tgagacactg    2400
gtttaaatga aaatggatat aaggtatgta taactggggg tggggtgagg gtaggaggca    2460
tttacaactc agatttttatt tattttgaaa ttatcaattg tataaatcta atttattacc   2520
aaataggggtc ttttaaaaaa tattttatc gttgaaaccct tgacaggtac ttcatattct   2580
tctaataatt taaacagtcc aataatgtgg tatacactt gacatccaag aactcaccaa    2640
gatgttttc agagatttat tctcgattta actatcatag catttaatga atctgatttg    2700
tagttcaata aattgtgggt tgaactactt atccctgtgt gaacattgaa ttactttctg    2760
tcactgaaac tgaggtattt gggtgtggta agtacttcga aaattgtaat actgtttggg   2820
cattgtctaa attattaaag gttaaaatag aaaataaagt cagaattttt cttttccatt   2880
ccaaaggtgt acttagagat ctctattagt attcattcga gatgacatag cagctcatat   2940
catggttgtt tattggattt atctgttcta attatataag tgtgtttact gtctgtgttt   3000
tcacacaaac tgctagaatt tttaatgtta agacgaaaac atctgaagtt ctccatggca   3060
aattgaattt ttcagtcatt ttcttttctt ttttggtac aattacttca tctgaatgt     3120
cttcattgaa ctcgttattc tattttttctt agaattaaaa gtggattaat gtgggttttt  3180
ctgttcattt tattgcagta ttaaatgctt aagcttatta ggaccataat tcactttaaa   3240
tataattgta tagaatatat ttgcgtcgat caaataattg cttcagatga attcttagac   3300
```

```
tcttgataat atcacaccta atttaacttg attttacaag ctgtacaatc cagttttagt      3360
tttctattgt gataataact ttttcaaac cagtttcaca tcttaatgaa ataacattct       3420
ctgactgcac ttgcttcagt actctcttgc ctgcctgttt ttgacctctg catgagttgg     3480
attagatgtt tttcttactg tcacttctaa atagaaaatg acagtgttat aaaaaaggga     3540
aggataaaac ctttgacatc cccttgtgtc tcaaaagtcc acagttattc aaacaatggc     3600 ttttttttgtg atgagagtat tgttaaaaa aaaaaaaaga cttcaagaaa aataaaagtt    3660
cagtggagct gcaaataaat ctggtgaata atttcatctt tggtaatctc ccatttcctg     3720
agttcttcct caatccaagc tgtcctgtgt agtatataac atttgggcat tttctctgat    3780
atactatact ctcatgttct ataaatttct gtcccgtaat ctaacactt tacatttttt     3840 ctttgctatc agctatagct attcatggaa gggaagaatc actaaatact tgtctagtta    3900
tagcatgatg tgagcatctc ctccttatcc ctcgatgcct ggcttggtgt ctggcaaaca    3960
gtccataatt agcagatgtt gaaagaccgt ttacaaagca gaatttgggg atttaaagtg   4020
caatgataca acaaaaagat ttaattacag cttccagtgt tttgactatg tgaaccatat    4080
ccaactactt ttttgaaaat ctagttctat gtaatatatt tctgtggcat caaattttag    4140
ttgattgtat tagtcaatag gaagtggtgg aaaatttcta aataaattca actattaaa     4199
```

<210> SEQ ID NO 79
<211> LENGTH: 541
<212> TYPE: DNA
<213> ORGANISM: Homo sapiens

<400> SEQUENCE: 79

```
ttttgagagg ctagtaacat cagttttatt gggttggggt ggcaacatag cctggctggg       60
ggtggggctg gcctcacagg ttgttgagtt ccagcagggt ctggtccaag gtctggtgaa      120
tctcgacgtt ctcctccttg gcactggcaa ggtctcttct aggtcatcga tggttttctc      180
caactttgcc acagacctct cggcaaactc tgctcgggtc tcagcctcct tcagcttctc      240
ctccaacagt ttgatctcct cttcatattt atcttctttg gtggaatact tgtccgcctg      300
ggcctccagg gatttcaagt tgttggtaac aattttcagc tcctcctcta ggtccccaca     360
tttactcctc ctctgaggcc atcagggact tgagggcctg gtccatggtt cgaagttcct    420
cctccagctg tctggctcgg ctctcggcca cctcagccct ctcctccgag cgctccagct    480
ctccttccag gatcaccagc ttcctggcca cctcttcata tttgcggtct gaatcctcag    540
c                                                                        541
```

<210> SEQ ID NO 80
<211> LENGTH: 368
<212> TYPE: DNA
<213> ORGANISM: Homo sapiens

<400> SEQUENCE: 80

```
ccgaccccccc ggcgcggccg tgcttctgcc cctacaaggt ttgggccgag gtggggagg       60 gtcctggttg ccggccccgc cgtcacctcc ccgccttta ggcaccgcgt ggccgggacg       120
tcccagtcgc ctccgtcctc ctcgcctgcc accggtgcac ccagtccgct cacccagccc     180
agtccgtccg gtcctcaccg cctgccggcc ggcccacccc ccaccgcagc catggacgcc     240
atcaagaaga agatgcagat gctgaagctg gacaaggaga acgccatcga ccgcgccgag    300
caggcgaagc cgacaagaag caagctgagg accgctgcaa cagctggagg aggagcagca    360
```

<210> SEQ ID NO 81
<211> LENGTH: 1044
<212> TYPE: DNA
<213> ORGANISM: Homo sapiens

<400> SEQUENCE: 81

```
ggccctcc                                                                  368 tgctgctctc ctcccgctcc gtcctcctcg cctgccaccg gtgcacccag tccgctcacc          60
cagcccagtc cgtccggtcc tcaccgcctg ccggccggcc cacccccac cgcaggccat          120
ggacgccatc aagaagaaga tgcagatgct gaagctggaa aaggagaacg ccatcgaccg         180
cgccgagcag gccgaagccg acaagaagca agctgaggac cgctgcaagc agctggagga         240
ggagcagcag gccctccaga agaagctgaa ggggacagag gatgaggtgg aaaagtattc         300
tgaatccgtg aaggaggccc aggagaaact ggagcaggcc gagaagaagg ccactgatgc         360
tgaggcagat gtggcctccc tgaaccgccg cattcagctg gttgaggagg agctggaccg         420
ggcccaggag cgcctggcta cagccctgca gaagctggag gaggccgaga aggcggctga         480
tgagagcgag agaggaatga aggtcatcga aaaccgggcc atgaaggatg aggagaagat         540
ggaactgcag gagatgcagc tgaaggaggc caagcacatc gctgaggatt cagaccgcaa         600
atatgaagag gtggccagga agctggtgat cctggaagga gagctggagc gctcggagga         660
gagggctgag gtggccgaga gccgagccag acagctggag gaggaacttc gaaccatgga         720
ccaggccctc aagtccctga tggcctcaga ggaggagtat tccaccaaag aagataaata         780
tgaagaggag atcaaactgt ggaggagaa gctgaaggag gctgagaccc gagcagagtt         840
tgccgagagg tctgtggcaa agttggagaa aaccatcgat gacctagaag agaccttggc         900
cagtgccaag gaggagaacg tcgagattca ccagaccttg gaccagaccc tgctggaact         960
caacaacctg tgagggccag ccccacccc agccaggcta tggttgccac cccaacccaa        1020
taaaactgat gttactagcc tctc                                              1044
```

<210> SEQ ID NO 82
<211> LENGTH: 447
<212> TYPE: DNA
<213> ORGANISM: Homo sapiens

<400> SEQUENCE: 82

```
taggttggac tcttcacaga aattggggcc atgtcctgct tcatccctcg acaatccatc          60
ccttcagaga tggagtttga atctaactcc aacccaccat gttacaagac aatggatgag         120
gatattgtga ttcagcagga cgatgagatc cgcttaaaga ttgtggggac ccgtgtggac         180
aagaatgaca ttttttgctat tggctccctg atggacgatt acttgggact tgtaagctga         240
gcctggtggc ctcctaccct tggtcctact ctaggaagtg tgattgtcac acttatcatg         300
ttgtccagag gtccagtctg gctgctgttg tggaggcaag gaaggcaact catcccagaa         360
ggcatctggt gcttcttgta gcttaactac tgcctcctca ttttttcagta tgtgttctaa         420
gtataaaaag tccttggttc tcaaaaa                                             447
```

<210> SEQ ID NO 83
<211> LENGTH: 433
<212> TYPE: DNA
<213> ORGANISM: Homo sapiens

<400> SEQUENCE: 83

```
gagaaccaag gactttttat acttagaaca catactgaaa aatgaggagg caggagttaa          60
```

```
gccacaagaa gcaccagatg ccctctggga agaggtgccc tcccggcctc cacaacagca      120
gccagactgg acctctggac aacatgataa gtgtgacaat cacacttcct agagtaggac      180
caagggtagg aggccaccag gctcagctta caagccccaa gtaatcgtcc atcagggagc      240
caatagcaaa aatgtcattc ttgtccacac gggtccccac aatctttaag cggatctcat      300
cgtcctgctg aatcacaata tcctcatcca ttgtcttgta acatggtggg ttggagttag      360
gatcaaactc catctctgaa gggatggaat gtcgagagat gtagccagac atgggcccca      420
tttctggtga gag                                                        433

<210> SEQ ID NO 84
<211> LENGTH: 828
<212> TYPE: DNA
<213> ORGANISM: Homo sapiens

<400> SEQUENCE: 84
tagtcgcacc aagcgcggaa ctggggttgc ggcgtctaag tgtttccggt ggattcccag       60
ggactgtcgg aggtgtggac tctgcctgcc tacctggtct gggaagatgt tctaccatat      120
ctccctagag cacgaaatcc tgctgcaccc gcgctacttc ggccccaact tgctcaacac      180
ggtgaagcag aagctcttca ccgaggtgga ggggacctgc acaggaagt atggctttgt       240 aattgctgtc accaccattg acaatattgg tgctggtgtg atccagccag gccgaggctt      300
tgtcctttat ccagttaagt acaaggccat tgttttccgg ccatttaaag gggaggtcgt      360
ggatgctgtt gtcactcagg tcaacaaggt tggactcttc acagaaattg gcccatgtc      420 ttgcttcatc tctcgacatt ccatcccttc agagatggag tttgatccta actccaaccc      480
accatgttac aagacaatgg atgaggatat tgtgattcag caggacgatg agatccgctt      540
aaagattgtg gggacccgtg tggacaagaa tgacatttt gctattggct ccctgatgga      600
cgattacttg gggcttgtaa gctgagcctg gtggcctcct acccttggtc ctactctagg      660
aagtgtgatt gtcacactta tcatgttgtc cagaggtcca gtctggctgc tgttgtggag      720
gcaaggaagg caactcatcc cagaaggcat ctggtgcttc ttgtagctta actactgcct      780
cctcattttt cagtatgtgt tctaagtata aaaagtcctt tggttctc                   828

<210> SEQ ID NO 85
<211> LENGTH: 336
<212> TYPE: DNA
<213> ORGANISM: Homo sapiens

<400> SEQUENCE: 85
tttgacgaat tcaggagtcc tttattagcc ggcagccgag agacagctag cgctcgaaat       60
tctcttggcc ccgaagaagg agctagattt ctttttatac tttggtttag acaggaggag      120
agggggagtc tagttgaaac aatcttacag aagtaaagta ggcaaaaagt taaaggata       180 aacggttaca ggaaagtaaa cagttccagg tgcagaggct ttaagtctat cctaaggtga      240
tggacgccgg gctttgggcg ttatcaaccg gacacaaacg caggggctct gggtgctatt      300
aaccgggcga attcctggga actgcggata tagctt                                336

<210> SEQ ID NO 86
<211> LENGTH: 391
<212> TYPE: DNA
<213> ORGANISM: Homo sapiens

<400> SEQUENCE: 86
```

```
gaagagccca catgtagccc tgaggtttcc ttcccaggac agctgcaggg tagagatcat      60
tttaagtgct tgtggagttg acatccctat tgactctttc ccagctgata tcagagactt     120
agacccagca ctccttggat tagctctgca gagtgtcttg gttgagagaa taacctcata     180
gtaccaacat gacatgtgac ttggaaagag actagaggcc acacttgata aatcatgggg     240
cacagatatg ttcccaccca acaaatgtga taagtgattg tgcagccaga gccagccttc     300
cttcaatcaa ggtttccagg cagagcaaat accctagaga ttctctgtga tataggaaat     360
ttggatcaag gaagctaaaa gaattacagg g                                    391

<210> SEQ ID NO 87
<211> LENGTH: 440
<212> TYPE: DNA
<213> ORGANISM: Homo sapiens

<400> SEQUENCE: 87
gcattattaa cacatttatt gaacaactag aacttgacaa ccacttgcca agtagagggg      60
atacagtggt gagcaataat agtgatgata atgaggagca gttttcccta gcaggcagca     120
gttgaaagga atatgggttt aacatccacc aatgaccagg agtggacaga cctatttcca     180
ggagactgag tccatagtgg gattaaaaac atccctgtaa ttcttttagc ttccttgatc     240
caaatttcct atatcacaga gaatctctag ggtatttgct ctgcctggaa accttgattg     300
aaggaaggct ggctctggct gcacaatcac ttatcacatt tgttgggtgg aacatatct     360 gtgccccatg atttatcaag tgtggcctct agtctctttc caagtcacat gtcatgttgg     420
tactatgagg ttattctctc                                                 440

<210> SEQ ID NO 88
<211> LENGTH: 2937
<212> TYPE: DNA
<213> ORGANISM: Homo sapiens

<400> SEQUENCE: 88
acgcgtccgc ttcggaatga gagactcaac cataatagaa agaatggaga actattaacc      60
accattcttc agtgggctgt gattttcaga ggggaatact aagaaatggt tttccatact     120
ggaacccaaa ggtaaagaca ctcaaggaca gacattttg gcagagcata gatgaaaatg      180
gcaagttccc tggcttttcct tctgctcaac tttcatgtct ccctcttctt ggtccagctg     240
ctcactcctt gctcagctca gttttctgtg cttggaccct ctgggcccat cctggccatg     300
gtgggtgaag acgctgatct gccctgtcac ctgttcccga ccatgagtgc agagaccatg     360
gagctgaggt gggtgagttc agcctaagg caggtggtga acgtgtatgc agatggaaag      420
gaagtggaag acaggcagag tgcaccatat cgagggagaa cttcgattct gcgggatggc     480
atcactgcag gaaggctgc tctccgaata cacaacgtca cagcctctga cagtggaaag      540
tacttgtgtt atttccaaga tggtgacttc tacgaaaaag ccctggtgga gctgaaggtt     600
gcagcattgg ttctgatct tcacattgaa gtgaagggtt atgaggatgg agggatccat     660
ctggagtgca ggtccactgg ctggtacccc caacccaaa taaagtggag cgacaccaag      720
ggagagaaca tcccggctgt ggaagcacct gtggttgcag atggagtggg cctgtatgca     780
gtagcagcat ctgtgatcat gagaggcagc tctggtgggg gtgtatcctg catcatcaga     840
aattccctcc tcggcctgga aaagacagcc agcatatcca tcgcagaccc cttcttcagg     900
agcgcccagc cctggatcgc ggccctggca gggaccctgc ctatctcgtt gctgcttctc     960
gcaggagcca gttacttctt gtggagacaa cagaaggaaa aaattgctct gtccagggag    1020
```

| | |
|---|---|
| acagaaagag agcgagagat gaaagaaatg ggatacgctg caacagagca agaaataagc | 1080 |
| ctaagagaga agctccagga ggaactcaag tggaggaaaa tccagtacat ggctcgtgga | 1140 |
| gagaagtctt tggcctatca tgaatggaaa atggccctct tcaaacctgc ggatgtgatt | 1200 |
| ctggatccag acacggcaaa cgccatcctc cttgtttctg aggaccagag gagtgtgcag | 1260 |
| cgtgctgaag agccgcggga tctgccagac aaccctgaga gatttgaatg gcgttactgt | 1320 |
| gtccttggct gtgaaaactt cacatcaggg agacattact gggaggtgga agtgggggac | 1380 |
| agaaaagagt ggcatattgg ggtatgtagt aagaacgtgg agaggaaaaa aggttgggtc | 1440 |
| aaaatgacac cggagaacgg atactggact atgggcctga ctgatgggaa taagtatcgg | 1500 |
| gctctcactg agcccagaac caacctgaaa cttcctgagc ctcctaggaa agtggggatc | 1560 |
| ttcctggact atgagactgg agagatctcg ttctataatg ccacagatgg atctcatatc | 1620 |
| tacacctttc cgcacgcctc tttctctgag cctctatatc ctgttttcag aattttgacc | 1680 |
| ttggagccca ctgccctgac catttgccca ataccaaaag aagtagagag ttcccccgat | 1740 |
| cctgacctag tgcctgatca ttccctggag acaccactga ccccgggctt agctaatgaa | 1800 |
| agtggggagc ctcaggctga agtaacatct ctgcttctcc ctgcccaccc tggagctgag | 1860 |
| gtctccccct ctgcaacaac caatcagaac cataagctac aggcacgcac tgaagcactt | 1920 |
| tactgatatt cattccatta ttccatatga cagttgtttt gagtttcgta ccaccttatt | 1980 |
| gtcccctttt acagataagg aaactggggt gcagaaaggt gaattaactt tacaaagtag | 2040 |
| acatgacaag tgaacagcag agctgggatc taaacagcaa taactaacat taacagagaa | 2100 |
| tttaaaatgt tcttagtgct gtgttataag ctttggtgga tgtcactcct ttaatcctca | 2160 |
| caacaccctg tcgggtagtc atattttgca agtatggaag ctgaggcagg gcaacatgaa | 2220 |
| gtaacttaca taattcatac agtaatttgt gcagttggga gatgttcagc cttagtccct | 2280 |
| ggctaattgc ctgttctttt ccagcctgat tttttttccc acaggaagag cccacatgta | 2340 |
| gccctgaggt ttccttccca ggacagctgc agggtagaga tcattttaag tgcttgtgga | 2400 |
| gttgacatcc ctattgactc tttcccagct gatatcagag acttagaccc agcactcctt | 2460 |
| ggattagctc tgcagagtgt cttggttgag agaataacct catagtacca acatgacatg | 2520 |
| tgacttggaa agagactaga ggccacactt gataaatcat ggggcacaga tatgttccca | 2580 |
| cccaacaaat gtgataagtg attgtgcagc cagagccagc cttccttcaa tcaaggtttc | 2640 |
| caggcagagc aaataccctga gattctct gtgatatagg aaatttggat caaggaagct | 2700 |
| aaaagaatta cagggatgtt tttaatccca ctatggactc agtctcctgg aaataggtct | 2760 |
| gtccactcct ggtcattggt ggatgttaaa cccatattcc tttcaactgc tgcctgctag | 2820 |
| ggaaaactgc tcctcattat catcactatt attgctcacc actgtatccc ctctacttgg | 2880 |
| caagtggttg tcaagttcta gttgttcaat aaatgtgtta ataatgaaaa aaaaaaa | 2937 |

<210> SEQ ID NO 89
<211> LENGTH: 490
<212> TYPE: DNA
<213> ORGANISM: Homo sapiens
<220> FEATURE:
<221> NAME/KEY: misc_feature
<222> LOCATION: 108, 110, 111, 188
<223> OTHER INFORMATION: n = A,T,C or G

<400> SEQUENCE: 89

| | |
|---|---|
| tattttaat tttgttaaat tttattatt agggtttgaa ataaattcag tgttcacatt | 60 |

| | |
|---|---:|
| tctataaaga agtaacccag tttcaggaaa ccctgcccca gcagcagntn naagcaacac | 120 |
| tctccctgcc cacatctagt ttgatttcac gccctgatgc ttcaaggtgc ccagaaaagc | 180 |
| ggcacttngt ggaagaggaa atctatgccc ggcccgtgct tggggcccag ggctcagtaa | 240 |
| gctttcgaga aagcagaggg gaagactagc ttactgcaaa aaccttttta aaaatattc | 300 |
| atacacttca gtgagcgcct gttgagacgt tagggaaca agagcttgga aacatcccgt | 360 |
| ccaggccatt gggaggcagc gtcttcctca caccccgtcc ctggatgtcg ggggtgcagg | 420 |
| gggaaggtcc cggctcttcc actggagaaa ggagactcac ctggcttcct agttcatgtt | 480 |
| tgactatttc | 490 |

<210> SEQ ID NO 90
<211> LENGTH: 484
<212> TYPE: DNA
<213> ORGANISM: Homo sapiens

<400> SEQUENCE: 90

| | |
|---|---:|
| attgaagccc acccgtggct gaagcattaa ccggtgggcc ccgtgcctcc ccgccccact | 60 |
| ttcccttctt caaaggacaa agtgccctca aagggaattg aatttttttt tttacacact | 120 |
| taatcttagc ggattacttc agatgttttt aaaaagtata ttaagatgcc ttttcactgt | 180 |
| agtatttaaa tatctgttac aggtttccaa ggtggacttg aacagatggc cttatattac | 240 |
| caaaactttt atattctagt tgtttttgta cttttttgc atacaagccg aacgtttgtg | 300 |
| cttcccgtgc atgcagtcaa agactcagca caggttttag aggaaatagt caaacatgaa | 360 |
| ctaggaagcc aggtgagtct cctttctcca gtggaagagc cgggaccttc cccctgcacc | 420 |
| cccgacatcc agggacgggg tgtgaggaag acgctgcctc ccaatggcct ggacgggatg | 480 |
| tttc | 484 |

<210> SEQ ID NO 91
<211> LENGTH: 501
<212> TYPE: DNA
<213> ORGANISM: Homo sapiens

<400> SEQUENCE: 91

| | |
|---|---:|
| tttacccaaa tttagtcgaa ttttagcaac tttgggatat aaaccagcac agatgacagc | 60 |
| tttaattatc ttctcattat ctgaatttat attagattct ggatctttag gatttctact | 120 |
| gcttacaaat ccagctccaa gaagatgctc agcaaactgt cctttcatgt tatgcagcat | 180 |
| ctgcagtgtg tttgaagaca gaaaatattc ccagcaatag tccttttcgt atctgaaacc | 240 |
| acgtcgccta gcctcttccc agccctcaaa cgcattcaca actgttaagt gatcacttct | 300 |
| agtatccttt gccaattcct ttcttcttgc atctgcaatc ttttcttttc ccagtggaat | 360 |
| gacaaatgga tctttgaaac tgagactagc agcaatagtg agtactgggt ctaagcagca | 420 |
| gaacagtgct ccaaaaagaa tcattttcc aatatgtggc tcaacgggta atcgtgccaa | 480 |
| gtggacttca agaggtgtca a | 501 |

<210> SEQ ID NO 92
<211> LENGTH: 502
<212> TYPE: DNA
<213> ORGANISM: Homo sapiens

<400> SEQUENCE: 92

| | |
|---|---:|
| gagagggagg gggaagagca gaagttagag aaaaaaagcc accggagaag aggaaaaaac | 60 |
| atcggccaac ctagaaacgt ttcattcgt cattccaaga gagagagagg aaagaaaaat | 120 |

| | |
|---|---|
| acaactttca ttctttcttt gcacgttcat aaacattcta catacgtatt ctcttttgtc | 180 |
| tcttcattta taactgctgt gaattgtaca tttctgtgtt ttttggaggt gcagttaaac | 240 |
| ttttaagctt aagtgtgaca ggactgataa atagaagatc aagagtagat ccgactttag | 300 |
| aagcctactt tgtgaccaag gagctcaatt tttgtttga agctttacta atctaccaga | 360 |
| gcattgtaga tattttttt ttacatctat tgtttaaaat agatgattat aacgggcag | 420 |
| agaactttct tttctctgca agaatgttac atattgtata gataaatgag tgacatttca | 480 |
| taccatgtat atatagagat gt | 502 |

<210> SEQ ID NO 93
<211> LENGTH: 425
<212> TYPE: DNA
<213> ORGANISM: Homo sapiens

<400> SEQUENCE: 93

| | |
|---|---|
| tacaagacag agaaatctac tttaatattc acatgtaaaa gttacacatc acaagagatt | 60 |
| ggacagtagc ttagcgtaac atagctatag tgaaaatcat ttttataaaa aaataatcta | 120 |
| gatgcggtca tcagaatttt tggtctgctt aagttaatgt ttgaagatcg acttttatcc | 180 |
| ctgcttgaag gatttgccat tatgcctttt ttttctccc actgttgcct attaattctt | 240 |
| tggaggaagg aaagcagaaa gtgttcattt ccaagagttt gtcctttggt agcaagcaga | 300 |
| gaacattttt ttcatttcca tgatttaaat aatctgtaca gacatgaaac ttagtgacat | 360 |
| taagctttag tgtaaaatga agagtaataa gcaattttt tcactttga taaaacagca | 420 |
| gattc | 425 |

<210> SEQ ID NO 94
<211> LENGTH: 1322
<212> TYPE: DNA
<213> ORGANISM: Homo sapiens

<400> SEQUENCE: 94

| | |
|---|---|
| ggaattccgg gcgcggttgt gagtagtacc gggagtgggg tgatcccggg ctaggggagc | 60 |
| gcggcgcccg atcgggctta gtcggagctc cgaagggagt gactaggaca cccgggtggg | 120 |
| ctactttcct tccggtgctt ttgcttttt tttccttggg gctcgggctg agtgtcgccc | 180 |
| actgagcaaa gattccctcg taaacccag agcgaccctc ccgtcaattg ttgggctcgg | 240 |
| gagtgtcgcg gtgccccgag cgcgccgggc gcggaggcaa agggagcgga gccggccgcg | 300 |
| gacggggccc ggagcttgcc tgcctccctc gctcgcccca gcgggttcgc tcgcgtagag | 360 |
| cgcagggcgc gcgcgatgaa ggcggtgagc ccggtgcgcc cctcgggccg caaggcgccg | 420 |
| tcgggctgcg gcggcgggga gctggcgctg cgctgcctgg ccgagcacgg ccacagcctg | 480 |
| ggtggctccg cagccgcggc ggccgcggcg cggcagcgc gctgtaaggc ggccgaggcg | 540 |
| gcggccgacg agccggcgct gtgcctgcag tgcgatatga acgactgcta tagccgcctg | 600 |
| cggaggctgg tgcccaccat cccgcccaac aagaaagtca gcaaagtgga gatcctgcag | 660 |
| cacgttatcg actacatcct ggacctgcag ctggcgctgg agacgcaccc ggccctgctg | 720 |
| aggcagccac caccgcccgc gccgccacac caccggccg ggacctgtcc agccgcgccg | 780 |
| ccgcggaccc cgctcactgc gctcaacacc gacccggccg cgcgggtgaa caagcagggc | 840 |
| gacagcattc tgtgccgctg agccgcgctg tccaggtgtg cggccgcctg agcccgagcc | 900 |
| aggagcacta gagagggagg gggaagagca gaagttagag aaaaaaagcc accggaggaa | 960 |

```
aggaaaaaac atcggccaac ctagaaacgt tttcattcgt cattccaaga gagagagagg    1020
aaagaaaaat acaactttca ttctttcttt gcacgttcat aaacattcta catacgtatt    1080
ctcttttgtc tcttcattta taactgctgt gaattgtaca tttctgtgtt ttttggaggt    1140
gcagttaaac ttttaagctt aagtgtgaca ggactgataa atagaagatc aagagtagat    1200
ccgactttag aagcctactt tgtgaccaag gagctcaatt tttgttttga agctttacta    1260
atctaccaga gcattgtaga tattttttt ttacatctat gtttaaaat agccggaatt     1320 cc                                                                   1322

<210> SEQ ID NO 95
<211> LENGTH: 397
<212> TYPE: DNA
<213> ORGANISM: Homo sapiens

<400> SEQUENCE: 95 ttttttttt tttttttttt tttttcattt taaagagctt tattacagga tattaatatt      60
taggacactt cagagcacct tatacttcta atcagatttt gggtaactgg ttttaaagtg    120
ttacttgaat atttttctca tactgtcttt caggtaaagt acttctcaga gactgtttaa    180
gagatgttaa tttgattaaa cagtttatcc ttaataacct gagacatcaa tccatggata    240
gcttctatgg tagttttaca gctgtctctt gtagctttgg caagtttgtc ttctgatttt    300
cggtcatgcg tttctaaacc caacatgaaa ctccctcgtc ccagctgggc ttctgactgc    360
tctaactttt cagacaaatc aaagacctga ccagtgg                             397

<210> SEQ ID NO 96
<211> LENGTH: 505
<212> TYPE: DNA
<213> ORGANISM: Homo sapiens

<400> SEQUENCE: 96
atagctgccc gctgctctcg gttcgccagt acgctggccg gggacttggt caactcgttc     60
tcctgctgtg cccaggggct attaaactgt gggggccact tctcaggcta aatctattgc    120
agcctctcca gccgtcccat gcaccagcca gcttaggaac agttcaccat tactttaagt    180
actgcaaaat ctcagcattg gctctgctga agatggtgat gcatgccaga tcggaggca     240 acttggaagt gatgggtctg atgctaggaa aggtggatgg tgaaccatga tcattatgga    300
cagttttgct ttgcctgtgg agggcactga aacccgagta aatgctcagg ctgctgcata    360
tgaatacatg gctgcataca tagaaaatgc aaaacaggtt ggccgccttg aaaatgcaat    420
cgggtggtat catagccacc ctggctatgg ctgctggctt tctgggattg atgttagtac    480
tcagatgctc aatcagcagt tccag                                          505

<210> SEQ ID NO 97
<211> LENGTH: 1277
<212> TYPE: DNA
<213> ORGANISM: Homo sapiens

<400> SEQUENCE: 97
caagagtcta ggtaagagtt tgttcccgtg gtgcggaggg tcaaggccca cacccggaaa     60
cctagcgagg taaagttgcg tcttggttgt agagacgaca acttctccgc ttcctcggcg    120
atggcggcgt ccgggagcgg tatggcccag aaaacctggg aactggccaa caacatgcag    180
gaagctcaga gtatcgatga aatctacaaa tacgacaaga acagcagca agaaatcctg    240 gcggcgaacc ttgggactaa ggatcaccat tactttaagt actgcaaaat ctcagcattg    300
```

```
gctcttctga agatggtgat gcatgccaga tcgggaggca atttggaagt gatgggtctg      360
atgctaggaa aggtggatgg tgaaaccatg atcattatgg acagttttgc tttgcctgtg      420
gagggcactg aaacccgagt aaatgctcag gctgctgcat atgaatacat ggctgcatac      480
atagaaaatg caaaacaggt tggccgcctt gaaaatgcaa tcgggtggta tcatagccac      540
cctggctatg gctgctggct ttctgggatt gatgttagta ctcagatgct caatcagcag      600
ttccaggaac catttgtagc agtggtgatt gatccaacaa gaacaatatc cgcagggaaa      660
gtgaatcttg gcgcctttag gacataccca aagggctaca aacctcctga tgaaggacct      720
tctgagtacc agactattcc acttaataaa atagaagatt ttggtgtaca ctgcaaacaa      780
tattatgcct tagaagtctc atatttcaaa tcctctttgg atcgcaaatt gcttgagctg      840
ttgtggaata atactgggt gaatacgttg agttcttcta gcttgcttac taatgcagac      900
tataccactg gtcaggtctt tgatttgtct gaaaagttag agcagtcaga agcccagctg      960
ggacgaggga gtttcatgtt gggtttagaa acgcatgacc gaaaatcaga agacaaactt     1020
gccaaagcta caagagacag ctgtaaaact accatagaag ctatccatgg attgatgtct     1080
caggttatta aggataaact gtttaatcaa attaacatct cttaaacagt ctctgagaag     1140
tactttacct gaaagacagt atgagaaaaa tattcaagta acactttaaa accagttacc     1200
caaaatctga ttagaagtat aaggtgctct gaagtgtcct aaatattaat atcctgtaat     1260
aaagctcttt aaaatga                                                    1277

<210> SEQ ID NO 98
<211> LENGTH: 247
<212> TYPE: DNA
<213> ORGANISM: Homo sapiens

<400> SEQUENCE: 98
gttctggatc tcaaagcggc tgtgagtact ttggctgtga gcaaaaaagg agaatttatg       60
atatcaccaa tgtcttagag ggaattgact tgattgaaaa aaagtcaaaa aacagtatcc      120
agtggaaagg tgtaggtgct ggctgtaata ctaaagaagt catagataga ttaagatatc      180
ttaaagctga aattgaagat ctagaactga aggaaagaga acttgatcag cagaagttgt      240
ggctaca                                                               247

<210> SEQ ID NO 99
<211> LENGTH: 342
<212> TYPE: DNA
<213> ORGANISM: Homo sapiens

<400> SEQUENCE: 99
tgaatgtttt atacaatttt attttaaaa atcttgttaa tgtacaggca ttggcacatt        60
ttaaaaacaa actacataaa cagatctttc ctataaccta ggaaagtgga atgtcagaag      120
tcaacaaaat gtgataaact taagtgctaa aacagaagg cacttcacaa aatctgttca       180
ctgaaacagt tatatatcct cgtttacatc cttcacttta caagtggcag tgaacgtctg      240
tttggataga aggacataca gaaatacagg cagtttagtg gcagtaaaaa tataagacaa      300
gtaatgagtc cttggccaac ttgttttga tgacctgtag tg                          342

<210> SEQ ID NO 100
<211> LENGTH: 1752
<212> TYPE: DNA
<213> ORGANISM: Homo sapiens
```

<400> SEQUENCE: 100

```
cgggggggcc cgaccaccgc ggggccggga cgcgatggcg gcggcagagc ccgcgagctc      60
gggccagcag gcgccggcag ggcaggggca gggccagcgg ccgccgccgc agcctccgca     120
ggcgcaagcc ccgcagccgc ccccgccgcc gcagctcggg ggcgcggggg gcggcagcag     180
caggcacgag aagagcctgg ggctgctcac taccaagttc gtgtcgctgc tgcaggaggc     240
caaggacggc gttctggatc tcaaagcggc tgctgatact ttggctgtga ggcaaaaaag     300
gagaatttat gatatcacca atgtcttaga gggaattgac ttgattgaaa aaaagtcaaa     360
aaacagtatc cagtggaaag gtgtaggtgc tggctgtaat actaaagaag tcatagatag     420
attaagatat cttaaagctg aaattgaaga tctagaactg aaggaaagag aacttgatca     480
gcagaagttg ttgctacagc aaagcatcaa aatgtgatg gacgattcca ttaataatag     540
attttcctat gtaactcatg aagacatctg taattgcttt aatggtgata cacttttggc     600
cattcaggca ccttctggta cacaactgga ggtacccatt ccagaaatgg gtcagaatgg     660
acaaaagaaa taccagatca atctaaagag tcattcagga cctatccatg tgctgcttat     720
aaataaagag tcgagttcat ctaagcccgt ggttttcct gttcccccac ctgatgacct     780
cacacagcct tcctcccagt ccttgactcc agtgactcca cagaaatcca gcatggcaac     840
tcaaaatctg cctgagcaac atgtctctga agaagccag gctctgcagc agacatcagc     900
tacagatata tcttcagcag gatctattag tggagatatc attgatgagt taatgtcttc     960
tgacgtgttt cctctcttaa ggctttctcc tacccggca gatgactaca actttaattt    1020
agatgataac gaaggagttt gtgatctgtt tgatgtccag atactaaatt attagattcc    1080
atggaaactt gggactgtta tctacctcta actgtgtaac attttagact tcttaataac    1140
ctaaatattt aaaataatga atgtaacacc ttttttagtt cactgattct gaagtgttct    1200
tccctaatac tttctttact tcacaaaact tcaaccataa aaacaaaggg ctctgattgc    1260
tttaggggat aagtgattta atattcacaa acgtccccac tcccaaaagt aactatattc    1320
tggatttcaa cttttcttct aattgtgaat ccttccgttt tttcttctta aggaggaaag    1380
ttaaaggaca ctacaggtca tcaaaaacaa gttggccaag gactcattac ttgtcttata    1440
tttttactgc cactaaactg cctgtatttc tgtatgtcct tctatccaaa cagacgttca    1500
ctgccacttg taaagtgaag gatgtaaacg aggatatata actgtttcag tgaacagatt    1560
ttgtgaagtg ccttctgttt tagcacttta agtttatcac attttgttga cttctgacat    1620
tccactttcc taggttatag gaaagatctg tttatgtagt ttgtttttaa aatgtgccaa    1680
tgcctgtaca ttaacagatt tttaaaaata aaattgtata aacattaaa aaaaaaaaa    1740
aaaaaaaaaa aa                                                        1752
```

<210> SEQ ID NO 101
<211> LENGTH: 456
<212> TYPE: DNA
<213> ORGANISM: Homo sapiens

<400> SEQUENCE: 101

```
tgtgttccaa caaaacttta tttacaaaaa caggaagcag gcacgtttgg ccctcagact      60
gtaatcttcc catcactact cttaatgata ctcagatgac ctggctgcct gagggggctg     120
tggccatgtc tgattctctg tgagatggaa accactctag ggtctcctgg tgcgctgagg     180
ctttacacac cggcagaaca gggcactgcg tttggaagtt tctgaccaag tggtgacagc     240
agagggcaaa acgtgaaggc tgtgctggat aaggctgaac cttcctcata agcaacacca     300
```

```
actgctttat tccaggtcag ggccaactct tccgccatga tacatacatg gtccctggcg    360
ggcactgtcc ttactgggcc cctaggagtc cctgcgttgt ggcctgacca ccagcccctc    420
tctggtgatg gcccagttgt agttcttccg ggagtc                              456

<210> SEQ ID NO 102
<211> LENGTH: 317
<212> TYPE: DNA
<213> ORGANISM: Homo sapiens

<400> SEQUENCE: 102
tgcggccgca agacccgcca cgacccgctg gccaaatcca agatcgagcg agtgaacatg     60
ccgcccgccg tggaccctgc ggagttcttc gtgctgatgg agcgttacca gcactaccgc    120
cagaccgtgc gcgccctcag gatggagttc gtgtccgagg tgcagaggaa ggtgcacgag    180
gcccgagccg ggttctggc ggacggcaag gccctgaagg acgccgccga gcaccgcgag    240
ctgatggcct ggaaccaggc ggagaaccgg cggctgcacg agctgcggat agcgaggctg    300
cggcaggagg agcggga                                                   317

<210> SEQ ID NO 103
<211> LENGTH: 1038
<212> TYPE: DNA
<213> ORGANISM: Homo sapiens

<400> SEQUENCE: 103
ggcacgaggc tcggccatgc tacgcgcgct gagccgcctg ggcgcgggga ccccgtgcag     60
gccccgggcc cctctggtgc tgccagcgcg cggccgcaag accgccacg acccgctggc    120 caaatccaag atcgagcgag tgaacatgcc gcccgcggtg gaccctgcgg agttcttcgt    180
gctgatggag cgttaccagc actaccgcca gaccgtgcgc gccctcagga tggagttcgt    240
gtccgaggtg cagaggaagg tgcacgaggc ccgagccggg ttctggcgg agcgcaaggc    300 cctgaaggac gccgccgagc accgcgagct gatggcctgg aaccaggcgg agaaccggcg    360
gctgcacgag ctgcggatag cgaggctgcg gcaggaggag cgggagcagg agcagcggca    420
ggcgttggag caggcccgca aggccgaaga ggtgcaggcc tgggcgcagc gcaaggagcg    480
ggaagtgctg cagctgcagg aagaggtgaa aaacttcatc acccgagaga acctggaggc    540
acgggtggaa gcagcattgg actcccggaa gaactacaac tgggccatca ccagagaggg    600
gctggtggtc aggccacaac gcagggactc ctaggggccc agtaaggaca gtgcccgcca    660
gggaccatgt atgtatcatg gcggaagagt tggccctgac ctggaataaa gcagttggtg    720
ttgcttatga ggaaggttca gccttatcca gcacagcctt cacgttttgc cctctgctgt    780
caccacttgg tcagaaactt ccaaacgcag tgccctgttc tgccggtgtg tacagcctca    840
gcgcaccagg agaccctaga gtggtttcca tctcacagag aatcagacag gccacagcc    900 ccctcaggca gccaggtcat ctgagtatca ttaagagtag tgatgggaag attacagtct    960
gagggccaaa cgtgcctgct tcctgttttt gtaaataaag ttttgttgga acacaaaaaa   1020
aaaaaaaaaa aaaaaaaa                                                 1038

<210> SEQ ID NO 104
<211> LENGTH: 405
<212> TYPE: DNA
<213> ORGANISM: Homo sapiens

<400> SEQUENCE: 104
```

| | |
|---|---|
| agtttgattt agaattgttt tatttgtgtt cctcatgcta caacacaacc ttcaaagtca | 60 |
| gcgaagtttta taacattaat atgcttcctc aaaacatcaa tttaggcaac ccatagccag | 120 |
| agcttctaaa cttctacaat gcaacttcaa cattcacaag agcacaatat gcttcaaatc | 180 |
| ccatctcaat gcaaatttaa gaaaagcaaa gcaaattgta ttatcagtct accaaaactc | 240 |
| agtaagattc tgtaatttaa tatacctact tctcaactct ctaaatttgt ttctcaacac | 300 |
| tggggagttt ttaaagatat caatgcctga attctactcc aagccaatta aatcagaaca | 360 |
| attaaaatca gaatctctgt ggggcatctt tttttttttt taaag | 405 |

<210> SEQ ID NO 105
<211> LENGTH: 1278
<212> TYPE: DNA
<213> ORGANISM: Homo sapiens

<400> SEQUENCE: 105

| | |
|---|---|
| ggcacgagga ggtgtggacg ctgtgtatga aatgtctttc ctccaggacc caagtttctt | 60 |
| caccatgggg atgtggtcca ttggtgcagg agccctgggg gctgctgcct tggcattgct | 120 |
| gcttgccaac acagacgtgt ttctgtccaa gccccagaaa gcggccctgg agtacctgga | 180 |
| ggatatagac ctgaaaacac tggagaagga accaaggact ttcaaagcaa aggagctatg | 240 |
| ggaaaaaaat ggagctgtga ttatggccgt cggaggcca ggctgttttcc tctgtcgaga | 300 |
| ggaagctgcg gatctgtcct ccctgaaaag catgttggac cagctgggcg tccccctcta | 360 |
| tgcagtggta aaggagcaca tcaggactga agtgaaggat ttccagcctt atttcaaagg | 420 |
| agaaatcttc ctggatgaaa agaaaaagtt ctatggtcca caaaggcgga agatgatgtt | 480 |
| tatgggattt atccgtctgg gagtgtggta caacttcttc cgagcctgga acggaggctt | 540 |
| ctctggaaac ctggaaggag aaggcttcat ccttggggga gttttcgtgg tgggatcagg | 600 |
| aaaagcagggc attcttcttg agcaccgaga aaaagaattt ggagacaaag taaacctact | 660 |
| ttctgttctg gaagctgcta agatgatcaa accacagact ttggcctcag agaaaaaatg | 720 |
| attgtgtgaa actgcccagc tcagggataa ccagggacat tcacctgtgt tcatgggatg | 780 |
| tattgttttcc actcgtgtcc ctaaggagtg agaaacccat ttatactcta ctctcagtat | 840 |
| ggattattaa tgtatttttaa tattctgttt aggcccacta aggcaaaata gcccaaaaac | 900 |
| aagactgaca aaaatctgaa aaactaatga ggattattaa gctaaaacct gggaaatagg | 960 |
| aggcttaaaa ttgactgcca ggctgggtgc agtggctcac acctgtaatc ccagcacttt | 1020 |
| gggaggccaa ggtgagcaag tcacttgagg tcgggagttc gagaccagcc tgagcaacat | 1080 |
| ggcgaaaccc cgtctctact aaaaatacaa aaatcacccg ggtgtggtgg caggcacctg | 1140 |
| tagtcccagc tacccgggag gctgaggcag gagaatcact tgaacctggg aggtggaggt | 1200 |
| tgcggtgagc tgagatcaca ccactgtatt ccagcctggg tgactgagac tctaactaaa | 1260 |
| aaaaaaaaaa aaaaaaaa | 1278 |

<210> SEQ ID NO 106
<211> LENGTH: 330
<212> TYPE: DNA
<213> ORGANISM: Homo sapiens

<400> SEQUENCE: 106

| | |
|---|---|
| gcgtgtggtt ttgatggtgg ttgtagttttt gtttcgtttt gtttttaaga gatgagtctt | 60 |
| gaaggcagag ttgtaatggc cctcctctct ccctcccat tccgaaaatt agggtagctt | 120 |
| aacagaaagc caccttgacc acatggccag ggactgagat tcaatgggga aagaaagact | 180 |

```
gtagctggaa tgtgaagaat ttgatttgca gttgattgca ggttgggttt ccggaagggc      240
agacagctca atgtagtgcc atcatagggc ctcagatgcc cacactccac ccccagagct      300
tcacaaaatg gaaggaccct ggagtcaccc                                      330

<210> SEQ ID NO 107
<211> LENGTH: 390
<212> TYPE: DNA
<213> ORGANISM: Homo sapiens

<400> SEQUENCE: 107
tttcacagcg taggcaacag agtgagaacc tagggctacc ctagctgatg gatgtgaggc       60
tgctgtctac aggagctcat cccagccctg ttaactggca gtggcaagga tactcgtcat      120
cggccattgc actggggaac tccctcaccc catggcttcc caacttgaaa cccagattta      180
cctccaggga gaggtgagaa aaaaattgta aatagacttg ctaaagagca actcaggggtt     240 ggggtgtgtt ttaattctcc tgatcacttg aaataatctg taggctgagt gcttatgggg      300
gtgggggaga agggtgactc cagggtcctt ccattttgtg aagctctggg ggtggagtgt      360
gggcatctga ggccctatga tggcactaca                                      390

<210> SEQ ID NO 108
<211> LENGTH: 380
<212> TYPE: DNA
<213> ORGANISM: Homo sapiens
<220> FEATURE:
<221> NAME/KEY: misc_feature
<222> LOCATION: 48, 58
<223> OTHER INFORMATION: n = A,T,C or G

<400> SEQUENCE: 108
cagcaggcac tccggagtgc acggcgaggg gggcctccta gagaccangc agggcccngg       60 gagccccac ccagcctgcc accgagcgac tccccgtgcg caaggcccag cagccaccga      120
cgcgccctcc cgccccggca gactcgcagg cagggtccaa gcgtccaggt ttattgaccc      180
ggctgggtct cactcctcct tctcctcccc gtgggtgatc acgtagctga gcgccttgta      240
gtccaggttg cccgccacat cgatggaggc gaactggaac atctggtcca cctgcgggcg      300
ggggcgaaag ggctccttgc gggctccggg agcgaattac aagcgcgcac ctgcaaaaaa      360
aaaaaaaaaa aaaaaacccg                                                380

<210> SEQ ID NO 109
<211> LENGTH: 325
<212> TYPE: DNA
<213> ORGANISM: Homo sapiens

<400> SEQUENCE: 109
tttgcaggtg cgcgcttgta attcgctccc ggagcccgca aggagcccctt tcgccccgc       60 ccgcaggtgg accagatgtt ccagttcgcc tccatcgatg tggcgggcaa cctggactac      120
aaggcgctca gctacgtgat cacccacggg gaggagaagg aggagtgaga cccagccggg      180
tcaataaacc tggacgcttg gaccctgcct gcgagtctgc cggggcggga gggcgcgtcg      240
gtggctgctg ggccttgcgc acggggagtc gctcggtggc aggctgggtg ggggctcccg      300
ggccctctgg ggtcctctag cgagg                                           325

<210> SEQ ID NO 110
<211> LENGTH: 1619
<212> TYPE: DNA
```

<213> ORGANISM: Homo sapiens

<400> SEQUENCE: 110

| | | | | | |
|---|---|---|---|---|---|
| cagtagtcct | tggggcggaa | ctggccccc | gtggcccggc | ccggctcggc | cccacctccg | 60 |
| cccgcaggcg | gtcccggccc | acgcgggaag | gtccttaagc | ccggcggcc | ggcgggaccg | 120 |
| gcggagaccc | gtggaggccg | ccgacgatgg | cggggccgac | ggaggccgag | acggggttgg | 180 |
| ccgagccccg | ggccctgtgc | gcgcagcggg | gccaccgcac | ctacgcgcgc | cgctgggtgt | 240 |
| tcctgctcgc | gatcagcctg | ctcaactgct | ccaacgccac | gatcaactgg | ctgtcactgg | 300 |
| tctacctcgt | ggtatccacc | ccatttggcg | tggcggccat | ctggatcctg | gactccgtcg | 360 |
| ggctccgtgc | ggcgctcggt | gtctatacca | tccctgctgg | cgtcgtctgc | ctgctgtcca | 420 |
| ccatctgcct | gtgggagagt | gtgccccca | ccccgccctc | tgccggggct | gccagctcca | 480 |
| cctcagagaa | gttcctggat | gggctcaagc | cgcagctcat | gtggaacaag | gcctatgtca | 540 |
| tcctggctgt | gtgcttgggg | ggaatgatcg | ggatctctgc | cagcttctca | gccctcctgg | 600 |
| agcagatcct | ctgtgcaagc | ggccactcca | gtgggttttc | cggcctctgt | ggcgctctct | 660 |
| tcatcacgtt | tgggatcctg | ggggcactgg | ctctcggccc | ctatgtggac | cggaccaagc | 720 |
| acttcactga | ggccaccaag | attggcctgt | gcctgttctc | tctggcctgc | gtgcccttttg | 780 |
| ccctggtgtc | ccagctgcag | ggacagaccc | ttgccctggc | tgccacctgc | tcgtgctcg | 840 |
| ggctgtttgg | cttctcggtg | ggccccgtgg | ccatggagtt | ggcggtcgag | tgttccttcc | 900 |
| ccgtggggga | gggggctgcc | acaggcatga | tcttttgtgct | ggggcaggcc | gagggaatac | 960 |
| tcatcatgct | ggcaatgacg | gcactgactg | tgcgacgctc | ggagctgtcc | ttgtccacct | 1020 |
| gccagcaggg | ggaggatcca | cttgactgga | cagtgtctct | gctgctgatg | gccggcctgt | 1080 |
| gcaccttctt | cagctgcatc | ctggcggtct | tcttccacac | cccataccgg | cgcctgcagg | 1140 |
| ccgagtctgg | ggagcccccc | tccacccgta | acgccgtggg | cggcgcagac | tcagggccgg | 1200 |
| gtgtggaccg | agggggagca | ggaagggctg | gggtcctggg | gccagcacg | gcgactccgg | 1260 |
| agtgcacggc | gaggggggcc | tcgctagagg | accccagagg | gcccgggagc | ccccacccag | 1320 |
| cctgccaccg | agcgactccc | cgtgcgcaag | gcccagcagc | caccgacgcg | ccctcccgcc | 1380 |
| ccggcagact | cgcaggcagg | gtccaagcgt | ccaggtttat | tgacccggct | gggtctcact | 1440 |
| cctccttctc | ctccccgtgg | gtgatcacgt | agctgagcgc | cttgtagtcc | aggttgcccg | 1500 |
| ccacatcgat | ggaggcgaac | tggaacatct | ggtccacctg | cgggcggggg | cgaaagggct | 1560 |
| ccttgcgggc | tccgggagcg | aattacaagc | gcgcacctgc | aaaaaaaaaa | aaaaaaaaa | 1619 |

<210> SEQ ID NO 111
<211> LENGTH: 338
<212> TYPE: DNA
<213> ORGANISM: Homo sapiens

<400> SEQUENCE: 111

| | | | | | |
|---|---|---|---|---|---|
| accccaacaa | caaaaaagaa | tgttttggta | taggagaagg | gatggtcagt | tagcctgtct | 60 |
| gtcacacgac | ggaatggata | ctgggcccgg | ggaccacttt | catactcacg | tcctcatcct | 120 |
| tggatacccca | ggggagggcg | aaccgttttc | gctcgtgtgt | ctgtacgcag | catgttggga | 180 |
| tcgggagttt | cggcacagac | tatcccatca | agccgttggt | cctttcagct | actacgttac | 240 |
| cacgttccta | aaacgcaagc | tctccggacc | agacggacac | agggagaagc | tagtttcttt | 300 |
| catgtgattg | aaatgatgac | tctactccta | aaagggaa | | | 338 |

<210> SEQ ID NO 112
<211> LENGTH: 413
<212> TYPE: DNA
<213> ORGANISM: Homo sapiens

<400> SEQUENCE: 112

```
tttttttttt tttttaagt ttaatacaaa ttttatacaa agaaaatgtg aaaaaatact      60
tccatatgct aaaagcaatt atgcttcaca ataaggcca gctaggctat tttttttttt     120
gacaactgca attcacaaat gttctttctc tcctgttttc ttctaatact ctcttatttc    180
ttctctaata tgggtaacta gctggaaact gtacagttcg catcctctta acaatgaaga    240
gaaagtaaac aagactaaaa tgtacaacaa aacgtactgg aatgatatcg tacaattaat    300
tttctcatat acatacatca ccttttgctt tttcatcaat gcttttttgtt ttacacaaca   360
tacaaaatgg ctctacagca tacgtagtgt tacggacagc atgacgggcc ttg           413
```

<210> SEQ ID NO 113
<211> LENGTH: 1845
<212> TYPE: DNA
<213> ORGANISM: Homo sapiens

<400> SEQUENCE: 113

```
atggatttga aggagctgag cgagtcggtc cagcaacagt ccaccectgt tcctctcatc      60
tctcccaagc gccagattcg tagcaggttc cagctgaatc ttgacaagac catagagagt    120
tgcaaagcac aattaggcat aaatgaaatc tcggaagatg tctataccggc cgtagagcac   180
agcgattcgg aggattctga agtcagat agtagcgata gtgagtatat cagtgatgat      240
gagcagaagt ctaagaacga gccagaagac acagaggaca agaaggttg tcagatggac     300
aaagagccat ctgctgttaa aaaaaagccc aagcctacaa acccagtgga gattaaagag    360
gagctgaaaa gcacgtcacc agccagcgag aaggcagacc ctggagcagt caaggacaag    420
gccagccctg agcctgagaa ggacttttcc gaaaaggcaa aaccttcacc tcaccccata    480
aaggataaac tgaagggaaa agatgagacg gattccccaa cagtccattt gggcctggac    540
tctgattcag agagcgaact tgtcatagat ttaggagaag accattctgg gcgggagggt    600
cgaaaaaata gaaggaacc caaagaacca tctcccaaac aggatgttgt aggtaaaaca    660
ccaccatcca cgacggtggg cagccattct ccccgggaaa caccggtgct cacccgctct    720
tccgcccaaa cttccgcggc tggcgccaca gccaccacca gcacgtcctc cacggtcacc    780
gtcacggccc cggcccccgc cgccacagga agcccagtga aaaagcagag gccgcttta    840
ccgaaggaga ctgccccggc cgtgcagcgg gtcgtgtgga actcatcaag tgtccagcag    900
aaggagatca cacagagccc atccacgtcc accatcaccc tggtgaccag cacacagtca    960
tcgcccctgg tcaccagctc ggggtccatg agcacccttg tgtcctcagt caacgctgac   1020
ctgcccatcg ccactgcctc agctgatgtc ccgctgata ttgccaagta cactagcaaa     1080
atgatggatg caataaaagg aacaatgaca gaaatataca acgatctttc taaaaacact    1140
actggaagca caatagctga gattcgcagg ctgaggatcg agatagagaa gctccagtgg   1200
ctgcaccagc aagagctctc cgaaatgaaa cacaacttag agctgaccat ggcggagatg    1260
cggcagagcc tggagcagga gcgggaccgg ctcatcgccg aggtgaagaa gcagctggag    1320
ttggagaagc agcaggcggt ggatgagacc aagaagaagc agtggtgcgc caactgcaag    1380
aaggaggcca tctttactg ctgttggaac accagctact gtgactaccc ctgccagcaa    1440
gcccactggc ctgagcacat gaagtcctgc acccagtcag ctactgctcc tcagcaggaa    1500
```

```
gcggatgctg aggtgaacac agaaacacta aataagtcct cccaggggag ctcctcgagc   1560
acacaatcag caccttcaga acggccagc gcctccaaag agaaggagac gtcagctgag    1620
aaaagcaagg agagtggctc gacccttgac ctttctggct ccagagagac gccctcctcc   1680
attctcttag gctccaacca aggctctgac cattcccgga gtaataaatc cagttggagc   1740
agcagtgatg agaagagggg atcgacacgt tccgatcaca acaccagtac cagcacgaag   1800
agcctcctcc cgaaagagtc tcggctggac accttctggg actag                  1845
```

<210> SEQ ID NO 114
<211> LENGTH: 348
<212> TYPE: DNA
<213> ORGANISM: Homo sapiens

<400> SEQUENCE: 114

```
gaaaaagttg caagcctttt aattcattga cctcttttga ctgattggaa ttttttaccat    60 tctgtacact ctgaattata actaaacaac tacatgttac tgacaaattt gtgattcttt     120
gagtctaaac aacacagaaa ctagaagatc cctttcctag atttatatac ttgattttct     180
tataaaaata acttcagtta ttatgtcaat atttatctga aaaaggcagc cctctgacag     240
taaactagta actggaataa ctacagtatc attataagct acagtaaaac aacctgtaaa     300 gtaattttc ctatttgaat aataaataga ctggacagga gtgaaaaa                   348
```

<210> SEQ ID NO 115
<211> LENGTH: 186
<212> TYPE: DNA
<213> ORGANISM: Homo sapiens

<400> SEQUENCE: 115

```
tttttttttt tttttttttt ttttttttga cgttaagaca tttattacat acagagcaga    60
tatgtgggtt tgcttgcagg gccaaagcct gaggagaatc gtcaccctc ccccagccgc     120 cccactgctc agcccggagt cacttcgaga tcctggggga acagacgagg gagcggacat    180
tcatca                                                               186
```

<210> SEQ ID NO 116
<211> LENGTH: 355
<212> TYPE: DNA
<213> ORGANISM: Homo sapiens

<400> SEQUENCE: 116

```
agttcttacg gaaacacccc aggacacaat tgaattaaac agattgaatt tagaatcttc    60
caattcaaag tactccttga atacagattc ctcagtgtct tatattgatt cagctgtaat    120
ttcacctgat actgtcccac tgggaacagg aacttccata ttatctatac aggttcaaaa    180
taaaccaaaa actggtcgaa gtttattagg aggaccagca gctcttagtc cattaacccc   240
aagttttggg attttgccat tagaaacccc aagtcctgga gatgggtcta tttacgaaac   300
tacactaata caccctcctgt aattggtgtg cctccatcgg ggcccttcag aaaag       355
```

<210> SEQ ID NO 117
<211> LENGTH: 4029
<212> TYPE: DNA
<213> ORGANISM: Homo sapiens

<400> SEQUENCE: 117

```
atgatggaga tccagatgga cgagggcggc ggcgtggtgg tgtaccagga cgactactgc    60
tccggctcgg tgatgtcgga gcgggtgtcg ggcctggcgg gctccatcta ccgcgagttc   120
```

```
gagcgcctca tccactgcta cgacgaggag gtggtcaagg agctcatgcc gctggtggtg      180
aacgtgctgg agaacctaga ctcggtgctc agcgagaacc aggagcacga ggtggagctg      240
gagctgctgc gcgaggacaa cgagcagctg ctcacccagt acgagcgtga gaaggcgctg      300
cgcaggcagg cggaggagaa attcattgag tttgaagatg ctctggaaca agagaagaaa      360
gagctgcaaa tccaggtgga gcactacgag ttccagacgc gccagctgga gctgaaggcc      420
aagaactatg ccgatcagat ttcccggttg gaggagcggg agtcggagat gaagaaggag      480
tacaatgccc tgcaccagcg gcacacagag atgatacaga cctacgtgga gcacattgag      540
aggtccaaga tgcagcaggt cggaggaaac agccagaccg agagcagcct gccggggcgg      600
agcaggaagg agcgccccac ctccctgaac gtgttccccc tggctgacgg cacggtacgt      660
gcacagatcg ggggcaagct cgtgcctgcg ggggaccact ggcacctgag tgacctcggc      720
cagctgcagt ccagctccag ctaccagtgt ccacaggatg aaatgtccga gtcaggccag      780
tcctcggcgg ccgccacacc cagcaccaca ggcaccaagt ccaacacgcc cacatcctcc      840
gtgccctcgg ccgccgtcac acccctcaac gagagcctgc agccctgggg ggactatggc      900
gtgggctcca agaacagcaa gcgtgcccgg gagaagcgcg acagccgcaa catggaagta      960
caggtcaccc aggagatgcg caacgtcagt ataggcatgg gcagcagtga cgagtggtct     1020
gatgttcaag acattattga ctccacgcca gagctggaca tgtgtccaga gacccgcctg     1080
gaccgcacag gaagcagccc aaccccaggc atcgtgaaca agctttcgg catcaacacc     1140 gactccctgt accatgagct gtcgacggca gggtctgagg tcatcgggga tgtggacgaa     1200
ggggccgacc tcctaggtga aacctccgca ccttctgttt caggaatggg caaagaagtg     1260
gggaatctgc tactggaaaa actcacagct tctggaaacca aaaacgcctt gaatgtggtg     1320
aagaatgacc tgattgccaa ggtcgaccag ctgtccgggg agcaggaggt gctgaggggc     1380
gagttggagg ctgctaagca ggccaaagtc aagctggaaa accgtatcaa ggagctggaa     1440
gaggaactga aaagagtgaa gtccgaggcc atcatcgccc gccgtgaacc caaagaagag     1500
gcggaggatg taagcagcta tctctgtaca gaatcggaca aaatccccat ggcccagcgc     1560
cgccgcttca cgcgggtgga gatggcccgt gtgctcatgg agcggaacca gtacaaggag     1620
cggctgatgg agctgcagga ggctgtgcgg tggactgaga tgatcagagc gtcccgagag     1680
cacccatccg tccaggagaa gaagaagtcg accatctggc agttcttcag ccgcctcttc     1740
agctcttcct ccagcccccc tccggccaag cgccccctatc cctcggtgaa catccactac     1800
aagtcaccca ccactgccgg cttcagccag cgccgcaacc atgccatgtg cccgatctcg     1860
gcaggcagcc ggcccctgga attcttccct gacgacgact gcacgtcctc cgcccgtcga     1920
gagcagaagc gcgagcagta ccgccaggtg cgtgagcacg tgcgtaacga cgacggccgt     1980
ctgcaggcct gcgctggag cctgcccgcc aagtacaagc agctgagtcc caacggggc     2040 caggaggaca cgcggatgaa gaacgtgccg gtgccggtgt actgccgccc tctggtggag     2100
aaggacccca ccatgaagct gtggtgtgcc gcgggcgtca acctgagcgg gtggaggccc     2160
aatgaggacg acgctgggaa tggagtcaag ccagcgccag gccgcgatcc cctgacctgc     2220
gaccgcgaag gagacggcga gcccaagagc gcccacacgt ctcccgagaa gaagaaggcc     2280
aaggagctcc ctgaaatgga cgccacctcc agccgggtgt ggatcctgac cagcacccctg    2340 accaccagca aggtggtgat catcgacgcc aaccagccgg gcacggtggt ggaccagttc     2400
accgtctgca acgcgcacgt gctgtgcatc tccagcatcc ccgcggccag cgacagcgac     2460
```

```
tacccteccg gggagatgtt cctggacagc gacgtgaacc cagaggaccc gggcgcagat      2520
ggcgtgctgg ccggtatcac cctggtgggc tgtgccaccc gctgcaacgt gccgcggagc      2580
aactgctcct cccgagggga cacccagtg ctagacaagg gcaggggga ggtggccacc        2640
atcgccaacg ggaaggtcaa cccgtcccag tccacagagg aggccacaga ggccacggag      2700
gtgccagacc ctgggcccag cgagccagag acagccacat tgcggcccgg gcctctcaca      2760
gagcacgtct tcactgaccc agccccgacc ccgtcctctg gccccagcc tggcagcgag       2820
aacgggccag agcctgacag cagcagcaca cggccagagc cagagcccag cggggacccc      2880
acgggagcag gcagcagtgc tgcacccacc atgtggctgg agcccagaa cggctggctc       2940
tatgtgcact cggctgtggc caactggaag aagtgcctgc actccatcaa gctgaaggat      3000
tctgtgctga gcctggtgca tgtcaaaggc cgtgtgctgg tggctctggc ggacgggacc      3060
ctggccatct tccaccgtgg tgaagatggc cagtgggatc tgagcaacta tcacctaatg      3120
gacctgggcc acccgcacca ctccatccgc tgcatggctg ttgtgtacga ccgcgtgtgg      3180
tgtggctaca agaacaaggt gcacgtcatc cagcccaaga ccatgcagat agaggcgacc      3240
atgactccac agaagtcatt tgacgcccac ccgcggcggg agagccaggt gcggcagctg      3300
gcgtggatcg gcgatggcgt atgggtgtcc atccgcctgg actccaccct gaggctctac      3360
catgcacaca cgcaccagca tctacaggac gtggacattg agccctacgt cagcaagatg      3420
ctaggcactg gcaagctggg ttttctcctt cgtacgcatca cggccctgct tgtcgcgggc      3480
agccggctct gggtgggcac cggcaacgga gtggtcatct ccatcccct gacagagact       3540
gtggtcctgc accgaggcca gctcctgggg ctccgagcca ataagacatc ccccacctct      3600
ggggagggcg cccgtcccgg gggcatcatc cacgtgtatg gcgatgacag cagtgacagg      3660
gcggccagca gcttcatccc ctactgctcc atggcccagg cccagctatg cttccatggg      3720
caccgcgatg ccgtgaagtt ctttgtctcg gtgccaggga acgtgctggc caccctgaat      3780
ggcagtgtgc tggacagccc agccgagggc cctgggccag ctgcccctgc ctcggaggtc      3840
gagggccaga agctgcggaa cgtgctggtg ctgagcggcg ggagggcta catcgacttc       3900
cgcattggag acgagagga cgacgagacg gaggagggcg caggggacat gagccaggtg       3960
aagcccgtgc tgtccaaggc agagcgcagt cacatcatcg tgtggcaggt gtcctacacc      4020
cccgagtga                                                              4029
```

<210> SEQ ID NO 118  
<211> LENGTH: 385  
<212> TYPE: DNA  
<213> ORGANISM: Homo sapiens

<400> SEQUENCE: 118

```
actcaaattg accctggaca acagtagtct agtctcctgg aagacatggt gcaaacagaa        60
atgcaatgtg gtggtatact catagtcaaa gtgggtgcac aagtgatggt ccaactttgt       120
ggaatggtaa ggattttag ggttgtttgg ccagaacaag agaaataact gcagaaaaca        180
catatggttg gaaaccatgc gcttgtgact ttttctgtag cctatgggag tggacagagt       240
gggtaaccca agatgttttt aagactgact ggactaagaa tgacgtactt atagccaact       300
actttccccc taatgtgact gaagggattc ataatgatca caattagcat tacggttaag      360
tatttttaggg ttgacgtcta agctc                                            385
```

<210> SEQ ID NO 119  
<211> LENGTH: 438

```
<212> TYPE: DNA
<213> ORGANISM: Homo sapiens

<400> SEQUENCE: 119
aggtcctcct tggggacgcc gcctgccgca gccacccgcc cccttggtgc tcagttctgg      60
ttctgttaat tcgccccacc aaaacgtgcc gagcacgctc tgtgctgggg ttgcggaagt     120
gactgaacgc ggctccgtgg gcgcagtggt gggggttggg ctagctgtcc ccggcagttg     180
gtgcagagcc attttcattc ccggcggttt ccttgttttt gttggggaac taagatggac     240
ggatacagtc gtcttattgt acttaaagcg gatgatattt aatacacagt ttgatttcac     300
aggtaagcca agatgggtgc atacaagtac atccaggagc tatggagaaa gaagcagtct     360
gatgtcatgc gctttcttct gagggtccgc tgctggcagt accgccagct ctctgctctc     420
cacagggctc ccgcccca                                                   438

<210> SEQ ID NO 120
<211> LENGTH: 2018
<212> TYPE: DNA
<213> ORGANISM: Homo sapiens

<400> SEQUENCE: 120
cctttccgtc tggcggcagc catcaggtaa gccaagatgg gtgcatacaa gtacatccag      60
gagctatgga gaaagaagca gtctgatgtc atgcgctttc ttctgagggt ccgctgctgg     120
cagtaccgcc agctctctgc tctccacagg gctccccgcc ccacccggcc tgataaagcg     180
cgccgactgg gctacaaggc caagcaaggt tacgttatat ataggattcg tgttcgccgt     240
ggtggccgaa aacgcccagt tcctaagggt gcaacttacg gcaagcctgt ccatcatggt     300
gttaaccagc taaagtttgc tcgaagcctt cagtccgttg cagaggagcg agctggacgc     360
cactgtgggg ctctgagagt cctgaattct tactgggttg gtgaagattc cacatacaaa     420
tttttttgagg ttatcctcat tgatccattc cataaagcta tcagaagaaa tcctgacacc     480
cagtggatca ccaaaccagt ccacaagcac agggagatgc gtgggctgac atctgcaggc     540
cgaaagagcc gtgccttgg aaagggccac aagttccacc acactattgg tggctctcgc     600
cgggcagctt ggagaaggcg caatactctc cagctccacc gttaccgcta atataagtaa     660
agtttgtaaa attcatactt aataaacaat ttaggacagt catgtctgct tacaggtgtt     720
atttgtctgt taaaactagt ctgcagatgt ttcttgaatg cttttgtcaaa ttaagaaagt     780
taaagtgcaa taatgtttga agacaataag tggtggtgta tcttgttct aataagataa     840
acttttttgt ctttgcttta tcttattagg gagttgtatg tcagtgtata aaacatactg     900
tgtggtataa caggcttaat aaattcttta aaggagaga actgaaacta gccctgtaga     960
tttgtctggt gcatgtgatg aaacctgcag ctttatcgga gtgatggcaa tgctctgctg    1020
gtttattttc aagtggctgc gttttttttta gtttggcagg tgtagacttt ttaagttggg    1080
ctttagaaaa tctggttag cctgaagaaa attgcctcag cctccacagt accattttaa    1140
attcacataa aaggtgaaag ctcctggttc agtgccatgg cttcatggca ttcagtgatt    1200
agtggtaatg gtaaacactg gtgtgttttg aagttgaatg tgcgataaaa ttattagcct    1260
taagattggt aagctagcaa tgaatgctag ggtgggaagc tggtgagcca gtggccatta    1320
gataaatacc tttcaagtgt gagcttagac gtcaacccta aaatacttaa ccgtaatgct    1380
aattgtgatc attatgaatc ccttcagtca cattagggggg aaagtagttg gctataagta    1440
cgtcattctt agtccagtca gtcttaaaaa catcttgggt tacccactct gtccactccc    1500
```

| | |
|---|---|
| ataggctaca gaaaaagtca caagcgcatg gttttccaacc atatgtgttt tctgcagtta | 1560 |
| tttctcttgt tctggccaaa caaccctaaa aatccttacc attccacaaa gttggaccat | 1620 |
| cacttgtgca cccactttga ctatgagtat accaccacat tgcatttctg tttgcaccat | 1680 |
| gtcttccagg agactagact actgttgtcc agggtcaatt tgagtgtaaa gaaaatgtag | 1740 |
| acaaggaatt gcccaatttt aaattctgac tttgctgact taatttaaat gctcgttctg | 1800 |
| aaccaattttt ctcctatctt ctctaggggt ttcaaaagac tcagttaatt gatttccagg | 1860 |
| aagtactcat agcaagttca taaaagttct tgagacctaa atttcttcac aaaaaaagaa | 1920 |
| aagatcttaa gtcatacatt ttaattgtgt agaggttgtt caactgaagg aataaatgtc | 1980 |
| tattaaacta aaaaaaaaa aaaaaaaaa aaaaaaa | 2018 |

<210> SEQ ID NO 121
<211> LENGTH: 720
<212> TYPE: DNA
<213> ORGANISM: Homo sapiens

<400> SEQUENCE: 121

| | |
|---|---|
| tttttttttt ttttttagt gtaaagtgta gcatgatgtt aagccatttt agcttttgca | 60 |
| catacatgtt gcacttctgg ctgataatgg aggaaaattt gcagcattat actgttaagc | 120 |
| taggttgcat ccatcccttt aaatggcatc aatatcgatg tcgtcatcct tgttgtctga | 180 |
| ctttacagtc tcaactttcg gtacactggc agccttcgaa tacaccacct caatgttctc | 240 |
| atcttcatct tcttcttcgc caccagaaga ttcttcctct gcctccttca accatttttat | 300 |
| aaatggttct gctttgacac gaatctcttt ggcaagttct ttggagacat atttcttaga | 360 |
| ggccttttcc gaccagctga tgaagaaccc ctcctccaaa aaggtcgaat cgtaaatctc | 420 |
| cttcaagaaa tgtggaatct tggagataag ctgagcttga tgcattgcta ccacacactc | 480 |
| caaaccatga agaaggtacc gttgggcttt tttgttgttg tgacaaaatc gtaggaaatg | 540 |
| gcgcctgtat ttcttaatct gttctctaat cttctcatta aaaagaactt cagttagaac | 600 |
| aagagggccc atggctttta catccagtcc ttctgcttca gcaacgattt ccttgtcaga | 660 |
| tgaatcaata acaccctctg tcttcctttt cttaacaaaa tcaaagagga tattgagcct | 720 |

<210> SEQ ID NO 122
<211> LENGTH: 1826
<212> TYPE: DNA
<213> ORGANISM: Homo sapiens

<400> SEQUENCE: 122

| | |
|---|---|
| tacctgaccc cagccatttc ccttctagaa attgttctac agacatatgt aataacatat | 60 |
| acaaaaggtt attctttcag cagtgtttgt cagagcgaga acattccaga gagctgttgc | 120 |
| gcagccattg gtacctgtat tggggaaaca tagcatacaa tcaagaagct tacagcctca | 180 |
| gtggcgaaaa ttttttcatg tcagagaccg agaactcttg cagtcgttta tgtcatccct | 240 |
| tcttctccag acagaagata ccaaaaagtt gcaatcaaag atctcttcat cttattgata | 300 |
| aagccactaa taagccaaaa tgtctgtcaa tgtcaaccgc agcgtgtcag accagttcta | 360 |
| tcgctacaag atgccccgtc tgattgccaa ggttgagggc aaaggcaatg gaatcaagac | 420 |
| agttatagtc aacatggttg acgttgcaaa ggcgcttaat cggcctccaa cgtatcccac | 480 |
| caaatatttt ggttgtgagc tgggagcaca gacccagttt gatgttaaga atgaccgtta | 540 |
| cattgtcaat ggatctcatg aggcgaataa gctgcaagac atgttggatg gattcattaa | 600 |
| aaaatttgtt ctctgtcctg aatgtgagaa tcctgaaaca gatttgcatg tcaatccaaa | 660 |

| | |
|---|---|
| gaagcaaaca ataggtaatt cttgtaaagc ctgtggctat cgaggcatgc ttgacacaca | 720 |
| tcataaactc tgcacattca ttctcaaaaa cccacctgag aatagtgaca gtggtacagg | 780 |
| aaagaaagaa aaagaaaaga aaaacagaaa gggcaaagac aaggaaaatg gctccgtatc | 840 |
| cagcagtgag acaccaccac caccaccacc accaaatgaa attaatcctc ctccacatac | 900 |
| aatggaagaa gaggaggatg atgactcggg agaagataca actgaggaag ctcaaaggcg | 960 |
| tcgaatggat gaaatcagtg accatgcaaa agttctgaca ctcagtgatg atttggaaag | 1020 |
| aacaattgag gagagggtca atatcctctt tgattttgtt aagaaaaaga agaagaggg | 1080 |
| tgttattgat tcatctgaca aagaaatcgt tgctgaagca gaaagactgg atgtaaaagc | 1140 |
| catgggccct cttgttctaa ctgaagttct ttttaatgag aagattagag aacagattaa | 1200 |
| gaaatacagg cgccatttcc tacgattttg tcacaacaac aaaaaagccc aacggtacct | 1260 |
| tcttcatggt ttggagtgtg tggtagcaat gcatcaagct cagcttatct ccaagattcc | 1320 |
| acatatcttg aaggagatgt acgatgcaga cctttagaa gaagaggtca tcatcagctg | 1380 |
| gtcggaaaag gcctctaaga aatatgtctc caaagaactt gccaaagaga ttcgtgtcaa | 1440 |
| agcagaacca tttataaaat ggttgaagga ggcagaggaa gaatcttctg gtggcgaaga | 1500 |
| agaagatgaa gatgagaaca ttgaggtggt gtattcgaag gctgccagtg taccgaaagt | 1560 |
| tgagactgta aagtcagaca caaggatga cgacatcgat attgatgcca tttaaaggga | 1620 |
| tggatgcaac ctagcttaac agtataatgc tgcaaatttt cctccattat cagccagaag | 1680 |
| tgcaacatgt atgtgcaaaa gctaaaatgg cttaacatca tgctacactt tacactaaaa | 1740 |
| atctattact gtgagtgtga aaaactagtg gtggacacat ttggatcaca tttatacagt | 1800 |
| tataaaaata aaggtttgat tttggt | 1826 |

<210> SEQ ID NO 123
<211> LENGTH: 486
<212> TYPE: DNA
<213> ORGANISM: Homo sapiens

<400> SEQUENCE: 123

| | |
|---|---|
| tggttgtttt gccttaaaac atcaatatgc tggattgtgg cgtgaggtat ttttattccc | 60 |
| tttgttagta ctggaaaccg tctggtacat cttgtaaggc aaatgattaa cacacggcag | 120 |
| gctcttcgtc cgtttgcaag ttgctgtttg tttccaggta caccagtcag agctccacag | 180 |
| agagggtgcg ttcctggttc tcaggtgggc aggtgctatg gtgcggggcg ctggaaagaa | 240 |
| tggggttgaa ttggccctcg cctccgcttg tttgagactc tcgttagaaa gggcttagga | 300 |
| aaaccaaggg aatggcagcc accccatcac catcgagaac aggcagacgt ttcccgagta | 360 |
| ggggccaaag cactggaaac cgtgttccct gtgcagtccg actgacacta ccccatgcct | 420 |
| gggggggaatg agtataaaaa ggtaaatgtt tttgaagaca ggcacgatat atactactag | 480 |
| agaatg | 486 |

<210> SEQ ID NO 124
<211> LENGTH: 3442
<212> TYPE: DNA
<213> ORGANISM: Homo sapiens

<400> SEQUENCE: 124

| | |
|---|---|
| cgccgcagcc gccggcgctg tgagatatt ctctaagccg ctttcatcat gggagaaata | 60 |
| gagcagaggc cgaccccagg atcacgactg ggggcccccgg aaaattcggg gatcagtacc | 120 |

```
ttggaacgtg gacagaagcc gcccccaaca ccttcaggaa aactcgtgtc catcaaaatc    180
cagatgctgg atgacaccca ggaggcattt gaagttccac aaagagctcc tgggaaggtg    240
ctgctggatg cagtttgcaa ccacctcaac ctcgtggaag gtgactattt tggcctcgag    300
tttcctgatc acaaaaagat cacggtgtgg ctggatctcc taaaacccat tgtgaaacag    360
attagaaggc caaagcacgt tgttgttaag tttgtggtga aattcttttc gcctgaccac    420
acacaactcc aagaagaact cacaaggtac ctgttcgcgc tgcaggtgaa gcaggacttg    480
gctcaaggca ggttgacgtg taatgacacc agcgcagctc tcttgatttc acacattgtg    540
caatctgaga ttggggattt tgatgaagcc ttggacagag agcacttagc aaaaaataaa    600
tacataccct cagcaagacg cactagagga c aaaatcgtgg aatttcacca taaccacatt    660
ggacaaacac cagcagaatc agatttccag ctcctagaga ttgcccgtcg gctagagatg    720
tatggaatcc ggttgcaccc ggccaaggac agggaaggca cgaagatcaa tctggccgtt    780
gccaacacgg gaattctagt gtttcagggt ttcactaaga tcaatgcctt caactgggcc    840
aaggtgcgga agctgagctt caagaggaag cgctttctca tcaagctccg gccagatgcc    900
aatagtgcgt accaggatac cttggaattc ctgatggcca gtcgggattt ctgcaagtcc    960
ttctggaaaa tctgtgttga acatcatgcc ttctttagac ttttttgaaga gcccaaacca   1020 aagcccaagc ccgtcctctt tagccggggg tcatcatttc ggttcagtgg tcggactcag   1080
aagcaggttc tcgactatgt taaagaagga ggacataaga aggtgcagtt tgaaaggaag   1140
cacagcaaga ttcattctat ccggagcctt gcttcacagc ctacagaact gaattcggaa   1200
gtgctggagc agtctcagca gagcaccagc cttacatttg gagaaggtgc cgaatctcca   1260
gggggccaga gctgccggcg aggaaaggaa ccgaaggttt ccgccgggga gccggggtcg   1320
cacccgagcc ctgcgccgag gagaagcccc gcgggtaaca agcaggcgga cggagccgcc   1380
tcggcgccca cggaggaaga ggaggaggtc gttaaggata ggacccagca gagtaaaacct   1440 cagccccgc agccaagcac aggctccctg actggcagtc ctcacctttc cgagctgtct   1500
gtgaactcgc aggggggagt ggcccctgcc aacgtgacct tgtctcccaa cctgagcccc   1560
gacaccaagc aggcctctcc cttgatcagc ccgctgctga atgaccaggc ctgccccgg   1620 acggacgatg aggatgaggg ccggaggaag agattcccaa ctgataaagc gtacttcata   1680
gctaaggaag tgtctaccac cgagcgaaca tatctgaagg atctcgaagt tatcacttcg   1740
tggtttcaga gcacagtgag caaagaggac gccatgccgg aagcactgaa aagtctcata   1800
ttcccgaatt ttgaaccttt gcacaaattt catactaatt ttctcaagga aattgagcaa   1860
cgacttgccc tgtgggaagg ccgctcaaat gcccaaatca gagattacca aagaatcggc   1920
gatgtcatgc tgaagaacat tcagggcatg aagcacctgg cggctcacct gtggaagcac   1980
agcgaggcct tggaggccct ggagaatgga atcaagagct cccggcggct ggagaacttc   2040
tgcagagact ttgagctgca aaggtgtgt tacctaccgc tcaacacctt cctcctgcgg   2100
ccactgcacc ggctcatgca ctacaagcag gtcctggagc ggctgtgcaa acaccacccg   2160
ccgagccacg ccgacttcag ggactgccga gccgctttgg cagagatcac ggagatggtg   2220
gcacagctcc acgtacgat gatcaagatg gagaatttcc agaagctgca cgaactcaag   2280
aaagatttga ttggcattga caatcttgtg gttccgggaa gggagttcat ccgtctgggc   2340
agcctcagca agctctcggg gaaggggctc cagcagcgca tgttcttcct gttcaacgac   2400
gtcctgctat acacgagccg ggggctgacg gcctccaatc agtttaaagt ccacgggcag   2460
ctcccgctct atggcatgac gattgaggag agcgaagacg agtgggggt gccccactgc   2520
```

```
ctgaccctcc ggggccagcg gcagtccatc atcgtggccg ccagttctcg gtccgagatg    2580
gagaagtggg ttgaggacat ccagatggcc attgacctgg cggagaagag cagcagcccc    2640
gcccctgagt tcctggccag cagccccccct gacaacaagt cccctgatga agccaccgcg    2700
gctgaccagg agtcagagga tgacctgagc gcctcgcgca catcgctgga gcgccaggcc    2760
ccgcaccgcg gcaacacaat ggtgcacgtg tgctggcacc gcaacaccag cgtctccatg    2820
gtggacttca gcatcgcagt ggagaatcag ttgtctggaa acctgctgag gaaattcaaa    2880
aacagcaacg ggtggcagaa gctgtgggtg tgttcacaa acttctgcct gttcttctac    2940
aaatcacacc aggacaatca tccccttgcc agcctgcctc tgctcggcta ctcgctcacc    3000 atccctctg agtccgagaa catccagaaa gactacgtgt tcaagctgca cttcaagtcc    3060
cacgtctact acttcagggc ggaaagcgag tacacgttcg aaaggtggat ggaagtgatc    3120
cgcagtgcca ccagctctgc ctcgcgaccc cacgtgttga gccacaaaga gtctcttgtg    3180
tattgatggc cggacacact cgtttccgca gtggctgctt tcctggaaga cgtttccttt    3240
cttctgtatt aatgaagcct ggtaaaatta cacctgtct gaaaatcaaa acatggctt     3300 cccagcagct ctcctgtctc cacagccgcg ttttttaacc ccgacctctc agcgtttgaa    3360
tgaacagcgc tcccacctcc agtcctggca tccgctgggg gcgctgttct ttagctagtg    3420
ccagtattaa aacattgtca tt                                              3442

<210> SEQ ID NO 125
<211> LENGTH: 360
<212> TYPE: DNA
<213> ORGANISM: Homo sapiens

<400> SEQUENCE: 125
tttacattta caaatattaa atttattata actaaaatga atttaattgt tctcagattt      60 ggccaccttaa tagctccgtt taaggagggg atttgttaaa aacaaaaatg cattataact    120
tggtcaaatt actttcacat taaggaaaaa aacttctaaa aaggaaaaca agaaaagcaa    180
ctcttcagtt tcacataatt aaaagaacag gagaaagcac gcaagctaca tatagctaaa    240
tttacgaaac caaccaaagc caggggggatt tctcttctga ttatgtgtca taaaaaggtc    300
cactgtctta tatacacatg tatataatgt tacattccat cactgtaaaa agtccccttt    360

<210> SEQ ID NO 126
<211> LENGTH: 3624
<212> TYPE: DNA
<213> ORGANISM: Homo sapiens

<400> SEQUENCE: 126
gcaggttggg agggaaagtc gggggaggac gcggaagagg agctgtggga aggggaggga     60
gggagggagg aaaagaggag gagacggagg agaactgagc agagcagagc atcgagccaa    120
aggggagatg agtttgtctg tcctctgctg aggctacggc cgggcctagg gaactgggag    180
cttgggtgga agcgacaccc gtggaagtgg gaggaggtgg cgccgggact ttaacccctt    240
gtgggctctg cggcagggga tttaaccctt tgtggatctg gccctcgga ggcagcgtca    300 tcggtagttt taacccttc ggggctgggt ttcacgcact ggacttaccc tcatcacctt    360
gctcaccaac tcctttattg gggtgctccg cttggaggtt tgaggcccac ctccgcccat    420
tacgtactgt tcctgccgct gcaccccctt ggacccgcta gctggccgca ctgtgggcgc    480 ttaaccctt actgacttga gctccccaga ttgcagttgg agtttgctga tagaaggact    540
```

```
agctaaaggc gtcactgcag gaattacaaa ctgaagagga ctctgttgga ctgttttttt      600 tttcttttc ttttttttaa gaaaaaccca ttttttcct taaggactta ctagccaaaa        660
tttcttaaac ttcgaggact ctactagcca tggccgagcc attcttgtca gaatatcaac      720
accagcctca aactagcaac tgtacaggtg ctgctgctgt ccaggaagag ctgaaccctg      780 agcgccccc aggcgcggag gagcgggtgc ccgaggagga cagtaggtgg caatcgagag       840
cgttccccca gttgggtggc cgtccgggc cggaggggga agggagcctg gaatcccaac       900
cacctccctt gcagacccag gcctgtccag aatctagctg cctgagagag ggcgagaagg      960
gccagaatgg ggacgactcg tccgctggcg gcgacttccc gccgccggca gaagtggaac     1020
cgacgcccga ggccgagctg ctcgcccagc cttgtcatga ctccgaggcc agtaagttgg     1080
gggctcctgc cgcaggggc gaagaggagt ggggacagca gcagagacag ctggggaaga      1140 aaaacatag gagacgcccg tccaagaaga agcggcattg gaaaccgtac tacaagctga      1200
cctgggaaga gaagaaaaag ttcgacgaga aacagagcct tcgagcttca aggatccgag     1260
ccgagatgtt cgccaagggc cagccggtcg cgccctataa caccacgcag ttcctcatgg     1320
atgatcacga ccaggaggag ccggatctca aaaccggcct gtactccaag cgggccgccg     1380
ccaaatccga cgacaccagc gatgacgact tcatggaaga agggggtgag gaggatgggg     1440
gcagcgatgg gatgggaggg gacggcagcg agtttctgca gcgggacttc tcggagacgt     1500
acgagcggta ccacacggag agcctgcaga acatgagcaa gcaggagctc atcaaggagt     1560
acctggaact ggagaagtgc ctctcgcgca tggaggacga gaacaaccgg ctgcggctgg     1620
agagcaagcg gctgggtggc gacgacgcgc gtgtgcggga gctggagctg agctggacc      1680 ggctgcgcgc cgagaacctc cagctgctga ccgagaacga actgcaccgg cagcaggagc     1740
gagcgccgct ttccaagttt ggagactaga ctgaaacttt ttgggggag ggggcaaagg      1800 ggactttta cagtgatgga atgtaacatt atatacatgt gtatataaga cagtggacct      1860
ttttatgaca cataatcaga agagaaatcc ccctggcttt ggttggtttc gtaaatttag     1920
ctatatgtag cttgcgtgct ttctcctgtt cttttaatta tgtgaaactg aagagttgct     1980
tttcttgttt tcctttttag aagtttttt ccttaatgtg aaagtaattt gaccaagtta     2040
taatgcattt ttgttttaa caaatccct ccttaaacgg agctataagg tggccaaatc      2100
tgagaacaat taaattcatt ttagttataa taaatttaat atttgtaaat gtaacatagt     2160
ttcagtgtga tttctagagc taattcaaaa tagtattgat atattttatg tgactgcatt     2220
tttggggagg ggtaccgaaa tcgttaaatt tgtcagtttg caaaaatatc aatctttaat     2280
gggagaattt tcaatttgcc aatttttcc ttgaatgggt ttaagtatgc tacaatatac      2340
agttcaggca aaatttaaga tgtaattatc ttcaatactt aagtgtgctt gctttctagt     2400
gccttggttt tctttcttga tgctggaaaa ataaacaaac cggtattgag tgtttaggcg     2460
agtggaaagt ggctacaatc caaaatttta aatttaactc tgcctcggcc attcaaaagt     2520
ctaataacaa aaatgtaaa cctaatttgg cagtttgtta ggttagacaa ctgacagcct      2580
catttcattc ctacaagttg gttttcagta atctcttcct tcccccagt aaggctggaa      2640 gaggctcttg gcaaacttct tagcgcaagc aatggttaga ttaatttgtg aggcagctct     2700
ttaagacgtt cagaggtaag aaatactgga tttataaagc aaatggctgt ttgggggatt     2760
ccaaggattt acctaattgt ccaattctac gtgctctcta taccaaaaca aaaaaaaagc     2820
tatccacctt tccatgtggg tcaaactaaa attagaaatg tcccctcact gcagatcaaa     2880
tgtaaagctt ccagttaagg agctaaatga ggtcctcagc tgaatgagga accctgtaca     2940
```

```
tccccttgca cagccctatt ctaaatcgct taaactatgc tgatagctgc ttaggttctt    3000
gagtagttct gctcttaaac gtagggaggc cctgagaact aaattttgcc ccaaaataaa    3060
aacagaaatt atgagattgc ctcctgtcat tttggttaac ccagtccttc acctgccctg    3120
tgtcagtgtc ttctgagggc aattgcgttg ctcaaatcac tagcacagag gttccttaat    3180
ttggggcctt agaaaccatt gtgggccttg ggtccatga accccatgaa attatttgta    3240
gacttgtatg tacatttttc tggggagaag gttcaagaga ttcataagat tgtcaaactc    3300
cttgaaggtt cagaacctct gcagggaagg gggaagaaaa ccctcccatt aggaagcatg    3360
cttttgcagt taaatggcga tggtggaggt gatagggact tcaagagtaa aatgcacctt    3420
gtattgcata agaagcatac acaaatcaat aaatcaaggg agattatacc agtaggactg    3480
aatcagggcc ttcaaagctg gactgagttg gtcctgttct ggcacatatg gtccactgga    3540
gacaatgtat gattgagctt ttctttggtc taaaaattat attaaacatt tattttgaaa    3600
aaaaaaaaaa aaaaaaaaa aaaa                                            3624

<210> SEQ ID NO 127
<211> LENGTH: 316
<212> TYPE: DNA
<213> ORGANISM: Homo sapiens

<400> SEQUENCE: 127
tagtggtgcc atgaagttta ctaggaagtg attgtgaata agtaatagat ctaacattcg    60
cgtcatagag gaggtgttgg gacaccacag aatcttgttt gaatttatga attgagtcca    120
gttccccagt actttcagtg tctccaatcc tcctgcacac ctgtgtggtt tgtcttagga    180
ctcagtggtc tttgaggatg tggctgtgga cttcaccctg gaggagtggg ctttgctgga    240
ttctgctcag agggacctct acagagatgt gatgctggag accttccgga acctggcctc    300
agtaggtgag gatggc                                                    316

<210> SEQ ID NO 128
<211> LENGTH: 270
<212> TYPE: DNA
<213> ORGANISM: Homo sapiens

<400> SEQUENCE: 128
caaccgcatc gaggtggcca acctcaatgg cacatcccgg aaggtgctct tctggcagga    60
ccttgaccag ccgagggcca tcgccttgga ccccgctcac gggtacatgt actgacagga    120
ctggggtgag acgccccgga ttgagcgggc agggatggat ggcagcaccc ggaagatcat    180
tgtggactcg acatttact ggcccaatgg actgaccatc gacctggagg agcagaagct    240
ctactgggct gacgcaagct cagcttcatc                                     270

<210> SEQ ID NO 129
<211> LENGTH: 5100
<212> TYPE: DNA
<213> ORGANISM: Homo sapiens

<400> SEQUENCE: 129
atggagcccg agtgagcgcg gcgcggggcc gtccggccgc cggacaacat ggaggcagcg    60
ccgcccgggc cgccgtggcc gctgctgctg ctgctgctgc tgctgctggc gctgtgcggc    120
tgccccgccc ccgccgcggc ctcgccgctc ctgctatttg ccaaccgccg ggacgtacgg    180
ctggtggacg ccggcggagt caagctggag tccaccatcg tggtcagcgg cctggaggat    240
```

-continued

| | |
|---|---|
| gcggccgcag tggacttcca gttttccaag ggagccgtgt actggacaga cgtgagcgag | 300 |
| gaggccatca agcagaccta cctgaaccag acggggggccg ccgtgcagaa cgtggtcatc | 360 |
| tccggcctgg tctctcccga cggcctcgcc tgcgactggg tgggcaagaa gctgtactgg | 420 |
| acggactcag agaccaaccg catcgaggtg gccaacctca atggcacatc ccggaaggtg | 480 |
| ctcttctggc aggaccttga ccagccgagg ccatcgcct tggacccgc tcacgggtac | 540 |
| atgtactgga cagactgggg tgagacgccc cggattgagc gggcagggat ggatggcagc | 600 |
| acccggaaga tcattgtgga ctcggacatt tactggccca atggactgac catcgacctg | 660 |
| gaggagcaga agctctactg ggctgacgcc aagctcagct tcatccaccg tgccaacctg | 720 |
| gacggctcgt tccggcagaa ggtggtggag ggcagcctga cgcacccctt cgccctgacg | 780 |
| ctctccgggg acactctgta ctggacagac tggcagaccc gctccatcca tgcctgcaac | 840 |
| aagcgcactg gggggaagag gaaggagatc ctgagtgccc tctactcacc catggacatc | 900 |
| caggtgctga gccaggagcg gcagccttc ttccacactc gctgtgagga ggacaatggc | 960 |
| ggctgctccc acctgtgcct gctgtcccca agcgagcctt tctacacatg cgcctgcccc | 1020 |
| acgggtgtgc agctgcagga caacggcagg acgtgtaagg caggagccga ggaggtgctg | 1080 |
| ctgctggccc ggcggacgga cctacggagg atctcgctgg acacgccgga ctttaccgac | 1140 |
| atcgtgctgc aggtggacga catccggcac gccattgcca tcgactacga cccgctagag | 1200 |
| ggctatgtct actggacaga tgacgaggtg cgggccatcc gcagggcgta cctggacggg | 1260 |
| tctggggcgc agacgctggt caacaccgag atcaacgacc ccgatggcat cgcggtcgac | 1320 |
| tgggtggccc gaaacctcta ctggaccgac acgggcacgg accgcatcga ggtgacgcgc | 1380 |
| ctcaacggca cctcccgcaa gatcctggtg tcggaggacc tggacgagcc ccgagccatc | 1440 |
| gcactgcacc ccgtgatggg cctcatgtac tggacagact ggggagagaa ccctaaaatc | 1500 |
| gagtgtgcca acttggatgg gcaggagcgg cgtgtgctgg tcaatgcctc cctcgggtgg | 1560 |
| cccaacggcc tggccctgga cctgcaggag gggaagctct actggggaga cgccaagaca | 1620 |
| gacaagatcg aggtgatcaa tgttgatggg acgaagaggc ggaccctcct ggaggacaag | 1680 |
| ctcccgcaca ttttcgggtt cacgctgctg ggggacttca tctactggac tgactggcag | 1740 |
| cgccgcagca tcgagcgggt gcacaaggtc aaggccagcc gggacgtcat cattgaccag | 1800 |
| ctgcccgacc tgatggggct caaagctgtg aatgtggcca aggtcgtcgg aaccaacccg | 1860 |
| tgtgcggaca ggaacggggg gtgcagccac ctgtgcttct tcacaccca cgcaacccgg | 1920 |
| tgtggctgcc ccatcggcct ggagctgctg agtgacatga gacctgcat cgtgcctgag | 1980 |
| gccttcttgg tcttcaccag cagagccgcc atccacagga tctccctcga gaccaataac | 2040 |
| aacgacgtgg ccatcccgct cacgggcgtc aaggaggcct cagccctgga ctttgatgtg | 2100 |
| tccaacaacc acatctactg gacagacgtc agcctgaaga ccatcagccg cgccttcatg | 2160 |
| aacgggagct cggtggagca cgtggtggag tttggccttg actacccga gggcatggcc | 2220 |
| gttgactgga tgggcaagaa cctctactgg gccgacactg ggaccaacag aatcgaagtg | 2280 |
| gcgcggctga cgggcagtt ccggcaagtc ctcgtgtgga gggacttgga caacccgagg | 2340 |
| tcgctggccc tggatcccac caagggctac atctactgga ccgagtgggg cggcaagccg | 2400 |
| aggatcgtgc gggccttcat ggacgggacc aactgcatga cgctggtgga caaggtgggc | 2460 |
| cgggccaacg acctcaccat tgactacgct gaccagcgcc tctactggac cgacctggac | 2520 |
| accaacatga tcgagtcgtc caacatgctg ggtcaggagc gggtcgtgat tgccgacgat | 2580 |
| ctccccgcacc cgttcggtct gacgcagtac agcgattata tctactggac agactggaat | 2640 |

```
ctgcacagca ttgagcgggc cgacaagact agcggccgga accgcaccct catccagggc   2700
cacctggact tcgtgatgga catcctggtg ttccactcct cccgccagga tggcctcaat   2760
gactgtatgc acaacaacgg gcagtgtggg cagctgtgcc ttgccatccc cggcggccac   2820
cgctgcggct gcgcctcaca ctacaccctg gaccccagca gccgcaactg cagcccgccc   2880
accaccttct tgctgttcag ccagaaatct gccatcagtc ggatgatccc ggacgaccag   2940
cacagcccgg atctcatcct gcccctgcat ggactgagga acgtcaaagc catcgactat   3000
gacccactgg acaagttcat ctactgggtg gatgggcgcc agaacatcaa gcgagccaag   3060
gacgacggga cccagcccct tgttttgacc tctctgagcc aaggccaaaa cccagacagg   3120
cagccccacg acctcagcat cgacatctac agcggacacc tgttctggac gtgcgaggcc   3180
accaatacca tcaacgtcca caggctgagc ggggaagcca tggggtggt gctgcgtggg   3240 gaccgcgaca agcccagggc catcgtcgtc aacgcggagc gagggtacct gtacttcacc   3300
aacatgcagg accgggcagc caagatcgaa cgcgcagccc tggacggcac cgagcgcgag   3360
gtcctcttca ccaccggcct catccgcccct gtggccctgg tggtagacaa cacactgggc   3420
aagctgttct gggtggacgc ggacctgaag cgcattgaga gctgtgacct gtcaggggcc   3480
aaccgcctga ccctggagga cgccaacatc gtgcagcctc tgggcctgac catccttggc   3540
aagcatctct actggatcga ccgccagcag cagatgatcg agcgtgtgga gaagaccacc   3600
ggggacaagc ggactcgcat ccagggccgt gtcgcccacc tcactggcat ccatgcagtg   3660
gaggaagtca gcctggagga gttctcagcc cacccatgtg cccgtgacaa tggtggctgc   3720
tcccacatct gtattgccaa gggtgatggg acaccacggt gctcatgccc agtccacctc   3780
gtgctcctgc agaacctgct gacctgtgga gagccgccca cctgctcccc ggaccagttt   3840
gcatgtgcca gggggagat cgactgtatc cccggggcct ggcgctgtga cggctttccc   3900
gagtgcgatg accagagcga cgaggagggc tgccccgtgt gctccgccgc ccagttcccc   3960
tgcgcgcggg gtcagtgtgt ggacctgcgc ctgcgctgcg acggcgaggc agactgtcag   4020
gaccgctcag acgaggcgga ctgtgacgcc atctgcctgc ccaaccagtt ccggtgtgcg   4080
agcggccagt gtgtcctcat caaacagcag tgcgactcct tccccgactg tatcgacggc   4140
tccgacgagc tcatgtgtga aatcaccaag ccgccctcag acgacagccc ggcccacagc   4200
agtgccatcg ggcccgtcat tggcatcatc ctctctctct tcgtcatggg tggtgtctat   4260
tttgtgtgcc agcgcgtggt gtgccagcgc tatgcgggg ccaacgggcc cttcccgcac   4320
gagtatgtca gcgggacccc gcacgtgccc ctcaattcca tagccccggg cggttcccag   4380
catggcccct tcacaggcat cgcatgcgga aagtccatga tgagctccgt gagcctgatg   4440
gggggccggg gcggggtgcc cctctacgac cggaaccacg tcacagggc ctcgtccagc   4500 agctcgtcca gcacgaaggc cacgctgtac ccgccgatcc tgaacccgcc gccctcccccg   4560 gccacggacc cctccctgta caacatggac atgttctact cttcaaacat tccggccact   4620
gtgagaccgt acaggcccta catcattcga ggaatggcgc cccgacgac gccctgcagc   4680 accgacgtgt gtgacagcga ctacagcgcc agccgctgga aggccagcaa gtactacctg   4740
gatttgaact cggactcaga cccctatcca ccccacccca cgccccacag ccagtacctg   4800
tcggcggagg acagctgccc gccctcgccc gccaccgaga ggagctactt ccatctcttc   4860 ccgcccctc cgtccccctg cacggactca tcctgacctc ggccgggcca ctctggcttc   4920
tctgtgcccc tgtaaatagt tttaaatatg aacaagaaa aaaatatatt ttatgattta   4980
```

```
aaaaataaat ataattggga ttttaaaaac atgagaaatg tgaactgtga tggggtgggc      5040
agggctggga gaactttgta cagtggaaca aatatttata aacttaattt tgtaaaacag      5100

<210> SEQ ID NO 130
<211> LENGTH: 282
<212> TYPE: DNA
<213> ORGANISM: Homo sapiens

<400> SEQUENCE: 130
tttaaataaa aatgctgcaa ggtttccgcc tctgcgttcc ccttgtgatg gctggcaggt        60
ggtctggaag cgtcccggat ggcggccaag cgacaatggg gcaggtgtcc tggcagcgaa       120
gggcagcccg ccgcacgcg atacactgca cagcggcgtc cgggtggctc tggtatcgct        180
gcctccaaac ctcctggatc ttcctgcacc acttgtgtgc gttcccgctg gggtccatca       240
gataatacgt cctgttaggc gtgtggacaa agaaagtttt aa                          282

<210> SEQ ID NO 131
<211> LENGTH: 1891
<212> TYPE: DNA
<213> ORGANISM: Homo sapiens

<400> SEQUENCE: 131
ccgcttcggg gaggaggacg ctgaggaggc gccgagccgc gcagcgctgc ggggggaggcg       60 cccgcgccga cgcggggccc atggccagga ccaccagcca gctgtatgac gccgtgccca      120
tccagtccag cgtggtgtta tgttcctgcc catccccatc aatggtgagg acccagactg      180
agtccagcac gcccctggc attcctggtg gcagcaggca gggccccgcc atggacggca       240
ctgcagccga gcctcggccc ggcgccggct ccctgcagca tgcccagcct ccgccgcagc      300
ctcggaagaa gcggcctgag gacttcaagt ttgggaaaat ccttgggaa ggctctttt        360 ccacggttgt cctggctcga gaactggcaa cctccagaga atatgcgatt aaaattctgg      420
agaagcgaca tatcataaaa gagaacaagg tcccctatgt aaccagagag cgggatgtca      480
tgtcgcgcct ggatcacccc ttctttgtta agctttactt cacatttcag gacgacgaga      540
agctgtattt cggccttagt tatgccaaaa atggagaact acttaaatat attcgcaaaa      600
tcggttcatt cgatgagacc tgtacccgat tttacacggc tgagatcgtg tctgctttag      660
agtacttgca cggcaagggc atcattcaca gggaccttaa accggaaaac attttgttaa      720
atgaagatat gcacatccag atcacagatt ttggaacagc aaaagtctta tccccagaga      780
gcaaacaagc caggccaac tcattcgtgg aacagcgca gtacgtttct ccagagctgc        840
tcacggagaa gtccgcctgt aagagttcag acctttgggc tcttggatgc ataatatacc      900 agcttgtgg aggactccca ccattccgag ctggaaacga gtatcttata tttcagaaga      960
tcattaagtt ggaatatgac tttccagaaa aattcttccc taaggcaaga gacctcgtgg     1020
agaaactttt ggttttagat gccacaaagc ggttaggctg tgaggaaatg gaaggatacg     1080
gacctcttaa agcacacccg ttcttcgagt ccgtcacgtg ggagaacctg caccagcaga     1140
cgcctccgaa gctcaccgct tacctgccgg ctatgtcgga agacgacgag gactgctatg     1200
gcaattatga caatctcctg agccagtttg gctgcatgca ggtgtcttcg tcctcctcct     1260
cacactccct gtcagcctcc gacacgggcc tgccccagag gtcaggcagc aacatagagc     1320
agtacattca cgatctggac tcgaactcct tgaactgga cttacagttt tccgaagatg     1380
agaagaggtt gttgttggag aagcaggctg gcggaaaccc ttggcaccag tttgtagaaa     1440
ataatttaat actaaagatg ggcccagtgg ataagcggaa gggtttattt gcaagacgac     1500
```

-continued

```
gacagctgtt gctcacagaa ggaccacatt tatattatgt ggatcctgtc aacaaagttc    1560
tgaaaggtga aattccttgg tcacaagaac ttcgaccaga ggccaagaat tttaaaactt    1620
tctttgtcca cacgcctaac aggacgtatt atctgatgga ccccagcggg aacgcacaca    1680
agtggtgcag gaagatccag gaggtttgga ggcagcgata ccagagccac ccggacgccg    1740
ctgtgcagtg acgtggcctg cggccgggct gccctccgct gccaggacac ctgccccagc    1800
gcggcttggc cgccatccgg gacgcttcca gaccacctgc cagccatcac aaggggaacg    1860
cagaggcgga aaccttgcag catttttatt t                                   1891

<210> SEQ ID NO 132
<211> LENGTH: 410
<212> TYPE: DNA
<213> ORGANISM: Homo sapiens

<400> SEQUENCE: 132
cacaatataa accttaattt taatgacata ttggctagtc aataaacaag tcttatctca      60
tctcatctct tttctgataa caaacacccg atgtgttcaa tttgctttca tatttaagtc    120
tttcctgaat tgctgtcatc attcaacaac agttgcatgt cgccttgcta gctgtcaaag    180
tagacttcat ccccaaatgg atatctgtaa tgaaagaata caaggtgaaa attttattta    240 aaaattttt aaaagaattt ggttttggat taaaaggcat gcaagcagca ttaattccac     300
tcacagttac agtctatcac ctggggcatt cactactttt cagagtcaga tcacagttca    360
aaagacagct ctcaccttgg gggcatattc cccagtcagt gtgaacatgt                410

<210> SEQ ID NO 133
<211> LENGTH: 278
<212> TYPE: DNA
<213> ORGANISM: Homo sapiens

<400> SEQUENCE: 133
tttttttttt ttatcaaaag tttgttttat ttcaataca agataaatac catgcttgtt       60
actagtgcag tttaaggccg acaatggcca tatatcaaac tgccgaacag tcacctaaat     120
gctaaagaaa ggaaagacaa agtaaacatt aaacacaaaa ttgcaattac aaacatttta    180
ataaaatgga atgagctttt taattgaagc taatatgaag tctaattctc atggacagca    240
aaaaaaaaaa aaaaaaaaag tctattagat caattatc                             278

<210> SEQ ID NO 134
<211> LENGTH: 414
<212> TYPE: DNA
<213> ORGANISM: Homo sapiens

<400> SEQUENCE: 134 tttttttta agaaatttgt tcttttcatt tcattactta ggaattacaa gagactttgc       60
agaagggtaa aaatggtgag aactgaagag taatgccatt gttctaacag tgtcggggag     120
ttcacctggg ccagagaatg actctttttt cactactgcc cctgtaggg gagcgacatc     180 cctctgatag aaatgagatg caaagaccac gtgagttacc tgcccggtcc cagtaaggta    240
agtcataggt gccttcagtt ttttttcttt tgtttctcca gtgccaagca cacactaata    300
tgagaatgag agtagtgagg accatgacca gcacagggac aagaactgca ggcagcgcta    360
catctttggt tacatttgga gttacggtag tatttctgat atcaggactg gcag          414

<210> SEQ ID NO 135
```

<210> SEQ ID NO 135
<211> LENGTH: 697
<212> TYPE: DNA
<213> ORGANISM: Homo sapiens

<400> SEQUENCE: 135

| | | | | | |
|---|---|---|---|---|---|
| aattattaaa | aacactttat | tatgtataat | ttgtacatgc | ttcaatttgt | gtcacttagg | 60 |
| gtgatttatt | ttccaggttg | taatgacatc | taccgagatt | agctagatct | aattttcatt | 120 |
| ctgccatgcc | acatacaaaa | atacaatttt | caaacaaagc | ttcccttctt | tacacaaagg | 180 |
| tacacaagag | tttgtcagac | aaataaaata | agaatacttc | acacgtat | caacaccata | 240 |
| caaggcatta | ttcttcacac | agtaacatct | aatgtgttct | tttattttg | aaacagcagg | 300 |
| aaaagagccc | tttcccttca | gaggaaaata | aaaactttat | ctgttgctta | agccaaactc | 360 |
| cagggaggaa | ggtgtggtcc | tctggggaaa | gcagagggga | ggggatgtat | ggaggagaat | 420 |
| ggacgcccct | tcataagcac | ttcaggagga | aggaattgca | ggaggttcct | cggggacagt | 480 |
| cacacagctt | cccgatcctt | gccccttttcc | tcactgcaca | ctgctcaccg | gcgtcacaca | 540 |
| tggggacttg | gccatacttc | ttctcataga | tgggaacacg | tttactcttg | agcttcttca | 600 |
| agacttcttg | cagcgcttcg | atcagctcct | tctcgtggga | ggcatcatcc | acggcagaat | 660 |
| agatgtccag | agctcggggc | tggagcttcg | cgttctc | | | 697 |

<210> SEQ ID NO 136
<211> LENGTH: 796
<212> TYPE: DNA
<213> ORGANISM: Homo sapiens

<400> SEQUENCE: 136

| | | | | | |
|---|---|---|---|---|---|
| aacgacgagt | ttcagaacga | tggagagctc | ccgcgtgagg | ctgctgcccc | tcctgggcgc | 60 |
| cgccctgctg | ctgatgctac | ctctgttggg | tacccgtgcc | caggaggacg | ccgagctcca | 120 |
| gccccgagcc | ctggacatct | actctgccgt | ggatgatgcc | tcccacgaga | aggagctgat | 180 |
| cgaagcgctg | caagaagtct | tgaagaagct | caagagtaaa | cgtgttccca | tctatgagaa | 240 |
| gaagtatggc | caagtcccca | tgtgtgacgc | cggtgagcag | tgtgcagtga | ggaaggggc | 300 |
| aaggatcggg | aagctgtgtg | actgtccccg | aggaacctcc | tgcaattcct | tcctcctgaa | 360 |
| gtgcttatga | agggcgtcc | attctcctcc | atacatcccc | atccctctac | tttccccaga | 420 |
| ggaccacacc | ttcctccctg | gagtttggct | taagcaacag | ataaagtttt | tattttcctc | 480 |
| tgaagggaaa | gggctctttt | cctgctgttt | caaaaataaa | agaacacatt | agatgttact | 540 |
| gtgtgaagaa | taatgcctgt | atggtgttga | tacgtgtgtg | aagtatctat | ttattgtctg | 600 |
| acaaactctt | gtgtaccttt | gtgtaaagaa | gggaagcttt | gtttgaaaat | tgtattttg | 660 |
| tatgtggcat | ggcagaatga | aaattagatc | tagctaatct | cggtagatgt | cattacaacc | 720 |
| tggaaaataa | atcaccctaa | gtgacacaaa | ttgaagcatg | tacaaattat | acataataaa | 780 |
| gtgttttttaa | taatta | | | | | 796 |

<210> SEQ ID NO 137
<211> LENGTH: 333
<212> TYPE: DNA
<213> ORGANISM: Homo sapiens

<400> SEQUENCE: 137

| | | | | | |
|---|---|---|---|---|---|
| tttttttggat | gcacatttga | ttttactggg | ggtaggggac | agggctgggc | gttcaggagt | 60 |
| tctccgctat | ggtgtcctcg | atccacttca | cataagacag | cactctgacg | gcgacagaag | 120 |
| gcttattggg | ggtgccacaa | gggacgtagc | cccatgatgt | gacaccttgg | agcacaccat | 180 |

```
cacacatcag cgggccccct gaatcaccca cacaggtgtc tttgccacct tccaggtgtc     240
cgacacacag catgaagtct gtcaccttct ggacgtggct cggggtcgc gtaactagtt     300 agcatgccag agtctcgttc gttatcggaa tta                                 333
```

<210> SEQ ID NO 138
<211> LENGTH: 871
<212> TYPE: DNA
<213> ORGANISM: Homo sapiens

<400> SEQUENCE: 138

```
tcctccacct gctggcccct ggacacctct gtcaccatgt ggttcctggt tctgtgcctc     60
gccctgtccc tggggggac tggtgctgcg cccccgattc agtcccggat gtgggaggc     120 tgggagtgtg agcagcattc ccagccctgg caggcggctc tgtaccattt cagcactttc    180
cagtgtgggg gcatcctggt gcaccgccag tgggtgctca cagctgctca ttgcatcagc    240
gacaattacc agctctggct gggtcgccac aacttgtttg acgacgaaaa cacagcccag    300
tttgttcatg tcagtgagag cttcccacac cctggcttca acatgagcct cctggagaac    360
cacacccgcc aagcagacga ggactacagc cacgacctca tgctgctccg cctgacagag    420
cctgctgata ccatcacaga tgctgtgaag gtcgtggagt tgcccaccga ggaacccgaa    480
gtggggagca cctgtttggc ttccggctgg ggcagcatcg aaccagagaa tttctcattt    540
ccagatgatc tccagtgtgt ggacctcaaa atcctgccta atgatgagtg caaaaaagcc    600
cacgtccaga aggtgacaga cttcatgctg tgtgtcggac acctggaagg tggcaaagac    660
acctgtgtgg gtgattcagg gggcccgctg atgtgtgatg gtgtgctcca aggtgtcaca    720
tcatggggct acgtcccttg tggcacccc aataagcctt ctgtcgccgt cagagtgctg    780
tcttatgtga agtggatcga ggacaccata gcggagaact cctgaacgcc cagccctgtc    840
ccctaccccc agtaaaatca aatgtgcatc c                                   871
```

<210> SEQ ID NO 139
<211> LENGTH: 395
<212> TYPE: DNA
<213> ORGANISM: Homo sapiens

<400> SEQUENCE: 139

```
cctacatttt tgttcaacta agagtgctta tttcttcttg aaggttaaca ttatgtttat     60
taagtatcaa aatggaatta tcttttaaaa aagaagacaa gttttccata ctgtcacagt    120
aagctccaaa gaactttgtc tttctcataa agtaatattc tttatttgca tccatttact    180
atgattccgt taatttgttg aattaaatgc ctttataaaa atatttacaa atgttttctt    240
gccttaaaat gtaacatttt ctacttaaat ttaatttcca agagagtgat tatttgcatt    300
acaaaggaat tcttaataat tcctgtaagc ctaggaaata ggaatgccaa agtaacattt    360
aatgtacttc tctataactt ttcataatca gaaat                               395
```

<210> SEQ ID NO 140
<211> LENGTH: 483
<212> TYPE: DNA
<213> ORGANISM: Homo sapiens
<220> FEATURE:
<221> NAME/KEY: misc_feature
<222> LOCATION: 446, 470
<223> OTHER INFORMATION: n = A,T,C or G

<400> SEQUENCE: 140

```
ttgctaatga catcacttgc tgtttatgtt tattttagac tatggaaatg atgttagaca      60
aaaacaaatc caagcgattt tcttatttga gttcaaaatg ggtcgtaaaa gaagcgcaga     120
caactcacga tataaacaaa gcatttgtct caggaattgc taacgaacat acagtgcatt     180
caagaagttc aagaagtttt gcaaaggaaa agagatcctt gtagatgagg agcatagtgg     240
ccagacatcg gaagtccaca atgaccattt gagagcaatc attgaagctg tttctctaac     300
aaccacatga gaagttgcca aaagaactca aacctttgac gattctacag ccctttaagc     360
attttggaag ccaaatttgg gaaagctggg gaaaatctcc gctaagtggg gtgcctcatg     420
agctgagcga aaatttaaaa aatccncgtt tttgaagtgg tcatccttcn cctaattcta     480
cac                                                                   483

<210> SEQ ID NO 141
<211> LENGTH: 452
<212> TYPE: DNA
<213> ORGANISM: Homo sapiens
<220> FEATURE:
<221> NAME/KEY: misc_feature
<222> LOCATION: 64, 68, 418
<223> OTHER INFORMATION: n = A,T,C or G

<400> SEQUENCE: 141
gtctccagtg gttaaaaaga aaaagaaac aaggaacatg tttaatatct taaaaaacag      60
cacntaancc tgcaaaaatg tgaattattt gataaatact taaaaaacat gttaatcatg     120
tttagatttg aaaatgtggc atcaatgtga agcagtgcat tcaaccctct gtatcaggag     180
acagcggtgc tgcctgccca agactgcaga gagcagagac acagctgcat ctctcagcac     240
tctccccggc ccccaagaag agattccaat cacagcatat tcatttaaaa agcattctaa     300
tatagtaatt agactcatca aatacaaact ttttttcccc tttaaactat actctaaatt     360
tggccaaact aagtacttga tataaaaatc ctggcaaaga gcaggggtcc ctgcgggntt     420
ggtggtgggc aaacccagac attctctcgc cc                                   452

<210> SEQ ID NO 142
<211> LENGTH: 355
<212> TYPE: DNA
<213> ORGANISM: Homo sapiens

<400> SEQUENCE: 142
tttggctgta caaaagcttt tatggttttg taatcccaca tgtccatttt tgcttttgtg      60
gcctgtgatt ttcatatcca tgaaatcatt accaagacta atgtgatgaa gctttcccct     120
atgttttctt ctgaaagttt tacagtttca gttcttatgt tcaagttttt aatccatttt     180
gaattgattt tttgtgtatg atgtaagatt ggggcccaat tttattcttt tgtatgggga     240
tatccagttt tgctaacact atttgttgaa gagactatcc tttccacttt gcgtattctt     300
ggcactcttg tcaaacatca gttgaccgta tcatgtgtgg atttatttgt gaact          355

<210> SEQ ID NO 143
<211> LENGTH: 412
<212> TYPE: DNA
<213> ORGANISM: Homo sapiens
<220> FEATURE:
<221> NAME/KEY: misc_feature
<222> LOCATION: 392, 393, 394
<223> OTHER INFORMATION: n = A,T,C or G

<400> SEQUENCE: 143
tacacagtaa tgatataatt atgtgatgca aatattaact tcatcccttt ccttgtaaat      60
```

| | |
|---|---:|
| tcagcttttc tcaccagagc tcaggggcag tcatgacaat aaaaataaca atagtaatta | 120 |
| caagaaatgt gctctgagta cagagaaacc acaaggccca tctcaacaca caaatacaaa | 180 |
| aacaactcgc atttacgggg cgtttccagg agttaatagc atacagtacc atgggtaggg | 240 |
| tgtggttggc agaagctgtc cacttttttct aagtgcaggt gttcgttgct gaggatcttg | 300 |
| ttgctctcct cccttcgttt tctagagtaa cttcccagag gaccctgcct ggagcctgcc | 360 |
| aagccagagt ccagcgtaaa ggcccggagg tnnnttgtgt ctttctggcc ct | 412 |

<210> SEQ ID NO 144
<211> LENGTH: 4700
<212> TYPE: DNA
<213> ORGANISM: Homo sapiens

<400> SEQUENCE: 144

| | |
|---|---:|
| atggccccct cggcctgggc catttgctgg ctgctagggg gcctcctgct ccatggggt | 60 |
| agctctggcc ccagccccgg ccccagtgtg cccgcctgc ggctctccta ccgagacctc | 120 |
| ctgtctgcca accgctctgc catctttctg gccccagg gctccctgaa cctccaggcc | 180 |
| atgtacctag atgagtaccg agaccgcctc tttctgggtg gcctggacgc cctctactct | 240 |
| ctgcggctgg accaggcatg gccagatccc cgggaggtcc tgtggccacc gcagccagga | 300 |
| cagagggagg agtgtgttcg aaagggaaga gatcctttga cagagtgcgc caacttcgtg | 360 |
| cgggtgctac agcctcacaa ccggacccac ctgctagcct gtggcactgg ggccttccag | 420 |
| cccacctgtg ccctcatcac agttggccac cgtggggagc atgtgctcca cctggagcct | 480 |
| ggcagtgtgg aaagtggccg ggggcggtgc cctcacgagc ccagccgtcc ctttgccagc | 540 |
| accttcatag acgggagct gtacacgggt ctcactgctg acttcctggg gcgagaggcc | 600 |
| atgatcttcc gaagtggagg tcctcggcca gctctgcgtt ccgactctga ccagagtctc | 660 |
| ttgcacgacc cccggtttgt gatggccgcc cggatccctg agaactctga ccaggacaat | 720 |
| gacaaggtgt acttcttctt ctcggagacg gtcccctcgc ccgatggtgg ctcgaaccat | 780 |
| gtcactgtca gccgcgtggg ccgcgtctgc gtgaatgatg ctgggggcca gcgggtgctg | 840 |
| gtgaacaaat ggagcacttt cctcaaggcc aggctggtct gctcggtgcc cggccctggt | 900 |
| ggtgccgaga cccactttga ccagctagag gatgtgttcc tgctgtggcc aaggccgggg | 960 |
| aagagcctcg aggtgtacgc gctgttcagc accgtcagtg ccgtgttcca gggcttcgcc | 1020 |
| gtctgtgtgt accacatggc agacatctgg gaggttttca acgggcccctt tgcccaccga | 1080 |
| gatgggcctc agcaccagtg ggggccctat gggggcaagg tgcccttccc tcgccctggc | 1140 |
| gtgtgcccca gcaagatgac cgcacagcca ggacggcctt ttggcagcac caaggactac | 1200 |
| ccagatgagg tgctgcagtt tgcccgagcc cacccctca tgttctggcc tgtgcggcct | 1260 |
| cgacatggcc gccctgtcct tgtcaagacc cacctggccc agcagctaca ccagatcgtg | 1320 |
| gtggaccgcg tggaggcaga ggatgggacc tacgatgtca ttttcctggg gactgactca | 1380 |
| gggtctgtgc tcaaagtcat cgctctccag gcagggggct cagctgaacc tgaggaagtg | 1440 |
| gttctggagg agctccaggt gtttaaggtg ccaacaccta tcaccgaaat ggagatctct | 1500 |
| gtcaaaaggc aaatgctata cgtgggctct cggctgggtg tggcccagct gcggctgcac | 1560 |
| caatgtgaga cttacggcac tgcctgtgca gagtgctgcc tggcccggga ccatactgt | 1620 |
| gcctgggatg gtgcctcctg tacccactac cgccccagcc ttgcaagcg ccggttccgc | 1680 |
| cggcaggaca tccggcacgg caaccctgcc ctgcagtgcc tgggccagag ccaggaagaa | 1740 |

```
gaggcagtgg gacttgtggc agccaccatg gtctacggca cggagcacaa tagcaccttc    1800
ctggagtgcc tgcccaagtc tccccaggct gctgtgcgct ggctcttgca gaggccaggg    1860 gatgagggc  ctgaccaggt gaagacggac gagcgagtct tgcacacgga gcggggctg     1920 ctgttccgca ggcttagccg tttcgatgcg ggcacctaca cctgcaccac tctggagcat    1980
ggcttctccc agactgtggt ccgcctggct ctggtggtga ttgtggcctc acagctggac    2040
aacctgttcc ctccggagcc aaagccagag gagcccccag cccggggagg cctggcttcc    2100
accccaccca aggcctggta caaggacatc ctgcagctca ttggcttcgc caacctgccc    2160
cgggtggatg agtactgtga gcgcgtgtgg tgcaggggca ccacggaatg ctcaggctgc    2220
ttccggagcc ggagccgggg caagcaggcc aggggcaaga gctgggcagg gctggagcta    2280
ggcaagaaga tgaagagccg ggtgcatgcc gagcacaatc ggacgccccg ggaggtggag    2340
gccacgtaga agggggcaga ggaggggtgg tcaggatggg ctgggggcc  cactagcagc    2400 ccccagcatc tcccacccac ccagctaggg cagaggggtc aggatgtctg tttgcctctt    2460
agagacaggt gtctctgccc ccacaccgct actgggtct  aatggagggg ctgggttctt    2520
gaagcctgtt ccctgccctt ctctgtgctc ttagacccag ctggagccag cacctctgg    2580 ctgctggcag ccccaaggga tctgccattt gttctcagag atggcctggc ttccgcaaca    2640
catttccggt gtgcccaga  ggcaagaggg ttgggtggtt cttcccagc  ctacagaaca    2700 atggccattc tgagtgaccc tcagagtggg tgtgtgggtg cgtctagggg gtatcccggt    2760 aggggggcctg cagggagcca gagggtggaa atggcctcta agctagcacc ccgtaagaag    2820
agcctacctg accgacttgg ggagggaaca cagaggtgtt gggaaggtgg agcaacaatg    2880
cacctcccct cctgtcgcgc cgtgatatct tggtggctcc ctgccactgc ccaccgcctc    2940
ttctccatct gagaatcacg gagaggtgta gataatctag aggcatagac tgctagagcc    3000
cccagggatc tggggtggtc agggctcagg cttcactttg taaaccaggt gggggcatct    3060
cacagcctga cttcccttcc ccaggccagg gttgctggga tgcctgcccc tcctgagagg    3120
accccctccc cattgtcagg ctctccatgt ccacgagcgg ggaggggtgg gttctgggc     3180 attgttgtcc cttgtgtctg tggactagag ataggggtggg ggagctgggg aagggtgcag    3240
gcgggaagag tgggctgtct ttcccagggt gatgcaagca tgccgcagcc ctggaggctg    3300
ggaatgtgga ggctctgtga gccctgcagc cctcagaatc agggccaggg atgcagaaga    3360
ttgagaggat atgagatgg  atagagggca ggagacccctt aggatagatt gtgggaccca    3420
ggcaggaaca ggtgtccaca agaactcagg atggcatcag ttagctcaga agccacctgg    3480
aagacccagt gtttccatct ctggaatctc tgtttatgc  taaatggatt taggaagact    3540 gttttttcttt taagggggaa acaaggtaga aaaaggacg  aagaagtgta agtcccgctg    3600
attctcgggg gtaaggctcg gatgcaagg  acgcgttctg cctgggcatg taggggaggt    3660 gttttgcca  tcaccagttt ctcaggctgg ggagcacaga ggggaggagg aggactaaat    3720
gaaaagttgt tcccagcctg cacatgaaca cattcatgac acacaaaact ggctggaagg    3780
agataagagc actgggtttg agattccctc cattaaaaca accaagacaa agaaaggagg    3840
ggaaaaaaag ataaaaagca agccagggtt ccctgcccta ttgaaactca aacccagact    3900
gccttgggtt ttatctttcc cttacccctg gcacctccag agaactggga cctgaaatag    3960
tccctccgtt ctccccttg  accatgtaat aaatgaacca gaagcactga gattaaccta    4020
tcaacgccct gagaagcctt ccagcctgcg gtgctgtctg ctgggaggtc agctggtcaa    4080
ggcagaggag gagaggagga aaggatgggg gctgaagagc agaagggagg ggagacagag    4140
```

-continued

```
gggattaaag aggggaggag agagtgcaga gctccaggaa agggtatcag agctgcagcc    4200
agctctgccc tctaccctag ggaggccaga agacacaaa cagccctccg ggcctttacg    4260
ctggactctg gcttggcagg ctccaggcag ggtcctctgg gaagttactc tagaaaacga    4320
agggaggagg agcacaagat cctcagcaac gaacacctgc acttagaaaa agtggacagc    4380
ttctgccaac cacaccctac ccatggtact gtatgctatt aactcctgga aacgccccgt    4440
aaatgcgagt tgttttttgta tttgtgtgtt gagatgggcc ttgtggtttc tctgtactca    4500
gagcacattt cttgtaatta ctattgttat ttttattgtc atgactgccc ctgagctctg    4560
gtgagaaaag ctgaatttac aaggaaaggg atgaagttaa tatttgcatc acataattat    4620
atcattactg tgtatctgtg tattgtacta aatggactga tgctgcgcac atgagctgaa    4680
aatgaagagc cctcccatcc                                               4700
```

<210> SEQ ID NO 145
<211> LENGTH: 453
<212> TYPE: DNA
<213> ORGANISM: Homo sapiens
<220> FEATURE:
<221> NAME/KEY: misc_feature
<222> LOCATION: 68
<223> OTHER INFORMATION: n = A,T,C or G

<400> SEQUENCE: 145

```
tttgtttaaa ggcaatctaa cagattggaa ccctgataag atcatgcctg tgcagccctg     60
caccgacnga aggagactgt gatcaagtct gttactcgtt acagtactgt gaacgtcaac    120
aagaagaatt gctgcatgga aaacactgaa tataggcaga caatctctc gcttacgata    180 ctgtgtgttg caaataatgc ctagaccaga gcaatgcagg cgctatgatt catcacaggc    240
aagatcaaca aaggaattgt taggacaaag aagaggctgc atgcagacct cccctgtcaa    300
aacacctcgc agctcattgg cttcatacag cctgccaaat gcaagggaag cagagagagg    360
gatggtgggt aggaagagaa actttttttg cctgacaagc aacagccctc ttccccacaa    420
agcaggacag ttccttataa ctaagagtaa gtt                                 453
```

<210> SEQ ID NO 146
<211> LENGTH: 290
<212> TYPE: DNA
<213> ORGANISM: Homo sapiens

<400> SEQUENCE: 146

```
attgattacc catgtagtac aagtgtcgga tttaatgttc acacaccata gagaggcggc     60
agggacagat ggtgccttaa ctcttctttg atagatttta atggtgaaat attgatttct    120
gtctggccaa gacctgctgt tagggccaa agtcatttgt tgggtattgc cggacaccca    180
gttgccccag cgtaatcaat catttttggc aaggcaggtg aaaatccaga gagaagcacc    240
ttggaaccca aactggagcg tgatgtgtct gagtccagcc acctggattg               290
```

<210> SEQ ID NO 147
<211> LENGTH: 487
<212> TYPE: DNA
<213> ORGANISM: Homo sapiens

<400> SEQUENCE: 147

```
ttcggcactt gggagaagat gtttgaaaaa actgactctg ctaatgagcc tggactcaga     60
gctcaagtct gaactctacc tccagacaga atgaagttca tctcgacatc tctgcttctc    120
```

```
atgctgctgg tcagagcctc tctccagtcc aaggtgttct ggaggtctat tacacaagct    180
tgaggtgtag atgtgtccaa gagagctcag tctttatccc tagacgcttc attgatcgaa    240
ttcaaatctt gcccccgtgg taatggttgt ccaagaaaag aaatcatagt ctggaagaag    300
aacaagtcaa ttgtgtgtgt ggaccctcaa gctgaatgga tacaagaat gatggaagta     360 ttgagaaaaa gaagttcttc aactctacca gttccagtgt ttaagagaaa gattccctga    420
tgctgatatt tccactaaga acacctgcat tcttcccttta tccctgctct ggattttagt    480
tttgtgc                                                              487
```

<210> SEQ ID NO 148
<211> LENGTH: 415
<212> TYPE: DNA
<213> ORGANISM: Homo sapiens
<400> SEQUENCE: 148

```
aagtaaaatg tttgctcaac tttattgaat gtcattagat ttataggaat cattaaagaa     60
ttagatacca gagtcccccc ggcccagacc cccacaaaaa aagtcagtga aaaagatgtg    120
agtgaaagaa gtttgtcaag gcaaatgtgt gaaaggatac atgtgtacat cacccttaa    180 atgctttccc tgagtattct atgaagtctg gggatcttcg aatgctatta atcttagaca    240
gtaaatttta taagaaatt cttaaaagt aggacttaat tctcctccgt agtgagtttt      300
taagcagagg atatctacta catggattcc tttgcctctt gacaggctca agttccatct    360
gcctcccagg cagcttttg agtctttcat agaagcctgc ttttaatata tgcca         415
```

<210> SEQ ID NO 149
<211> LENGTH: 1216
<212> TYPE: DNA
<213> ORGANISM: Homo sapiens
<400> SEQUENCE: 149

```
ttcggcactt gggagaagat gtttgaaaaa actgactctg ctaatgagcc tggactcaga     60
gctcaagtct gaactctacc tccagacaga atgaagttca tctcgacatc tctgcttctc    120
atgctgctgg tcagcagcct ctctccagtc caaggtgttc tggaggtcta ttacacaagc    180
ttgaggtgta gatgtgtcca agagagctca gtctttatcc ctagacgctt cattgatcga    240
attcaaatct tgcccccgtgg gaatggttgt ccaagaaaag aaatcatagt ctggaagaag    300
aacaagtcaa ttgtgtgtgt ggaccctcaa gctgaatgga tacaagaat gatggaagta     360 ttgagaaaaa gaagttcttc aactctacca gttccagtgt ttaagagaaa gattccctga    420
tgctgatatt tccactaaga acacctgcat tcttcccttta tccctgctct ggattttagt    480
tttgtgctta gttaaatctt ttccagggag aaagaacttc cccatacaaa taaggcatga    540
ggactatgtg aaaataacc ttgcaggagc tgatggggca aactcaagct tcttcactca     600
cagcacccta tatacacttg gagtttgcat tcttattcat cagggaggaa agtttctttg    660
aaaatagtta ttcagttata agtaatacag gattattttg attatatact tgttgtttaa    720
tgtttaaaat ttcttagaaa acaatggaat gagaatttaa gcctcaaatt tgaacatgtg    780
gcttgaatta agaagaaaat tatggcatat attaaaagca ggcttctatg aaagactcaa    840
aaagctgcct gggaggcaga tggaacttga gcctgtcaag aggcaaagga atccatgtag    900
tagatatcct ctgcttaaaa actcactacg gaggagaatt aagtcctact tttaaagaat    960
ttctttataa aatttactgt ctaagattaa tagcattcga agatcccag acttcataga    1020 atactcaggg aaagcattta aagggtgatg tacacatgta tcctttcaca catttgcctt   1080
```

```
gacaaacttc tttcactcac atctttttca ctgactttttt ttgtgggggc ggggccgggg    1140
ggactctggt atctaattct ttaatgattc ctataaatct aatgacattc aataaagttg    1200
agcaaacatt ttactt                                                    1216

<210> SEQ ID NO 150
<211> LENGTH: 405
<212> TYPE: DNA
<213> ORGANISM: Homo sapiens

<400> SEQUENCE: 150
tttgtgtcaa aggccttta ttcattaact gaacaatcat tggttgattt cttaaaaaat     60
tgtggtgaac caataaaagc taaagttcct tctaattgtg ggcttaactg aattacagtt   120
ttaaaatgtg gtgtcttcat tgccactcag ttcaatatat tttctaactt ccacttgatt   180
taaaagtcat gtttgatagt gtattgccag tttgtttaag acaggtatga ttaactgcat   240
cttagagaac tcgtctgtcc tggactgact gaagaatttc tgcactttgc catgttccat   300
ttttccatgg aaacagtgct ctgcagtgag cctctctctt caactccacc atgtcactgg   360
tctacctggt ctgggagcca gtagacttag ctgagacggg ctgta                   405

<210> SEQ ID NO 151
<211> LENGTH: 343
<212> TYPE: DNA
<213> ORGANISM: Homo sapiens

<400> SEQUENCE: 151
ccgagaagga ggtccagcag tggtacaaag gcttcatcaa ggactgcccc agtggcagct    60
ggatgcggca ggctaccaga agatctacaa gcaattcttc ccgttcggag accccaccaa   120
gtttgccaca tttgttttca acgtctttga tgaaaacaag gacgggcgaa ttgagttctc   180
cgagttcatc caggcgctgt cggtgacctc acggggaacc ctggatgaga agctacggtg   240
ggccttcaag ctctacgact tggacaatga tggctacatc accaggaatg agatgctgga   300
cattgtggat gccatttacc agatggtggg gaataccgtg gag                     343

<210> SEQ ID NO 152
<211> LENGTH: 4341
<212> TYPE: DNA
<213> ORGANISM: Homo sapiens

<400> SEQUENCE: 152
ccggcccggc ccgcccggcc cagccgctcc tgctgggcgc cccaaccggg tccggcccgg    60
gggggcgggg gccgcggccg ccgaggatgg ggaaatccaa cagcaagttg aagcccgaag   120
ttgtggagga gctgaccagg aagacctact ttaccgagaa ggaggtccag cagtggtaca   180
aaggcttcat caaggactgc cccagtgggc agctggatgc ggcaggcttc agaagatct    240 acaagcaatt cttcccgttc ggagacccca ccaagtttgc cacatttgtt ttcaacgtct   300
ttgatgaaaa caaggacggg cgaattgagt tctccgagtt catccaggcg ctgtcggtga   360
cctcacgggg aaccctggat gagaagctac ggtgggcctt caagctctac gacttggaca   420
atgatggcta catcaccagg aatgagatgc tggacattgt ggatgccatt taccagatgg   480
tggggaatac cgtggagctc ccagaggagg agaacactcc tgagaagagg gtggaccgga   540
tctttgccat gatggataag aatgccgacg ggaagctgac cctgcaggag ttccaggagg   600
ggtccaaggc agacccgtcc attgtgcagg cgctgtccct ctacgacggg ctggtatagt   660
```

-continued

```
cccaggctgg agctggatgc ctgggaacca ctcacctcct tctgtgccat gaggccacct       720
cagccctgac accaaccccg tgcgtccacc cagccttctt ccgcatccac acacagccgg       780
ctgcccttga cccggggaggc cccggctctc ctctcccctg tcctgcaccc atccccgcc       840 tgaagccacc ggctccaatt gccagcaacc tctgcttgtc cggaaaacga caacacgaaa       900
tggaaaaggc tacagccctc tgcataaacc aaggacttgg ctgcctcgca ggcagcctcc       960
gttcctcccg ctctcttgcg cgtgtgcttt tgttttttat tttgaacaga cgttttaaaa      1020
gaaaaaaaaa caactacctt ctgtcctaga agacacagac tgacagatgg ggtgaaggcc      1080
tggggacctc agagaactct gccttgccct cgtccctcgt ccttcggcag ccggagaggc      1140
tgtgggtggg ccgagggtgt ctaggggttc tgcctagtca acgttatttg tcgtcccatc      1200
ttttggcagc aaaaccacct gcgtggctag gatgattaat tatgaggatg atgatttttt      1260
ttgtgataac agtattgtgc ttttttgtggg gaaagtgagg tttttttttt atatacatat      1320
ataattgata tctttaattt attggttgtt aactgttgct gctgcctggt gtgtcctcag      1380
ctcccagggc tgcgggccca ccgtttacat gtgcacgccc tgacccacct gcccacgccg      1440
acttgggagg atggtggcct gcagcggcca agaagccaaa aaaaattttt ttttttttcag      1500 atactgtgct tgattttttgg agaggggaga ggtggaaatt cctaaatggc taatgcactg      1560
ttccctccag cccgaatgcc tcctgccaaa ccccttttcc ctgctgcctc tgtccccgca      1620
tccttgttct cccctgggtc cgtaacattt tttccgagga tgaacagggg acatctttag      1680
gtttctcaac tcttgctttg gtgtttgccg cagcatggaa aacagggcgc ctaaggctgg      1740
gagctggaag aaggggcatt gggtacccag gcagagtcag gagaggtggt ctttgaagta      1800
agttagcaga aatcaagggg accccgcct cctgggctg gggaggggat ttcaagatag      1860
ttcataactc tctcccgctc tgccttccct ccttcctatc tgcttttttcc agtaaactgc      1920 atggtgtcct tccctggcct tctcttggct caaaggctgg gagggaggga aggagagaag      1980
agttccaggc aatcccatca atatagtccc tacacctggg gctgcggccc acatgtcttc      2040
acggaggctt ccagcggtgc ctgccactga ggcaggtgcg gccccaggac catcaccagg      2100
aatgcgaggc caccctggac cagaggtagg agcccaaggt ccggcccttg ctctttgatt      2160
gtgggcagcc tcctgccctc tctgggtctc agttgcccca tctgcagagc gaggaggccc      2220
gggctggttg gtcttgaagg ccttttttcca tgccgacatc atgtcactct aggcctgggg      2280 ttcagttttcc tgtggctggt gatgctgtgg ttaagtttgc ttgacccag cagcccgagg      2340 gactgtctga gtcacagcac agcccctatt gcgtggctgc tggtgtgtgg ggtcagttcc      2400
agcagatgaa tgtgtcatgt ggcacacctt gtcccttccc gcagcatttc ctggttcccc      2460 ccagacccctt gagcgctctt tgggacccag aaggagtcct tgcacaggga aggcttgagg      2520
tgagaagccg cttcccagac tgtcagggcc aggcctgggt ctagaattct tgctgctgct      2580
ttgcagagtc aacagcccat cagcccatgt tttagagggg acactttggt cctcggttcc      2640 cacccctcagc aagcaggcct ccagcccgag gaaggcctct gccgtagtga cgttgccgtg      2700
tggggctgcg tggctgttcc ccttggctgg agcattcagc caaccccagc gtcccccctg      2760
aggcgttcat tggcagcccc ctaggactgc acgctggccc cacggtaacc cccctcccc      2820 caccaacatc ctgcagggat ggggtcagtg gttccacctt cacaggccac tttgaagggt      2880
ggattctttg aggcccctgc cagtcggctc cctgctcagc tgctggcccg ggcgacctgg      2940
gactcagcac caacgctga agtttctcag ctgggtctg acctggggtc tggggcaggg      3000
aacgaacatg gtggctttgg gctgagagga tgagggaggt cttccccagg tcaaaattact      3060
```

```
ttcctttggc ctctgcctga ggctcgattt gcctctctgg tccaatggga ctgacactgt      3120
tgtacaacct gacctgtggc tgagggtgtc tgggcttaag catgtggacc ccttcggtgt      3180
gtctggcctt cctccatcgt cctgcccttt ggccttttgg tttgaagcca caggtgtggc      3240
ttctggcctt agcagatggt atgcttgcgg accgcagccc agcatgccgg tgggcccaca      3300
gcccgagcca gcccagagct gccggaaggg ccgcccttcc cggccctggc ggggtgctgg      3360
acactggcca ttttcactag agtttgcctg gcagggaccg atctctgccc cctcctctcc      3420
ccaggcctct ggctgcagtg atgccgcaga atcctgagcc aggtgcctcc tgagcagccc      3480
gtgcgcctct ccacagcggc gtttgccacc caatgcggct cgcttcagat gctctgatgc      3540
agagggcacg cccatagtcc ctctgcagag cctcgcactg gggccagggc aggcaccagc      3600
cccaggcggc cagtcggcca cggcctgtcc tcttcctcgt agcgtctgct cctcactttg      3660
tgttgatggt gacttaggag aatgttccga ttttccatga tctaagcagg ccacgtttaa      3720
aataacatca aggcaagcgt acgtgtcacc ctctgtactg acatctcctc ccctgaaatg      3780
cttttcagtt tgacagcccg tttcctagac aagtgcacct ggggtttcag gaactttgtg      3840
ttttttcgga gggggttggt ggggaggtcg ggatgcctgg gatcccttcc tggagaggca      3900
ggctgtctct ggaaaaagcc tccattgccc acccgccagg cggaaagtca ccctgttccc      3960
agcgcggttt cagcatttaa ttttaaggga gctaaggaag cgcggcgcgc ccctggtgg      4020 tggtaagccg ccaacgcacc tggggctgc aaccccaccg gacgggtggt ccggagggag      4080
gctggagcgg ggaggcgagg aggggctgt gagtcctcag aggccctggg ccaccacatt      4140
tctggcagcg tttcccagac acccctctgc taggccatcc ctggatagca agtgaattaa      4200
cttaagggca ctgtgatggg aagccttgcc cccctctttt ttttttttt tttaatatct      4260 gcggaataaa cccaatggtt aattttttgaa tgaataaaag cttttgttg aataaaaaaa      4320 aaaaaaaaa aaaaaaaaa a                                                  4341

<210> SEQ ID NO 153
<211> LENGTH: 355
<212> TYPE: DNA
<213> ORGANISM: Homo sapiens

<400> SEQUENCE: 153
gctgacaccc tgctctccta ccgcattcct cttgctgaga cactgaaaat ggtaatcaat       60
aaactgaggg aactcagagg ccggtgcggt gctggtcctc cgtatgctga gtgccggtct      120
cctgggcccg ctgttctttc tctgtacttt gtctccgtgt cttatttctt ttctcagtct      180
ctcatcccac atatgaagaa ttctaatctt caaaaaattt tagaactcag tcagaacttg      240
agaacttctt tcagtaggtg tagtcccagg tagacaaaca acacggcctt cctcagcctc      300
tacccgagtc gtttcagaag agtgtgagcc atgagaaatc agagctgtta ttttc          355

<210> SEQ ID NO 154
<211> LENGTH: 372
<212> TYPE: DNA
<213> ORGANISM: Homo sapiens
<220> FEATURE:
<221> NAME/KEY: misc_feature
<222> LOCATION: 149, 187, 290, 351, 361
<223> OTHER INFORMATION: n = A,T,C or G

<400> SEQUENCE: 154
ggctgctcca ccacagttag aggaggcagc cctgcttaca gactatagca ggttttata       60
```

```
gggccagaac taggtcgggg tgggggagct gagttgggggg tgcaggagaa ctgggttggg      120
gtgggggagc tgagtcgagg gtgcaggtnt cttgtctgca tcctggagat gttttttgcc      180
agctttntta tgcgaggtga acagacatgt taaccgcatc ctgtaactgt ctggacagtt      240
actggaggga tcagtgaagg ggggtttgtt ttttgccctg ggggtagctn tgcggagagc      300
aaaaggggac cctattgtaa gtccccttgg gaggggaagg gaaccggtct natcaagggt      360
naaccccaaa ca                                                          372

<210> SEQ ID NO 155
<211> LENGTH: 230
<212> TYPE: DNA
<213> ORGANISM: Homo sapiens
<220> FEATURE:
<221> NAME/KEY: misc_feature
<222> LOCATION: 207
<223> OTHER INFORMATION: n = A,T,C or G

<400> SEQUENCE: 155
acaagtctat ctttatttgt aaaaaataat atacaactaa agctaatttg attttttaaaa     60 tcgaagttca tttagtgata atgtacactt tataataaaa ttgtagtaaa atactgacat     120
ttgatagtta taaacaaagt atcattcatg taaaaatcat gttatagcat gtaaaattta     180
attagaaaat tcatagctca caaaagnaca tatattttgt tgatagctcc               230

<210> SEQ ID NO 156
<211> LENGTH: 177
<212> TYPE: DNA
<213> ORGANISM: Homo sapiens
<220> FEATURE:
<221> NAME/KEY: misc_feature
<222> LOCATION: 153, 161, 168
<223> OTHER INFORMATION: n = A,T,C or G

<400> SEQUENCE: 156
ttgttttaaa gggggttttc acttacactt tttggtatga tgaattttttt gttaaataaa     60 cagatacaat agaattaaac taaggaccaa ttagtgcaaa aatgcattaa atacagctct    120
ccaggatttt taggatatgc ctcatttctg agnaataaaa nttttttangg ggaaaca       177

<210> SEQ ID NO 157
<211> LENGTH: 327
<212> TYPE: DNA
<213> ORGANISM: Homo sapiens

<400> SEQUENCE: 157
ctttagatga tgttgccatg gtacttgatg aagaagcaga agttttttata gtcaaaatgt    60 ggagattatt gatatatgaa acagaagcca agaaaattgg tcttgtgaag taaaacttttt  120 tatatttaga gttccatttc agatttcttc tttgccaccc ttttaaggac tttgaatttt   180 tcttttgtctt tgaagacatt tgtgagatctg taatttttttt tttttgtaga aaatgtgaat   240
tttttggtcc tctaatttgt tgttgccctg tgtactccct tggttgtaaa gtcatctgaa     300
tccttggttc tctttatact caccagg                                         327

<210> SEQ ID NO 158
<211> LENGTH: 512
<212> TYPE: DNA
<213> ORGANISM: Homo sapiens

<400> SEQUENCE: 158
tgtatctttt tttaacttat taaatggcta gtgggaaaga tttgtgcttg tgatcagctc      60
```

```
ttaacttcaa tttttacatc aaaacgtccc tgaaaacggt ctttctcact gtacccaatg      120
ttctcaccgt acgccttaca ctctatgcga atttcagtgt ccatggtaag attggtgaac      180
tgtacggcca gcaggggctg caggtatttg ggctgcagga gtttgccata gtacggataa      240
tactgcagag gaaaaccagg ggagttgcac agtccaaaat actccacatt ccaacttta       300 tccttatctt catctcgctt gccagtgcac tgaacgggaa ggacatttgg gttatacttc      360
atcactgggt aagtctccaa ggactcattc aatgggggct taggtttgaa gcctataaat      420
cggttgagcc ttataataat gcaagggttg tcctctttgt agccataagt ttcatcattt      480
aatccgagca atttcccggc catgcaaact tg                                    512

<210> SEQ ID NO 159
<211> LENGTH: 2208
<212> TYPE: DNA
<213> ORGANISM: Homo sapiens

<400> SEQUENCE: 159
gaattcatgc taaattgctg gaaggctgcg tctctgctgt ggtgtcagtt ccggatgcct       60
catcgccagg ggcgcgccgc agccacccac cctccggacc gcggcagctg ctgacccgcc      120
atcgccatgg cccgcgggaa agccaaggag gagggcagct ggaagaaatt catctggaac      180
tcagagaaga aggagtttct gggcaggacc ggtggcagtt ggtttaagat ccttctattc      240
tacgtaatat tttatggctg cctggctggc atcttcatcg gaaccatcca agtgatgctg      300
ctcaccatca gtgaatttaa gcccacatat caggaccgag tggccccgcc aggattaaca      360
cagattcctc agatccagaa gactgaaatt cctttcgtc ctaatgatcc caagagctat       420
gaggcatatg tactgaacat agttaggttc ctggaaaagt acaaagattc agcccagagg      480
gatgacatga ttttgaaga ttgtggcgat gtgcccagtg aaccgaaaga acgaggagac       540
tttaatcatg aacgaggaga gcgaaaggtc tgcagattca gcttgaatg gctgggaaat       600 tgctctggat taaatgatga aacttatggc tacaaagagg gcaaaccgtg cattattata      660
aagctcaacc gagttctagg cttcaaacct aagcctccca agaatgagtc cttggagact      720
tacccagtga tgaagtataa cccaaatgtc cttcccgttc agtgcactgg caagcgagat      780
gaagataagg ataaagttgg aaatgtggag tattttggac tgggcaactc ccctggtttt      840
cctctgcagt attatccgta ctatggcaaa ctcctgcagc ccaaatacct gcagcccctg      900
ctggccgtac agttcaccaa tcttaccatg gacactgaaa ttcgcataga gtgtaaggcg      960
tacggtgaga acattgggta cagtgagaaa gaccgttttc agggacgttt tgatgtaaaa     1020
attgaagtta gagctgatc acaagcacaa atctttccca ctagccattt aataagttaa     1080
aaaaagatac aaaaacaaaa acctactagt cttgaacaaa ctgtcatacg tatgggacct     1140
acacttaatc tatatgcttt acactagctt tctgcattta ataggttaga atgtaaatta     1200
aagtgtagca atagcaacaa atatttatt ctactgtaaa tgacaaaaga aaagaaaaa       1260 ttgagccttg ggacgtgccc attttttactg taaattatga ttccgtaact gaccttgtag     1320
taagcagtgt ttctggcccc taagtattgc tgccttgtgt attttattta gtgtacagta     1380
ctacaggtgc atactctggt cattttttcaa gccatgtttt attgtatctg ttttctactt     1440
tatgtgagca aggtttgctg tccaaggtgt aaatattcaa cgggaataaa actggcatgg     1500
taattttttt tttttgtttg ttttttgttt tttggctctt tcaaaggtaa tggcccatcg     1560
atgagcattt ttaacatact ccatagtctt ttcctgtggt gttaggtctt tattttatt      1620
```

```
tttttcctgg gggctggggt gggggtttgt catgggggaa ctgcccttta aattttaagt    1680
gacactacag aaaaacacaa aaaggtgatg ggttgtgtta tgcttgtatt gaatgctgtc    1740
ttgacatctc ttgccttgtc ctccggtatg ttctaaagct gtgtctgaga tctggatctg    1800
cccatcactt tggcctaggg acagggctaa ttaatttgct ttatacattt tcttttactt    1860
tccttttttc ctttctggag gcatcacatg ctggtgctgt gtctttatga atgttttaac    1920
cattttcatg gtggaagaat tttatattta tgcagttgta caattttatt tttttctgca    1980
agaaaaagtg taatgtatga aataaaccaa agtcacttgt ttgaaaataa atctttattt    2040
tgaactttat aaaagcaatg cagtacccca tagactggtg ttaaatgttg tctacagtgc    2100
aaaatccatg ttctaacata tgtaataatt gccaggagta cagtgctctt gttgatcttg    2160
tattcagtca ggttaaaaca acggacaata aaagaatgaa ccgaattc                2208
```